(12) United States Patent
Matsuda et al.

(10) Patent No.: US 8,975,256 B2
(45) Date of Patent: *Mar. 10, 2015

(54) 1,2,3,4-TETRAHYDROQUINOXALINE COMPOUNDS HAVING GLUCOCORTICOID RECEPTOR BINDING ACTIVITY

(71) Applicant: Santen Pharmaceutical Co., Ltd., Osaka (JP)

(72) Inventors: Mamoru Matsuda, Ikoma (JP); Toshiyuki Mori, Ikoma (JP); Kenji Kawashima, Ikoma (JP); Minoru Yamamoto, Ikoma (JP); Masatomo Kato, Ikoma (JP); Miwa Takai, Ikoma (JP); Masato Nagatsuka, Ikoma (JP); Sachiko Kobayashi, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/937,447

(22) Filed: Jul. 9, 2013

(65) Prior Publication Data

US 2013/0303537 A1 Nov. 14, 2013

Related U.S. Application Data

(62) Division of application No. 12/225,010, filed as application No. PCT/JP2007/055122 on Mar. 14, 2007, now Pat. No. 8,551,991.

(30) Foreign Application Priority Data

Mar. 14, 2006 (JP) .................................. 2006-069739
Aug. 22, 2006 (JP) .................................. 2006-255039

(51) Int. Cl.
| | | |
|---|---|---|
| *A61K 31/535* | (2006.01) | |
| *A61K 31/44* | (2006.01) | |
| *A01N 43/40* | (2006.01) | |
| *C07D 241/46* | (2006.01) | |
| *C07D 241/44* | (2006.01) | |
| *C07D 401/12* | (2006.01) | |
| *C07D 401/14* | (2006.01) | |
| *C07D 405/12* | (2006.01) | |
| *C07D 409/12* | (2006.01) | |
| *C07D 409/14* | (2006.01) | |
| *C07D 413/12* | (2006.01) | |
| *C07D 417/12* | (2006.01) | |
| *C07D 417/14* | (2006.01) | |

(52) U.S. Cl.
CPC ............ *C07D 241/46* (2013.01); *C07D 241/44* (2013.01); *C07D 401/12* (2013.01); *C07D 401/14* (2013.01); *C07D 405/12* (2013.01); *C07D 409/12* (2013.01); *C07D 409/14* (2013.01); *C07D 413/12* (2013.01); *C07D 417/12* (2013.01); *C07D 417/14* (2013.01)

USPC ......................................... 514/234.8; 514/354

(58) Field of Classification Search
None
See application file for complete search history.

(56) References Cited

U.S. PATENT DOCUMENTS

| | | | |
|---|---|---|---|
| 6,153,607 | A | 11/2000 | Pflugfelder et al. |
| 6,340,758 | B1 | 1/2002 | Kornberg et al. |

(Continued)

FOREIGN PATENT DOCUMENTS

| | | |
|---|---|---|
| EP | 1 944 290 A1 | 7/2008 |
| EP | 2151436 A1 | 2/2010 |

(Continued)

OTHER PUBLICATIONS

International Search Report for PCT/JP2007/055122 mailed Apr. 17, 2007.
Supplementary European Search Report for EP 07738592 mailed Jul. 6, 2010.
Nawata, Hajime, "new horizone of glucocorticoid therapy in 21$^{st}$ century", Sougou Rinsyou, 2005, 1951-2076, 54(7), Japan.

(Continued)

*Primary Examiner* — Anna Pagonakis
(74) *Attorney, Agent, or Firm* — Holtz, Holtz, Goodman & Chick PC

(57) ABSTRACT

A 1,2,3,4-tetrahydroquinoxaline compound represented by the following formula:

(1)

In the formula (1), $R^1$ represents substituents such as a halogen, an alkyl, a cycloalkyl, an aryl or a heterocyclic group; p represents 0 to 5; $R^2$ represents substituents such as a halogen, an alkyl, a hydroxyl or an alkoxy group; q represents 0 to 2; $R^3$ represents substituents such as hydrogen, an alkyl, an alkenyl, an alkylcarbonyl or an arylcarbonyl group; $R^4$ and $R^5$ independently represent substituents such as hydrogen, a halogen, an alkyl, an alkenyl, an alkynyl, a cycloalkyl, an aryl or a heterocyclic group; $R^6$ represents substituents such as hydrogen, an alkyl, an alkenyl, an alkynyl, a cycloalkyl, an aryl or a heterocyclic group; A represents an alkylene; $R^7$ represents $OR^8$, $NR^8R^9$, $SR^8$, $S(O)R^8$, $S(O)_2R^8$; $R^8$ and $R^9$ independently represent substituents such as hydrogen, an alkyl or an alkenyl; and X represents O or S.

5 Claims, No Drawings

(56) References Cited

U.S. PATENT DOCUMENTS

| | | | |
|---|---|---|---|
| 6,369,057 | B1 | 4/2002 | Billhardt et al. |
| 6,852,719 | B2 | 2/2005 | Liu et al. |
| 7,235,662 | B2 | 6/2007 | Hadida-Ruah et al. |
| 8,193,187 | B2 * | 6/2012 | Matsuda et al. ............ 514/249 |
| 8,551,991 | B2 * | 10/2013 | Matsuda et al. ........... 514/234.8 |
| 2004/0266758 | A1 | 12/2004 | Hadida-Ruah et al. |
| 2007/0249611 | A1 | 10/2007 | Feng et al. |
| 2009/0298826 | A1 | 12/2009 | Matsuda et al. |
| 2009/0298827 | A1 | 12/2009 | Matsuda et al. |
| 2010/0056504 | A1 | 3/2010 | Matsuda et al. |

FOREIGN PATENT DOCUMENTS

| | | |
|---|---|---|
| JP | 2002-193955 A | 7/2002 |
| JP | 2008-74829 A | 4/2008 |
| WO | 2004/099192 A2 | 11/2004 |
| WO | WO 2006/015259 A2 | 2/2006 |
| WO | WO 2007/105766 A1 | 9/2007 |
| WO | WO 2008/111632 A1 | 9/2008 |
| WO | WO 2008/146871 A1 | 12/2008 |
| WO | WO 2009/035067 A1 | 3/2009 |
| WO | WO 2009/035068 A1 | 3/2009 |

OTHER PUBLICATIONS

Jeffrey N. Miner et al., "New and improved glucocorticoid receptor ligands," Expert Opinion on Investigational Drugs, Ashley Publications Ltd., London, GB, vol. 14, No. 12, Dec. 1, 2005, pp. 1527-1545.

Jordan, V.C., "Tamoxifen: A Most Unlikely Pioneering Medicine," *Nature Reviews*: Drug Discovery, 2, 2003, 205.

Hackam, et al., "Translation of Research Evidence from Animals to Humans," *JAMA*, 296(14), 2006, 1731-1732.

Igaku Daijiten, Nanzando (Nanzando's Medical Dictionary), The 17$^{th}$ Edition, 1038-1040, 1990.

Patani et al., "Biosterism: A Rational Approach in Drug Design," *Chem. Rev.*, 1996, 96, 3146-3176.

Nagelhout et al., "Preservation of Tear Film Integrity and Inhibition of Corneal Injury by Dexamethasone in a Rabbit Model of Lacrimal Gland Inflammation-Induced Dry Eye," *Jour. of Ocular Pharmacology and Therapeutics*, vol. 21, No. 2, (2005), pp. 139 to 148.

Health, "Optometric Management of Anterior Segment Eye Disease: Dry Eye and Eyelid Disease," Continuing Education and Training: 2007, pp. 1 to 9, Johnson & Johnson Vision Care.

* cited by examiner

1,2,3,4-TETRAHYDROQUINOXALINE COMPOUNDS HAVING GLUCOCORTICOID RECEPTOR BINDING ACTIVITY

CROSS-REFERENCE TO RELATED APPLICATIONS

This application is a continuation application of application Ser. No. 12/225,010 filed Sep. 11, 2008 (U.S. Pat. No. 8,551,991), which is the United States national phase application of International application PCT/JP2007/055122 filed Mar. 14, 2007. The entire contents of each of application Ser. No. 12/225,010 and International application PCT/JP2007/055122 are hereby incorporated by reference herein.

TECHNICAL FIELD

The present invention relates to a novel 1,2,3,4-tetrahydroquinoxaline derivative or a salt thereof, which is useful as a pharmaceutical. The derivative has a glucocorticoid receptor binding activity and is useful as a glucocorticoid receptor modulator having a nonsteroidal structure (a glucocorticoid receptor agonist and/or a glucocorticoid receptor antagonist).

BACKGROUND ART

A glucocorticoid receptor is a 94 kDa ligand-activated intracellular transcriptional factor that is a member of the nuclear receptor superfamily. This receptor is a mediator of glucocorticoid action which effects the metabolism of carbohydrates, proteins, fats and the like, the suppression of the immune or inflammatory responses, the activation of the central nervous system, the regulation of the cardiovascular function and the basal and stress-related homeostasis and the like.

As glucocorticoid action-related diseases, metabolic disorders such as diabetes and obesity, inflammatory diseases such as arthritis, enteritis and chronic obstructive pulmonary diseases, autoimmune diseases such as connective tissue diseases, allergic diseases such as asthma, atopic dermatitis, allergic rhinitis and conjunctivitis, central nervous system diseases such as psychiatric disorders, Alzheimer's disease and drug use disorders, cardiovascular diseases such as hypertension, hypercalcemia, hyperinsulinemia and hyperlipidemia, homeostasis-related diseases causing an abnormality of neuro-immune-endocrine balance, glaucoma and the like are known. (SOUGOU RINSYOU, 54(7), 1951-2076 (2005), JP-A-2002-193955.)

Therefore, a compound having a glucocorticoid receptor binding activity is considered to be useful as a preventive and/or therapeutic agent for these diseases.

As such a compound having a glucocorticoid receptor binding activity, glucocorticoid receptor agonists synthesized in the living body such as cortisol and corticosterone, synthetic glucocorticoid receptor agonists such as dexamethasone, prednisone and prednisilone, non-selective glucocorticoid receptor antagonists such as RU486 and the like are known. (JP-A-2002-193955)

On the other hand, compounds having a 1,2,3,4-tetrahydroquinoxaline structure are disclosed in WO 04/099192 and JP-A-5-148243 and the like. The compounds disclosed in WO 04/099192 are protein thyrosine phosphatase inhibitors essentially having a carboxylic group. On the other hand, a large number of compounds having 1,2,3,4-tetrahydroquinoxaline structure are disclosed as anti-virus agents in JP-A-5-148243. However, the present compound has not been specifically disclosed in any of patents.

DISCLOSURE OF THE INVENTION

Problems to be Solved

It is a very interesting subject to study synthesis of a novel 1,2,3,4-tetrahydroquinoxaline derivative and to find a pharmacological action of the derivative.

Means of Solving Problems

The present inventors conducted studies about the synthesis of 1,2,3,4-tetrahydroquinoxaline derivatives having a novel chemical structure, and succeeded in producing a large number of novel compounds. Further, the present inventors studied the pharmacological actions of the derivatives and as a result, they found that the derivatives have a glucocorticoid receptor binding activity and are useful as a pharmaceutical, and thus the present invention has been completed.

That is, the present invention relates to a compound represented by the following general formula (1) or a salt thereof (hereinafter referred to as "the present compound") and a pharmaceutical composition containing the same. Further, a preferred invention in its pharmaceutical use relates to a glucocorticoid receptor modulator, and its target diseases are glucocorticoid receptor-related diseases, that is, metabolic disorders such as diabetes and obesity, inflammatory diseases such as arthritis, enteritis and chronic obstructive pulmonary diseases, autoimmune diseases such as connective tissue diseases, allergic diseases such as asthma, atopic dermatitis, allergic rhinitis and conjunctivitis, central nervous system diseases such as psychiatric disorders, Alzheimer's disease and drug use disorders; cardiovascular diseases such as hypertension, hypercalcemia, hyperinsulinemia and hyperlipidemia, homeostasis-related diseases causing an abnormality of neuro-immune-endocrine balance, glaucoma and the like. A particularly preferred invention is an invention relating to a preventive or a therapeutic agent for these diseases.

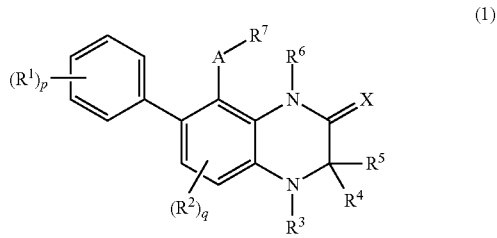

(1)

[wherein $R^1$ represents a halogen atom, a lower alkyl group which may have at least a substituent, a lower cycloalkyl group which may have at least a substituent, an aryl group which may have at least a substituent, a heterocyclic group which may have at least a substituent, a hydroxy group, an ester of a hydroxy group, a lower alkoxy group which may have at least a substituent, a lower cycloalkyloxy group which may have at least a substituent, an aryloxy group which may have at least a substituent, a heterocyclic oxy group which may have at least a substituent, a mercapto group, an ester of a mercapto group, a lower alkylthio group which may have least a substituent, a lower cycloalkylthio group which may have at least a substituent, an arylthio group which may have at least a substituent, a heterocyclic thio group which may have at least a substituent, an amino group, a lower alkylamino group which may have at least a substituent, a lower cycloalkylamino group which may have at least a substituent, an arylamino group which may have at least a substituent, a heterocyclic amino group which may have at least a substituent, an amide of an amino group, an amide of a lower alkylamino group which may have at least a substituent, an amide of a lower cycloalkylamino group which may have at least a substituent, an amide of an arylamino group which may have at least a substituent, an amide of heterocyclic amino group which may have at least a substituent, a formyl group, a lower alkylcarbonyl group which may have at least a substituent, a lower cycloalkylcarbonyl group which may have at least a substituent, an arylcarbonyl group which may have at least a substituent, a heterocyclic carbonyl group which may have at least a substituent, a carboxy group, an ester of a carboxy group, an amide of a carboxy group, a lower alkylsulfonyl group which may have at least a substituent, a lower cycloalkylsulfonyl group which may have at least a substituent, an arylsulfonyl group which may have at least a substituent, a heterocyclic sulfonyl group which may have at least a substituent, a sulfonic acid group, an ester of a sulfonic acid group, an amide of a sulfonic acid group, a nitro group or a cyano group;

p represents an integer of 0 to 5;

in the case where p is 2 to 5, each $R^1$ may be the same or different;

$R^2$ represents a halogen atom, a lower alkyl group which may have at least a substituent, a hydroxy group, an ester of a hydroxy group or a lower alkoxy group which may have at least a substituent;

q represents an integer of 0 to 2;

in the case where q is 2, each $R^2$ may be the same or different;

$R^3$ represents a hydrogen atom, a lower alkyl group which may have at least a substituent, a lower alkenyl group which may have at least a substituent, a lower alkylcarbonyl group which may have at least a substituent, a lower alkenylcarbonyl group which may have at least a substituent or an arylcarbonyl group which may have at least a substituent;

$R^4$ and $R^5$ may be the same or different and represent a hydrogen atom, a halogen atom, a lower alkyl group which may have at least a substituent, a lower alkenyl group which may have at least a substituent, a lower alkynyl group which may have at least a substituent, a lower cycloalkyl group which may have at least a substituent, an aryl group which may have at least a substituent or a heterocyclic group which may have at least a substituent;

$R^4$ and $R^5$ may be combined together to form a 3- to 8-membered lower cycloalkane ring which may have at least a substituent;

$R^6$ represents a hydrogen atom, a lower alkyl group which may have at least a substituent, a lower alkenyl group which may have at least a substituent, a lower alkynyl group which may have at least a substituent, a lower cycloalkyl group which may have at least a substituent, an aryl group which may have at least a substituent or a heterocyclic group which may have at least a substituent;

A represents a lower alkylene group which may have at least a substituent;

$R^7$ represents $OR^8$, $NR^8R^9$, $SR^8$, $S(O)R^8$ or $S(O)_2R^8$;

$R^8$ and $R^9$ may be the same or different and represent a hydrogen atom, a lower alkyl group which may have at least a substituent, a lower alkenyl group which may have at least a substituent, a lower alkynyl group which may have at least a substituent, a lower cycloalkyl group which may have at least a substituent, an aryl group which may have at least a substituent, a heterocyclic group which may have at least a substituent, a formyl group, a lower alkylcarbonyl group which may have at least a substituent, a lower alkenylcarbonyl group which may have at least a substituent, a lower alkynylcarbonyl group which may have at least a substituent, a lower cycloalkylcarbonyl group which may have at least a substituent, an arylcarbonyl group which may have at least a substituent, a heterocyclic carbonyl group which may have at least a substituent, a carboxy group, a lower alkoxycarbonyl group which may have at least a substituent, a lower alkenyloxycarbonyl group which may have at least a substituent, a lower alkynyloxycarbonyl group which may have at least a substituent, a lower cycloalkyloxycarbonyl group which may have at least a substituent, an aryloxycarbonyl group which may have at least substituent, a heterocyclic oxycarbonyl group which may have at least a substituent, a lower alkylsulfonyl group which may have at least a substituent, a lower alkenylsulfonyl group which may have at least a substituent, a lower alkynylsulfonyl group which may have at least a substituent, a lower cycloalkylsulfonyl group which may have at least a substituent, an arylsulfonyl group which may have at least a substituent, a heterocyclic sulfonyl group which may have at least a substituent, an aminocarbonyl group, a lower alkylaminocarbonyl group which may have at least a substituent, a lower alkenylaminocarbonyl group which may have at least a substituent, a lower alkynylaminocarbonyl group which may have at least a substituent, a lower cycloalkylaminocarbonyl group which may have at least a substituent, an arylaminocarbonyl group which may have at least a substituent or a heterocyclic aminocarbonyl group which may have at least a substituent;

in the case where $R^7$ is $NR^8R^9$, $R^8$ and $R^9$ may be combined together to form a 3- to 8-membered nitrogen-containing heterocyclic ring which may have at least a substituent; and X represents O or S. Hereinafter the same shall apply.]

Advantage of the Invention

The present invention provides a 1,2,3,4-tetrahydroquinoxaline derivative or a salt thereof, which is useful as a pharmaceutical. The present compound has an excellent glucocorticoid receptor binding activity and is useful as a glucocorticoid receptor modulator. In particular, the present compound is useful as a preventive or therapeutic agent for glucocorticoid action related diseases, that is, metabolic disorders such as diabetes and obesity, inflammatory diseases such as arthritis, enteritis and chronic obstructive pulmonary diseases, autoimmune diseases such as connective tissue diseases, allergic diseases such as asthma, atopic dermatitis, allergic rhinitis and conjunctivitis, central nervous system diseases such as psychiatric disorders, Alzheimer's disease and drug use disorders, cardiovascular diseases such as hypertension, hypercalcemia, hyperinsulinemia and hyperlipidemia, homeostasis-related diseases causing an abnormality of neuro-immune-endocrine balance, glaucoma and the like.

BEST MODE FOR CARRYING OUT THE INVENTION

Hereinafter, definitions of terms and phrases (atoms, groups, rings and the like) to be used in this specification will be described in detail.

The "halogen atom" refers to a fluorine, chlorine, bromine or iodine atom.

The "lower alkyl group" refers to a straight chain or branched alkyl group having 1 to 8 carbon atoms. Specific examples thereof include methyl, ethyl, n-propyl, n-butyl, n-pentyl, n-hexyl, n-heptyl, n-octyl, isopropyl, isobutyl, sec-butyl, tert-butyl and isopentyl groups and the like.

The "lower alkenyl group" refers to a straight chain or branched alkenyl group having 2 to 8 carbon atoms. Specific examples thereof include vinyl, propenyl, butenyl, pentenyl, hexenyl, heptenyl, octenyl, isopropenyl, 2-methyl-1-propenyl and 2-methyl-2 butenyl groups and the like.

The "lower alkynyl group" refers to a straight chain or branched alkynyl group having 2 to 8 carbon atoms. Specific examples thereof include ethynyl, propynyl, butynyl, pentynyl, hexynyl, heptynyl, octynyl, isobutynyl and isopentynyl groups and the like.

The "lower cycloalkyl group" refers to a cycloalkyl group having 3 to 8 carbon atoms. Specific examples thereof include cyclopropyl, cyclobutyl, cyclopentyl, cyclohexyl, cycloheptyl and cyclooctyl groups.

The "lower cycloalkane ring" refers to a cycloalkane ring having 3 to 8 carbon atoms. Specific examples thereof include cyclopropane, cyclobutane, cyclopentane, cyclohexane, cycloheptane and cyclooctane rings.

The "aryl group" refers to a residue formed by removing one hydrogen atom from a monocyclic aromatic hydrocarbon group, or bicyclic or tricyclic condensed polycyclic aromatic hydrocarbon having 6 to 14 carbon atoms. Further, A residue formed by removing one hydrogen atom from bicyclic or tricyclic condensed polycyclic hydrocarbon having 6 to 14 carbon atoms is also included in the scope of the "aryl group". Specific examples thereof include phenyl, naphthyl, anthryl, phenanthryl and fluorenyl groups and the like.

The "heterocyclic group" refers to a residue formed by removing one hydrogen atom from a saturated or unsaturated monocyclic heterocyclic ring, or a bicyclic or tricyclic condensed polycyclic heterocyclic ring having one or a plurality of heteroatoms selected from a nitrogen atom, an oxygen atom and a sulfur atom in the ring.

Specific examples of the saturated monocyclic heterocyclic ring include pyrrolidine, pyrazolidine, imidazolidine, triazolidine, piperidine, hexahydropyridazine, hexahydropyrimidine, piperazine, homopiperidine and homopiperazine rings and the like having a nitrogen atom in the ring, tetrahydrofuran and tetrahydropyran rings and the like having an oxygen atom in the ring, tetrahydrothiophene and tetrahydrothiopyran rings and the like having a sulfur atom in the ring, oxazolidine, isoxazolidine and morpholine rings and the like having a nitrogen atom and an oxygen atom in the ring, and thiazolidine, isothiazolidine and thiomorpholine rings and the like having a nitrogen atom and a sulfur atom in the ring.

Further, such a saturated monocyclic heterocyclic ring can be condensed with a benzene ring or the like to form a bicyclic or tricyclic condensed polycyclic heterocyclic ring such as a dihydroindole, dihydroindazole, dihydrobenzimidazole, tetrahydroquinoline, tetrahydroisoquinoline, tetrahydrocinnoline, tetrahydrophthalazine, tetrahydroquinazoline, tetrahydroquinoxaline, dihydrobenzofuran, dihydroisobenzofuran, chromane, isochromane, dihydrobenzothiophene, dihydroisobenzothiophene, thiochromane, isothiochromane, dihydrobenzoxazole, dihydrobenzisoxazole, dihydrobenzoxazine, dihydrobenzothiazole, dihydrobenzisothiazole, dihydrobenzothiazine, xanthene, 4a-carbazole and perimidine rings and the like.

Specific examples of the unsaturated monocyclic heterocyclic ring include dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine and pyrazine rings and the like having a nitrogen atom in the ring, dihydrofuran, furan, dihydropyran and pyran rings and the like having an oxygen atom in the ring, dihydrothiophene, thiophene, dihydrothiopyran and thiopyran rings and the like having a sulfur atom in the ring, dihydrooxazole, oxazole, dihydroisoxazole, isoxazole, dihydrooxazine and oxazine rings and the like having a nitrogen atom and an oxygen atom in the ring, dihydrothiazole, thiazole, dihydroisothiazole, isothiazole, dihydrothiazine and thiazine rings and the like having a nitrogen atom and a sulfur atom in the ring.

Further, such an unsaturated monocyclic heterocyclic ring can be condensed with a benzene ring or the like to form a bicyclic or tricyclic condensed polycyclic heterocyclic ring such as an indole, indazole, benzimidazole, benzotriazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromene, isochromene, benzothiophene, isobenzothiophene, thiochromene, isothiochromene, benzoxazole, benzisoxazole, benzoxazine, benzothiazole, benzisothiazole, benzothiazine, phenoxanthin, carbazole, β-carboline, phenanthridine, acridine, phenanthroline, phenazine, phenothiazine or phenoxazine rings and the like.

The "lower alkoxy group" refers to a group formed by replacing the hydrogen atom of a hydroxy group with a lower alkyl group. Specific examples thereof include methoxy, ethoxy, n-propoxy, n-butoxy, n-pentoxy, n-hexyloxy, n-heptyloxy, n-octyloxy, isopropoxy, isobutoxy, sec-butoxy, tert-butoxy and isopentoxy groups and the like.

The "lower alkenyloxy group" refers to a group formed by replacing the hydrogen atom of a hydroxy group with a lower alkenyl group. Specific examples thereof include vinyloxy, propenyloxy, butenyloxy, pentenyloxy, hexenyloxy, heptenyloxy, octenyloxy, isopropenyloxy, 2-methyl-1-propenyloxy and 2-methyl-2-butenyloxy groups and the like.

The "lower alkynyloxy group" refers to a group formed by replacing the hydrogen atom of a hydroxy group with a lower alkynyl group. Specific examples thereof include ethynyloxy, propynyloxy, butynyloxy, pentynyloxy, hexynyloxy, heptynyloxy, octynyloxy, isobutynyloxy and isopentynyloxy groups and the like.

The "lower cycloalkyloxy group" refers to a group formed by replacing the hydrogen atom of a hydroxy group with a lower cycloalkyl group. Specific examples thereof include cyclopropyloxy, cyclobutyloxy, cyclopentyloxy, cyclohexyloxy, cycloheptyloxy and cyclooctyloxy groups.

The "aryloxy group" refers to a group formed by replacing the hydrogen atom of a hydroxy group with an aryl group. Specific examples thereof include phenoxy, naphthoxy, anthryloxy and phenanthryloxy groups and the like.

The "heterocyclic oxy group" refers to a group formed by replacing the hydrogen atom of a hydroxy group with a heterocyclic group.

The "lower alkylthio group" refers to a group formed by replacing the hydrogen atom of a mercapto group with a lower alkyl group. Specific examples thereof include methylthio, ethylthio, n-propylthio, n-butylthio, n-pentylthio, n-hexylthio, n-heptylthio, n-octylthio, isopropylthio, isobutylthio, sec-butylthio, tert-butylthio and isopentylthio groups and the like.

The "lower cycloalkylthio group" refers to a group formed by replacing the hydrogen atom of a mercapto group with a lower cycloalkyl group. Specific examples thereof include cyclopropylthio, cyclobutylthio, cyclopentylthio, cyclohexylthio, cycloheptylthio and cyclooctylthio groups.

The "arylthio group" refers to a group formed by replacing the hydrogen atom of a mercapto group with an aryl group. Specific examples thereof include phenylthio, naphthylthio, anthrylthio and phenanthrylthio groups and the like.

The "heterocyclic thio group" refers to a group formed by replacing the hydrogen atom of a mercapto group with a heterocyclic group.

The "lower alkylamino group" refers to a group formed by replacing one or both of the hydrogen atoms of an amino group with a lower alkyl group. Specific examples thereof include methylamino, ethylamino, propylamino, dimethylamino, diethylamino and ethyl(methyl)amino groups and the like.

The "lower cycloalkylamino group" refers to a group formed by replacing one or both of the hydrogen atoms of an amino group with a lower cycloalkyl group, or a group formed by replacing one of the hydrogen atoms of an amino group with a lower cycloalkyl group and the other hydrogen atom with a lower alkyl group, a lower alkenyl group or a lower alkynyl group. Specific examples thereof include cyclopropylamino, cyclobutylamino, cyclopentylamino, cyclohexylamino, cycloheptylamino, cyclooctylamino, dicyclohexylamino, cyclohexyl(methyl)amino, cyclohexyl(vinyl)amino and cyclohexyl(ethynyl)amino groups and the like.

The "arylamino group" refers to a group formed by replacing one or both of the hydrogen atoms of an amino group with an aryl group, or a group formed by replacing one of the hydrogen atoms of an amino group with an aryl group and the other hydrogen atom with a lower alkyl group, a lower alkenyl group, a lower alkynyl group or a lower cycloalkyl group. Specific examples thereof include phenylamino, naphthylamino, anthrylamino, phenanthrylamino, diphenylamino, methyl(phenyl)amino, ethyl(phenyl)amino, phenyl(vinyl)amino, ethynyl(phenyl)amino and cyclohexyl(phenyl)amino groups and the like.

The "heterocyclic amino group" refers to a group formed by replacing one or both of the hydrogen atoms of an amino group with a heterocyclic group, or a group formed by replacing one of the hydrogen atoms of an amino group with a heterocyclic group and the other hydrogen atom with a lower alkyl group, a lower alkenyl group, a lower alkynyl group, a lower cycloalkyl group or an aryl group.

The "lower alkylcarbonyl group" refers to a group formed by replacing the hydrogen atom of a formyl group with a lower alkyl group. Specific examples thereof include methylcarbonyl, ethylcarbonyl, n-propylcarbonyl, n-butylcarbonyl, n-pentylcarbonyl, n-hexylcarbonyl, n-heptylcarbonyl, n-octylcarbonyl, isopropylcarbonyl, isobutylcarbonyl, sec-butylcarbonyl, tert-butylcarbonyl and isopentylcarbonyl groups and the like.

The "lower alkenylcarbonyl group" refers to a group formed by replacing the hydrogen atom of a formyl group with a lower alkenyl group. Specific examples thereof include vinylcarbonyl, propenylcarbonyl, butenylcarbonyl, pentenylcarbonyl, hexenylcarbonyl, heptenylcarbonyl, octenylcarbonyl, isopropenylcarbonyl, 2-methyl-1-propenylcarbonyl and 2-methyl-2-butenylcarbonyl groups and the like.

The "lower alkynylcarbonyl group" refers to a group formed by replacing the hydrogen atom of a formyl group with a lower alkynyl group. Specific examples thereof include ethynylcarbonyl, propynylcarbonyl, butynylcarbonyl, pentynylcarbonyl, hexynylcarbonyl, heptynylcarbonyl, octynylcarbonyl, isobutynylcarbonyl and isopentynylcarbonyl groups and the like.

The "lower cycloalkylcarbonyl group" refers to a group formed by replacing the hydrogen atom of a formyl group with a lower cycloalkyl group. Specific examples thereof include cyclopropylcarbonyl, cyclobutylcarbonyl, cyclopentylcarbonyl, cyclohexylcarbonyl, cycloheptylcarbonyl and cyclooctylcarbonyl groups.

The "arylcarbonyl group" refers to a group formed by replacing the hydrogen atom of a formyl group with an aryl group. Specific examples thereof include phenylcarbonyl, naphthylcarbonyl, anthrylcarbonyl and phenanthrylcarbonyl groups and the like.

The "heterocyclic carbonyl group" refers to a group formed by replacing the hydrogen atom of a formyl group with a heterocyclic group.

The "lower alkoxycarbonyl group" refers to a group formed by replacing the hydrogen atom of a formyl group with a lower alkoxy group. Specific examples thereof include methoxycarbonyl, ethoxycarbonyl, n-propoxycarbonyl, n-butoxycarbonyl, n-pentoxycarbonyl, n-hexyloxycarbonyl, n-heptyloxycarbonyl, n-octyloxycarbonyl, isopropoxycarbonyl, isobutoxycarbonyl, sec-butoxycarbonyl, tert-butoxycarbonyl and isopentoxycarbonyl groups and the like.

The "lower alkenyloxycarbonyl group" refers to a group formed by replacing the hydrogen atom of a formyl group with a lower alkenyloxy group. Specific examples thereof include vinyloxycarbonyl, propenyloxycarbonyl, butenyloxycarbonyl, pentenyloxycarbonyl, hexenyloxycarbonyl, heptenyloxycarbonyl, octenyloxycarbonyl, isopropenyloxycarbonyl, 2-methyl-1-propenyloxycarbonyl and 2-methyl-2-butenyloxycarbonyl groups and the like.

The "lower alkynyloxycarbonyl group" refers to a group formed by replacing the hydrogen atom of a formyl group with a lower alkynyloxy group. Specific examples thereof include ethynyloxycarbonyl, propynyloxycarbonyl, butynyloxycarbonyl, pentynyloxycarbonyl, hexynyloxycarbonyl, heptynyloxycarbonyl, octynyloxycarbonyl, isobutynyloxycarbonyl and isopentynyloxycarbonyl groups and the like.

The "lower cycloalkyloxycarbonyl group" refers to a group formed by replacing the hydrogen atom of a formyl group with a lower cycloalkyloxy group. Specific examples thereof include cyclopropyloxycarbonyl, cyclobutyloxycarbonyl, cyclopentyloxycarbonyl, cyclohexyloxycarbonyl, cycloheptyloxycarbonyl and cyclooctyloxycarbonyl groups.

The "aryloxycarbonyl group" refers to a group formed by replacing the hydrogen atom of a formyl group with an aryloxy group. Specific examples thereof include phenoxycarbonyl, naphthoxycarbonyl, anthryloxycarbonyl and phenanthryloxycarbonyl groups and the like.

The "heterocyclic oxycarbonyl group" refers to a group formed by replacing the hydrogen atom of a formyl group with a heterocyclic oxy group.

The "lower alkylaminocarbonyl group" refers to a group formed by replacing the hydrogen atom of a formyl group with a lower alkylamino group. Specific examples thereof include methylaminocarbonyl, ethylaminocarbonyl, propylaminocarbonyl, dimethylaminocarbonyl, diethylaminocarbonyl and ethylmethylaminocarbonyl groups and the like.

The "lower alkenylaminocarbonyl group" refers to a group formed by replacing the hydrogen atom of a formyl group with a lower alkenylamino group. Specific examples thereof include vinylaminocarbonyl, propenylaminocarbonyl, butenylaminocarbonyl, pentenylaminocarbonyl, hexenylaminocarbonyl, heptenylaminocarbonyl, octenylaminocarbonyl, isopropenylaminocarbonyl, 2-methyl-1-propenylaminocarbonyl, 2-methyl-2-butenylaminocarbonyl, divinylaminocarbonyl and methyl(vinyl)aminocarbonyl groups and the like.

The "lower alkynylaminocarbonyl group" refers to a group formed by replacing the hydrogen atom of a formyl group with a lower alkynylamino group. Specific examples thereof include ethynylaminocarbonyl, propynylaminocarbonyl, butynylaminocarbonyl, pentynylaminocarbonyl, hexynylaminocarbonyl, heptynylaminocarbonyl, octynylaminocarbonyl, isobutynylaminocarbonyl, isopentynylaminocarbonyl, diethynylaminocarbonyl, ethynyl(methyl)aminocarbonyl and ethynyl(vinyl)aminocarbonyl groups and the like.

The "lower cycloalkylaminocarbonyl group" refers to a group formed by replacing the hydrogen atom of a formyl group with a lower cycloalkylamino group. Specific examples thereof include cyclopropylaminocarbonyl, cyclobutylaminocarbonyl, cyclopentylaminocarbonyl, cyclohexylaminocarbonyl, cycloheptylaminocarbonyl, cyclooctylaminocarbonyl, dicyclohexylaminocarbonyl, cyclohexyl(methyl)aminocarbonyl, cyclohexyl(vinyl)aminocarbonyl and cyclohexyl(ethynyl)aminocarbonyl groups and the like.

The "arylaminocarbonyl group" refers to a group formed by replacing the hydrogen atom of a formyl group with an arylamino group. Specific examples thereof include phenylaminocarbonyl, naphthylaminocarbonyl, anthrylaminocarbonyl, phenanthrylaminocarbonyl, diphenylaminocarbonyl, methylphenylaminocarbonyl ethylphenylaminocarbonyl, phenyl(vinyl)aminocarbonyl, ethynyl(phenyl)aminocarbonyl and cyclohexyl(phenyl)aminocarbonyl groups and the like.

The "heterocyclic aminocarbonyl group" refers to a group formed by replacing the hydrogen atom of a formyl group with a heterocyclic amino group.

The "lower alkylsulfonyl group" refers group formed by replacing the hydroxy group of a sulfonic acid group with a lower alkyl group. Specific examples thereof include methylsulfonyl, ethylsulfonyl, n-propylsulfonyl, n-butylsulfonyl, n-pentylsulfonyl, n-hexylsulfonyl, n-heptylsulfonyl, n-octylsulfonyl, isopropylsulfonyl, isobutylsulfonyl, sec-butylsulfonyl, tert-butylsulfonyl and isopentylsulfonyl groups and the like.

The "lower alkenylsulfonyl group" refers to group formed by replacing the hydroxy group of a sulfonic acid group with a lower alkenyl, group. Specific examples thereof include vinylsulfonyl, propenylsulfonyl, butenylsulfonyl, pentenylsulfonyl, hexenylsulfonyl, heptenylsulfonyl, octenylsulfonyl, isopropenylsulfonyl, 2-methyl-1-propenylsulfonyl and 2-methyl-2-butenylsulfonyl groups and the like.

The "lower alkynylsulfonyl group" refers to a group formed by replacing the hydroxy group of a sulfonic acid group with a lower alkynyl group. Specific examples thereof include ethynylsulfonyl, propynylsulfonyl, butynylsulfonyl, pentynylsulfonyl, hexynylsulfonyl, heptynylsulfonyl, octynylsulfonyl, isobutynylsulfonyl and isopentynylsulfonyl groups and the like.

The "lower cycloalkylsulfonyl group" refers to a group formed by replacing the hydroxy group of a sulfonic acid group with a lower cycloalkyl group. Specific examples thereof include cyclopropylsulfonyl, cyclobutylsulfonyl, cyclopentylsulfonyl, cyclohexylsulfonyl, cycloheptylsulfonyl and cyclooctylsulfonyl groups.

The "arylsulfonyl group" refers to a group formed by replacing the hydroxy group of a sulfonic acid group with an aryl group. Specific examples thereof include phenylsulfonyl, naphthylsulfonyl, anthrylsulfonyl and phenanthrylsulfonyl groups and the like.

The "heterocyclic sulfonyl group" refers to a group formed by replacing the hydroxy group of a sulfonic acid group with a heterocyclic group.

The "3- to 8-membered nitrogen-containing heterocyclic ring" refers to a saturated monocyclic heterocyclic ring containing one or two nitrogen atoms in the ring. Specific examples thereof include aziridine, azetidine, pyrrolidine, imidazolidine, pyrazolidine, piperazine and morpholine rings and the like.

The "lower alkylene group" refers to a straight chain or branched alkylene group having 1 to 8 carbon atoms. Specific examples thereof include methylene, ethylene, trimethylene, tetramethylene, pentamethylene, hexamethylene, heptamethylene, octamethylene, methylmethylene and ethylmethylene groups and the like.

The "ester of a hydroxy group" refers to an ester formed from a hydroxy group and a carboxylic acid and/or a group represented by —OCO—R.

Herein, R represents a hydrogen atom, a lower alkyl group which may have at least a substituent, a lower alkenyl group which may have at least a substituent, a lower alkynyl group which may have at least a substituent, a lower cycloalkyl group which may have at least a substituent, an aryl group which may have at least a substituent, a heterocyclic group which may have at least a substituent, a lower alkoxy group which may have at least a substituent, a lower alkenyloxy group which may have at least a substituent, a lower alkynyloxy group which may have at least a substituent, a lower cycloalkyloxy group which may have at least a substituent, an aryloxy group which may have at least a substituent, a heterocyclic oxy group which may have at least a substituent, an amino group, a lower alkylamino group which may have at least a substituent, a lower cycloalkylamino group which may have at least a substituent, an arylamino group which may have at least a substituent or a heterocyclic amino group which may have at least a substituent. R is the same as below.

The "ester of a mercapto group" refers to a thioester formed from a mercapto group and a carboxylic acid and/or a group represented by —SCO—R. Herein, R is the same as the above.

The "amide of an amino group" refers to an amide formed from an amino group and a carboxylic acid and/or a group represented by —NHCO—R. Herein, R is the same as the above.

The "amide of a lower alkylamino group" refers to an amide formed from a lower alkylamino group and a carboxylic acid and/or a group represented by —NR'CO—R. Herein, R' represents a lower alkyl group which may have at least a substituent, and R is the same as the above.

The "amide of a lower cycloalkylamino group" refers to an amide formed from a lower cycloalkylamino group and a carboxylic acid and/or a group represented by —NR"CO—R. Herein, R" represents a lower cycloalkyl group which may have at least a substituent, and R is the same as the above.

The "amide of an arylamino group" refers to an amide formed from an arylamino group and a carboxylic acid and/or a group represented by —NR'"CO—R. Herein, R'" represents an aryl group which may have at least a substituent, and R is the same as the above.

The "amide of a heterocyclic amino group" refers to an amide formed from a heterocyclic amino group and a carboxylic acid and/or a group represented by —NR""CO—R. Herein, R"" represents a heterocyclic group which may have at least a substituent, and R is the same for the above.

The "carboxylic acid" refers to a saturated aliphatic carboxylic acid, an unsaturated aliphatic carboxylic acid, an aryl carboxylic acid, a heterocyclic carboxylic acid or the like represented by $R^a$COOH ($R^a$ represents a hydrogen atom, a lower alkyl group which may have at least a substituent, a lower alkenyl group which may have at least a substituent, a lower alkynyl group which may have at least a substituent, a lower cycloalkyl group which may have at least a substituent, an aryl group which may have at least a substituent, a heterocyclic group which may have at least a substituent and the like). Specific examples thereof include saturated aliphatic carboxylic acids such as formic acid, acetic acid, propionic acid, butyric acid, isobutyric acid, valeric acid, isovaleric acid, pivalic acid, cyclopropanecarboxylic acid, cyclobutanecarboxylic acid, cyclopentanecarboxylic acid and cyclohexanecarboxylic acid; unsaturated aliphatic carboxylic acids such as acrylic acid, propionic acid, crotonic acid, cinnamic acid, cyclopentenecarboxylic acid and cyclohexenecarboxylic acid; aryl carboxylic acids such as benzoic acid, phthalic acid, isophthalic acid, terephthalic acid, naphthoic acid and toluic acid; heterocyclic carboxylic acids such as furancarboxylic acid, thiophenecarboxylic acid, nicotinic acid and isonicotinic acid; and the like.

The "ester of a carboxy group" refers to an ester formed from a carboxy group and an alcohol or a phenol.

The "ester of a sulfonic acid group" refers to an ester formed from a sulfonic acid group and an alcohol or a phenol.

The "alcohol" refers to a saturated aliphatic hydroxy compound, an unsaturated aliphatic hydroxy compound, a heterocyclic hydroxyl compound or the like represented by $R^b OH$ ($R^b$ represents a lower alkyl group which may have at least a substituent, a lower alkenyl group which may have at least a substituent, a lower alkynyl group which may have at least a substituent, a lower cycloalkyl group which may have at least a substituent, a heterocyclic group which may have at least a substituent or the like). Specific examples thereof include saturated aliphatic hydroxy compounds such as methanol, ethanol, propanol, butanol, isopropanol, cyclopropanol, cyclobutanol, cyclopentanol, cyclohexanol, benzylalcohol and phenethylalcohol; unsaturated aliphatic hydroxy compounds such as vinyl alcohol, allylalcohol, propagylalcohol, cyclopentenol and cyclohexenol; heterocyclic hydroxy compounds such as hydroxypiperidine and hydroxytetrahydropyran.

The "phenol" refers to an aryl hydroxy compound, a heterocyclic hydroxyl compound or the like represented by $R^c OH$ ($R^c$ represents an aryl group which may have at least a substituent, a heterocyclic group which may have at least a substituent or the like). Specific examples thereof include aryl hydroxyl compounds such as phenol, naphthol, anthrol and phenanthrol; heterocyclic hydroxyl compounds such as hydroxypyridine, hydroxyfuran and hydroxythiophen.

The "amide of a carboxy group" refers to an acid amide formed from a carboxy group and an amine.

The "amide of a sulfonic acid group" refers to an acid amide formed from a sulfonic acid group and an amine.

The "amine" refers to ammonia, a saturated aliphatic amine compound, an unsaturated aliphatic amine compound, an aryl amine compound, heterocyclic amine compound, a saturated cyclic amine compound or the like represented by $HNR^d R^e$ ($R^d$ and $R^e$ may be the same or different and represent a hydrogen atom, a lower alkyl group which may have at least a substituent, a lower alkenyl group which may have at least a substituent, a lower alkynyl group which may have at least a substituent, a lower cycloalkyl group which may have at least a substituent, an aryl group which may have at least a substituent, a heterocyclic group or the like, or $R^d$ and $R^e$ may be combined together to form a saturated cyclic amine). Specific examples thereof include ammonia; saturated aliphatic amine compounds such as methylamine, ethylamine, propylamine, pentylamine, dimethylamine, diethylamine, ethylmethylamine, cyclopropylamine, cyclobutylamine, cyclopentylamine, cyclohexylamine, benzylamine and phenetylamine; unsaturated aliphatic amine compounds such as allylamine and propagylamine; aryl amine compounds such as phenylamine, naphthylamine, anthrylamine, phenanthrylamine, diphenylamine, methylphenylamine and ethylphenylamine; heterocyclic amine compounds such as furylamine, thienylamine, pyrrolidylamine, pyridylamine, quinolylamine and methylpyridylamine; saturated cyclic amine compounds such as aziridine, azetidine, pyrrolidine, piperidine and 4-methylpiperidine.

The "lower alkyl group which may have at least a substituent", "lower alkenyl group which may have at least a substituent", "lower alkynyl group which may have at least a substituent", "lower alkoxy group which may have at least a substituent", "lower alkylthio group which may have at least a substituent", "lower alkylamino group which may have at least a substituent", "lower alkylcarbonyl group which may have at least a substituent", "lower alkenylcarbonyl group which may have at least a substituent", "lower alkynylcarbonyl group which may have at least a substituent", "lower alkoxycarbonyl group which may have at least a substituent", "lower alkenyloxycarbonyl group which may have at least a substituent", "lower alkynyloxycarbonyl group which may have at least a substituent", "lower alkylaminocarbonyl group which may have at least a substituent", "lower alkenylaminocarbonyl group which may have at least a substituent", "lower alkynylaminocarbonyl group which may have at least a substituent", "lower alkylsulfonyl group which may have at least a substituent", "lower alkenylsulfonyl group which may have at least a substituent", "lower alkynylsulfonyl group which may have at least a substituent" and "amide of lower alkylamino group which may have at least a substituent" refer to a "lower alkyl group", a "lower alkenyl group", a "lower alkynyl group", a "lower alkoxy group", a "lower alkylthio group", a "lower alkylamino group", a "lower alkylcarbonyl group", a "lower alkenylcarbonyl group", a "lower alkynylcarbonyl group", a "lower alkoxycarbonyl group", a "lower alkenyloxycarbonyl group", a "lower alkynyloxycarbonyl group", a "lower alkylaminocarbonyl group", a "lower alkenylaminocarbonyl group", a "lower alkynylaminocarbonyl group", a "lower alkylsulfonyl group", a "lower alkenylsulfonyl group", a "lower alkynylsulfonyl group" and an "amide of the lower alkylamino group" which may have one or a plurality of substituents selected from the following $\alpha^1$ group, respectively.

[$\alpha^1$ Group]

A halogen atom, a lower cycloalkyl group, an aryl group, a heterocyclic group, a hydroxy group, an ester of a hydroxy group, a lower alkoxy group, a lower alkoxy group substituted by a halogen atom, a lower alkenyloxy group, a lower alkynyloxy group, a lower cycloalkyloxy group, an aryloxy group, a heterocyclic oxy group, a mercapto group, an ester of a mercapto group, a lower alkylthio group, a lower alkenylthio group, a lower alkynylthio group, a lower cycloalkylthio group, an arylthio group, a heterocyclic thio group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, an ester of a carboxy group, an amide of a carboxy group, a lower alkylsulfinyl group, an arylsulfinyl group, a lower alkylsulfonyl group, a lower cycloalkylsulfonyl group, an arylsulfonyl group, a heterocyclic sulfonyl group, a sulfinic acid group, an ester of a sulfinic acid group, an amide of a sulfinic acid group, a sulfonic acid group, an ester of a sulfonic acid group, an amide of a sulfonic acid group, a nitro group and a cyano group.

The "lower cycloalkyl group which may have at least a substituent", "aryl group which may have at least a substituent", "heterocyclic group which may have at least a substituent", "lower cycloalkyloxy group which may have at least a substituent", "aryloxy group which may have at least a substituent", "heterocyclic oxy group which may have at least a substituent", "lower cycloalkylthio group which may have at least a substituent", "arylthio group which may have at least a substituent", "heterocyclic thio group which may have at least substituent", "lower cycloalkylamino group which may have at least a substituent", "arylamino group which may have at least a substituent", "heterocyclic amino group which may have at least a substituent", "lower cycloalkylcarbonyl group which may have at least a substituent", "arylcarbonyl group which may have at least a substituent", "heterocyclic carbonyl group which may have at least a substituent", "lower cycloalkyloxycarbonyl group which may have at least a substituent", "aryloxycarbonyl group which may have at least a substituent", "heterocyclic oxycarbonyl group which may have at least a substituent", "lower cycloalkylaminocarbonyl group which may have at least a substituent", "arylaminocarbonyl group which may have at least a substituent", "heterocyclic aminocarbonyl group which may have at least a substituent", "lower cycloalkylsulfonyl group which may have at least a substituent", "arylsulfonyl group which may have at least a substituent", "heterocyclic sulfonyl group which may have at least a substituent", "amide of lower cycloalkylamino group which may have at least a substituent", "amide of arylamino group which may have at least a substituent" and "amide of heterocyclic amino group which may have at least a substituent" refer to a "lower cycloalkyl group", an "aryl group", a "heterocyclic group", a "lower cycloalkyloxy group", an "aryloxy group", a "heterocyclic oxy group", a "lower cycloalkylthio group", an "arylthio group", "heterocyclic thio group", a "lower cycloalkylamino group", an "arylamino group", a "heterocyclic amino group", a "lower cycloalkylcarbonyl group", an "arylcarbonyl group", a "heterocyclic carbonyl group", an "lower cycloalkyloxycarbonyl group", an "aryloxycarbonyl group", a "heterocyclic oxycarbonyl group", a "lower cycloalkylaminocarbonyl group", an "arylaminocarbonyl group", a "heterocyclic aminocarbonyl group", a "lower cycloalkylsulfonyl group", an "arylsulfonyl group", a "heterocyclic sulfonyl group", an "amide of lower cycloalkylamino group", an "amide of arylamino group" and an "amide of heterocyclic amino group" which may have one or a plurality of substituents selected from the following $\beta^1$ group, respectively.

[$\beta^1$ Group]

A halogen atom, a lower alkyl group, a lower alkyl group substituted by a halogen atom, a lower alkenyl group, a lower alkynyl group, a lower cycloalkyl group, an aryl group, a heterocyclic group, a hydroxy group, an ester of a hydroxy group, a lower alkoxy group, lower alkoxy group substituted by a halogen atom, a lower alkenyloxy group, a lower alkynyloxy group, a lower cycloalkyloxy group, an aryloxy group, a heterocyclic oxy group, a mercapto group, an ester of a mercapto group, a lower alkylthio group, a lower alkenylthio group, lower alkynylthio group, a lower cycloalkylthio group, an arylthio group, a heterocyclic thio group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, an ester of a carboxy group, an amide of a carboxy group, a lower alkylsulfinyl group, an arylsulfinyl group, a lower alkylsulfonyl group, a lower cycloalkylsulfonyl group, an arylsulfonyl group, a heterocyclic sulfonyl group, a sulfinic acid group, an ester of a sulfinic acid group, an amide of a sulfinic acid group, a sulfonic acid group, an ester of a sulfonic acid group, an amide of a sulfonic acid group, a nitro group, a cyano group, lower alkylaminocarbonyloxy group and an arylaminocarbonyloxy group.

The term "a plurality of groups" as used herein means that each group may be the same or different and the number of groups is preferably 2. Further, a hydrogen atom and a halogen atom are also included in the concept of the "group".

The "glucocorticoid receptor modulator" as used herein refers to a modulator that exhibits a pharmaceutical action by binding to glucocorticoid receptor. Examples thereof include glucocorticoid receptor agonists, glucocorticoid receptor antagonists and the like.

The "salt" of the present compound is not particularly limited as long as it is pharmaceutically acceptable salt, and examples thereof include salts with an inorganic acid such as hydrochloric acid, hydrobromic acid, hydroiodic acid, nitric acid, sulfuric acid or phosphoric acid; salts with an organic acid such as acetic acid, fumalic acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate ester, methyl sulfate, naphthalenesulfonic acid or sulfosalicylic acid; quaternary ammonium salts with methyl bromide, methyl iodide or the like; salts with a halogen ion such as a bromine ion, a chlorine ion or an iodine ion; salts with an alkali metal such as lithium, sodium or potassium; salts with an alkaline earth metal such as calcium or magnesium; salts with a metal such as iron or zinc; salts with ammonia; salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine or N,N-bis(phenylmethyl)-1,2-ethanediamine; and the like.

In the case where there are geometrical isomers or optical isomers in the present compound, these isomers are also included in the scope of the present invention.

Further, the present compound may be in the form of a hydrate or a solvate.

In the case where there is proton tautomerism in the present compound, the tautomeric isomers thereof are also included in the present invention.

In the case where there are crystalline polymorphisms in the present compound, the crystalline polymorphisms thereof are also included in the present invention.

(a) Preferred examples of the present compound include compounds in which the respective groups are groups as defined below and salts thereof in the compounds represented by the general formula (1) and salts thereof.

In the general formula (1), (a1) $R^1$ represents a halogen atom, a lower alkyl group, a lower cycloalkyl group, an aryl group, a heterocyclic group, a hydroxy group, an ester of a hydroxy group, a lower alkoxy group, a lower cycloalkyloxy group, an aryloxy group, a heterocyclic oxy group, a mercapto group, an ester of a mercapto group, a lower alkylthio group, a lower cycloalkylthio group, an arylthio group, a heterocyclic thio group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxy group, an ester of a carboxy group, an amide of a carboxy group, a lower alkylsulfonyl group, a lower cycloalkylsulfonyl group, an arylsulfonyl group, a heterocyclic sulfonyl group, a sulfonic acid group, an ester of a sulfonic acid group, an amide of a sulfonic acid group, a nitro group or a cyano group;

in the case where $R^1$ is a lower alkyl group, a lower alkoxy group, a lower alkylthio group, a lower alkylamino group, an amide of a lower alkylamino group, a lower alkylcarbonyl group or a lower alkylsulfonyl group, the lower alkyl group, lower alkoxy group, lower alkylthio group, lower alkylamino group, amide of a lower alkylamino group, lower alkylcarbonyl group or lower alkylsulfonyl group may have one or a plurality of groups selected from a halogen atom, a lower cycloalkyl group, an aryl group, a heterocyclic group, a hydroxy group, an ester of a hydroxy group, a lower alkoxy group, a lower alkoxy group substituted with a halogen atom, lower cycloalkyloxy group, an aryloxy group, a heterocyclic oxy group, a lower alkylthio group, lower cycloalkylthio group, an arylthio group, a heterocyclic thio group, an amino group, a lower alkylamino group, lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxy group, an ester of a carboxy group, an amide of a carboxy group, a lower alkylsulfonyl group, a lower cycloalkylsulfonyl group, an arylsulfonyl group, a heterocyclic sulfonyl group, a sulfonic acid group, an ester of a sulfonic acid group, an amide of a sulfonic acid group, a nitro group and a cyano group as substituents;

in the case where $R^1$ is a lower cycloalkyl group, an aryl group, a heterocyclic group, a lower cycloalkyloxy group, an aryloxy group, a heterocyclic oxy group, a lower cycloalkylthio group, an arylthio group, a heterocyclic thio group, a lower cycloalkylamino group, an arylamino group, a heterocyclic amino group, an amide of a lower cycloalkylamino group, an amide of an arylamino group, an amide of a heterocyclic amino group, a lower cycloalkylcarbonyl group, an arylcarbonyl group, a heterocyclic carbonyl group, a lower cycloalkylsulfonyl group, an arylsulfonyl group or a heterocyclic sulfonyl group, the lower cycloalkyl group, aryl group, heterocyclic group, lower cycloalkyloxy group, aryloxy group, heterocyclic oxy group, lower cycloalkylthio group, arylthio group, heterocyclic thio group, lower cycloalkylamino group, arylamino group, heterocyclic amino group, amide of a lower cycloalkylamino group, amide of an arylamino group, amide of a heterocyclic amino group, lower cycloalkylcarbonyl group, arylcarbonyl group, heterocyclic carbonyl group, lower cycloalkylsulfonyl group, arylsulfonyl group or heterocyclic sulfonyl group may have one or a plurality of groups selected from a halogen atom, a lower alkyl group, a lower alkyl group substituted with a halogen atom, a hydroxy group, an ester of a hydroxy group, a lower alkoxy group, a lower alkoxy group substituted with a halogen atom, a lower alkylthio group, an amino group, a lower alkylamino group, an amide of an amino group, an amide of a lower alkylamino group, a lower alkylcarbonyl group, a carboxy group, an ester of a carboxy group, an amide of a carboxy group, a lower alkylsulfonyl group, a sulfonic acid group, an ester of a sulfonic acid group, an amide of a sulfonic acid group, a nitro group and a cyano group as substituents; and/or (a2) p represents an integer of 0 to 3;
in the case where p is 2 or 3, each $R^1$ may be the same or different; and/or (a3) $R^2$ represents a halogen atom, a lower alkyl group, a hydroxy group or a lower alkoxy group; and/or (a4) q represents an integer of 0 to 2;
in the case where q is 2, each $R^2$ may be the same or different;
and/or (a5) $R^3$ represents a hydrogen atom, a lower alkyl group, a lower alkenyl group, a lower alkylcarbonyl group, a lower alkenylcarbonyl group or an arylcarbonyl group;

in the case where $R^3$ is a lower alkyl group or a lower alkylcarbonyl group, the lower alkyl group or lower alkylcarbonyl group may have one or a plurality of groups selected from a halogen atom and an aryl group as substituents;

in the case where $R^3$ is an arylcarbonyl group, the arylcarbonyl group may have one or a plurality of groups selected from a halogen atom, a lower alkyl group, a lower alkyl group substituted with a halogen atom, a lower alkoxy group and a lower alkoxy group substituted with a halogen atom as substituents; and/or (a6) $R^4$ and $R^5$ may be the same or different and represent a hydrogen atom, a halogen atom, a lower alkyl group, a lower cycloalkyl group, aryl or heterocyclic group;

in the case where $R^4$ or $R^5$ is a lower alkyl group, the lower alkyl group may have one or a plurality of groups selected from a halogen atom, a lower cycloalkyl group, an aryl group, a heterocyclic group, a hydroxy group, an ester of a hydroxy group, a lower alkoxy group, lower alkoxy group substituted with a halogen atom, a lower cycloalkyloxy group, an aryloxy group, a heterocyclic oxy group, a lower alkylthio group, a lower cycloalkylthio group, an arylthio group, a heterocyclic thio group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxy group, an ester of a carboxy group, an amide of a carboxy group, a nitro group and a cyano group as substituents;

in the case where $R^4$ or $R^5$ is a lower cycloalkyl group, aryl or a heterocyclic group, the lower cycloalkyl group, aryl or heterocyclic group may have one or a plurality of groups selected from a halogen atom, a lower alkyl group, a lower alkyl group substituted with a halogen atom, a hydroxy group, an ester of a hydroxy group, a lower alkoxy group, a lower alkoxy group substituted with a halogen atom, a lower alkylthio group, an amino group, a lower alkylamino group, an amide of an amino group, an amide of a lower alkylamino group, a lower alkylcarbonyl group, a carboxy group, an ester of a carboxy group, an amide of a carboxy group, a lower alkylsulfonyl group, a sulfonic acid group, an ester of a sulfonic acid group, an amide of a sulfonic acid group, a nitro group and a cyano group as substituents;

$R^4$ and $R^5$ may be combined together to form a 3- to 8-membered lower cycloalkane ring; and/or (a7) $R^6$ represents a hydrogen atom, a lower alkyl group, a lower alkenyl group, a lower alkynyl group or a lower cycloalkyl group;

in the case where $R^6$ is a lower alkyl group, a lower alkenyl group, a lower alkynyl group or a lower cycloalkyl group, the lower alkyl group, lower alkenyl group, lower alkynyl group or lower cycloalkyl group may have one or a plurality of groups selected from a halogen atom and an aryl group as substituents; and/or (a8) A represents a lower alkylene group which may be substituted with a hydroxy group or a halogen atom; and/or (a9) $R^7$ represents $OR^8$, $NR^8R^9$ or $SR^8$;

$R^8$ and $R^9$ may be the same or different and represent a hydrogen atom, a lower alkyl group, a lower alkenyl group, a lower alkynyl group, a lower cycloalkyl group, an aryl group, a heterocyclic group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, a lower alkoxycarbonyl group, a lower alkenyloxycarbonyl group, a lower alkynyloxycarbonyl group, a lower cycloalkyloxycarbonyl group, an aryloxycarbonyl group, a heterocyclic oxycarbonyl group, a lower alkylsulfonyl group, a lower alkenylsulfonyl group, a lower alkynylsulfonyl group, a lower cycloalkylsulfonyl group, an arylsulfonyl group, a heterocyclic sulfonyl group, an aminocarbonyl group, a lower alkylaminocarbonyl group, a lower alkenylaminocarbonyl group, a lower alkynylaminocarbonyl group, a lower cycloalkylaminocarbonyl group, an arylaminocarbonyl group or a heterocyclic aminocarbonyl group;

in the case where $R^8$ or $R^9$ is a lower alkyl group, a lower alkenyl group, a lower alkynyl group, a lower alkylcarbonyl group, a lower alkenylcarbonyl group, a lower alkynylcarbonyl group, a lower alkoxycarbonyl group, a lower alkenyloxycarbonyl group, a lower alkynyloxycarbonyl group, a lower alkylsulfonyl group, a lower alkenylsulfonyl group, a lower alkynylsulfonyl group, a lower alkylaminocarbonyl group, a lower alkenylaminocarbonyl group or a lower alkynylaminocarbonyl group, the lower alkyl group, lower alkenyl group, lower alkynyl group, lower alkylcarbonyl group, lower alkenylcarbonyl group, lower alkynylcarbonyl group, lower alkoxycarbonyl group, lower alkenyloxycarbonyl group, lower alkynyloxycarbonyl group, lower alkylsulfonyl group, lower alkenylsulfonyl group, lower alkynylsulfonyl group, lower alkylaminocarbonyl group, lower alkenylaminocarbonyl group or lower alkynylaminocarbonyl group may have one or a plurality of groups selected from a halogen atom, a lower cycloalkyl group, an aryl group, a heterocyclic group, a hydroxy group, an ester of a hydroxy group, a lower alkoxy group, a lower alkoxy group substituted with a halogen atom, a lower cycloalkyloxy group, an aryloxy group, a heterocyclic oxy group, a lower alkylthio group, a lower cycloalkylthio group, an arylthio group, heterocyclic thio group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxy group, an ester of a carboxy group, an amide of a carboxy group, a lower alkylsulfonyl group, a lower cycloalkylsulfonyl group, an arylsulfonyl group, a heterocyclic sulfonyl group, a sulfonic acid group, an ester of a sulfonic acid group, an amide of a sulfonic acid group, a nitro group and a cyano group as substituents;

in the case where $R^8$ or $R^9$ is a lower cycloalkyl group, an aryl group, a heterocyclic group, a lower cycloalkylcarbonyl group, an arylcarbonyl group, a heterocyclic carbonyl group, a lower cycloalkyloxycarbonyl group, an aryloxycarbonyl group, a heterocyclic oxycarbonyl group, a lower cycloalkylsulfonyl group, an arylsulfonyl group, a heterocyclic sulfonyl group, a lower cycloalkylaminocarbonyl group, an arylaminocarbonyl group or a heterocyclic aminocarbonyl group, the lower cycloalkyl group, aryl group, heterocyclic group, lower cycloalkylcarbonyl group, arylcarbonyl group, heterocyclic carbonyl group, lower cycloalkyloxycarbonyl group, aryloxycarbonyl group, heterocyclic oxycarbonyl group, lower cycloalkylsulfonyl group, arylsulfonyl group, heterocyclic sulfonyl group, lower cycloalkylaminocarbonyl group, arylaminocarbonyl group or heterocyclic aminocarbonyl group may have one or a plurality of groups selected from a halogen atom, a lower alkyl group, a lower alkyl group substituted with a halogen atom, a lower alkyl group substituted with a hydroxy group, a lower alkenyl group, a lower alkynyl group, a lower cycloalkyl group, an aryl group, a heterocyclic group, a hydroxy group, an ester of a hydroxy group, a lower alkoxy group, a lower alkoxy group substituted with a halogen atom, a lower alkenyloxy group, a lower alkynyloxy group, a lower cycloalkyloxy group, an aryloxy group, a heterocyclic oxy group, a lower alkylthio group, lower cycloalkylthio group, an arylthio group, a heterocyclic thio group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxy group, an ester of a carboxy group, an amide of a carboxy group, a lower alkylsulfonyl group, a lower cycloalkylsulfonyl group, an arylsulfonyl group, a heterocyclic sulfonyl group, a sulfonic acid group, an ester of a sulfonic acid group, an amide of a sulfonic acid group, a nitro group and a cyano group as substituents;

in the case where $R^7$ is $NR^8R^9$, $R^8$ and $R^9$ may be combined together form a 5- or 6-membered nitrogen-containing heterocyclic ring; and/or (a10) X represents O or S.

That is, in the compounds represented by the general formula (1), preferred examples include compounds that comprises one or a combination of two or more selected from the above (a1), (a2), (a3), (a4), (a5), (a6), (a7), (a8), (a9) and (a10), and salts thereof.

(b) More preferred examples of the present compound include compounds in which the respective groups are groups as defined below and salts thereof in the compounds represented by the general formula (1) and salts thereof.

In the general formula (1), (b1) $R^1$ represents a halogen atom, a lower alkyl group, a hydroxy group, an ester of a hydroxy group, a lower alkoxy group, a lower alkylthio group, an amino group, a lower alkylamino group, an amide of an amino group, an amide of a lower alkylamino group, a lower alkylcarbonyl group, a carboxy group, an ester of a carboxy group, an amide of a carboxy group, a lower alkylsulfonyl group, a nitro group or a cyano group;

in the case where $R^1$ is a lower alkyl group, a lower alkoxy group, a lower alkylthio group, a lower alkylamino group, an amide of a lower alkylamino group, a lower alkylcarbonyl group or a lower alkylsulfonyl group, the lower alkyl group, lower alkoxy group, lower alkylthio group, lower alkylamino group, amide of a lower alkylamino group, lower alkylcarbonyl group or lower alkylsulfonyl group may have one or a plurality of groups selected from a halogen atom, a lower cycloalkyl group, an aryl group, a heterocyclic group, a hydroxy group, an ester of a hydroxy group, a lower alkoxy group, a lower alkoxy group substituted with a halogen atom, a lower cycloalkyloxy group, an aryloxy group, a heterocyclic oxy group, a lower alkylthio group, a lower cycloalkylthio group, an arylthio group, a heterocyclic thio group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, carboxy group, an ester of a carboxy group, an amide of a carboxy group, a lower alkylsulfonyl group, a lower cycloalkylsulfonyl group, an arylsulfonyl group, a heterocyclic sulfonyl group, a sulfonic acid group, an ester of a sulfonic acid group, an amide of a sulfonic acid group, a nitro group and a cyano group as substituents; and/or (b2) p represents an integer of 0 to 3;

in the case where p is 2 or 3, each $R^1$ may be the same or different; and/or (b3) q represents 0; and/or (b4) $R^3$ represents a hydrogen atom, a lower alkyl group, lower alkenyl group, a lower alkylcarbonyl group, a lower alkenylcarbonyl group or an arylcarbonyl group;

in the case where $R^3$ is a lower alkyl group, the lower alkyl group may have one or a plurality of aryl groups as substituents;

in the case where $R^3$ is an arylcarbonyl group, the arylcarbonyl group may have one or a plurality of groups selected from a halogen atom and a lower alkyl group as substituents; and/or (b5) $R^4$ and $R^5$ may be the same or different and represent a hydrogen atom, a halogen atom, a lower alkyl group, a lower cycloalkyl group, aryl or a heterocyclic group;

in the case where $R^4$ or $R^5$ is a lower alkyl group, the lower alkyl group may have one or a plurality of groups selected from a halogen atom, a hydroxy group, an ester of a hydroxy group, a lower alkoxy group, a lower alkoxy group substituted with a halogen atom, a lower alkylthio group, an amino group, a lower alkylamino group, an amide of an amino group, an amide of a lower alkylamino group, a lower alkylcarbonyl group, a carboxy group, an ester of a carboxy group, an amide of a carboxy group, a nitro group and a cyano group as substituents;

in the case where $R^4$ or $R^5$ is a lower cycloalkyl group, aryl or heterocyclic group, the lower cycloalkyl group, aryl or heterocyclic group may have one or a plurality of groups selected from a halogen atom, a lower alkyl group, a lower alkyl group substituted with a halogen atom, a hydroxy group, an ester of a hydroxy group, a lower alkoxy group, a lower alkoxy group substituted with a halogen atom, lower alkylthio group, an amino group, a lower alkylamino group, an amide of an amino group, an amide of a lower alkylamino group, a lower alkylcarbonyl group, a carboxy group, an ester of a carboxy group, an amide of a carboxy group, a lower alkylsulfonyl group, a nitro group and a cyano group as substituents;

$R^4$ and $R^5$ may be combined together to form a 3- to 8-membered lower cycloalkane ring; and/or (b6) $R^6$ represents a hydrogen atom, a lower alkyl group, a lower alkenyl group, a lower alkynyl group or a lower cycloalkyl group;

in the case where $R^6$ is a lower alkyl group, a lower alkenyl group, a lower alkynyl group or a lower cycloalkyl group, the lower alkyl group, lower alkenyl group, lower alkynyl group or lower cycloalkyl group may have one or a plurality of groups selected from a halogen atom and an aryl group as substituents; and/or (b7) A represents a lower alkylene group; and/or (b8) $R^7$ represents $OR^8$, $NR^8R^9$ or $SR^8$;

$R^8$ and $R^9$ may be the same or different and represent a hydrogen atom, a lower alkyl group, a lower alkenyl group, a lower alkynyl group, a lower cycloalkyl group, an aryl group, a heterocyclic group, a formyl group, a lower alkylcarbonyl group, a lower alkenylcarbonyl group, a lower alkynylcarbonyl group, lower cycloalkylcarbonyl group, an arylcarbonyl group, a heterocyclic carbonyl group, a carboxy group, a lower alkoxycarbonyl group, a lower alkenyloxycarbonyl group, a lower alkynyloxycarbonyl group, a lower cycloalkyloxycarbonyl group, an aryloxycarbonyl group, a heterocyclic oxycarbonyl group, a lower alkylsulfonyl group, a lower alkenylsulfonyl group, a lower alkynylsulfonyl group, a lower cycloalkylsulfonyl group, an arylsulfonyl group, a heterocyclic sulfonyl group, an aminocarbonyl group, a lower alkylaminocarbonyl group, a lower alkenylaminocarbonyl group, a lower alkynylaminocarbonyl group, a lower cycloalkylaminocarbonyl group, an arylaminocarbonyl group or a heterocyclic aminocarbonyl group;

in the case where $R^8$ or $R^9$ is a lower alkyl group, a lower alkenyl group, a lower alkynyl group, a lower alkylcarbonyl group, a lower alkenylcarbonyl group, a lower alkynylcarbonyl group, a lower alkoxycarbonyl group, a lower alkenyloxycarbonyl group, a lower alkynyloxycarbonyl group, a lower alkylsulfonyl group, a lower alkenylsulfonyl group, a lower alkynylsulfonyl group, a lower alkylaminocarbonyl group, a lower alkenylaminocarbonyl group or a lower alkynylaminocarbonyl group, the lower alkyl group, lower alkenyl group, lower alkynyl group, lower alkylcarbonyl group, lower alkenylcarbonyl group, lower alkynylcarbonyl group, lower alkoxycarbonyl group, lower alkenyloxycarbonyl group, lower alkynyloxycarbonyl group, lower alkylsulfonyl group, lower alkenylsulfonyl group, lower alkynylsulfonyl group, lower alkylaminocarbonyl group, lower alkenylaminocarbonyl group or lower alkynylaminocarbonyl group may have one or a plurality of groups selected from a halogen atom, a lower cycloalkyl group, an aryl group, a heterocyclic group, a hydroxy group, an ester of a hydroxy group, a lower alkoxy group, a lower alkoxy group substituted with a halogen atom, a lower alkylthio group, an amino group, a lower alkylamino group, an amide of an amino group, an amide of a lower alkylamino group, a lower alkylcarbonyl group, a carboxy group, an ester of a carboxy group, an amide of a carboxy group, a lower alkylsulfonyl group, a nitro group and a cyano group as substituents;

in the case where $R^8$ or $R^9$ is a lower cycloalkyl group, an aryl group, a heterocyclic group, a lower cycloalkylcarbonyl group, an arylcarbonyl group, a heterocyclic carbonyl group, a lower cycloalkyloxycarbonyl group, an aryloxycarbonyl group, a heterocyclic oxycarbonyl group, a lower cycloalkylsulfonyl group, an arylsulfonyl group, a heterocyclic sulfonyl group, a lower cycloalkylaminocarbonyl group, an arylaminocarbonyl group or a heterocyclic aminocarbonyl group, the lower cycloalkyl group, aryl group, heterocyclic group, lower cycloalkylcarbonyl group, arylcarbonyl group, heterocyclic carbonyl group, lower cycloalkyloxycarbonyl group, aryloxycarbonyl group, heterocyclic oxycarbonyl group, lower cycloalkylsulfonyl group, arylsulfonyl group, heterocyclic sulfonyl group, lower cycloalkylaminocarbonyl group, arylaminocarbonyl group or heterocyclic aminocarbonyl group may have one or a plurality of groups selected from a halogen atom, a lower alkyl group, a lower alkyl group substituted with a halogen atom, a lower alkyl group substituted with a hydroxy group, a lower alkenyl group, a lower alkynyl group, a lower cycloalkyl group, an aryl group, a heterocyclic group, a hydroxy group, an ester of a hydroxy group, a lower alkoxy group, a lower alkoxy group substituted with a halogen atom, a lower alkenyloxy group, a lower alkynyloxy group, a lower alkylthio group, an amino group, a lower alkylamino group, an amide of an amino group, an amide of a lower alkylamino group, a lower alkylcarbonyl group, a carboxy group, an ester of carboxy group, an amide of a carboxy group, a lower alkylsulfonyl group, a nitro group and a cyano group as substituents;

in the case where $R^7$ is $NR^8R^9$, $R^8$ and $R^9$ may be combined together to form a 5- or 6-membered nitrogen-containing heterocyclic ring; and/or (b9) X represents O.

That is, in the compounds represented by the general formula (1), more preferred examples include compounds that comprises one or a combination of two or more selected from the above (b1), (b2), (b3), (b4), (b5), (b6), (b7), (b8) and (b9), and salts thereof.

(c) Further more preferred examples of the present compound include compounds in which the respective groups are groups as defined below and salts thereof in the compounds represented by the general formula (1) and salts thereof.

In the general formula (1), (c1) $R^1$ represents a halogen atom, a lower alkyl group, a hydroxy group, an ester of a hydroxy group, a lower alkoxy group, a lower alkylthio group, an amino group, an amide of an amino group, an amide of a lower alkylamino group, a lower alkylcarbonyl group, a carboxy group, an ester of a carboxy group, a nitro group or a cyano group;

in the case where $R^1$ is a lower alkyl group or a lower alkoxy group, the lower alkyl group or lower alkoxy group may have one or a plurality of groups selected from a halogen atom, a hydroxy group and a lower alkoxy group as substituents; and/or (c2) p represents 1, 2 or 3;

in the case where p is 2 or 3, each $R^1$ may be the same or different; and/or (c3) q represents 0; and/or (c4) $R^3$ represents a hydrogen atom; and/or (c5) $R^4$ and $R^5$ may be the same or different and represent a lower alkyl group; and/or (c6) $R^6$ represents a hydrogen atom, a lower alkyl group or a lower alkenyl group; and/or (c7) A represents a lower alkylene group; and/or (c8) $R^7$ represents $OR^8$ or $NR^8R^9$;

$R^8$ and $R^9$ may be the same or different and represent a hydrogen atom, an aryl group, an arylcarbonyl group or a heterocyclic carbonyl group;

in the case where $R^8$ or $R^9$ is an aryl group, an arylcarbonyl group or a heterocyclic carbonyl group, the aryl group, arylcarbonyl group or heterocyclic carbonyl group may have one or a plurality of groups selected from a halogen atom, a lower alkyl group, a lower alkyl group substituted with at least a halogen atom, a lower alkyl group substituted with at least a hydroxy group, a lower alkenyl group, an aryl group, a lower alkoxy group, a lower alkylcarbonyl group, an ester of a carboxy group, a nitro group and a cyano group as substituents; and/or (c9) X represents O.

That is, in the compounds represented by the general formula (1), further more preferred examples include compounds that comprises one or a combination of two or more selected from the above (c1), (c2), (c3), (c4), (c5), (c6), (c7), (c8) and (c9), and salts thereof.

(d) Further more preferred examples of the present compound include compounds in which the respective groups are groups as defined below and salts thereof in the compounds represented by the general formula (1) and salts thereof.

In the general formula (1), (d1) $R^1$ represents a halogen atom, a hydroxy group, an ester of a hydroxy group, a lower alkoxy group, an amide of an amino group or an amide of lower alkylamino group; and/or (d2) p represents 2 or 3, in this case, each $R^1$ may be the same or different; and/or (d3) q represents 0; and/or (d4) $R^3$ represents a hydrogen atom; and/or (d5) $R^4$ and $R^5$ may be the same or different and represent a lower alkyl group; and/or (d6) $R^6$ represents a lower alkyl group; and/or (d7) A represents a lower alkylene group; and/or (d8) $R^7$ represents $OR^8$ or $NR^8R^9$;

$R^8$ represents an aryl group, an arylcarbonyl group or a heterocyclic carbonyl group, in this case, the aryl group, arylcarbonyl group or heterocyclic carbonyl group may have one or a plurality of groups selected from a halogen atom, a lower alkyl group, a lower alkyl group substituted with at least a halogen atom, a lower alkyl group substituted with at least a hydroxy group, a lower alkenyl group, an aryl group, a lower alkoxy group, a lower alkylcarbonyl group, an ester of a carboxy group, a nitro group and a cyano group as substituents;

$R^9$ represents a hydrogen atom; and/or (d9) X represents O.

That is, in the compounds represented by the general formula (1), further more preferred examples include compounds that comprises one or a combination of two or more selected from the above (d1), (d2), (d3), (d4), (d5), (d6), (d7), (d8) and (d9), and salts thereof.

(e) Preferred examples of $R^1$ in the present compound include compounds that satisfy the following requirement and salts thereof.

A compound or a salt thereof wherein in the general formula (1), $R^1$ represents a halogen atom, a hydroxy group, an ester of a hydroxy group, a lower alkoxy group, an amide of an amino group or an amide of a lower alkylamino group; and satisfies the requirement of the above (a), (b) and/or (c).

(f) Preferred examples of $R^4$, $R^5$ and $R^6$ in the present compound include compounds that satisfy the following requirement and salts thereof.

A compound or a salt thereof wherein in the general formula (1), $R^4$, $R^5$ and $R^6$ each represent methyl group, and satisfies the requirement of the above (a), (b), (c) and/or (d).

(g) Preferred examples of $R^8$ in the present compound include compounds that satisfy the following requirement and salts thereof.

A compound or a salt thereof wherein in the general formula (1), represents an aryl group, an arylcarbonyl group or a heterocyclic carbonyl group, and the aryl group represents a phenyl group, the arylcarbonyl group represents a phenylcarbonyl group, and/or the heterocyclic carbonyl group represents a thiophenecarbonyl group, and satisfies the requirement of the above (a), (b), (c) and/or (d).

(h) Preferred examples of A in the present compound include compounds that satisfy the following requirement and salts thereof.

A compound or a salt thereof wherein in the general formula (1), A represent a methylene group, and satisfies the requirement of the above (a), (b), (c) and/or (d).

(i) Preferred examples of which $R^1$ is an ester of a hydroxyl group in the present compound include compounds that satisfy the following requirement and salts thereof.

In the $R^1$ of the general formula (1), the ester of a hydroxy group represents —OCO—$R^{a1}$, in which the $R^{a1}$ represents a hydrogen atom, a lower alkyl group which may have at least a substituent, a lower alkenyl group which may have at least a substituent, a lower alkynyl group which may have at least a substituent, a lower cycloalkyl group which may have at least a substituent, an aryl group which may have at least a substituent, a heterocyclic group which may have at least a substituent, a lower alkoxy group which may have at least a substituent, a lower alkenyloxy group which may have at least substituent, a lower alkynyloxy group which may have at least a substituent, a lower cycloalkyloxy group which may have at least a substituent, an aryloxy group which may have at least a substituent, a heterocyclic oxy group which may have at least a substituent, an amino group, a lower alkylamino group which may have at least a substituent, a lower cycloalkylamino group which may have at least a substituent, an arylamino group which may have at least a substituent or a heterocyclic amino group which may have at least a substituent, more preferred examples, the $R^{a1}$ represents a hydrogen atom, a lower alkyl group, a lower alkenyl group, lower cycloalkyl group, an aryl group, a heterocyclic group, a lower alkoxy group, a lower alkenyloxy group, a lower cycloalkyloxy group, an aryloxy group, a heterocyclic oxy group, an amino group, a lower alkylamino group, a lower cycloalkylamino group, an arylamino group or a heterocyclic amino group;

in the case where $R^{a1}$ is a lower alkyl group, lower alkenyl group, a lower alkoxy group, a lower alkenyloxy group or a lower alkylamino group, the lower alkyl group, lower alkenyl group, lower alkoxy group, lower alkenyloxy group or lower alkylamino group may have one or a plurality of groups selected from a halogen atom, an aryl group, a heterocyclic group, a hydroxy group, an ester of a hydroxy group, an amino group, a lower alkylamino group, a carboxy group and an ester of a carboxy group as substituents; and in the case where $R^{a1}$ is a lower cycloalkyl group, an aryl group, a heterocyclic group, a lower cycloalkyloxy group, an aryloxy group, a heterocyclic oxy group, a lower cycloalkylamino group, an arylamino group or a heterocyclic amino group, the lower cycloalkyl group, aryl group, heterocyclic group, lower cycloalkyloxy group, aryloxy group, heterocyclic oxy group, lower cycloalkylamino group, arylamino group or heterocyclic amino group may have one or a plurality of groups selected from a halogen atom, a lower alkyl group, a lower alkyl group substituted with at least a halogen atom, a hydroxy group, an ester of a hydroxy group, a lower alkoxy group, a mercapto group, a lower alkylthio group, formyl group, a lower alkylcarbonyl group, a carboxy group, an ester of a carboxy group, a nitro group and a cyano group as substituents, further more preferred examples, the $R^{a1}$ represents a lower alkyl group, a lower alkenyl group, a lower cycloalkyl group, an aryl group, a heterocyclic group, a lower alkoxy group, an aryloxy group, a lower alkylamino group, a lower cycloalkylamino group, an arylamino group or a heterocyclic amino group;

in the case where $R^{a1}$ is a lower alkyl group, the lower alkyl group may have one or a plurality of groups selected from an aryl group and a lower alkylamino group as substituents;

in the case where $R^{a1}$ is an aryl group, the aryl group may have one or a plurality of groups selected from a halogen atom, a lower alkyl group, a lower alkyl group substituted with at least a halogen atom, an ester of a hydroxy group, a lower alkoxy group, a lower alkylthio group, a lower alkylcarbonyl group, an ester of a carboxy group and a nitro group as substituents;

in the case where $R^{a1}$ is a heterocyclic group, the heterocyclic group may have one or a plurality of groups selected from a halogen atom, a lower alkyl group, a hydroxy group and a lower alkoxy group as substituents;

in the case where $R^{a1}$ is a lower alkylamino group, the lower alkylamino group may have one or a plurality of groups selected from an aryl group, a heterocyclic group and an ester of a carboxy group as substituents; and in the case where $R^{a1}$ is an arylamino group, the arylamino group may have one or a plurality of groups selected from a halogen atom, a lower alkyl group and a lower alkoxy group as substituents, and satisfies the requirement of the above (a), (b), (c) (d) and/or (e).

(j) Preferred examples of which $R^1$ is an amide of an amino group in the present compound include compounds that satisfy the following requirement and salts thereof.

In the $R^1$ of the general formula (1), the amide of an amino group represents —NHCO—$R^{b1}$, in which the $R^{b1}$ represents a hydrogen atom, a lower alkyl group which may have at least a substituent, a lower alkenyl group which may have at least a substituent, a lower alkynyl group which may have at least a substituent, a lower cycloalkyl group which may have at least a substituent, an aryl group which may have at least a substituent, a heterocyclic group which may have at least a substituent, a lower alkoxy group which may have at least a substituent, a lower alkenyloxy group which may have at least a substituent, a lower alkynyloxy group which may have at least a substituent, a lower cycloalkyloxy group which may have at least a substituent, an aryloxy group which may have at least a substituent, a heterocyclic oxy group which may have at least a substituent, an amino group, a lower alkylamino group which may have at least substituent, a lower cycloalkylamino group which may have at least a substituent, an arylamino group which may have at least a substituent or a heterocyclic amino group which may have at least a substituent, more preferred examples, $R^{b1}$ represents a hydrogen atom, a lower alkyl group, a lower alkenyl group, a lower cycloalkyl group, an aryl group, a heterocyclic group, a lower alkoxy group, a lower alkenyloxy group, a lower cycloalkyloxy group, an aryloxy group, a heterocyclic oxy group, an amino group, a lower alkylamino group, a lower cycloalkylamino group, an arylamino group or a heterocyclic amino group;

in the case where $R^{b1}$ is a lower alkyl group, a lower alkenyl group, a lower alkoxy group, a lower alkenyloxy group or a lower alkylamino group, the lower alkyl group, lower alkenyl group, lower alkoxy group, lower alkenyloxy group or lower alkylamino group may have one or a plurality of groups selected from a halogen atom, an aryl group, a heterocyclic group, a hydroxy group, an ester of a hydroxy group, an amino group, a lower alkylamino group, a carboxy group and an ester of a carboxy group as substituents; and in the case where $R^{b1}$ is lower cycloalkyl group, an aryl group, a heterocyclic group, a lower cycloalkyloxy group, an aryloxy group, a heterocyclic oxy group, a lower cycloalkylamino group, an arylamino group or a heterocyclic amino group, the lower cycloalkyl group, aryl group, heterocyclic group, lower cycloalkyloxy group, aryloxy group, heterocyclic oxy group, lower cycloalkylamino group, arylamino group or heterocyclic amino group may have one or a plurality of groups selected from a halogen atom, a lower alkyl group, a lower alkyl group substituted with at least a halogen atom, a hydroxy group, an ester of a hydroxy group, a lower alkoxy group, a mercapto group, a lower alkylthio group, a formyl group, a lower alkylcarbonyl group, a carboxy group, an ester of a carboxy group, a nitro group and a cyano group as substituents, further more preferred examples, the $R^{b1}$ represents a lower alkyl group, an aryl group, a heterocyclic group, an aryloxy group, a lower alkylamino group or an arylamino group;

in the case where $R^{b1}$ is a lower alkyl group, the lower alkyl group may have one or a plurality of amino groups as substituents;

in the case where $R^{b1}$ is an aryl group, the aryl group may have one or a plurality of groups selected from a halogen atom, a lower alkyl group, a lower alkyl group substituted with at least a halogen atom, an ester of a hydroxy group, a lower alkoxy group, a lower alkylthio group, a lower alkylcarbonyl group, an ester of a carboxy group and a nitro group as substituents;

in the case where $R^{b1}$ is a heterocyclic group, the heterocyclic group may have one or a plurality of groups selected from a halogen atom, a lower alkyl group, a hydroxy group and a lower alkoxy group as substituents; and in the case where $R^{b1}$ is a lower alkylamino group, the lower alkylamino group may have one or a plurality aryl groups as substituents, and satisfies the requirement of the above (a), (b), (c) (d) and/or (e).

(k) Preferred examples of which $R^1$ is an amide of a lower alkylamino group in the present compound include compounds that satisfy the following requirement and salts thereof.

In the $R^1$ of the general formula (1), the amide of a lower alkylamino group represents —$NR^{c1}CO$—$R^{c2}$, in which the $R^{c1}$ represents a lower alkyl group which may have at least a substituent, and the $R^{c2}$ represents a hydrogen atom, a lower alkyl group which may have at least a substituent, a lower alkenyl group which may have at least a substituent, a lower alkynyl group which may have at least a substituent, a lower cycloalkyl group which may have at least a substituent, an aryl group which may have at least a substituent, a heterocyclic group which may have at least a substituent, a lower alkoxy group which may have at least a substituent, a lower alkenyloxy group which may have at least a substituent, a lower alkynyloxy group which may have at least a substituent, a lower cycloalkyloxy group which may have at least a substituent, an aryloxy group which may have at least a substituent, a heterocyclic oxy group which may have at least a substituent, an amino group, a lower alkylamino group which may have at least a substituent, a lower cycloalkylamino group which may have at least a substituent, an arylamino group which may have at least a substituent or a heterocyclic amino group which may have at least a substituent, more preferred examples, the $R^{c1}$ represents a lower alkyl group, and the $R^{c2}$ represents a hydrogen atom, a lower alkyl group, a lower alkenyl group, a lower cycloalkyl group, an aryl group, a heterocyclic group, a lower alkoxy group, a lower alkenyloxy group, a lower cycloalkyloxy group, an aryloxy group, a heterocyclic oxy group, an amino group, a lower alkylamino group, lower cycloalkylamino group, an arylamino group or a heterocyclic amino group;

in the case where $R^{c2}$ is a lower alkyl group, a lower alkenyl group, a lower alkoxy group, a lower alkenyloxy group or a lower alkylamino group, the lower alkyl group, lower alkenyl group, lower alkoxy group, lower alkenyloxy group or lower alkylamino group may have one or a plurality of groups selected from a halogen atom, an aryl group, a heterocyclic group, a hydroxy group, an ester of a hydroxy group, an amino group, a lower alkylamino group, a carboxy group and an ester of a carboxy group as substituents; and in the case where $R^{c2}$ is a lower cycloalkyl group, an aryl group, a heterocyclic group, a lower cycloalkyloxy group, an aryloxy group, a heterocyclic oxy group, a lower cycloalkylamino group, an arylamino group or a heterocyclic amino group, the lower cycloalkyl group, aryl group, heterocyclic group, lower cycloalkyloxy group, aryloxy group, heterocyclic oxy group, lower cycloalkylamino group, arylamino group or heterocyclic amino group may have one or a plurality of groups selected from a halogen atom, a lower alkyl group, a lower alkyl group substituted with at least a halogen atom, a hydroxy group, an ester of a hydroxy group, a lower alkoxy group, a mercapto group, a lower alkylthio group, a formyl group, a lower alkylcarbonyl group, a carboxy group, an ester of a carboxy group, a nitro group and a cyano group as substituents, further more preferred examples, the $R^{c1}$ represents a lower alkyl group, and the $R^{c2}$ represents a lower alkyl group, an aryl group or a heterocyclic group;

in the case where $R^{c2}$ is a lower alkyl group, the lower alkyl group may have one or a plurality of amino groups as substituents;

in the case where $R^{c2}$ is an aryl group, the aryl group may have one or a plurality of groups selected from a halogen atom, a lower alkyl group, a lower alkyl group substituted with at least a halogen atom, an ester of a hydroxy group, a lower alkoxy group, a lower alkylthio group, a lower alkylcarbonyl group, an ester of a carboxy group and a nitro group as substituents;

in the case where $R^{c2}$ is a heterocyclic group, the heterocyclic group may have one or a plurality of groups selected from a halogen atom, a lower alkyl group, a hydroxy group and a lower alkoxy group as substituents; and in the case where $R^{c2}$ is a lower alkylamino group, the lower alkylamino group may have one or a plurality of aryl groups as substituents, and satisfies the requirement of the above (a), (b), (c) (d) and/or (e).

(l) Particularly preferred specific examples of the present compound include the following compounds and salts thereof. A compound or a salt thereof selected from 7-[2-Methoxy-4-(2-methylbenzoyloxy)phenyl]-8-(4-methoxybenzoyloxymethyl)-3,3-dimethyl-3,4-dihydro-1H-quinoxalin-2-one 7-(5-Fluoro-2-methoxyphenyl)-8-(4-methylbenzoyloxymethyl)-3,3-dimethyl-3,4-dihydro-1H-quinoxalin-2-one 7-(4-Fluoro-2-methoxyphenyl)-8-(5-methylthiophen-2-ylcarbonyloxymethyl)-1,3,3-trimethyl-3,4-dihydro-1H-quinoxalin-2-one 8-(5-Bromothiophen-2-ylcarbonyloxymethyl)-7-(4-fluoro-2-methoxyphenyl)-1,3,3-trimethyl-3,4-dihydro-1H-quinoxalin-2-one 7-(4-Fluoro-2-methoxyphenyl)-8-(2-methyl-5-nitrophenoxymethyl)-1,3,3-trimethyl-3,4-dihydro-1H-quinoxalin-2-one 7-(5-Chloro-2-methoxyphenyl)-8-[2-(2-hydroxyethyl)phenoxymethyl]-1,3,3-trimethyl-3,4-dihydro-1H-quinoxalin-2-one 8-(5-Chloro-2-methylphenoxymethyl)-7-(4-fluoro-2-methoxyphenyl)-1,3,3-trimethyl-3,4-dihydro-1H-quinoxalin-2-one 7-(4-Fluoro-2-methoxyphenyl)-8-(2-methoxy-5-nitrophenoxymethyl)-1,3,3-trimethyl-3,4-dihydro-quinoxalin-2-one 8-(2-Allylphenoxymethyl)-7-(4-fluoro-2-methoxyphenyl)-1,3,3-trimethyl-3,4-dihydro-1H-quinoxalin-2-one 7-(4-Fluoro-2-methoxyphenyl)-8-(2-methoxy-5-methylphenylaminomethyl)-1,3,3-trimethyl-3,4-dihydro-1H-quinoxalin-2-one 7-(5-Chloro-2-methoxyphenyl)-8-(5-fluoro-2-methylphenylaminomethyl)-1,3,3-trimethyl-3,4-dihydro-1H-quinoxalin-2-one 7-(5-Chloro-2-methoxyphenyl)-8-(2-isopropylphenylaminomethyl)-1,3,3-trimethyl-3,4-dihydro-1H-quinoxalin-2-one 7-(4-Fluoro-2-methoxyphenyl)-8-(2-methoxyphenylaminomethyl)-1,3,3-trimethyl-3,4-dihydro-1H-quinoxalin-2-one 8-Benzoyloxymethyl-7-(5-fluoro-2-methoxyphenyl)-1,3,3-trimethyl-3,4-dihydro-1H-quinoxalin-2-one 7-(5-Fluoro-2-methoxyphenyl)-8-phenoxymethyl-1,3,3-trimethyl-3,4-dihydro-1H-quinoxalin-2-one 7-(5-Fluoro-2-methoxyphenyl)-8-phenylaminomethyl-1,3,3-trimethyl-3,4-dihydro-1H-quinoxalin-2-one 1-Ethyl-7-(5-fluoro-2-methoxyphenyl)-8-(4-methylbenzoyloxymethyl)-3,3-dimethyl-3,4-dihydro-1H-quinoxalin-2-one 1-(Propen-3-yl)-7-(5-fluoro-2-methoxyphenyl)-8-(4-methylbenzoyloxymethyl)-3,3-dimethyl-3,4-dihydro-1H-quinoxalin-2-one 7-[2-Methoxy-4-(2-methylbenzoyloxy)phenyl]-8-(4-methoxybenzoyloxymethyl)-1,3,3-trimethyl-3,4-dihydro-1H-quinoxalin-2-one 7-[2-Methoxy-4-(2-methylbenzoyloxy)phenyl]-8-(2-methoxy-5-nitrophenoxymethyl)-1,3,3-trimethyl-3,4-dihydro-1H-quinoxalin-2-one 8-(3-Fluorobenzoyloxymethyl)-7-[2-methoxy-4-(2-methylbenzoyloxy)phenyl]-1,3,3-trimethyl-3,4-dihydro-1H-quinoxalin-2-one 7-(2-Chlorophenyl)-8-(5-fluoro-2-methylphenoxymethyl)-1,3,3-trimethyl-3,4-dihydro-1H-quinoxalin-2-one 8-(5-Fluoro-2-methylphenoxymethyl)-7-(2-methoxyphenyl)-1,3,3-trimethyl-3,4-dihydro-1H-quinoxalin-2-one 8-(5-Fluoro-2-methylphenoxymethyl)-7-(2-methylthiophenyl)-1,3,3-trimethyl-3,4-dihydro-1H-quinoxalin-2-one 7-(4-Fluoro-2-methoxyphenyl)-8-(5-fluoro-2-methylphenoxymethyl)-1,3,3-trimethyl-3,4-dihydro-1H-quinoxalin-2-one 7-(5-Chloro-2-methoxyphenyl)-8-(5-fluoro-2-methylphenoxymethyl)-1,3,3-trimethyl-3,4-dihydro-1H-quinoxalin-2-one 8-(5-Fluoro-2-methylphenoxymethyl)-7-(2-methoxy-5-trifluoromethylphenyl)-1,3,3-trimethyl-3,4-dihydro-1H-quinoxalin-2-one 7-(6-Fluoro-2-methoxyphenyl)-8-(5-fluoro-2-methylphenoxymethyl)-1,3,3-trimethyl-3,4-dihydro-1H-quinoxalin-2-one 8-(5-Fluoro-2-methylphenoxymethyl)-7-(2-methoxy-5-nitrophenyl)-1,3,3-trimethyl-3,4-dihydro-1H-quinoxalin-2-one 7-(5-Benzoyloxy-2-methoxyphenyl)-8-(5-fluoro-2-methylphenoxymethyl)-1,3,3-trimethyl-3,4-dihydro-1H-quinoxalin-2-one 8-(2-Methoxyphenylaminomethyl)-7-(2-methoxy-5-trifluoromethylphenyl)-1,3,3-trimethyl-3,4-dihydro-1H-quinoxalin-2-one 7-(4-Amino-2-methoxyphenyl)-8-(5-fluoro-2-methylphenoxymethyl)-1,3,3-trimethyl-3,4-dihydro-1H-quinoxalin-2-one 8-(5-Fluoro-2-methylphenoxymethyl)-7-(5-hydroxymethyl-2-methoxyphenyl)-1,3,3-trimethyl-3,4-dihydro-1H-quinoxalin-2-one 8-(5-Fluoro-2-methylphenoxymethyl)-7-(4-hydroxy-2-methoxyphenyl)-1,3,3-trimethyl-3,4-dihydro-1H-quinoxalin-2-one 7-(4-Hydroxy-2-methoxyphenyl)-8-(5-methylthiophen-2-ylcarbonyloxymethyl)-1,3,3-trimethyl-3,4-dihydro-1H-quinoxalin-2-one 8-(5-Fluoro-2-methylphenoxymethyl)-7-[2-methoxy-4-(2-methylbenzoyloxy)phenyl]-1,3,3-trimethyl-3,4-dihydro-1H-quinoxalin-2-one 7-[4-(2-Chlorobenzoyloxy)-2-methoxyphenyl]-8-(5-fluoro-2-methylphenoxymethyl)-1,3,3-trimethyl-3,4-dihydro-1H-quinoxalin-2-one 8-(5-Fluoro-2-methylphenoxymethyl)-7-[4-(furan-3-ylcarbonyloxy)-2-methoxyphenyl]-1,3,3-trimethyl-3,4-dihydro-1H-quinoxalin-2-one 8-(5-Fluoro-2-methylphenoxymethyl)-7-[2-methoxy-4-(pyridin-4-ylcarbonylamino)phenyl]-1,3,3-trimethyl-3,4-dihydro-1H-quinoxalin-2-one 7-[4-(2-Chlorobenzoylamino)-2-methoxyphenyl]-8-(5-fluoro-2-methylphenoxymethyl)-1,3,3-trimethyl-3,4-dihydro-1H-quinoxalin-2-one 8-(5-Fluoro-2-methylphenoxymethyl)-7-[2-methoxy-4-(4-methoxybenzoyloxy)phenyl]-1,3,3-trimethyl-3,4-dihydro-1H-quinoxalin-2-one 7-(4-Acryloyloxy-2-methoxyphenyl)-8-(5-fluoro-2-methylphenoxymethyl)-1,3,3-trimethyl-3,4-dihydro-1H-quinoxalin-2-one 8-(5-Fluoro-2-methylphenoxymethyl)-7-(2-methoxy-4-methoxycarbonyloxyphenyl)-1,3,3-trimethyl-3,4-dihydro-1H-quinoxalin-2-one 8-(5-Fluoro-2-methylphenoxymethyl)-7-(2-methoxy-4-phenoxycarbonyloxyphenyl)-1,3,3-trimethyl-3,4-dihydro-1H-quinoxalin-2-one 8-(5-Fluoro-2-methylphenoxymethyl)-7-(2-methoxy-4-phenoxycarbonylaminophenyl)-1,3,3-trimethyl-3,4-dihydro-1H-quinoxalin-2-one 7-[4-(2-Fluorobenzoyloxy)-2-methoxyphenyl]-8-(5-methylthiophen-2-ylcarbonyloxymethyl)-1,3,3-trimethyl-3,4-dihydro-1H-quinoxalin-2-one 8-(5-Fluoro-2-methylphenoxymethyl)-7-[2-methoxy-4-(3-methoxycarbonylbenzoyloxy)phenyl]-1,3,3-trimethyl-3,4-dihydro-1H-quinoxalin-2-one 8-(5-Fluoro-2-methylphenoxymethyl)-7-[2-methoxy-4-(2-methylpyridin-3-ylcarbonyloxy)phenyl]-1,3,3-trimethyl-3,4-dihydro-1H-quinoxalin-2-one 7-[4-(2-Acetoxybenzoyloxy)-2-methoxyphenyl]-8-(5-fluoro-2-methylphenoxymethyl)-1,3,3-trimethyl-3,4-dihydro-1H-quinoxalin-2-one 8-(5-Fluoro-2-methylphenoxymethyl)-7-[2-methoxy-4-(2-methylthiobenzoyloxy)phenyl]-1,3,3-trimethyl-3,4-dihydro-1H-quinoxalin-2-one 8-(5-Fluoro-2-methylphenoxymethyl)-7-[2-methoxy-4-(6-methylpyridin-3-ylcarbonyloxy)phenyl]-1,3,3-trimethyl-3,4-dihydro-1H-quinoxalin-2-one 8-(5-Fluoro-2-methylphenoxymethyl)-7-[2-methoxy-4-(oxazol-4-ylcarbonyloxy)phenyl]-1,3,3-trimethyl-3,4-dihydro-1H-quinoxalin-2-one 7-[4-(3-Acetylbenzoyloxy)-2-methoxyphenyl]-8-(5-fluoro-2-methylphenoxymethyl)-1,3,3-trimethyl-3,4-dihydro-1H-quinoxalin-2-one 7-[4-(3-Chlorothiophen-2-ylcarbonyloxy)-2-methoxyphenyl]-8-(5-fluoro-2-methylphenoxymethyl)-1,3,3-trimethyl-3,4-dihydro-1H-quinoxalin-2-one 8-(5-Fluoro-2-methylphenoxymethyl)-7-[2-methoxy-4-(2-methoxypyridin-3-ylcarbonyloxy)phenyl]-1,3,3-trimethyl-3,4-dihydro-1H-quinoxalin-2-one 7-[2-Methoxy-4-(2-methylthiobenzoyloxy)phenyl]-8-(5-methylthiophen-2-ylcarbonyloxymethyl)-1,3,3-trimethyl-3,4-dihydro-1H-quinoxalin-2-one 7-[4-(N-Acetyl-N-methylamino)-2-methoxyphenyl]-8-(5-fluoro-2-methylphenoxymethyl)-1,3,3-trimethyl-3,4-dihydro-1H-quinoxalin-2-one 8-(5-Fluoro-2-methylphenoxymethyl)-7-[2-methoxy-4-(pyridin-3-ylaminocarbonyloxy)phenyl]-1,3,3-trimethyl-3,4-dihydro-1H-quinoxalin-2-one 7-(2-Methoxy-4-phenylaminocarbonyloxyphenyl)-8-(5-methylthiophen-2-ylcarbonyloxymethyl)-1,3,3-trimethyl-3,4-dihydro-1H-quinoxalin-2-one 8-(5-Fluoro-2-methylphenoxymethyl)-7-[2-methoxy-4-(morpholin-4-ylcarbonyloxy)phenyl]-1,3,3-trimethyl-3,4-dihydro-1H-quinoxalin-2-one 7-(4-Dimethylaminocarbonyloxy-2-methoxyphenyl)-8-(5-fluoro-2-methylphenoxymethyl)-1,3,3-trimethyl-3,4-dihydro-1H-quinoxalin-2-one 7-(4-Hydroxy-2-methoxyphenyl)-8-(2-methoxyphenylaminomethyl)-1,3,3-trimethyl-3,4-dihydro-1H-quinoxalin-2-one 7-(4-Butyryloxy-2-methoxyphenyl)-8-(2-methoxyphenylaminomethyl)-1,3,3-trimethyl-3,4-dihydro-1H-quinoxalin-2-one 7-[2-Methoxy-4-(2-methylpyridin-3-ylcarbonyloxy)phenyl]-8-(2-methoxyphenylaminomethyl)-1,3,3-trimethyl-3,4-dihydro-1H-quinoxalin-2-one 8-(2-Methoxyphenylaminomethyl)-7-[2-methoxy-4-(thiazol-4-ylcarbonyloxy)phenyl]-1,3,3-trimethyl-3,4-dihydro-1H-quinoxalin-2-one 8-[N-(5-Fluoro-2-methylphenyl)-N-(9-fluorenylmethoxycarbonyl)aminomethyl]-7-(4-hydroxy-2-methoxyphenyl)-1,3,3-trimethyl-3,4-dihydro-1H-quinoxalin-2-one 7-[2-Methoxy-4-(2-methylbenzoyloxy)phenyl]-8-(2-methoxy-5-nitrophenoxymethyl)-3,3-dimethyl-3,4-dihydro-1H-quinoxalin-2-one 8-(5-Fluoro-2-methylphenoxymethyl)-7-(2-methylphenyl)-1,3,3-trimethyl-3,4-dihydro-1H-quinoxalin-2-one 7-(4-Benzoyloxy-2-methoxyphenyl)-8-(5-fluoro-2-methylphenoxymethyl)-1,3,3-trimethyl-3,4-dihydro-1H-quinoxalin-2-one 7-(4-Benzoyloxy-2-methoxyphenyl)-8-(5-methylthiophen-2-ylcarbonyloxymethyl)-1,3,3-trimethyl-3,4-dihydro-1H-quinoxalin-2-one 7-[4-(Furan-2-ylcarbonyloxy)-2-methoxyphenyl]-8-(5-methylthiophen-2-ylcarbonyloxymethyl)-1,3,3-trimethyl-3,4-dihydro-1H-quinoxalin-2-one 7-[2-Methoxy-4-(2-methoxybenzoyloxy)phenyl]-8-(5-methylthiophen-2-ylcarbonyloxymethyl)-1,3,3-trimethyl-3,4-dihydro-1H-quinoxalin-2-one 7-[2-Methoxy-4-(3-methoxycarbonylbenzoyloxy)phenyl]-8-(5-methylthiophen-2-ylcarbonyloxymethyl)-1,3,3-trimethyl-3,4-dihydro-1H-quinoxalin-2-one 7-[2-Methoxy-4-(3-methylfuran-2-ylcarbonyloxy)phenyl]-8-(5-methylthiophen-2-ylcarbonyloxymethyl)-1,3,3-trimethyl-3,4-dihydro-1H-quinoxalin-2-one 7-[4-(3-Benzylureido)-2-methoxyphenyl]-8-(5-fluoro-2-methylphenoxymethyl)-1,3,3-trimethyl-3,4-dihydro-1H-quinoxalin-2-one 8-(5-Fluoro-2-methylphenoxymethyl)-7-[2-methoxy-4-(3-phenylureido)phenyl]-1,3,3-trimethyl-3,4-dihydro-1H-quinoxalin-2-one 8-(2-Methoxyphenylaminomethyl)-7-[2-methoxy-4-(pyridine-3-ylcarbonyloxy)phenyl]-1,3,3-trimethyl-3,4-dihydro-1H-quinoxalin-2-one 7-[2-Methoxy-4-(2-methoxybenzoyloxy)phenyl]-8-(2-methoxyphenylaminomethyl)-1,3,3-trimethyl-3,4-dihydro-1H-quinoxalin-2-one 8-(2-Methoxyphenylaminomethyl)-7-[2-methoxy-4-(thiophen-3-ylcarbonyloxy)phenyl]-1,3,3-trimethyl-3,4-dihydro-1H-quinoxalin-2-one, and 7-[2-Methoxy-4-(2-methylbenzoyloxy)phenyl]-8-(2-methoxyphenylaminomethyl)-1,3,3-trimethyl-3,4-dihydro-1H-quinoxalin-2-one The present compound can be synthesized according to the following procedures. The individual concrete preparation procedures are explained in details in the following examples, [preparation examples]. These examples are intended to make the present invention more clearly understandable, and do not limit the scope of the present invention. The Hal shown in the following synthetic routes represents a halogen atom, MOM represents methoxymethyl group and Fmoc represents 9-fluorenylmethoxycarbonyl group.

The present compound (I)-(a) (the compound that A is methylene group, X is O in the general formula (1)) can be synthesized according to the synthetic route 1. Namely, the compound (I)-(a) can be given by the reaction of the present compound (I)-(b) (the compound that A is methylene group, X is O, $R^6$ is H in the general formula (1)) with a corresponding halide (II) in an organic solvent such as N,N-dimethylformamide (hereinafter referred to as DMF), tetrahydrofuran (hereinafter referred to as THF), 1,4-dioxane, methylene dichloride in the presence of a base such as cesium carbonate, potassium carbonate at 0° C. to 50° C. for 1 hour to 24 hours.

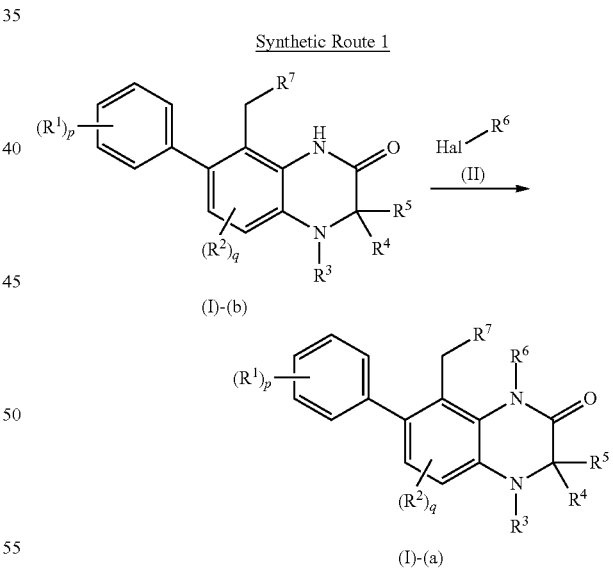

Synthetic Route 1

The present compound (I)-(b) (the compound that A is methylene group, X is O, $R^6$ is H, $R^7$ is $OR^8$, $NR^8R^9$ or $SR^8$ in the general formula (1)) can be synthesized according to the synthetic route 2. Namely, the compound (I)-(b) can be given by the reaction of the compound (III) with a corresponding alcohol, carboxylic acid, phenol, amine, thiol, thiophenol and the like (IV) in an organic solvent such as DMF, THF, ethanol in the presence of a base such as potassium carbonate, sodium hydride at 0° C. to 100° C. for 1 hour to 48 hours.

Synthetic Route 2

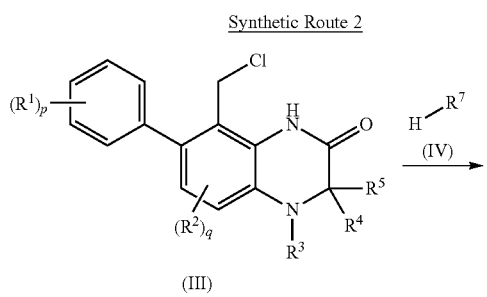

The present compound (I)-(c) (the compound that A is methylene group, X is O, $R^7$ is $OR^8$ in the general formula (1)) can be synthesized according to the synthetic route 3. Namely, the compound (I)-(c) can be given by the reaction of the compound (V) with a corresponding halide (VI) in an organic solvent such as DMF, THF, methylene dichloride in the presence of a base such as triethylamine, potassium carbonate at 0° C. to 50° C. for 1 hour to 48 hours.

Synthetic Route 3

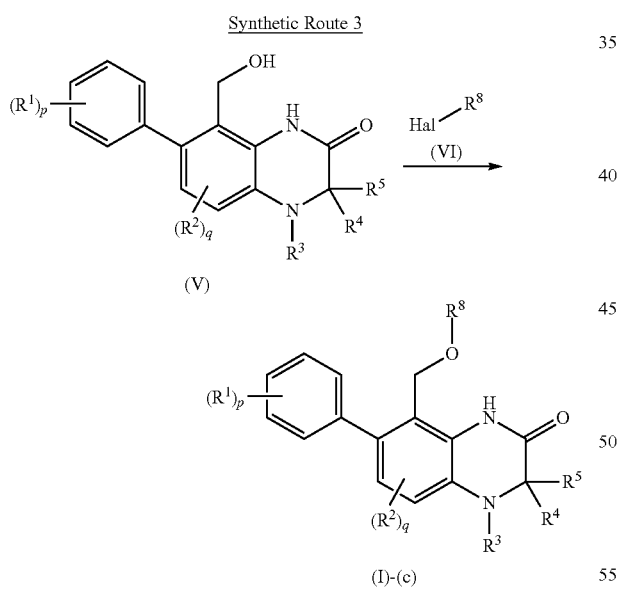

The compound (III) and (V) can be synthesized according to the synthetic route 4. Namely, the compound (IX) can be given by the reaction of the compound (VII) with a corresponding boronic acid or its ester (VIII) in a solvent such as DMF, 1,4-dioxane, ethanol, toluene, water and in the presence of a base such as cesium carbonate, sodium carbonate, sodium hydrogen carbonate, tripotassium phosphate and a catalyst such, as bis(triphenylphosphine)palladium (II) dichloride, tetrakis(triphenylphosphine)palladium (0) at 50° C. to 120° C. for 1 hour to 48 hours. The compound (V) can be given by the treatment of the compound (IX) in an organic solvent such as diethylether, THF in the presence of a reductive agent such as lithium aluminium hydride at −30° C. to room temperature for 1 hour to 24 hours. The compound (III) can be given by the treatment of the compound (V) with methanesulfonyl chloride in an organic solvent such as methylene dichloride, THF in the presence of base such as triethylamine, diisopropylethylamine (hereinafter referred to as DIEA) at 0° C. to room temperature for 30 minutes to 12 hours.

Synthetic Route 4

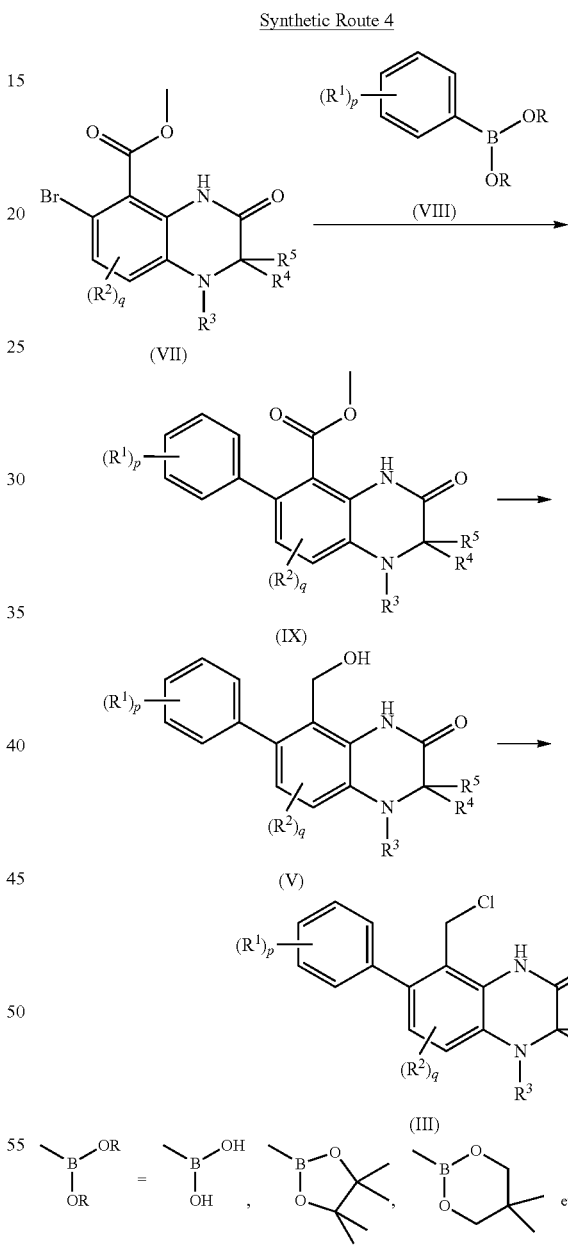

The compound (VII) can be synthesized according to the synthetic route 5. Namely, the compound (XI) can be given by the treatment of the compound (X) in an organic solvent such as methanol, ethanol, DMF in the presence of a reductive agent such as tin(II) chloride, ferric(II) chloride at 50° C. to 120° C. for 1 hour to 12 hours. The compound (XII) can be given by the treatment of the compound (XI) with an acetylation agent such as acetyl chloride, acetic anhydride in an, organic solvent such as methylene dichloride, THF in the presence of a base such as triethylamine, DIEA at 0° C. to 50° C. for 1 hour to 12 hours. The compound (XIII) can be given by the treatment of the compound (XII) with nitric acid in a solvent such as water in the presence of an acid such as sulfuric acid at −20° C. to room temperature for 30 minutes to 12 hours. The compound (XIV) can be given by the treatment of the compound (XIII) in an organic solvent such as methanol in the presence of an acid such as boron trifluoride ether complex at 50° C. to the temperature under reflux for 1 hour to 12 hours. The compound (XVI) can be given by the reaction of the compound (XIV) with a corresponding halide (XV) in the presence of a base such as cesium carbonate, potassium carbonate at 50° C. to 120° C. for 1 hour to 120 hours. The compound (VII) can be given by the treatment of the compound (XVI) in an organic solvent such as methanol, ethanol, DMF in the presence of reductive agent such as tin(II) chloride, ferric(II) chloride at 50° C. to 120° C. for 1 hour to 12 hours.

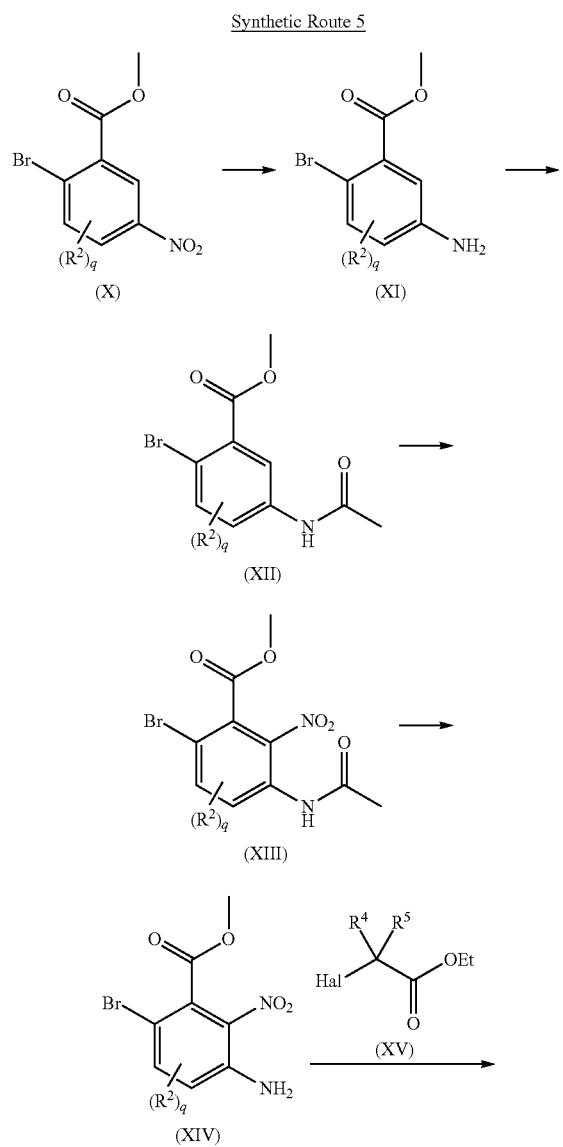

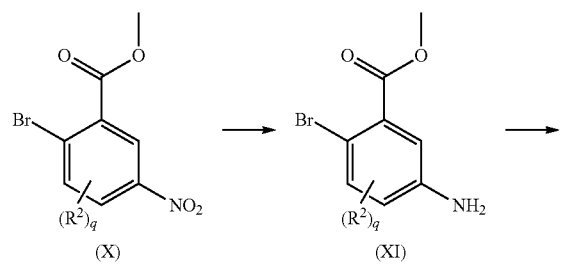

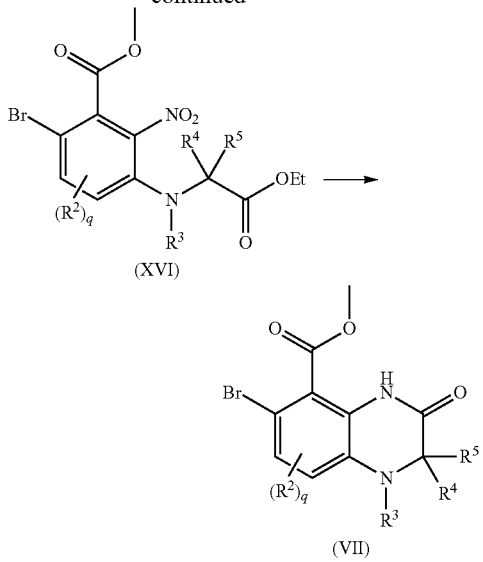

The present compound (I)-(a) (the compound that A is methylene group, X is O in the general formula (1)) can be also synthesized according to the synthetic route 6. Namely, the compound (I)-(a) can be given by the reaction of the compound (XVII) with a corresponding boronic acid or its ester (VIII) in a solvent such as DMF, 1,4-dioxane, ethanol, toluene, water and in the presence of a base such as cesium carbonate, sodium carbonate, sodium hydrogen carbonate, tripotassium phosphate and a catalyst such as bis(triphenylphosphine)palladium(II)dichloride, tetrakis(triphenylphosphine)palladium (0) at 50° C. to 120° C. for 1 hour to 48 hours.

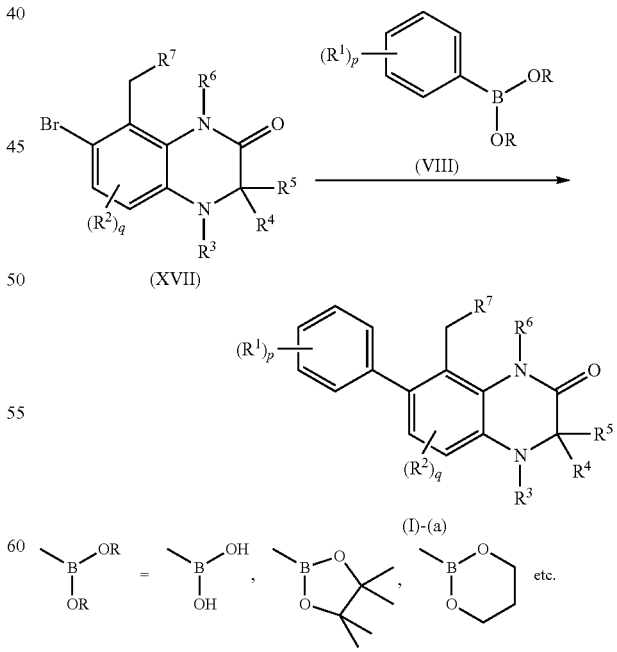

Moreover, the present compound (I)-(a) (the compound that A is methylene group, X is O in the general formula (1))

can be also synthesized according to the synthetic route 7. Namely, the compound (I)-(a) can be given by the reaction of the compound (XVIII) with a corresponding halide (XIX) in a solvent such as DMF, 1,4-dioxane, ethanol, toluene, water and in the presence of a base such as cesium carbonate, sodium carbonate, sodium hydrogen carbonate, tripotassium phosphate and a catalyst such as bis(triphenylphosphine)palladium(II)dichloride, tetrakis(triphenylphosphine)palladium (0) at 50° C. to 120° C. for 1 hour to 48 hours.

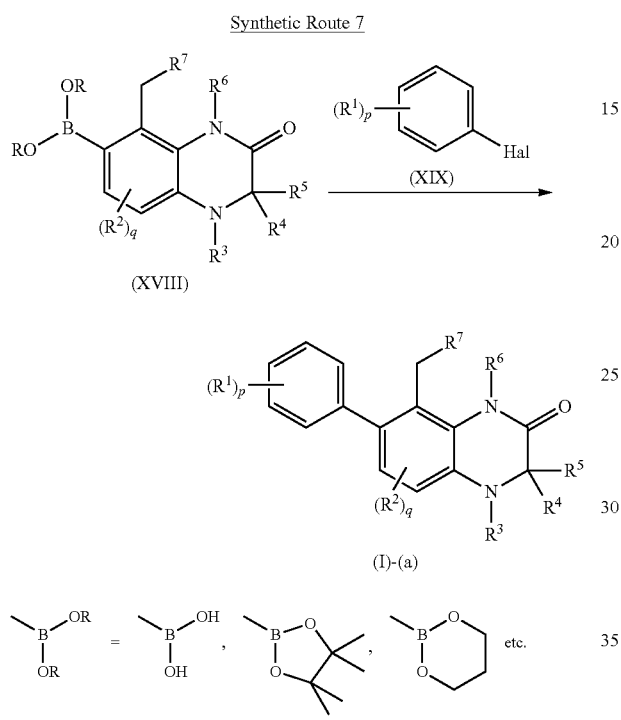

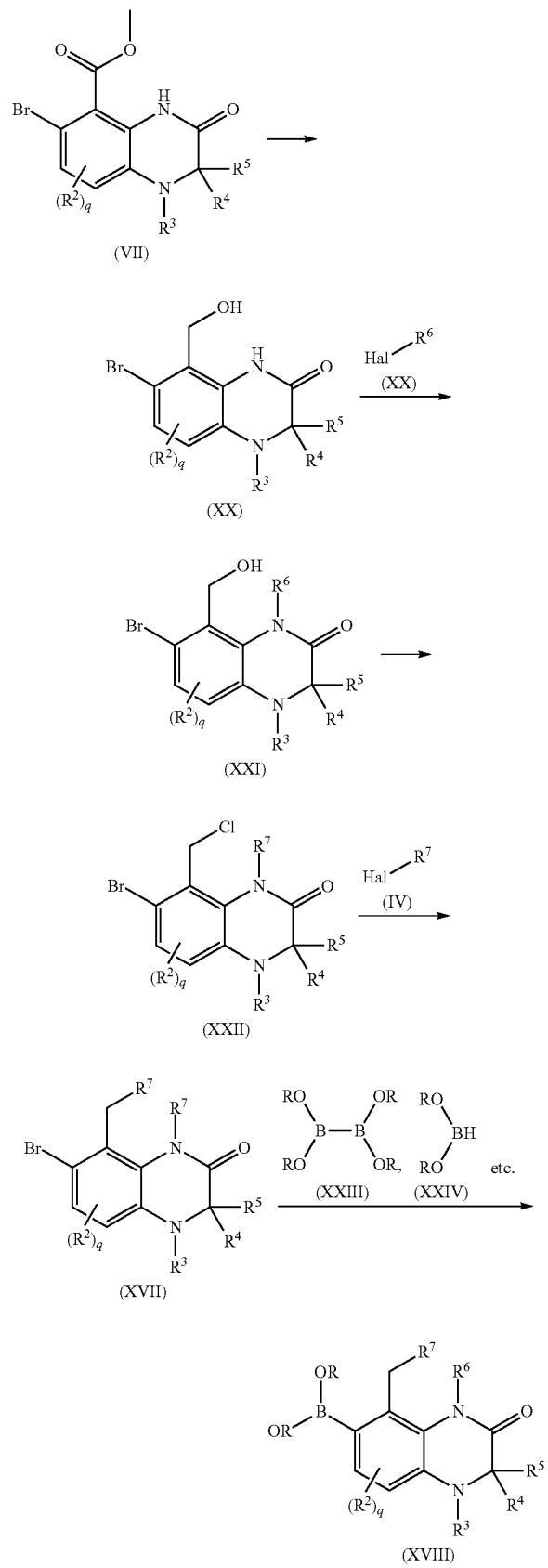

The compound (XVII) and (XVIII) can be synthesized according to the synthetic route 8. Namely, the compound (XX) can be given by the treatment of the compound (VII) in an organic solvent such as diethylether, THF in the presence of a reductive agent such as lithium aluminium hydride at 0° C. to 50° C. for 1 hour to 24 hours. The compound (XXI) can be given by the reaction of the compound (XX) with a corresponding halide (II) in an organic solvent such as DMF, THF, 1,4-dioxane, methylene dichloride in the presence of a base such as cesium carbonate, potassium carbonate at 0° C. to 50° C. for 1 hour to 24 hours. The compound (XXII) can be given by the treatment of the compound (XXI) with methanesulfonyl chloride in an organic solvent such as methylene dichloride, THF in the presence of base such as triethylamine, DIEA at 0° C. to room temperature for 30 minutes to 12 hours. The compound (XVII) can be given by the reaction of the compound (XXII) with a corresponding alcohol, carboxylic acid, phenol, amine, thiol, thiophenol (IV) in an organic solvent such as DMF, THF, ethanol in the presence of a base such as potassium carbonate, sodium hydride at 0° C. to 100° C. for 1 hour to 48 hours. The compound (XVIII) can be given by the reaction of the compound (XVII) with a corresponding diboron (XXIII) or borane (XXIV) in a solvent such as dimethylsulfoxide, DMF, 1,4-dioxane in the presence of a base such as potassium acetate, triethylamine and a catalyst such as [1,1'-bis(diphenylphosphino)ferrocene]palladium(II)dichloride, bis(triphenylphosphine)-palladium(II)dichloride at 50° C. to 120° C. for 10 minutes to 48 hours.

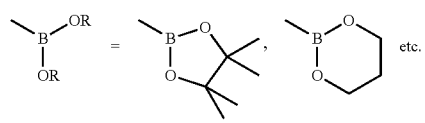

The present compound (I)-(d) (the compound that A is methylene group, X is O, one of $R^1$ is $OR^{10}$, $R^{10}$ is a lower alkyl group which may have at least a substituent, a lower alkylcarbonyl group which may have at least a substituent, an arylcarbonyl group which may have at least a substituent, a heterocyclic carbonyl group which may have at least a substituent, a lower alkoxycarbonyl group which may have at least a substituent or an aryloxycarbonyl group which may have at least a substituent, and the like in the general formula (1)) can be synthesized according to the synthetic route 9. Namely, the compound (I)-(d) can be given by the reaction of the present compound (I)-(e) (the compound that A is methylene group, X is O, one of $R^1$ is OH in the general formula (1)) with a corresponding halide (XXV) in an organic solvent such as THF, methylene dichloride, DMF in the presence of a base such as triethylamine, DIEA, potassium carbonate at 0° C. to 100° C. for 1 hour to 24 hours.

Synthetic Route 9

(I)-(e)

(I)-(d)

The present compound (I)-(f) (the compound that A is methylene group, X is O, one of the $R^1$ is $OCOR^{11}$, $R^{11}$ is a lower alkyl group which may have at least a substituent, an aryl group which may have at least a substituent or a heterocyclic group which may have at least a substituent, and the like in the general formula (1)) can be synthesized according to the synthetic route 10. Namely, the compound (I)-(f) can be given by the reaction of the present compound (I)-(e) (the compound that A is methylene group, X is O, one of $R^1$ is OH in the general formula (1)) with a corresponding carboxylic acid (XXVI) in an organic solvent such as DMF, methylene dichloride in the presence of a condensation agent such as N,N'-dicyclohexylcarbodiimide (hereinafter referred to as DCC), O-(7-azabenzotriazol-1-yl)-N,N,N,N-tetramethyluroniumhexafluorophosphate (hereinafter referred to as HATU) and a base such as DIEA at room temperature to 50° C. for 1 hour to 3 days.

Synthetic Route 10

(I)-(e)

(XXVI)

(I)-(f)

The present compound (I)-(g) (the compound that A is methylene group, X is O, one of the $R^1$ is $OCONR^{12}R^{13}$, $R^{12}$ and $R^{13}$ may be the same or different and are a lower alkyl group which may have at least a substituent, an aryl group which may have at least a substituent, and the like in the general formula (1)) can be synthesized according to the synthetic route 11. Namely, the compound (I)-(g) can be given by the reaction of the present compound (I)-(e) (the compound that A is methylene group, X is O, one of the $R^1$ is OH in the general formula (1)) with 1,1'-carbonyldiimidazole (hereinafter referred to as CDI) in an organic solvent such as methylene dichloride, THF at room temperature to 50° C. for 30 minutes to 12 hours followed by the reaction with a corresponding amine (XXVII).

Synthetic Route 11

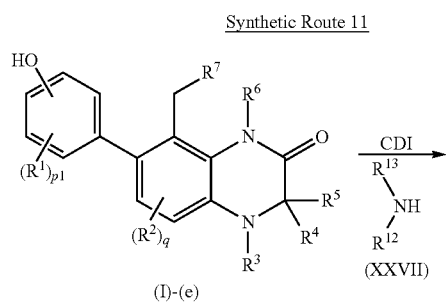

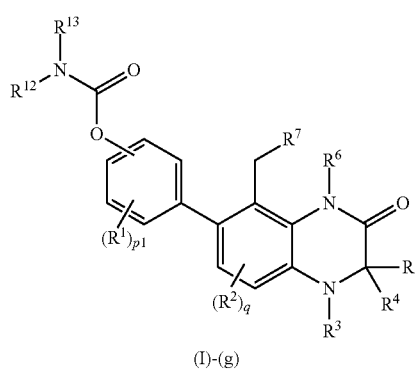

The present compound (I)-(e) (the compound that A is methylene group, X is O, one of the $R^1$ is OH in the general formula (1)) can be synthesized according to the synthetic route 12. Namely, the present compound (I)-(h) can be given by the reaction of the compound (XVII) with a corresponding boronic acid or its ester (XXVIII) in a solvent such as DMF, 1,4-dioxane, ethanol, toluene, water in the presence of a base such as cesium carbonate, sodium carbonate, sodium hydrogen carbonate, tripotassium phosphate and a catalyst such as bis(triphenylphosphine)palladium (II)dichloride, tetrakis (triphenylphosphine)palladium (0) at 50° C. to 120° C. for 1 hour to 48 hours. The compound (I)-(e) can be given by the treatment of the compound (I)-(h) in an organic solvent such as 1,4-dioxane, methylene dichloride in the presence of an acid such as hydrogen chloride, trifluoroacetic acid at 0° C. to 50° C. for 1 hour to 24 hours.

Synthetic Route 12

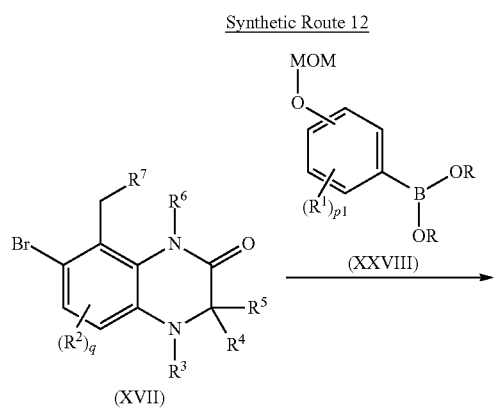

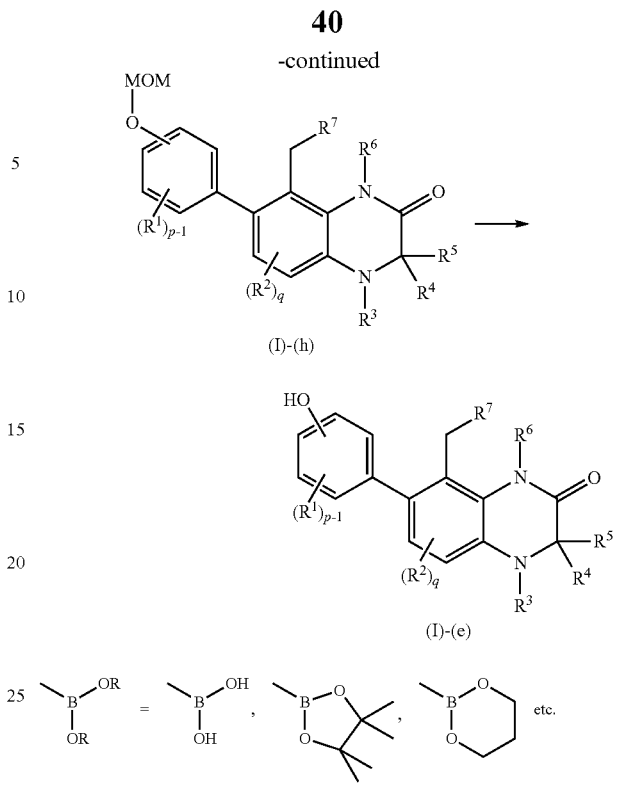

Further, the present compound (I)-(e) (the compound that A is methylene group, X is O, one of the $R^1$ is OH in the general formula (1)) can be also synthesized according to the synthetic route 13. Namely, the compound (XXIX) can be given by the reaction of the compound (VII) with a corresponding boronic acid or its ester (XXVIII) in a solvent such as DMF, 1,4-dioxane, ethanol, toluene, water in the presence of a base such as cesium carbonate, sodium carbonate, sodium hydrogen carbonate, tripotassium phosphate and a catalyst such as bis(triphenylphosphine)palladium(II)dichloride, tetrakis(triphenylphosphine)palladium (0) at 50° C. to 120° C. for 1 hour to 48 hours. The compound (XXX) can be given by the treatment of the compound (XXIX) in an organic solvent such as diethylether, THF in the presence of a reductive agent such as lithium aluminium hydride at −30° C. to room temperature for 1 hour to 24 hours. The compound (XXXI) can be given by the treatment of the compound (XXX) with methanesulfonyl chloride in an organic solvent such as methylene dichloride, THF in the presence of a base such as triethylamine, DIEA at 0° C. to room temperature for 30 minutes to 12 hours. The present compound (I)-(i) can be given by the reaction of the compound (XXXI) with a corresponding alcohol, carboxylic acid, phenol, amine, thiol, thiophenol and the like (IV) in an organic solvent such as DMF, THF, ethanol in the presence of a base such as potassium carbonate, sodium hydride at 0° C. to 100° C. for 1 hour to 48 hours. The present compound (I)-(h) can be given by the reaction of the compound (I)-(i) with a corresponding halide (II) in an organic solvent such as DMF, THF, 1,4-dioxane, methylene dichloride in the presence of a base such as cesium carbonate, potassium carbonate at 0° C. to 50° C. for 1 hour to 24 hours. The compound (I)-(e) can be given by the treatment of the compound (I)-(h) in an organic solvent such as 1,4-dioxane, methylene dichloride in the presence of an acid such as hydrogen chloride, trifluoroacetic acid at 0° C. to 50° C. for 1 hour to 24 hours.

Synthetic Route 13

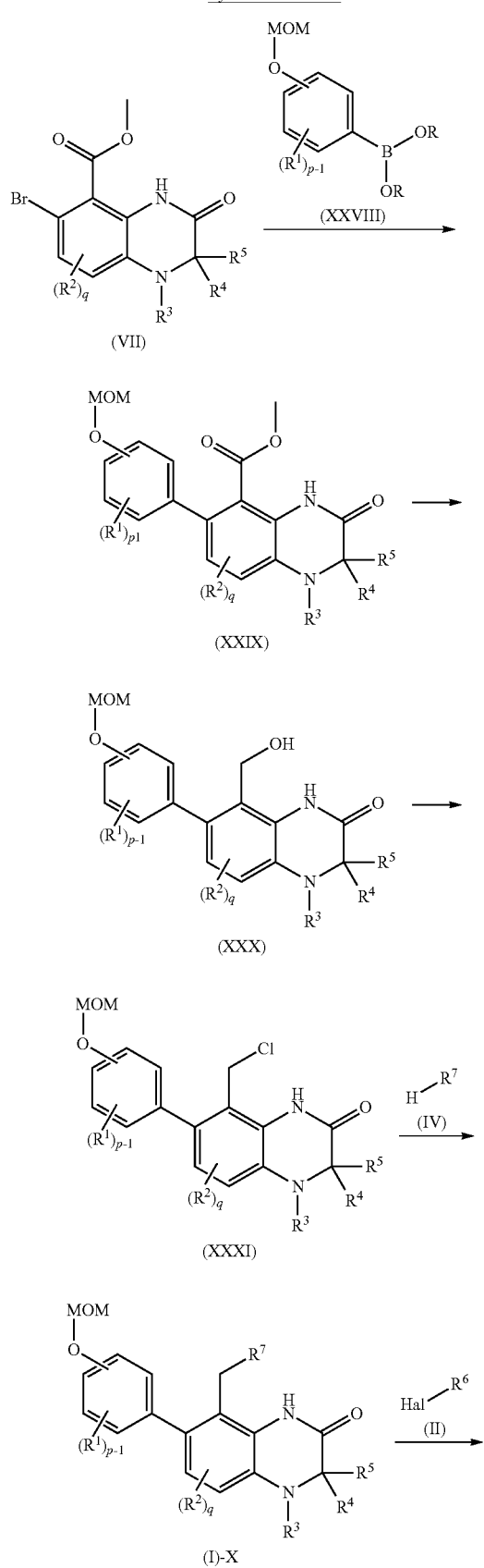

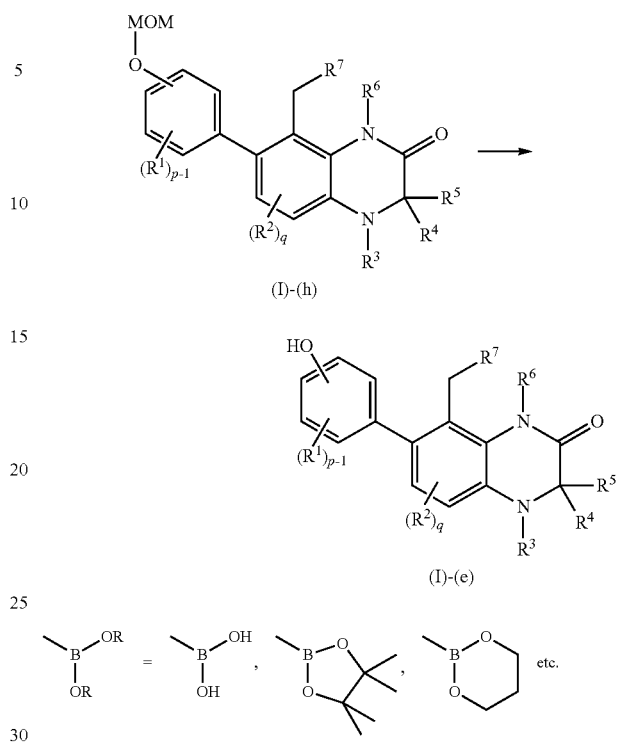

The present compound (I)-(j) (the compound that A is methylene group, X is O, one of the $R^1$ is $OR^{10}$, $R^7$ is $NHR^8$, $R^{10}$ is a lower alkyl group which may have at least a substituent, a lower alkylcarbonyl group which may have at least a substituent, an arylcarbonyl group which may have at least substituent, a heterocyclic carbonyl group which may have at least a substituent, a lower alkoxycarbonyl group which may have at least a substituent, an aryloxycarbonyl group which may have at least a substituent, and the like in the general formula (1)), the present compound (I)-(k) (the compound that A is methylene group, X is O, one of the $R^1$ is $OCOR^{11}$, $R^7$ is $NHR^8$, $R^{11}$ is a lower alkyl group which may have at least a substituent, an aryl group which may have at least a substituent, a heterocyclic group which may have at least a substituent, and the like in the general formula (1)) and the present compound (I)-(l) (the compound that A is methylene group, X is O, one of the $R^1$ is $OCONR^{12}R^{13}$, $R^7$ is $NHR^8$, $R^{12}$ and $R^{13}$ may be the same or different and are a lower alkyl group which may have at least a substituent, an aryl group which may have at least a substituent, and the like in the general formula (1)) can be synthesized according to the synthetic route 14. Namely, the compound (I)-(j), (I)-(k) and (I)-(l) can be given by the reaction of the present compound (I)-(m) (the compound that A is methylene group, X is O, one of the $R^1$ is OH, $R^7$ is $NR^8$(Fmoc) in the general formula (1)) with a corresponding halide (XXV), a carboxylic acid (XXVI) or an amine (XXVII) according to the method of synthetic route 9, 10 or 11 respectively, followed by the treatment in an organic solvent such as DMF, methylene dichloride in the presence of a base such as piperidine at 0° C. to 50° C. for 5 minutes to 24 hours.

Synthetic Route 14

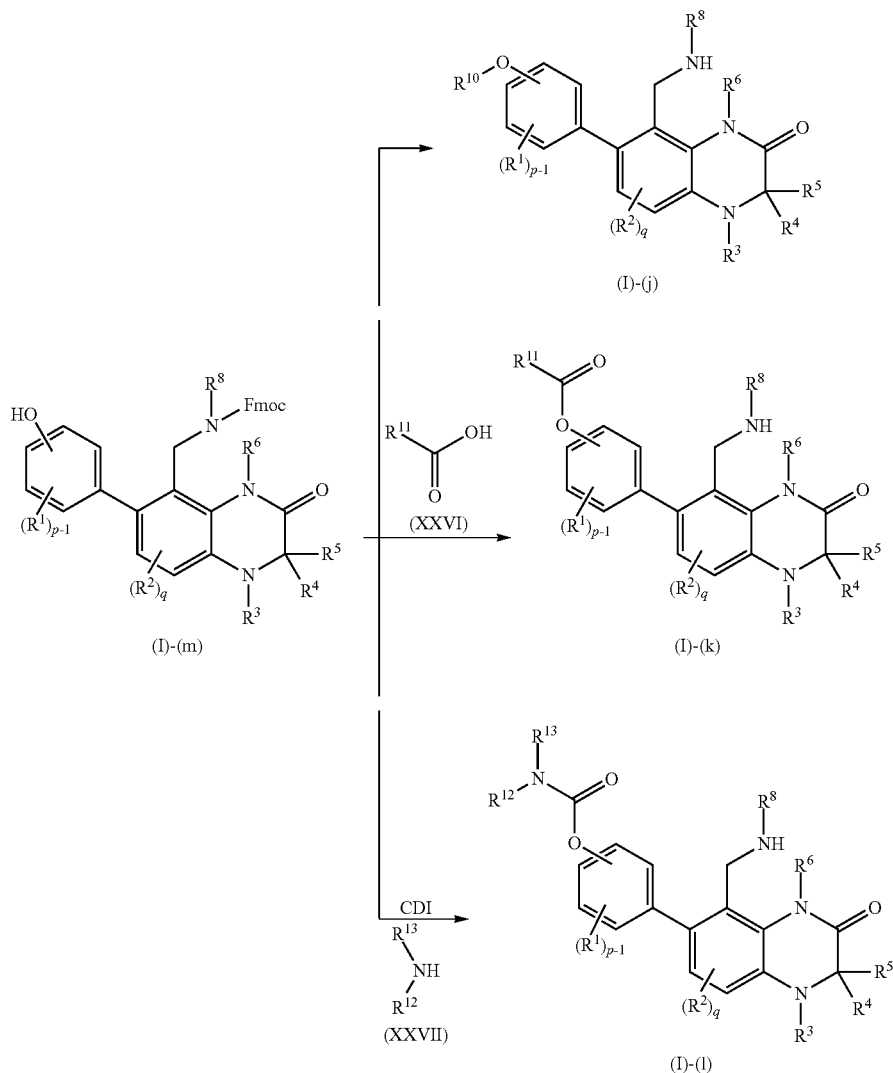

The present compound (I)-(m) (the compound that A is methylene group, X is O, one of the $R^1$ is OH, $R^7$ is $NR^8$ (Fmoc) in the general formula (1)) can be synthesized according to the synthetic route 15. Namely, the compound (XXXIII) can be given by the reaction of the compound (XXII) with a corresponding amine (XXXII) in an organic solvent such as DMF, THF, ethanol in the presence of a base such as potassium carbonate, sodium hydride at 0° C. to 100° C. for 1 hour to 48 hours. The present compound (I)-(o) can be given by the reaction of the compound (XXXIII) with a corresponding boronic acid or its ester (XXVIII) in a solvent such as DMF, 1,4-dioxane, ethanol, toluene, water in the presence of a base such as cesium carbonate, sodium carbonate, sodium hydrogen carbonate, tripotassium phosphate and a catalyst such as bis(triphenylphosphine)palladium(II) dichloride, tetrakis(triphenylphosphine)palladium (0) at 50° C. to 120° C. for 1 hour to 48 hours. The present compound (I)-(n) can be given by the reaction of the compound (I)-(o) with 9-fluorenylmethoxycarbonyl chloride in a solvent such as 1,4-dioxane, water in the presence of a base such as sodium hydrogen carbonate at 0° C. to 50° C. for 1 hour to 24 hours. The compound (I)-(m) can be given by the treatment of the compound (I)-(n) in an organic solvent such as 1,4-dioxane, methylene dichloride in the presence of an acid such as hydrogen chloride, trifluoroacetic acid at 0° C. to 50° C. for 1 hour to 24 hours.

Synthetic Route 15

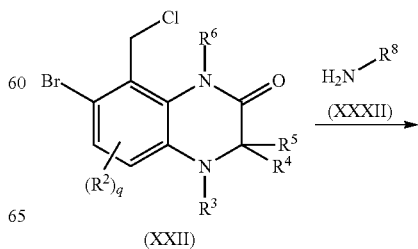

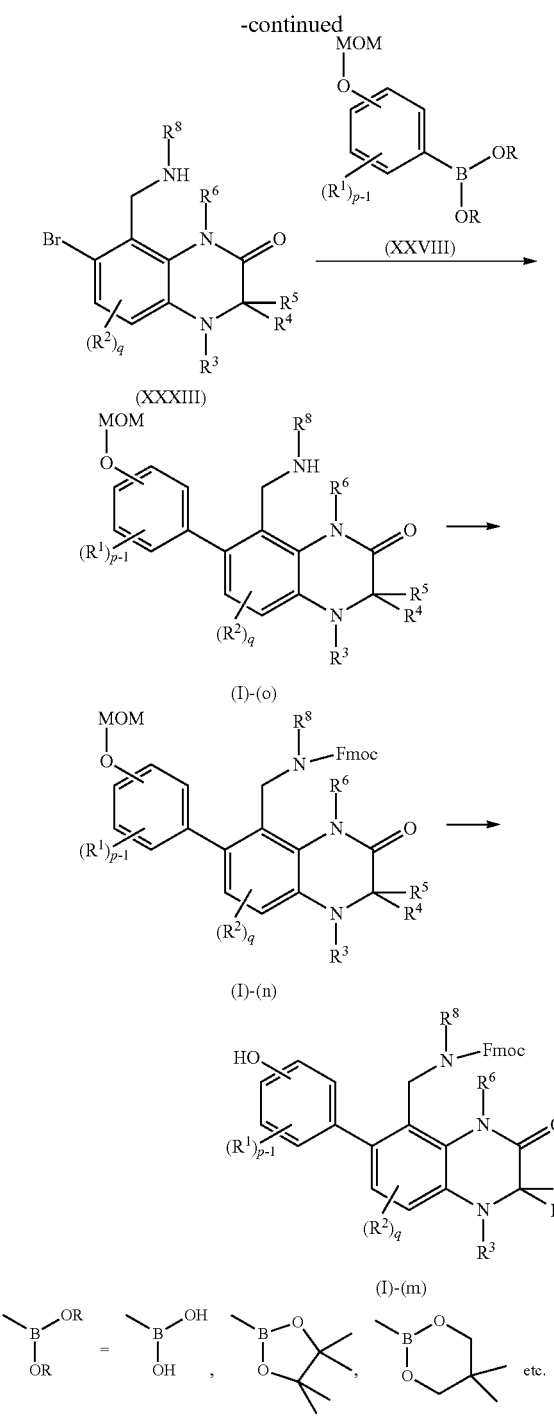

(XXXIII)

(I)-(o)

(I)-(n)

(I)-(m)

The present compound (I)-(p) (the compound that A is methylene group, X is O, one of the $R^1$ is $OR^{10}$, $R^7$ is $OR^8$, $R^{10}$ is a lower alkyl group which may have at least a substituent, a lower alkylcarbonyl group which may have at least a substituent, an arylcarbonyl group which may have at least a substituent, a heterocyclic carbonyl group which may have at least a substituent, a lower alkoxycarbonyl group which may have at least a substituent, an aryloxycarbonyl group which may have at least a substituent, and the like in the general formula (1)) can be synthesized according to the synthetic route 16. Namely, the compound (XXXIV) can be given by the treatment of the compound (XXX) in an organic solvent such as 1,4-dioxane, methylene dichloride in the presence of an acid such as hydrogen chloride, trifluoroacetic acid at 0° C. to 50° C. for 1 hour to 24 hours. The compound (XXXV) can be given by the reaction of the compound (XXXIV) with a corresponding halide (XXV) in an organic solvent such as THF, methylene dichloride, DMF in the presence of a base such as triethylamine, DIEA, potassium carbonate at 0° C. to 100° C. for 1 hour to 24 hours. The compound (I)-(q) can be given by the reaction of the compound (XXXV) with a corresponding halide (VI) in an organic solvent such as DMF, THF, methylene dichloride in the presence of a base such as triethylamine, potassium carbonate at 0° C. to 50° C. for 1 hour to 48 hours. The compound (I)-(p) can be given by the reaction of the compound (I)-(q) with a corresponding halide (II) in an organic solvent such as DMF, THF, 1,4-dioxane, methylene dichloride in the presence of a base such as cesium carbonate, potassium carbonate at 0° C. to 50° C. for 1 hour to 24 hours.

Synthetic Route 16

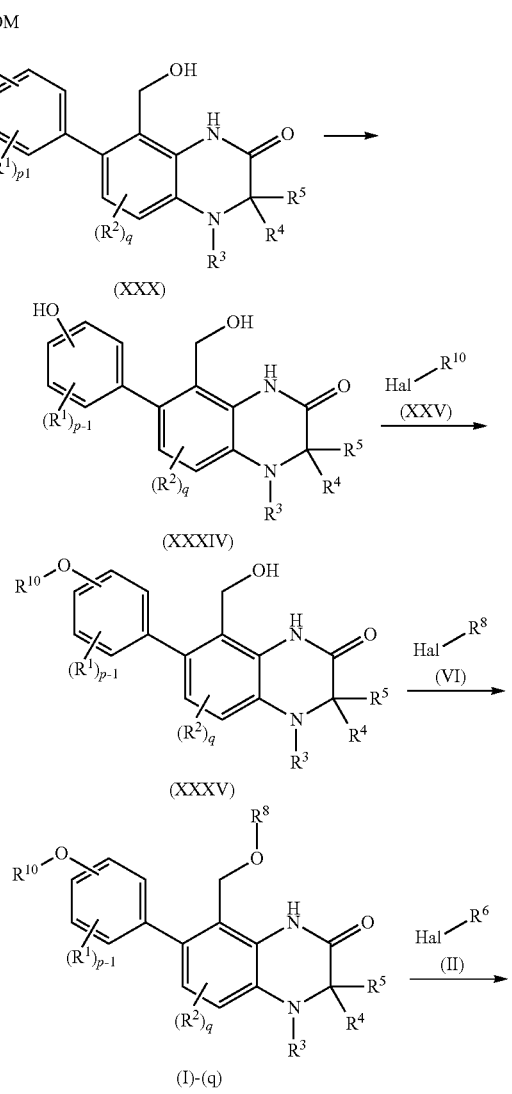

-continued

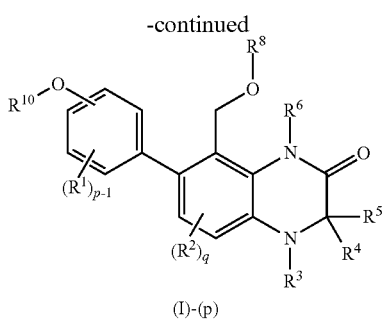

(I)-(p)

The present invention also relates to a method of preventing or treating a glucocorticoid receptor-related disease, for example, metabolic disorders such as diabetes and obesity, inflammatory diseases such as arthritis, enteritis and chronic obstructive pulmonary diseases, autoimmune diseases such as connective tissue diseases, allergic diseases such as asthma, atopic dermatitis, allergic rhinitis and conjunctivitis, central nervous system diseases such as psychiatric disorders, Alzheimer's disease and drug use disorders, cardiovascular diseases such as hypertension, hypercalcemia, hyperinsulinemia and hyperlipidemia, homeostasis-related diseases causing an abnormality of neuro-immune-endocrine balance, glaucoma, comprising administering to a patient a therapeutically effective amount of the present compound or a salt thereof.

In order to find the usefulness of the present compound as a pharmaceutical, by using glucocorticoid receptor competitor assay kit, a glucocorticoid receptor competitor assay was carried out by fluorescence polarization method. As a result, the present compound showed an excellent glucocorticoid receptor binding activity. Incidentally, the glucocorticoid receptor is associated with the occurrence of various diseases as described above, therefore, the present compound having an excellent binding activity to the glucocorticoid receptor is useful as a glucocorticoid receptor modulator.

A detailed explanation of this matter will be described in the section of "Pharmacological Test" in Examples described below.

The present compound can be administered either orally or parenterally. Examples of the dosage form include a tablet, a capsule, a granule, a powder, an injection, an eye drop and the like. Such preparation can be prepared using a commonly used technique.

For example, an oral preparation such as a tablet, a capsule, a granule or a powder can be prepared by optionally adding a necessary amount of an excipient such as lactose, mannitol, starch, crystalline cellulose, light silicic anhydride, calcium carbonate or calcium hydrogen phosphate; a lubricant such as stearic acid, magnesium stearate or talc; a binder such as starch, hydroxypropyl cellulose, hydroxypropylmethyl cellulose or polyvinylpyrrolidone; a disintegrant such as carboxymethyl cellulose, low-substituted hydroxypropylmethyl cellulose or calcium citrate; a coating agent such as hydroxypropylmethyl cellulose, macrogol or a silicone resin; a stabilizer such as ethyl p-hydroxybenzoate or benzyl alcohol; a corrigent such as a sweetener, a sour agent or a flavor, or the like.

A parenteral preparation such as an injection or an eye drop can be prepared by optionally adding a necessary amount of a tonicity agent such as sodium chloride, concentrated glycerin, propylene glycol, polyethylene glycol, potassium chloride, sorbitol or mannitol; a buffer such as sodium phosphate, sodium hydrogen phosphate, sodium acetate, citric acid, glacial acetic acid or trometamol; a surfactant such as polyoxyethylene sorbitan monoolate, polyoxy 40 stearate or polyoxyethylene hydrogenated castor oil 60; a stabilizer such as sodium citrate or sodium edetate; a preservative such as benzalkonium chloride, paraben, benzothonium chloride, p-hydroxybenzoate ester, sodium benzoate or chlorobutanol; a pH adjusting agent such as hydrochloric acid, citric acid, phosphoric acid, glacial acetic acid, sodium hydroxide, sodium carbonate or sodium hydrogen carbonate; a soothing agent such as benzyl alcohol, or the like.

The dose of the present compound can be appropriately selected depending on the symptoms, age, dosage form or the like. For example, in the case of an oral preparation, it can be administered in an amount of generally 0.01 to 1000 mg, preferably 1 to 100 mg per day in a single dose or several divided doses. Further, in the case of an eye drop, a preparation containing the present compound at a concentration of generally 0.0001% to 10% (w/v), preferably 0.01% to 5% (w/v) can be administered in a single dose or several divided doses.

Hereinafter, Production Examples of the present compound, Preparation Examples and results of Pharmacological Test will be described. However, these examples are described for the purpose of understanding the present invention better and are not meant to limit the scope of the present invention.

Fmoc in the chemical structure in Production Examples represents 9-fluorenylmethoxycarbonyl group.

Production Example

Reference Example 1

7-Bromo-8-methoxycarbonyl-3,3-dimethyl-3,4-dihydro-1H-quinoxalin-2-one (Reference Compound No. 1)

Methyl 5-amino-2-bromobenzoate (Reference Compound No. 1-(1))

Methyl 2-bromo-5-nitrobenzoate (25.3 g, 97.3 mmol) was dissolved in anhydrous methanol (500 mL), Tin (II) chloride (93.3 g, 487 mmol) was added thereto, and then the reaction mixture was refluxed for 2 hours. The reaction mixture was cooled down, ethyl acetate (500 mL) and water (100 mL) were added thereto, the mixture was neutralized with 4N aqueous sodium hydroxide solution, and then filtered on celite. The filtrate was concentrated under reduced pressure, ethyl acetate (200 mL) was added thereto, and then the mixture was washed with saturated aqueous sodium hydrogen carbonate solution (200 mL, 2 times), water (200 mL), and saturated brine (200 mL) successively. The organic layer was dried over anhydrous magnesium sulfate and the solvent was removed under reduced pressure to give the titled reference compound (21.0 g) as a pale yellow oil. (Yield 94%)

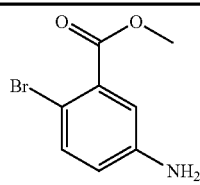

$^1$H-NMR (400 MHz, DMSO-d$_6$)
δ 3.80 (s, 3H), 5.55 (s, 2H),
6.63 (dd, J = 8.8, 2.8 Hz, 1H),
6.94 (d, J = 2.8 Hz, 1H),
7.29 (d, J = 8.8 Hz, 1H)

Methyl 5-acetylamino-2-bromobenzoate (Reference Compound No. 1-(2))

Methyl 5-amino-2-bromobenzoate (Reference Compound No. 1-(1), 21.0 g, 91.2 mmol) was dissolved in anhydrous dichloromethane (450 mL), triethylamine (19.0 mL, 137 mmol) and acetyl chloride (13.0 mL, 182 mmol) were added dropwise over 30 minutes successively, and then the mixture was stirred at 0° C. for 2 hours. The reaction mixture was washed with water (200 mL, 2 times), saturated aqueous sodium hydrogen carbonate solution (200 mL, 2 times), and saturated brine (200 mL) successively, dried over anhydrous magnesium sulfate, and then the solvent was removed under reduced pressure. The obtained residue was filtered with hexane-ethyl acetate (20:1) to give the titled reference compound (24.2 g) as a pale yellow solid. (Yield 98%)

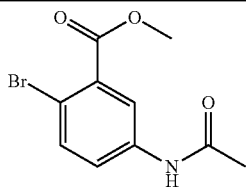

¹H-NMR (400 MHz, DMSO-d₆) δ 2.06 (s, 3H), 3.86 (s, 3H), 7.63-7.66 (m, 2H), 8.07 (s, 1H), 10.25 (s, 1H)

Methyl 3-acetylamino-6-bromo-2-nitrobenzoate (Reference Compound No. 1-(3))

To conc. sulfuric acid (150 mL), methyl 5-acetylamino-2-bromobenzoate (Reference Compound No. 1-(2), 18.5 g, 68.1 mmol) was added at 0° C. portionwise, and conc. nitric acid (150 mL) was added dropwise thereto over 1 hour. The reaction mixture was stirred for 30 minutes, poured into iced water (1 L), and then extracted with ethyl acetate (500 mL, 2 times). The organic layer was washed with water (1 L, 2 times), saturated aqueous sodium hydrogen carbonate solution (1 L), and saturated brine (1 L) successively, dried over anhydrous magnesium sulfate, and then the solvent was removed under reduced pressure. The obtained residue was purified by silica gel column chromatography (hexane-ethyl acetate) to give the titled reference compound (13.4 g) as a yellow solid. (Yield 62%)

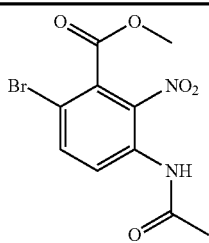

¹H-NMR (400 MHz, DMSO-d₆) δ 2.05 (s, 3H), 3.87 (s, 3H), 7.55 (d, J = 8.8 Hz, 1H), 8.02 (d, J = 8.8 Hz, 1H), 10.48 (s, 1H)

Methyl 3-amino-6-bromo-2-nitrobenzoate (Reference Compound No. 1-(4))

Methyl 3-acetylamino-6-bromo-2-nitrobenzoate (Reference Compound No. 1-(3), 13.4 g, 42.2 mmol) was dissolved in methanol (240 mL), boron trifluoride diethyl etherate complex (24.0 mL, 190 mmol) was added thereto, and then the mixture was refluxed for 2.5 hours. After the reaction mixture was neutralized with sodium hydrogen carbonate (48 g), the mixture was concentrated under reduced pressure. After ethyl acetate (500 mL) and water (700 mL) were added thereto and the mixture was partitioned, the ethyl acetate layer was washed with water (700 mL) and saturated brine (700 mL) successively, dried over anhydrous magnesium sulfate, and then the solvent was removed under reduced pressure to give the titled reference compound (11.6 g) as an orange solid. (Yield 100%)

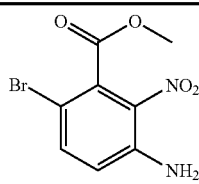

¹H-NMR (500 MHz, CDCl₃) δ 3.98 (s, 3H), 6.15 (br s, 2H), 6.78 (d, J = 9.2 Hz, 1H), 7.48 (d, J = 9.2 Hz, 1H)

Methyl 6-bromo-3-[(2-ethoxycarbonyl)propan-2-yl]amino-2-nitrobenzoate (Reference Compound No. 1-(5))

The mixture of methyl 3-amino-6-bromo-2-nitrobenzoate (Reference Compound No. 1-(4), 11.6 g, 42.0 mmol), ethyl 2-bromoisobutyrate (60.4 mL, 412 mmol), potassium iodide (7.76 g, 46.2 mmol) and cesium carbonate (56.1 g, 172 mmol) was stirred at 85° C. for 4 days. After the mixture was cooled down, ethyl acetate (500 mL) and water (500 mL) were added thereto, the mixture was partitioned, and then the water layer was extracted with ethyl acetate (300 mL). The organic layer was combined, washed with water (1 L, 2 times) and saturated brine (1 L) successively, dried over anhydrous magnesium sulfate, and then the solvent was removed under reduced pressure. The obtained residue was purified by silica gel column chromatography (hexane-ethyl acetate) to give the titled reference compound (5.08 g) as an orange oil. (Yield 31%)

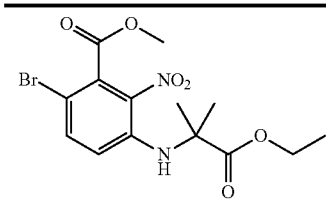

¹H-NMR (400 MHz, CDCl₃) δ 1.22 (t, J = 7.1 Hz, 3H), 1.65 (s, 6H), 3.98 (s, 3H), 4.20 (d, J = 7.1 Hz, 2H), 6.56 (d, J = 9.4 Hz, 1H), 7.49 (d, J = 9.4 Hz, 1H), 8.31 (s, 1H)

7-Bromo-8-methoxycarbonyl-3,3-dimethyl-3,4-dihydro-1H-quinoxalin-2-one (Reference Compound No. 1)

Methyl 6-bromo-3-[(2-ethoxycarbonyl)propan-2-yl]amino-2-nitrobenzoate (Reference Compound No. 1-(5), 105 mg, 0.26 mmol) was dissolved in anhydrous ethanol (4.5 mL), tin (II) chloride (247 mg, 1.30 mmol) was added thereto, and then the reaction mixture was refluxed for 5 hours. After the reaction mixture was cooled down, ethyl acetate (25 mL) was added thereto, the mixture was neutralized with aqueous sodium hydrogen carbonate solution, and then filtered on celite. After the filtrate was partitioned, the water layer was extracted with ethyl acetate (10 mL, 2 times), the combined organic layer was washed with water (50 mL, 2 times) and saturated brine (50 mL) successively, dried over anhydrous magnesium sulfate, and then the solvent was removed under reduced pressure. The obtained residue was purified by silica gel column chromatography (hexane-ethyl acetate) to give the titled reference compound (56.3 mg) as a pale yellow solid. (Yield 70%)

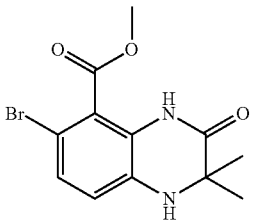 [SMILES: COC(=O)c1c(Br)ccc2c1NC(=O)C(C)(C)N2]

¹H-NMR (400 MHz, CDCl₃) δ 1.39 (s, 6H), 3.86 (s, 1H), 3.98 (s, 3H), 6.62 (d, J = 8.5 Hz, 1H), 7.13 (d, J = 8.5 Hz, 1H), 8.89 (s, 1H)

Reference Example 2

8-Methoxycarbonyl-7-(2-methoxyphenyl)-3,3-dimethyl-3,4-dihydro-1H-quinoxalin-2-one (Reference Compound No. 2-1)

A mixture of 7-bromo-8-methoxycarbonyl-3,3-dimethyl-3,4-dihydro-1H-quinoxalin-2-one (Reference Compound No. 1, 203 mg, 0.64 mmol), 2-methoxyphenylboronic acid (196 mg, 1.28 mmol), cessium carbonate (629 mg, 1.92 mmol) and bis(triphenylphosphine)palladium dichloride (II) (45.8 mg, 0.06 mmol) was suspended with anhydrous N,N-dimethylformamide (3 ml) and stirred at 80° C. for days. After the mixture was cooled down, ethyl acetate (30 mL) and water (30 mL) were added thereto and the mixture was partitioned. The organic layer was washed with water (30 mL) and saturated brine (30 mL) successively, dried over anhydrous magnesium sulfate, and then the solvent was removed under reduced pressure. The obtained residue was purified by silica gel column chromatography (hexane-ethyl acetate) to give the titled reference compound (116 mg) as a pale yellow amorphous product. (Yield 31%)

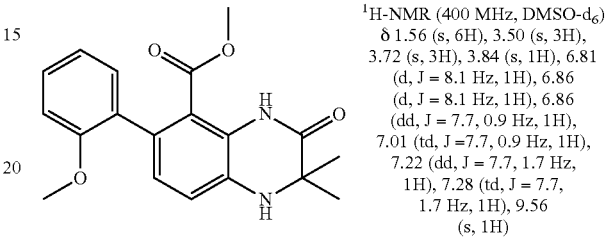

¹H-NMR (400 MHz, DMSO-d₆) δ 1.56 (s, 6H), 3.50 (s, 3H), 3.72 (s, 3H), 3.84 (s, 1H), 6.81 (d, J = 8.1 Hz, 1H), 6.86 (d, J = 8.1 Hz, 1H), 6.86 (dd, J = 7.7, 0.9 Hz, 1H), 7.01 (td, J =7.7, 0.9 Hz, 1H), 7.22 (dd, J = 7.7, 1.7 Hz, 1H), 7.28 (td, J = 7.7, 1.7 Hz, 1H), 9.56 (s, 1H)

Using any compounds among Reference Compounds No. 1, 18-3, 18-5 and available compounds, the following Reference Compounds (No. 2-2~2-5) were obtained by a method similar to that of Reference Compound No. 2-1.

7-(4-Fluoro-2-methoxyphenyl)-8-methoxycarbonyl-3,3-dimethyl-3,4-dihydro-1H-quinoxalin-2-one (Reference Compound No. 2-2)

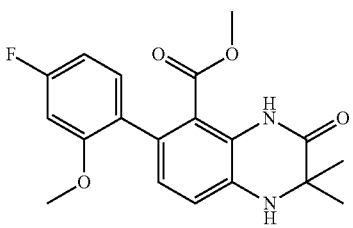 [SMILES: COC(=O)c1c(-c2ccc(F)cc2OC)ccc2c1NC(=O)C(C)(C)N2]

¹H-NMR (500 MHz, DMSO-d₆) δ 1.27 (s, 6H), 3.50 (s, 3H), 3.65 (s, 3H), 6.41 (s, 1H), 6.74 (d, J = 8.2 Hz, 1H), 6.78 (td, J = 8.5, 2.4 Hz, 1H), 6.87 (dd, J = 11.3, 2.4 Hz, 1H), 6.89 (d, J = 8.2 Hz, 1H), 7.14 (dd, J = 8.5, 7.0 Hz, 1H), 9.48 (s, 1H)

7-(5-Fluoro-2-methoxyphenyl)-8-methoxycarbonyl-3,3-dimethyl-3,4-dihydro-1H-quinoxalin-2-one (Reference Compound 2-3)

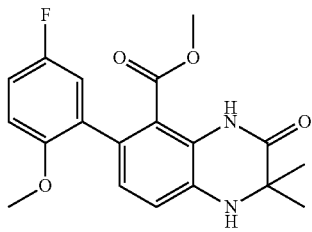 [SMILES: COC(=O)c1c(-c2cc(F)ccc2OC)ccc2c1NC(=O)C(C)(C)N2]

¹H-NMR (500 MHz, DMSO-d₆) δ 1.27 (s, 6H), 3.50 (s, 3H), 3.61 (s, 3H), 6.46 (s, 1H), 6.78 (d, J = 8.2 Hz, 1H), 6.90 (d, J = 8.2 Hz, 1H), 6.94 (dd, J = 8.8, 4.7 Hz, 1H), 7.00 (dd, J = 9.3, 3.2 Hz, 1H), 7.08 (td, J = 8.8, 3.2 Hz, 1H), 9.49 (s, 1H)

8-Methoxycarbonyl-7-(2-methoxy-4-methoxymethoxyphenyl)-3,3-dimethyl-3,4-dihydro-1H-quinoxalin-2-one (Reference Compound No. 2-4)

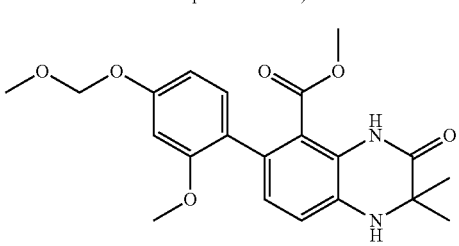

¹H-NMR (500 MHz, CDCl₃) δ 1.42 (br s, 6H), 3.52 (s, 3H), 3.54 (s, 3H), 3.70 (s, 3H), 3.81 (br s, 1H), 5.21 (s, 2H), 6.57 (d, J = 2.1 Hz, 1H), 6.69 (dd, J = 8.2, 2.1 Hz, 1H), 6.79 (d, J = 8.2 Hz, 1H), 6.82 (d, J = 8.2 Hz, 1H), 7.12 (d, J = 8.2 Hz, 1H), 9.51 (s, 1H)

| 7-(4-Benzoyloxy-2-methoxyphenyl)-8-methoxycarbonyl-3,3-dimethyl-3,4-dihydro-1H-quinoxalin-2-one (Reference Compound No. 2-5) | $^1$H-NHR (400 MHz, CDCl$_3$) δ 1.41 (br s, 3H), 1.48 (br s, 3H), 3.56 (s, 3H), 3.72 (s, 3H), 3.86 (s, 1H), 6.76 (d, J = 2.3 Hz, 1H), 6.82 (d, J = 8.2 Hz, 1H), 6.87 (d, J = 8.2 Hz, 1H), 6.89 (dd, J = 8.1, 2.3 Hz, 1H), 7.25 (d, J = 8.1 Hz, 1H), 7.52-7.56 (m, 2H), 7.66 (tt, J = 7.4, 1.4 Hz, 1H), 8.23 (dd, J = 8.2, 1.4 Hz, 2H), 9.60 (s, 1H) |
|---|---|
| 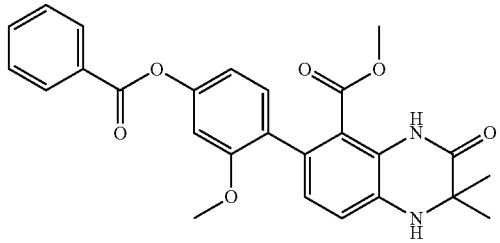 [SMILES: COC(=O)c1c(-c2ccc(OC(=O)c3ccccc3)cc2OC)ccc2c1NC(=O)C(C)(C)N2] | |

Reference Example 3

8-Hydroxymethyl-7-(2-methoxyphenyl)-3,3-dimethyl-3,4-dihydro-1H-quinoxalin-2-one (Reference Compound No. 3-1)

Lithium aluminium hydride (26.0 mg, 0.64 mmol) was suspended in anhydrous tetrahydrofuran (0.5 mL) under nitrogen atmosphere. An anhydrous tetrahydrofuran solution (1.5 mL) of 8-methoxycarbonyl-7-(2-methoxyphenyl)-3,3-dimethyl-3,4-dihydro-1H-quinoxalin-2-one (Reference Compound No. 2-1, 108 mg, 0.32 mmol) was added thereto at 0° C., and stirred for 3 hours at the same temperature. After ethyl acetate (3 mL) and water (3 mL) were added dropwise successively, ethyl acetate (30 mL), water (30 mL) and 1N aqueous hydro chloride solution (5 mL) were added thereto, and the mixture was partitioned. After the water layer was extracted with ethyl acetate (20 mL), the organic layer was combined. The organic layer was washed with water (50 mL, 2 times) and saturated brine (50 mL) successively, dried over anhydrous magnesium sulfate, and then the solvent was removed under reduced pressure. The obtained residue was purified by silica gel column chromatography (hexane-ethyl acetate) to give the titled reference compound (61.0 mg) as a pale yellow amorphous product. (Yield 61%)

| 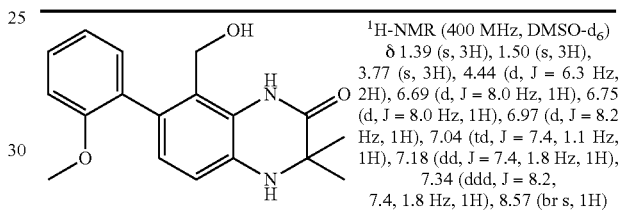 | $^1$H-NMR (400 MHz, DMSO-d$_6$) δ 1.39 (s, 3H), 1.50 (s, 3H), 3.77 (s, 3H), 4.44 (d, J = 6.3 Hz, 2H), 6.69 (d, J = 8.0 Hz, 1H), 6.75 (d, J = 8.0 Hz, 1H), 6.97 (d, J = 8.2 Hz, 1H), 7.04 (td, J = 7.4, 1.1 Hz, 1H), 7.18 (dd, J = 7.4, 1.8 Hz, 1H), 7.34 (ddd, J = 8.2, 7.4, 1.8 Hz, 1H), 8.57 (br s, 1H) |
|---|---|

Using any compounds among Reference Compounds No. 2-2~2-5, the following Reference Compounds (No. 3-2~3-5) were obtained by a method similar to that of Reference Compound No. 3-1.

| 7-(4-Fluoro-2-methoxyphenyl)-8-hydroxymethyl-3,3-dimethyl-3,4-dihydro-1H-quinoxalin-2-one (Reference Compound No. 3-2) | $^1$H-NMR (400 MHz, DMSO-d$_6$) δ 1.24 (s, 3H), 1.27 (s, 3H), 3.70 (s, 3H), 4.18 (dd, J = 12.9, 5.0 Hz, 1H), 4.44 (dd, J = 12.9, 5.0 Hz, 1H), 5.29 (t, J = 5.0 Hz, 1H), 6.07 (s, 1H), 6.57 (d, J = 8.1 Hz, 1H), 6.66 (d, J = 8.1 Hz, 1H), 6.79 (td, J = 8.4, 2.5 Hz, 1H), 6.94 (dd, J = 11.5, 2.5 Hz, 1H), 7.12 (dd, J = 8.4, 7.1 Hz, 1H), 9.24 (s, 1H) |
|---|---|
| 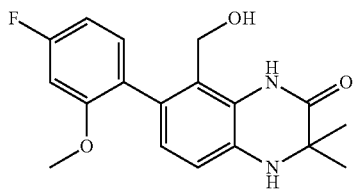 [SMILES: COc1cc(F)ccc1-c1ccc2c(c1CO)NC(=O)C(C)(C)N2] | |

| 7-(5-Fluoro-2-methoxyphenyl)-8-hydroxymethyl-3,3-dimethyl-3,4-dihydro-1H-quinoxalin-2-one (Reference Compound No. 3-3) | 1H-NMR (400 MHz, DMSO-d$_6$) δ 1.25 (s, 3H), 1.28 (s, 3H), 3.67 (s, 3H), 4.20 (dd, J = 12.8, 5.3 Hz, 1H), 4.46 (dd, J = 12.8, 5.3 Hz, 1H), 5.30 (t, J = 5.3 Hz, 1H), 6.11 (s, 1H), 6.61 (d, J = 8.1 Hz, 1H), 6.67 (d, J = 8.1 Hz, 1H), 6.97 (dd, J = 9.0, 3.2 Hz, 1H), 7.03 (dd, J = 8.9, 4.8 Hz, 1H), 7.14 (td, J = 8.9, 3.2 Hz, 1H), 9.25 (s, 1H) |
|---|---|
| 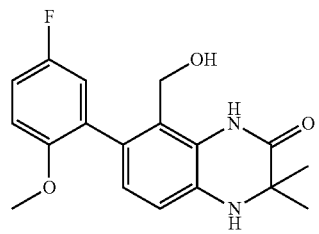 [SMILES: COc1ccc(F)cc1-c1ccc2c(c1CO)NC(=O)C(C)(C)N2] | |

| | |
|---|---|
| 8-Hydroxymethyl-7-(2-methoxy-4-methoxymethoxyphenyl)-3,3-dimethyl-3,4-dihydro-1H-quinoxalin-2-one (Reference Compound No. 3-4)<br />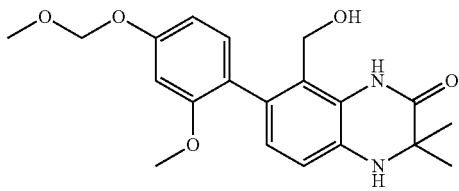 | ¹H-NMR (400 MHz, CDCl₃) δ 1.38 (s, 3H), 1.49 (s, 3H), 2.13 (t, J = 6.9 Hz, 1H), 3.53 (s, 3H), 3.75 (s, 4H), 4.45 (d, J = 6.9 Hz, 2H), 5.22 (s, 2H), 6.67 (d, J = 2.7 Hz, 1H), 6.67 (d, J = 8.1 Hz, 1H), 6.72 (dd, J = 8.0, 2.7 Hz, 1H), 6.72 (d, J = 8.0 Hz, 1H), 7.07 (d, J = 8.1 Hz, 1H), 8.57 (s, 1H) |
| 7-(4-Hydroxy-2-methoxyphenyl)-8-hydroxymethyl-3,3-dimethyl-3,4-dihydro-1H-quinoxalin-2-one (Reference Compound No. 3-5)<br />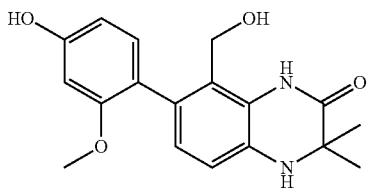 [SMILES: COc1cc(O)ccc1-c1ccc2c(c1CO)NC(=O)C(C)(C)N2] | ¹H-NMR (400 MHz, CDCl₃) δ 1.39 (s, 3H), 1.49 (s, 3H), 2.07 (t, J = 6.5 Hz, 1H), 3.74 (s, 4H), 4.45 (d, J = 6.5 Hz, 2H), 4.95 (s, 1H), 6.48 (dd, J = 7.8, 2.3 Hz, 1H), 6.50 (d, J = 2.3 Hz, 1H), 6.67 (d, J = 8.1 Hz, 1H), 6.72 (d, J = 8.1 Hz, 1H), 7.01 (d, J = 7.8 Hz, 1H), 8.56 (s, 1H) |

Reference Example 4

8-Chloromethyl-7-(4-fluoro-2-methoxyphenyl)-3,3-dimethyl-3,4-dihydro-1H-quinoxalin-2-one (Reference Compound No. 4-1)

7-(4-Fluoro-2-methoxyphenyl)-8-hydroxymethyl-3,3-dimethyl-3,4-dihydro-1H-quinoxalin-2-one (Reference Compound No. 3-2, 70.0 mg, 0.21 mmol) was dissolved in the mixed solvent of anhydrous dichloromethane (1 mL) and anhydrous tetrahydrofuran (1.5 mL), and triethylamine (35 μL, 0.25 mmol) and methanesulfonyl chloride (18 μL, 0.23 mmol) were added thereto successively. The reaction mixture was stirred at room temperature overnight. Ethyl acetate (30 mL) and water (30 mL) were added to the reaction mixture and partitioned. The organic layer was washed with water (30 mL) and saturated brine (30 mL) successively, dried over anhydrous magnesium sulfate, and then the solvent was removed under reduced pressure. The obtained residue was purified by silica gel column chromatography (hexane-ethyl acetate) to give the titled reference compound (49.5 mg) as pale yellow solid. (Yield 68%)

| | |
|---|---|
| 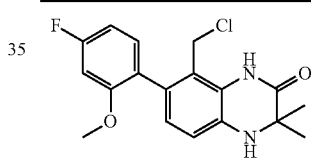 | ¹H-NMR (400 MHz, DMSO-d₆) δ 1.19 (s, 3H), 1.30 (s, 3H), 3.70 (s, 3H), 4.29 (d, J = 11.7 Hz, 1H), 4.91 (d, J = 11.7 Hz, 1H), 6.18 (s, 1H), 6.59 (d, J = 8.1 Hz, 1H), 6.74 (d, J = 8.1 Hz, 1H), 6.82 (td, J = 8.4, 2.4 Hz, 1H), 6.97 (dd, J = 11.5, 2.4 Hz, 1H), 7.14 (dd, J = 8.4, 7.1 Hz, 1H), 9.77 (s, 1H) |

Using any compounds among Reference Compounds No. 3-3 and 3-4, the following Reference Compounds (No. 4-2 and 4-3) were obtained by a method similar to that of Reference Compound No. 4-1.

| | |
|---|---|
| 8-Chloromethyl-7-(5-fluoro-2-methoxyphenyl)-3,3-dimethyl-3,4-dihydro-1H-quinoxalin-2-one (Reference Compound No. 4-2)<br />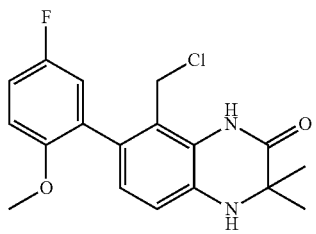 [SMILES: COc1ccc(F)cc1-c1ccc2c(c1CCl)NC(=O)C(C)(C)N2] | ¹H-NMR (400 MHz, DMSO-d₆) δ 1.19 (s, 3H), 1.30 (s, 3H), 3.67 (s, 3H), 4.31 (d, J = 11.7 Hz, 1H), 4.95 (d, J = 11.7 Hz, 1H), 6.22 (s, 1H), 6.63 (d, J = 8.1 Hz, 1H), 6.75 (d, J = 8.1 Hz, 1H), 6.99 (dd, J = 9.0, 3.2 Hz, 1H), 7.07 (dd, J = 8.9, 4.6 Hz, 1H), 7.19 (td, J = 8.9, 3.2 Hz, 1H), 9.80 (s, 1H) |

-continued

| | |
|---|---|
| 8-Chloromethyl-7-(2-methoxy-4-methoxymethoxyphenyl)-3,3-dimethyl-3,4-dihydro-1H-quinoxalin-2-one (Reference Compound No. 4-3)<br>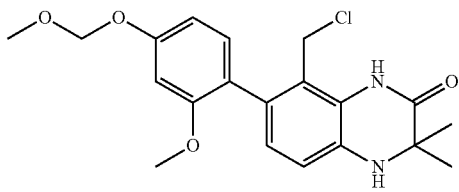 | $^1$H-NMR (400 MHz, CDCl$_3$) δ 1.44 (s, 3H), 1.45 (s, 3H), 3.53 (s, 3H), 3.74 (s, 4H), 4.42 (s, 2H), 5.22 (s, 2H), 6.66 (d, J = 2.3 Hz, 1H), 6.70 (d, J = 8.1 Hz, 1H), 6.70 (dd, J = 8.3, 2.3 Hz, 1H), 6.77 (d, J = 8.1 Hz, 1H), 7.11 (d, J = 8.3 Hz, 1H), 7.85 (br s, 1H) |

Reference Example 5

7-Bromo-8-hydroxymethyl-3,3-dimethyl-3,4-dihydro-1H-quinoxalin-2-one (Reference Compound No. 5)

Lithium aluminium hydride (38.5 mg, 1.01 mmol) was suspended in anhydrous tetrahydrofuran (0.5 mL) under nitrogen atmosphere. An anhydrous tetrahydrofuran solution (1.5 mL) of 7-bromo-8-methoxycarbonyl-3,3-dimethyl-3,4-dihydro-1H-quinoxalin-2-one (Reference Compound No. 1, 101 mg, 0.323 mmol) was added dropwise thereto at 0° C., and stirred for 1 hour at the same temperature. Ethyl acetate (10 mL), water (10 mL), and 1N aqueous hydrochloride solution (2 mL) were added thereto successively and the mixture was partitioned. The organic layer was washed with saturated brine (10 mL), dried over anhydrous magnesium sulfate, and then the solvent was removed under reduced pressure. The obtained residue was purified by silica gel column chromatography (hexane-ethyl acetate) to give the titled reference compound (67.4 mg) as an orange amorphous product. (Yield 74%)

| | |
|---|---|
| 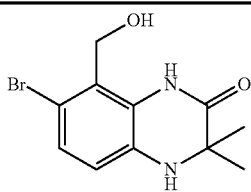 | $^1$H-NMR (400 MHz, CDCl$_3$) δ 1.39 (s, 6H), 3.18 (br s, 1H), 3.75 (s, 1H), 4.99 (d, J = 9.5 Hz, 2H), 6.51 (d, J = 8.3 Hz, 1H), 7.07 (d, J = 8.3 Hz, 1H), 9.40 (s, 1H) |

Reference Example 6

7-Bromo-8-hydroxymethyl-1,3,3-trimethyl-3,4-dihydro-1H-quinoxalin-2-one (Reference Compound No. 6)

A mixture of 7-bromo-8-hydroxymethyl-3,3-dimethyl-3,4-dihydro-1H-quinoxalin-2-one (Reference Compound No. 5, 62.7 mg, 0.220 mmol), methyl iodide (68.6 μL, 1.10 mmol), and cessium carbonate (180 mg, 0.552 mmol) was suspended in anhydrous N,N-dimethylformamide (1 mL) and stirred at room temperature for 2.5 hours. Ethyl acetate (10 mL) and water (10 mL) were added to the reaction mixture and partitioned. The organic layer was washed with saturated brine (10 mL), dried over anhydrous magnesium sulfate, and then the solvent was removed under reduced pressure. The obtained residue was purified by silica gel column chromatography (hexane-ethyl acetate) to give the titled reference compound (45.5 mg) as an orange amorphous product. (Yield 69%)

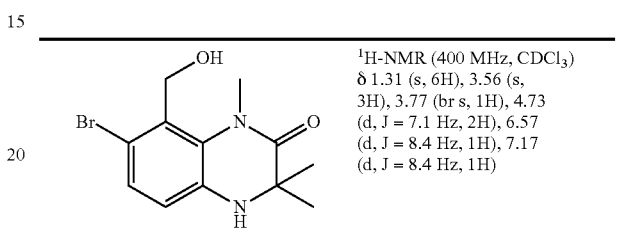

$^1$H-NMR (400 MHz, CDCl$_3$) δ 1.31 (s, 6H), 3.56 (s, 3H), 3.77 (br s, 1H), 4.73 (d, J = 7.1 Hz, 2H), 6.57 (d, J = 8.4 Hz, 1H), 7.17 (d, J = 8.4 Hz, 1H)

Reference Example 7

7-Bromo-8-chloromethyl-1,3,3-trimethyl-3,4-dihydro-1H-quinoxalin-2-one (Reference Compound No. 7)

7-Bromo-8-hydroxymethyl-1,3,3-trimethyl-3,4-dihydro-1H-quinoxalin-2-one (Reference Compound No. 6, 37.5 mg, 0.125 mmol 1) was dissolved in anhydrous dichloromethane (1 mL), and triethylamine (20.9 μL, 0.150 mmol) and methanesulfonyl chloride (10.7 μL, 0.138 mmol) were added thereto successively. The reaction mixture was stirred at room temperature overnight. Ethyl acetate (10 mL) and water (10 mL) were added to the reaction mixture and partitioned. The organic layer was washed with saturated brine (10 mL), dried over anhydrous magnesium sulfate, and then the solvent was removed under reduced pressure. The obtained residue was purified by silica gel column chromatography (hexane-ethyl acetate) to give the titled reference compound (28.7 mg) as an orange amorphous product. (Yield 72%)

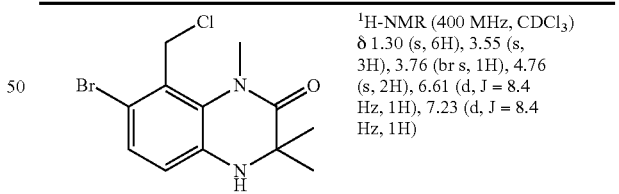

$^1$H-NMR (400 MHz, CDCl$_3$) δ 1.30 (s, 6H), 3.55 (s, 3H), 3.76 (br s, 1H), 4.76 (s, 2H), 6.61 (d, J = 8.4 Hz, 1H), 7.23 (d, J = 8.4 Hz, 1H)

Reference Example 8

7-Bromo-8-(5-fluoro-2-methylphenoxymethyl)-1,3,3-trimethyl-3,4-dihydro-1H-quinoxalin-2-one (Reference Compound No. 8-1)

A mixture of 7-bromo-8-chloromethyl-1,3,3-trimethyl-3,4-dihydro-1H-quinoxalin-2-one (Reference Compound No. 7, 801 mg, 2.52 mmol), 5-fluoro-2-methylphenol (330 μL, 3.02 mmol), and potassium carbonate (524 mg, 3.79 mmol) was suspended in anhydrous N,N-dimethylformamide (10 mL) and stirred at 80° C. overnight. After cooling down, ethyl acetate (80 mL) and water (50 mL) were added to the reaction mixture and partitioned. The organic layer was washed with saturated brine (50 mL), dried over anhydrous magnesium sulfate, and then the solvent was removed under reduced pressure. The obtained residue was purified by silica gel column chromatography (hexane-ethyl acetate) to give the titled reference compound (945 mg) as a colorless solid. (Yield 92%)

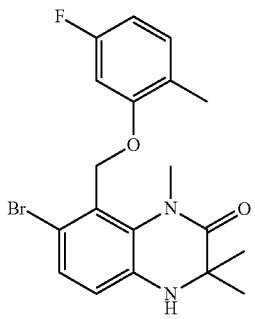

$^1$H-NMR (400 MHz, CDCl$_3$) δ 1.24 (s, 6H), 2.13 (s, 3H), 3.41 (s, 3H), 3.78 (br s, 1H), 5.16 (s, 2H), 6.54-6.57 (m, 1H), 6.58 (d, J = 9.5 Hz, 1H), 6.62 (d, J = 8.5 Hz, 1H), 7.05 (t, J = 7.6 Hz, 1H), 7.23 (d, J = 8.5 Hz, 1H)

Using any compounds among Reference Compounds No. 7 and available compounds, the following Reference Compounds (No. 8-2~8-4) were obtained by a method similar to that of Reference Compound No. 8-1.

| 7-Bromo-8-(2-methylphenoxymethyl)-1,3,3-trimethyl-3,4-dihydro-1H-quinoxalin-2-one (Reference Compound No. 8-2) 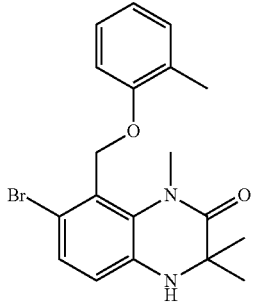 | $^1$H-NMR (400 MHz, CDCl$_3$) δ 1.23 (s, 6H), 2.20 (s, 3H), 3.43 (s, 3H), 3.76 (br s, 1H), 5.18 (s, 2H), 6.61 (d, J = 8.4 Hz, 1H), 6.83 (d, J = 8.1 Hz, 1H), 6.86 (t, J = 7.2 Hz, 1H), 7.12-7.16 (m, 1H), 7.23 (d, J = 8.4 Hz, 1H), 7.26-7.27 (m, 1H) |
|---|---|
| 7-Bromo-8-(2-methoxyphenylaminomethyl)-1,3,3-trimethyl-3,4-dihydro-1H-quinoxalin-2-one (Reference Compound No. 8-3) 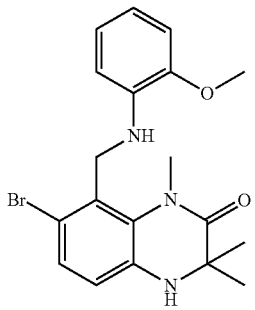 | $^1$H-NMR (400 MHz, CDCl$_3$) δ 1.29 (s, 6H), 3.50 (s, 3H), 3.74 (s, 1H), 3.84 (s, 3H), 4.30 (d, J = 5.6 Hz, 2H), 4.73 (t, J = 5.6 Hz, 1H), 6.57 (d, J = 8.3 Hz, 1H), 6.67 (dd, J = 7.8, 1.5 Hz, 1H), 6.72 (td, J = 7.8, 1.5 Hz, 1H), 6.80 (dd, J = 7.8, 1.5 Hz, 1H), 6.89 (td, J = 7.8, 1.5 Hz, 1H), 7.21 (d, J = 8.3 Hz, 1H) |
| 7-Bromo-8-(5-fluoro-2-methylphenylaminomethyl)-1,3,3-trimethyl-3,4-dihydro-1H-quinoxalin-2-one (Reference Compound No. 8-4) 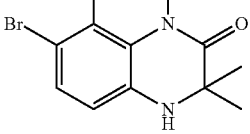 | $^1$H-NMR (500 MHz, CDCl$_3$) δ 1.30 (s, 6H), 2.11 (s, 3H), 3.47 (s, 3H), 3.78 (s, 1H), 4.12 (br s, 1H), 4.30 (d, J = 5.5 Hz, 2H), 6.35-6.40 (m, 2H), 6.60 (d, J = 8.6 Hz, 1H), 6.98 (t, J = 7.2 Hz, 1H), 7.22 (d, J = 8.6 Hz, 1H) |

Reference Example No. 9

7-Bromo-8-methoxycarbonyl-1,3,3-trimethyl-3,4-dihydro-1H-quinoxalin-2-one (Reference Compound No. 9)

A mixture of 7-bromo-8-methoxycarbonyl-3,3-dimethyl-3,4-dihydro-1H-quinoxalin-2-one (Reference Compound No. 1, 102 mg, 0.326 mmol), methyl iodide (100 μL, 1.60 mmol), and cessium carbonate (272 mg, 0.835 mmol) was suspended in anhydrous N,N-dimethylformamide (5 mL) and stirred at room temperature for 2 hours. Ethyl acetate (25 mL) and water (25 mL) were added to the reaction mixture and partitioned. The organic layer was washed with saturated brine (20 mL), dried over anhydrous magnesium sulfate, and then the solvent was removed under reduced pressure. The obtained residue was purified by silica gel column chromatography (hexane-ethyl acetate) to give the titled reference compound (86.0 mg) as a pale yellow solid. (Yield 83%)

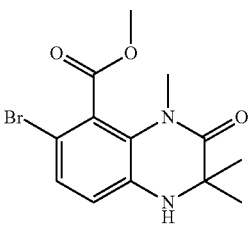 [SMILES: COC(=O)c1c(Br)ccc2c1N(C)C(=O)C(C)(C)N2]

$^1$H-NMR (500 MHz, CDCl$_3$) δ 1.34 (s, 6H), 3.27 (s, 3H), 3.85 (br s, 1H), 3.95 (s, 3H), 6.64 (d, J = 8.2 Hz, 1H), 7.15 (d, J = 8.2 Hz, 1H)

Reference Example 10

7-(5-Chloro-2-methoxyphenyl)-8-methoxycarbonyl-1,3,3-trimethyl-3,4-dihydro-1H-quinoxalin-2-one (Reference Compound No. 10-1)

A mixture of 7-bromo-8-methoxycarbonyl-1,3,3-trimethyl-3,4-dihydro-1H-quinoxalin-2-one (Reference Compound No. 9, 3.75 g, 11.5 mmol), 5-chloro-2-methoxyphenylboronic acid (2.57 g, 13.8 mmol), cessium carbonate (7.49 g, 23.0 mmol) and tetrakis(triphenylphosphine)palladium (0) (1.33 g, 1.16 mmol) was suspended in anhydrous N,N-dimethylformamide (70 ml) and stirred at 80° C. overnight under argon atmosphere. After cooling down, ethyl acetate (300 mL), diethylether (150 mL) and water (400 mL) were added and partitioned. The organic layer was washed with water (250 mL) and saturated brine (150 mL) successively, dried over anhydrous magnesium sulfate, and then the solvent was removed under reduced pressure. The obtained residue was purified by silica gel column chromatography (hexane-ethyl acetate) to give the titled reference compound (3.84 g) as a colorless amorphous product. (Yield 86%)

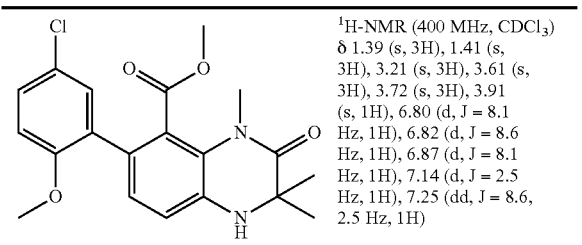

$^1$H-NMR (400 MHz, CDCl$_3$) δ 1.39 (s, 3H), 1.41 (s, 3H), 3.21 (s, 3H), 3.61 (s, 3H), 3.72 (s, 3H), 3.91 (s, 1H), 6.80 (d, J = 8.1 Hz, 1H), 6.82 (d, J = 8.6 Hz, 1H), 6.87 (d, J = 8.1 Hz, 1H), 7.14 (d, J = 2.5 Hz, 1H), 7.25 (dd, J = 8.6, 2.5 Hz, 1H)

Using any compounds among Reference Compounds No. 9 and available compounds, the following Reference Compound (No. 10-2) was obtained by a method similar to that of Reference Compound No. 10-1.

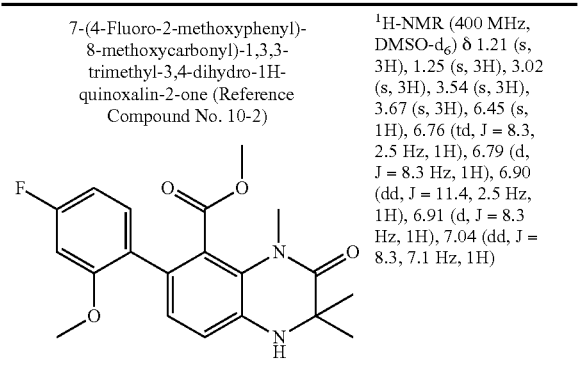

7-(4-Fluoro-2-methoxyphenyl)-8-methoxycarbonyl)-1,3,3-trimethyl-3,4-dihydro-1H-quinoxalin-2-one (Reference Compound No. 10-2)

$^1$H-NMR (400 MHz, DMSO-d$_6$) δ 1.21 (s, 3H), 1.25 (s, 3H), 3.02 (s, 3H), 3.54 (s, 3H), 3.67 (s, 3H), 6.45 (s, 1H), 6.76 (td, J = 8.3, 2.5 Hz, 1H), 6.79 (d, J = 8.3 Hz, 1H), 6.90 (dd, J = 11.4, 2.5 Hz, 1H), 6.91 (d, J = 8.3 Hz, 1H), 7.04 (dd, J = 8.3, 7.1 Hz, 1H)

Reference Example 11

9-Chloro-2,2,4-trimethyl-1,4-dihydro-2H-6-oxa-1,4-diazachrysen-3,5-dione (Reference Compound No. 11-1)

7-(5-Chloro-2-methoxyphenyl)-8-methoxycarbonyl-1,3,3-trimethyl-3,4-dihydro-1H-quinoxalin-2-one (Reference Compound No. 10-1, 3.81 g, 9.80 mmol) was dissolved in anhydrous dichloromethane (30 mL), boron tribromide (7.62 g, 30.4 mmol) was added thereto at −78° C., and then stirred at room temperature for 1 hour. The reaction mixture was poured into ice water (500 mL), ethyl acetate (500 mL) was added thereto and partitioned. The organic layer was washed with saturated brine (200 mL), dried over anhydrous magnesium sulfate, and then the solvent was removed under reduced pressure. The obtained residue was dissolved in N,N-dimethylformamide (50 mL), 60% sodium hydride (23.1 mg, 0.578 mmol) was added thereto, and then stirred at 70° C. overnight. 60% sodium hydride (31.2 mg, 0.780 mmol) was added more thereto and stirred at 80° C. overnight. After cooling down, ethyl acetate (200 mL), diethylether (200 mL) and water (300 mL) were added and partitioned. The organic layer was washed with water (200 mL) and saturated brine (200 mL) successively, dried over anhydrous magnesium sulfate, and then the solvent was removed under reduced pressure. The obtained residue was filtered with ethyl acetate/hexane (1/4, 30 mL) to give the titled reference compound (2.04 g) as a pale yellow solid. (Yield 61%)

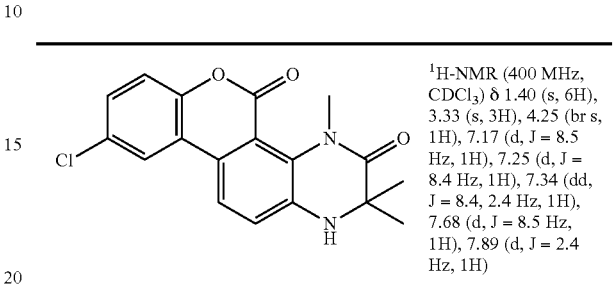

$^1$H-NMR (400 MHz, CDCl$_3$) δ 1.40 (s, 6H), 3.33 (s, 3H), 4.25 (br s, 1H), 7.17 (d, J = 8.5 Hz, 1H), 7.25 (d, J = 8.4 Hz, 1H), 7.34 (dd, J = 8.4, 2.4 Hz, 1H), 7.68 (d, J = 8.5 Hz, 1H), 7.89 (d, J = 2.4 Hz, 1H)

Using Reference Compound No. 10-2, the following Reference Compound (No. 11-2) was obtained by a method similar to that of Reference Compound No. 11-1.

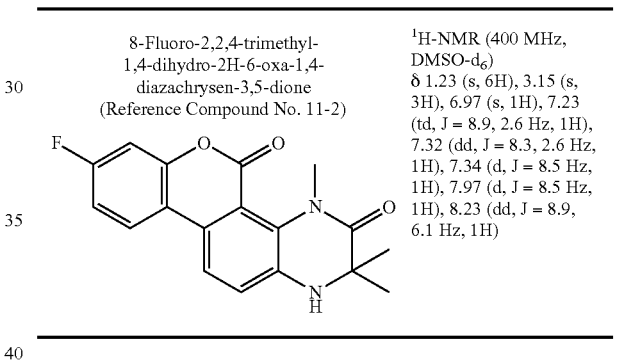

8-Fluoro-2,2,4-trimethyl-1,4-dihydro-2H-6-oxa-1,4-diazachrysen-3,5-dione (Reference Compound No. 11-2)

$^1$H-NMR (400 MHz, DMSO-d$_6$) δ 1.23 (s, 6H), 3.15 (s, 3H), 6.97 (s, 1H), 7.23 (td, J = 8.9, 2.6 Hz, 1H), 7.32 (dd, J = 8.3, 2.6 Hz, 1H), 7.34 (d, J = 8.5 Hz, 1H), 7.97 (d, J = 8.5 Hz, 1H), 8.23 (dd, J = 8.9, 6.1 Hz, 1H)

Reference Example 12

7-(5-Chloro-2-hydroxyphenyl)-8-hydroxymethyl-1,3,3-trimethyl-3,4-dihydro-1H-quinoxalin-2-one (Reference Compound No. 12-1)

Lithium aluminium hydride (442 mg, 11.7 mmol) was suspended in anhydrous tetrahydrofuran (10 mL) under nitrogen atmosphere. An anhydrous tetrahydrofuran solution (40 mL) of 9-chloro-2,2,4-trimethyl-1,4-dihydro-2H-6-oxa-1,4-diazachrysen-3,5-dione (Reference Compound No. 11-1, 1:99 g, 5.81 mmol) was added dropwise thereto at −10° C. and stirred for 10 minutes at the same temperature. After ethyl acetate (1 mL) and water (1 mL) were added thereto successively, ethyl acetate (300 mL) and saturated brine (300 mL) were added and partitioned. The organic layer was washed with saturated brine (150 mL), dried over anhydrous magnesium sulfate, and then the solvent was removed under reduced pressure. The obtained residue was purified by silica gel column chromatography (hexane-ethyl acetate) to give the titled reference compound (1.38 g) as a pale yellow solid. (Yield 69%)

| 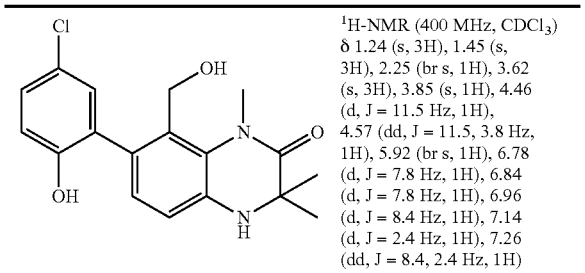 | ¹H-NMR (400 MHz, CDCl₃) δ 1.24 (s, 3H), 1.45 (s, 3H), 2.25 (br s, 1H), 3.62 (s, 3H), 3.85 (s, 1H), 4.46 (d, J = 11.5 Hz, 1H), 4.57 (dd, J = 11.5, 3.8 Hz, 1H), 5.92 (br s, 1H), 6.78 (d, J = 7.8 Hz, 1H), 6.84 (d, J = 7.8 Hz, 1H), 6.96 (d, J = 8.4 Hz, 1H), 7.14 (d, J = 2.4 Hz, 1H), 7.26 (dd, J = 8.4, 2.4 Hz, 1H) |
|---|---|

Using Reference Compound No. 11-2, the following Reference Compound (No. 12-2) was obtained by a method similar to that of Reference Compound No. 12-1.

| 7-(4-fluoro2-hydroxyphenyl)-8-hydroxymethyl)-1,3,3-trimethyl-3,4-dihydro-1H-quinoxalin-2-one (Reference Compound No. 12-2)<br>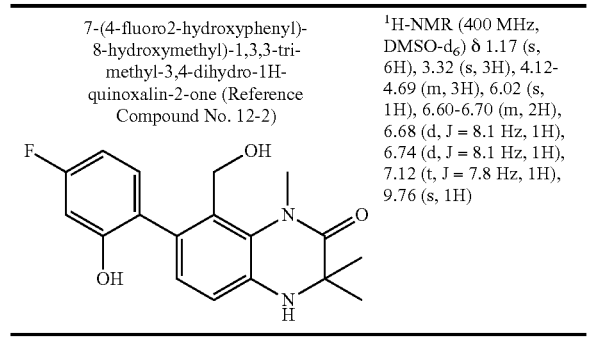 | ¹H-NMR (400 MHz, DMSO-d₆) δ 1.17 (s, 6H), 3.32 (s, 3H), 4.12-4.69 (m, 3H), 6.02 (s, 1H), 6.60-6.70 (m, 2H), 6.68 (d, J = 8.1 Hz, 1H), 6.74 (d, J = 8.1 Hz, 1H), 7.12 (t, J = 7.8 Hz, 1H), 9.76 (s, 1H) |
|---|---|

Reference Example 13

7-(5-Chloro-2-methoxyphenyl)-8-hydroxymethyl-1,3,3-trimethyl-3,4-dihydro-1H-quinoxalin-2-one (Reference Compound No. 13-1)

A mixture of 7-(5-chloro-2-hydroxyphenyl)-hydroxymethyl-1,3,3-trimethyl-3,4-dihydro-1H-quinoxalin-2-one (Reference Compound No. 12-1, 1.36 g, 3.92 mmol), methyl iodide (244 µL, 3.92 mmol), and potassium carbonate (1.08 g, 7.81 mmol) was suspended in anhydrous N,N-dimethylformamide (20 mL) and stirred at 50° C. for 1 hour. After cooling down, ethyl acetate (70 mL), diethylether (70 mL), and water (150 mL) were added and partitioned. The organic layer was washed with water (100 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled reference compound (1.36 g) as a pale yellow amorphous product. (Yield 96%)

| 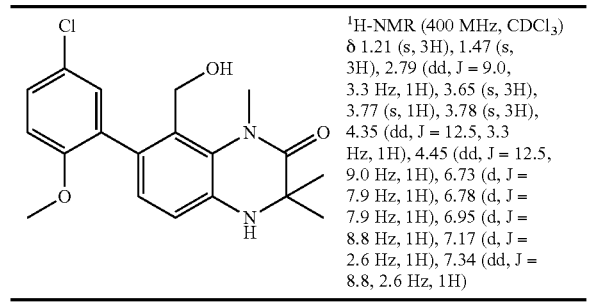 | ¹H-NMR (400 MHz, CDCl₃) δ 1.21 (s, 3H), 1.47 (s, 3H), 2.79 (dd, J = 9.0, 3.3 Hz, 1H), 3.65 (s, 3H), 3.77 (s, 1H), 3.78 (s, 3H), 4.35 (dd, J = 12.5, 3.3 Hz, 1H), 4.45 (dd, J = 12.5, 9.0 Hz, 1H), 6.73 (d, J = 7.9 Hz, 1H), 6.78 (d, J = 7.9 Hz, 1H), 6.95 (d, J = 8.8 Hz, 1H), 7.17 (d, J = 2.6 Hz, 1H), 7.34 (dd, J = 8.8, 2.6 Hz, 1H) |
|---|---|

Using Reference Compound No. 12-2, the following Reference Compound (No. 13-2) was obtained by a method similar to that of Reference Compound No. 13-1.

| 7-(4-Fluoro-2-methoxyphenyl)-8-hydroxymethyl)-1,3,3-trimethyl-3,4-dihydro-1H-quinoxalin-2-one (Reference Compound No. 13-2)<br>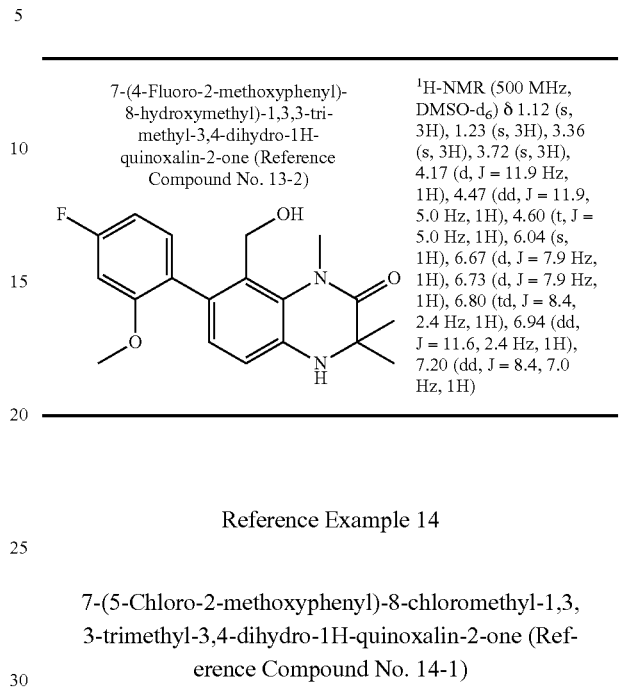 | ¹H-NMR (500 MHz, DMSO-d₆) δ 1.12 (s, 3H), 1.23 (s, 3H), 3.36 (s, 3H), 3.72 (s, 3H), 4.17 (d, J = 11.9 Hz, 1H), 4.47 (dd, J = 11.9, 5.0 Hz, 1H), 4.60 (t, J = 5.0 Hz, 1H), 6.04 (s, 1H), 6.67 (d, J = 7.9 Hz, 1H), 6.73 (d, J = 7.9 Hz, 1H), 6.80 (td, J = 8.4, 2.4 Hz, 1H), 6.94 (dd, J = 11.6, 2.4 Hz, 1H), 7.20 (dd, J = 8.4, 7.0 Hz, 1H) |
|---|---|

Reference Example 14

7-(5-Chloro-2-methoxyphenyl)-8-chloromethyl-1,3,3-trimethyl-3,4-dihydro-1H-quinoxalin-2-one (Reference Compound No. 14-1)

7-(5-Chloro-2-methoxyphenyl)-8-hydroxymethyl-1,3,3-trimethyl-3,4-dihydro-1H-quinoxalin-2-one (Reference Compound No. 13-1, 1.34 g, 3.71 mmol) was dissolved in anhydrous dichloromethane (19 mL), and triethylamine (621 µL, 4.46 mmol) and methanesulfonyl chloride (316 µL, 4.08 mmol) were added thereto successively. The reaction mixture was stirred at room temperature overnight. Ethyl acetate (200 mL) was added to the reaction mixture, washed with water (200 mL), dried over anhydrous magnesium sulfate, and then the solvent was removed under reduced pressure. The obtained residue was purified by silica gel column chromatography (hexane-ethyl acetate) to give the titled reference compound (1.14 g) as a colorless amorphous product. (Yield 81%)

| 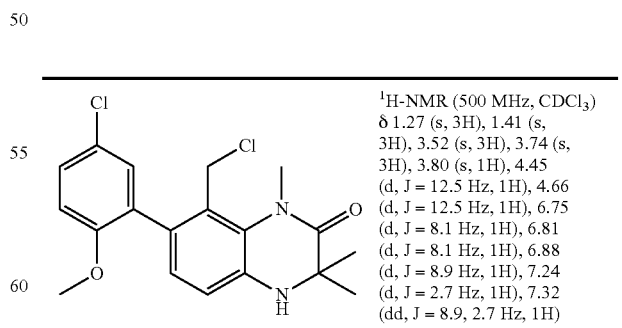 | ¹H-NMR (500 MHz, CDCl₃) δ 1.27 (s, 3H), 1.41 (s, 3H), 3.52 (s, 3H), 3.74 (s, 3H), 3.80 (s, 1H), 4.45 (d, J = 12.5 Hz, 1H), 4.66 (d, J = 12.5 Hz, 1H), 6.75 (d, J = 8.1 Hz, 1H), 6.81 (d, J = 8.1 Hz, 1H), 6.88 (d, J = 8.9 Hz, 1H), 7.24 (d, J = 2.7 Hz, 1H), 7.32 (dd, J = 8.9, 2.7 Hz, 1H) |
|---|---|

Using Reference Compound No. 13-2, the following Reference Compound (No. 14-2) was obtained by a method similar to that of Reference Compound No. 14-1.

| 8-Chloromethyl-7-(4-fluoro-2-methoxy-phenyl)-1,3,3-trimethyl-3,4-dihydro-1H-quinoxalin-2-one (Reference Compound No. 14-2) 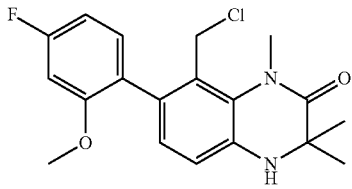 | $^1$H-NMR (400 MHz, DMSO-$d_6$) δ 1.11 (s, 3H), 1.24 (s, 3H), 3.36 (s, 3H), 3.74 (s, 3H), 4.44 (d, J = 12.8 Hz, 1H), 4.77 (d, J = 12.8 Hz, 1H), 6.24 (s, 1H), 6.74 (d, J = 8.1 Hz, 1H), 6.84 (d, J = 8.1 Hz, 1H), 6.85 (td, J = 8.4, 2.5 Hz, 1H), 6.99 (dd, J = 11.3, 2.5 Hz, 1H), 7.21 (dd, J = 8.4, 7.1 Hz, 1H) |

Reference Example 15

4-Benzoyloxyanisole (Reference Compound No. 15-1)

4-Hydroxyanisole (1.25 g, 10.1 mmol) was dissolved in anhydrous dichloromethane (10 mL), and triethylamine (4.25 mL, 30.5 mmol) and benzoyl chloride (1.40 mL, 12.1 mmol) were added thereto successively. The reaction mixture was stirred at room temperature for 4 hours. Chloroform (50 mL) and water (50 mL) were added to the reaction mixture and partitioned. The organic layer was washed with saturated brine (50 mL), dried over anhydrous magnesium sulfate, and then the solvent was removed under reduced pressure. The obtained residue was filtered with hexane (50 mL) to give the titled reference compound (2.24 g) as a colorless solid. (Yield 98%)

| 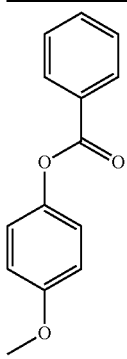 | $^1$H-NMR (400 MHz, DMSO-$d_6$) δ 3.78 (s, 3H), 7.01 (d, J = 9.1 Hz, 2H), 7.21 (d, J = 9.1 Hz, 2H), 7.61 (t, J = 7.8 Hz, 2H), 7.75 (t, J = 7.8 Hz, 1H), 8.13 (d, J = 7.8 Hz, 2H) |

Reference Example 16

2-Bromo-4-chloro-5-fluoroaisole (Reference Compound No. 16-1)

A mixture of 4-chloro-3-fluoroanisole (124 μL, 1.00 mmol) and N-bromosuccinimide was dissolved in mixed solvent of anhydrous N,N-dimethylformamide (0.5 mL) and anhydrous dichloromethane (1 mL), and stirred at 40° C. for 3 days. After cooling down, chloroform (30 mL) and water (30 mL) were added and partitioned. The water layer was extracted with chloroform (30 mL, 2 times). The combined organic layer was washed with saturated brine (30 mL), dried over anhydrous magnesium sulfate, and then the solvent was removed under reduced pressure. The obtained residue was purified by silica gel column chromatography (hexane-ethyl acetate) to give the titled reference compound (195 mg) as a colorless solid. (Yield 82%)

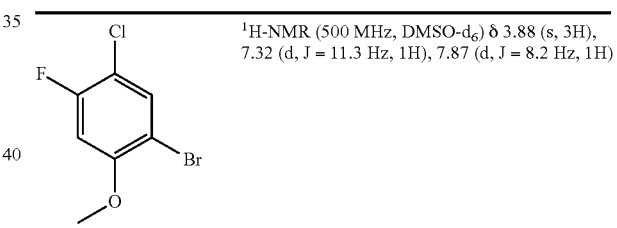

$^1$H-NMR (500 MHz, DMSO-$d_6$) δ 3.88 (s, 3H), 7.32 (d, J = 11.3 Hz, 1H), 7.87 (d, J = 8.2 Hz, 1H)

Using any compounds among Reference Compounds No. 15-1 and available compounds, the following Reference Compounds (No. 16-2~16-3) were obtained by a method similar to that of Reference Compound No. 16-1.

| 4-Benzoyloxy-2-bromoanisole (Reference Compound No. 16-2) 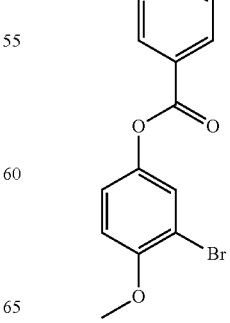 | $^1$H-NMR (400 MHz, DMSO-$d_6$) δ 3.88 (s, 3H), 7.19 (d, J = 9.0 Hz, 1H), 7.32 (dd, J = 9.0, 2.8 Hz, 1H), 7.59-7.63 (m, 3H), 7.75 (tt, J = 7.8, 1.5 Hz, 1H), 8.12 (dt, J = 7.8, 1.5 Hz, 2H) |

Using Reference Compound No. 16-3, the following Reference Compound (No. 15-2) was obtained by a method similar to that of Reference Compound No. 15-1.

| 5-Benzoyloxy-2-iodoanisole (Reference Compound No. 15-2) 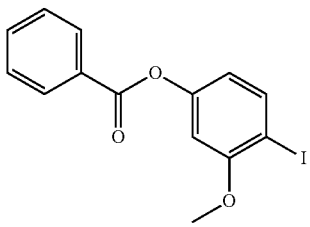 | $^1$H-NMR (400 MHz, CDCl$_3$) δ 3.89 (s, 3H), 6.65 (dd, J = 8.5, 2.4 Hz, 1H), 6.73 (d, J = 2.4 Hz, 1H), 7.50-7.54 (m, 2H), 7.63-7.68 (m, 1H), 7.80 (d, J = 8.5 Hz, 1H), 8.18-8.21 (m, 2H) |

67
-continued

| 5-Hydroxy-2-iodoanisole (Reference Compound No. 16-3) 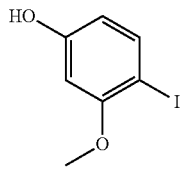 | $^1$H-NMR (400 MHz, CDCl$_3$) δ 3.85 (s, 3H), 4.82 (s, 1H), 6.25 (dd, J = 8.4, 2.7 Hz, 1H), 6.40 (d, J = 2.7 Hz, 1H), 7.56 (d, J = 8.4 Hz, 1H) |
|---|---|

Reference Example 17

5-Chloro-4-fluoro-2-methoxyphenylboronic acid (Reference Compound No. 17)

2-Bromo-4-chloro-5-fluoroanisole (Reference Compound No. 16-1, 239 mg, 1.00 mmol) was dissolved in mixed solvent of anhydrous toluene (2 mL) and anhydrous tetrahydrofuran (0.5 mL), 1.6M hexane solution of n-butyl lithium (750 μL, 1.20 mmol) was added thereto at −40° C., and then the reaction mixture was stirred at the same temperature for 30 minutes. Triisopropyl boronic acid (277 μL, 1.20 mmol) was added dropwise to the reaction mixture, warmed to −20° C. over 10 minutes, and then 2N aqueous HCl solution (1 mL) was added. After the reaction mixture was stirred at room temperature for 20 minutes, ethyl acetate (20 mL) and water (20 mL) were added and partitioned. The organic layer was washed with saturated brine (20 mL), dried over anhydrous magnesium sulfate, and then the solvent was removed under reduced pressure to give the titled reference compound (181 mg) as a colorless solid. (Yield 89%)

| 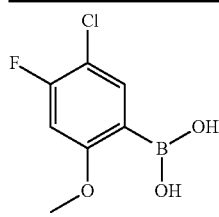 | $^1$H-NMR (400 MHz, DMSO-d$_6$) δ 3.81 (s, 3H), 7.10 (d, J = 12.2 Hz, 1H), 7.57 (d, J = 9.5 Hz, 1H), 7.86 (br s, 1H), 8.45 (br s, 1H) |
|---|---|

Reference Example 18

2-(5,5-Dimethyl[1,3,2]dioxaborinan-2-yl)-4-nitroanisole (Reference Compound No. 18-1)

A mixture of 2-Bromo-4-nitroanisole (100 mg, 0.431 mmol), bis(neopentylglycolate)diborane (151 mg, 0.668 mmol), potassium acetate (129 mg, 1.31 mmol), and [1,1'-bis(diphenylphosphino)ferrocene]palladium(II)dichloride dichloromethane complex (1:1) (35.5 mg, 0.0435 mmol) was suspended in dimethylsulfoxide (3 mL), and the reaction mixture was stirred at 80° C. for 10 minutes under microwave. After cooling down, ethyl acetate (30 mL) and water (30 mL) were added to the reaction mixture and partitioned. The organic layer was washed with saturated brine (30 mL), dried over anhydrous magnesium sulfate, and then the solvent was removed under reduced pressure to give the titled reference compound (72.5 mg) as a yellow solid. (Yield 85%)

| 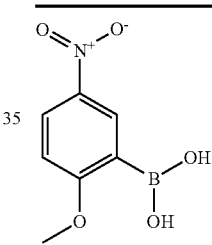 | $^1$H-NMR (500 MHz, DMSO-d$_6$) δ 3.89 (s, 3H), 7.35 (d, J = 9.4 Hz, 1H), 8.12 (d, J = 2.7 Hz, 1H), 8.34 (dd, J = 9.4, 2.7 Hz, 1H) |
|---|---|

Using any compounds among Reference Compounds No. 15-2, 16-2, 23 and available compounds, the following Reference Compounds (No. 18-2~18-7) were obtained by method similar to that of Reference Compound No. 18-1.

| 2-(5,5-Dimethyl[1,3,2]dioxaborinan-2-yl)-5-nitroanisole (Reference Compound No. 18-2) 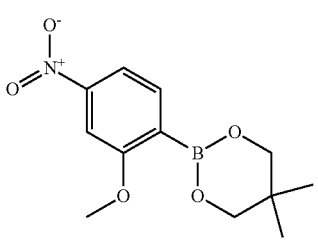 | $^1$H-NMR (500 MHz, DMSO-d$_6$) δ 0.98 (s, 6H), 3.47 (s, 4H), 3.86 (s, 3H), 7.67 (d, J = 1.9 Hz, 1H), 7.69 (d, J = 8.0 Hz, 1H), 7.77 (dd, J = 8.0, 1.9 Hz, 1H) |
|---|---|

-continued

| | |
|---|---|
| 4-Benzoyloxy-2-methoxyphenylboronic acid (Reference Compound No. 18-3) 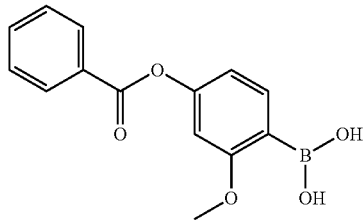 | $^1$H-NMR (500 MHz, CDCl$_3$) δ 3.93 (s, 3H), 5.63 (s, 2H), 6.83 (d, J = 2.1 Hz, 1H), 6.91 (dd, J = 8.0, 2.1 Hz, 1H), 7.53 (t, J = 7.9 Hz, 2H), 7.64-7.67 (m, 1H), 7.91 (d, J = 8.0 Hz, 1H), 8.20-8.22 (m, 2H) |
| 5-Benzoyloxy-2-methoxyphenyl-boronic acid (Reference Compound No. 18-4) 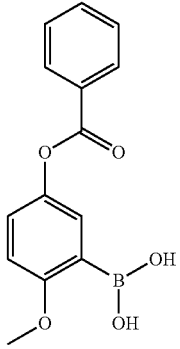 | $^1$H-NMR (400 MHz, CDCl$_3$) δ 3.94 (s, 3H), 5.92 (s, 2H), 6.96 (d, J = 8.9 Hz, 1H), 7.30 (dd, J = 8.9, 3.0 Hz, 1H), 7.51 (t, J = 7.8 Hz, 2H), 7.63 (tt, J = 7.8, 1.5 Hz, 1H), 7.66 (d, J = 3.0 Hz, 1H), 8.20 (dd, J = 7.8, 1.5 Hz, 2H) |
| 2-Methoxy-4-methoxymethoxyphenyl-boronic acid (Reference Compound No. 18-5) 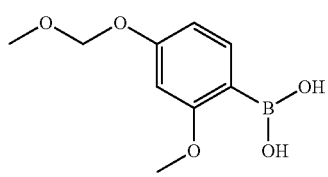 | $^1$H-NMR (400 MHz, CDCl$_3$) δ 3.49 (s, 3H), 3.90 (s, 3H), 5.21 (s, 2H), 5.58 (s, 2H), 6.60 (d, J = 2.0 Hz, 1H), 6.70 (dd, J = 8.2, 2.0 Hz, 1H), 7.75 (d, J = 8.2 Hz, 1H) |
| 2-Methoxy-4-nitrophenylboronic acid (Reference Compound No. 18-6) 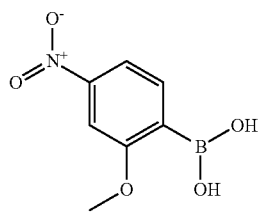 | $^1$H-NMR (500 MHz, CDCl$_3$) δ 4.03 (s, 3H), 5.68 (s, 2H), 7.75 (d, J = 1.8 Hz, 1H), 7.89 (dd, J = 8.1, 1.8 Hz, 1H), 8.03 (d, J = 8.1 Hz, 1H) |
| 2-(5,5-Dimethyl[1,3,2]dioxa-borinan-2-yl)-4-nitroanisole (Reference Compound No. 18-7) 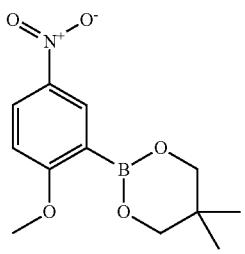 | $^1$H-NMR (400 MHz, CDCl$_3$) δ 1.06 (s, 6H), 3.81 (s, 4H), 3.94 (s, 3H), 6.91 (d, J = 9.2 Hz, 1H), 8.26 (dd, J = 9.2, 3.0 Hz, 1H), 8.55 (d, J = 3.0 Hz, 1H) |

Reference Example 19

5-Cyano-2-trifluoromethylsulfonyloxyanisole (Reference Compound No. 19-1)

A mixture of 5-cyano-2-hydroxyanisole (600 mg, 4.02 mmol) and triethylamine (1.40 mL, 10.0 mmol) was dissolved in anhydrous tetrahydrofuran (20 mL) under argon atmosphere. Trifluoromethanesulfonyl chloride (642 µL, 6.03 mmol) were added thereto at −10° C., and stirred at the same temperature for 1 hour. Ethyl acetate (100 mL) and water (100 mL) were added to the reaction mixture and partitioned. The organic layer was washed with saturated brine (50 mL), dried over anhydrous magnesium sulfate, and then the solvent was removed under reduced pressure. The obtained residue was purified by silica gel column chromatography (hexane-ethyl acetate) to give the titled reference compound (979 mg) as a colorless solid. (Yield 87%)

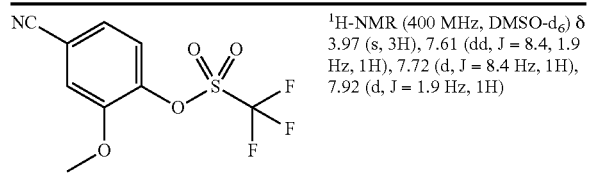

$^1$H-NMR (400 MHz, DMSO-$d_6$) δ 3.97 (s, 3H), 7.61 (dd, J = 8.4, 1.9 Hz, 1H), 7.72 (d, J = 8.4 Hz, 1H), 7.92 (d, J = 1.9 Hz, 1H)

Using available compounds, the following Reference Compounds (No. 19-2~19-4) were obtained by a method similar to that of Reference Compound No. 19-1.

5-Acetyl-2-trifluoromethylsulfonyloxyanisole (Reference Compound No. 19-2)

$^1$H-NMR (400 MHz, CDCl$_3$) δ 2.62 (s, 3H), 3.99 (s, 3H), 7.32 (d, J = 8.5 Hz, 1H), 7.57 (dd, J = 8.5, 2.0 Hz, 1H), 7.66 (d, J = 2.0 Hz, 1H)

5-Methyl-2-trifluoromethylsulfonyloxyanisole (Reference Compound No. 19-3)

$^1$H-NMR (400 MHz, CDCl$_3$) δ 2.37 (s, 3H), 3.89 (s, 3H), 6.75-6.77 (m, 1H), 6.83 (d, J = 1.7 Hz, 1H), 7.08 (d, J = 8.3 Hz, 1H)

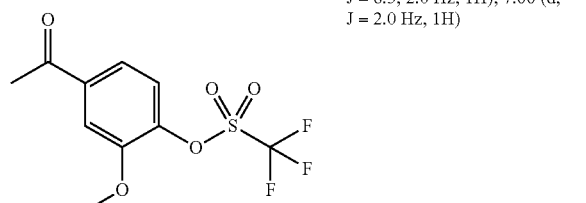

4-Methoxycarbonyl-2-trifluoromethylsulfonyloxyanisole (Reference Compound No. 19-4)

$^1$H-NMR (400 MHz, CDCl$_3$) δ 3.91 (s, 3H), 3.98 (s, 3H), 7.07 (d, J = 8.6 Hz, 1H), 7.89 (d, J = 2.1 Hz, 1H), 8.05 (dd, J = 8.6, 2.1 Hz, 1H)

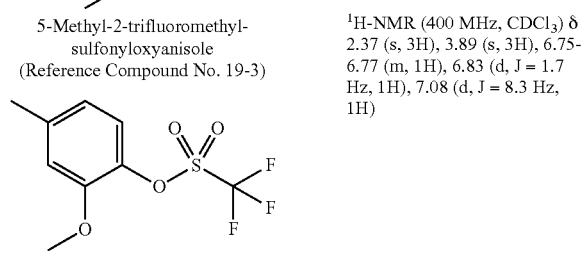

Reference Example 20

5-Cyano-2-(4,4,5,5-tetramethyl[1,3,2]dioxaborolan-2-yl)anisole (Reference Compound No. 20-1)

A mixture of 5-cyano-2-trifluoromethylsulfonyloxyanisole (Reference Compound No. 19-1, 200 mg, 0.711 mmol), bis(pinacolato)diboron (200 mg, 0.788 mmol), potassium acetate (213 mg, 2.17 mmol), and [1,1'-bis(diphenylphosphino)ferrocene] (20.0 mg, 0.0361 mmol), and [1,1'-bis(diphenylphosphino)ferrocene]palladium(II)dichloride dichloromethane complex (1:1) (29.4 mg, 0.0360 mmol) was suspended in 1,4-dioxane (4 mL), and the reaction mixture was stirred at 80° C. overnight. After cooling down, ethyl acetate (100 mL) and water (100 mL) were added and partitioned. The organic layer was washed with saturated brine (50 mL), dried over anhydrous magnesium sulfate, and then the solvent was removed under reduced pressure. The obtained residue was purified by silica gel column chromatography (hexane-ethyl, acetate) to give the titled reference compound (123 mg) as a colorless solid. (Yield 67%)

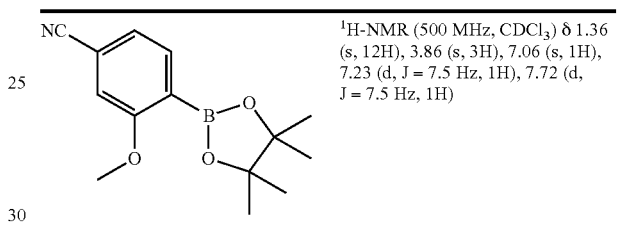

$^1$H-NMR (500 MHz, CDCl$_3$) δ 1.36 (s, 12H), 3.86 (s, 3H), 7.06 (s, 1H), 7.23 (d, J = 7.5 Hz, 1H), 7.72 (d, J = 7.5 Hz, 1H)

Using Reference Compound No. 19-4, the following Reference Compound (No. 20-2) was obtained by a method similar to that of Reference Compound No. 20-1.

4-Methoxycarbonyl-2-(4,4,5,5-tetramethyl[1,3,2]dioxaborolan-2-yl)anisole (Reference Compound No. 20-2)

$^1$H-NMR (500 MHz, CDCl$_3$) δ 1.36 (s, 12H), 3.88 (s, 3H), 3.89 (s, 3H), 6.88 (d, J = 8.8 Hz, 1H), 8.10 (dd, J = 8.8, 2.4 Hz, 1H), 8.34 (d, J = 2.4 Hz, 1H)

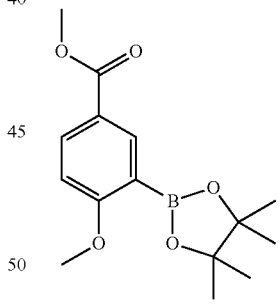

Reference Example 21

7-(5,5-Dimethyl[1,3,2]dioxaborinan-2-yl)-8-(5-fluoro-2-methylphenoxymethyl)-1,3,3-trimethyl-3,4-dihydro-1H-quinoxalin-2-one (Reference Compound 21)

A mixture of 7-bromo-8-(5-fluoro-2-methylphenoxymethyl)-1,3,3-trimethyl-3,4-dihydro-1H-quinoxalin-2-one (Reference Compound No. 8-1, 98.7 mg, 0.242 mmol), bis(neopentyl glycolate)diboron (170 mg, 0.753 mmol), potassium acetate (112 mg, 1.14 mmol), and [1,1'-bis(diphenylphosphino)ferrocene]palladium(II)dichloride dichloromethane complex (1:1) (20.7 mg, 0.0253 mmol) was suspended in dimethylsulfoxide (2 mL), and the reaction mixture was stirred at 80° C. for 15 minutes under microwave. After cooling down, ethyl acetate (15 mL) and water (15 mL) were added to the reaction mixture and partitioned. The organic layer was washed with saturated brine (15 mL), dried over anhydrous magnesium sulfate, and then the solvent was removed under reduced pressure. The obtained residue was purified by silica gel column chromatography (1st:hexane-ethyl acetate, 2nd:chloroform). The obtained residue was filtered with hexane (5 ml) to give the titled reference compound (70.2 mg) as a colorless solid. (Yield 65%)

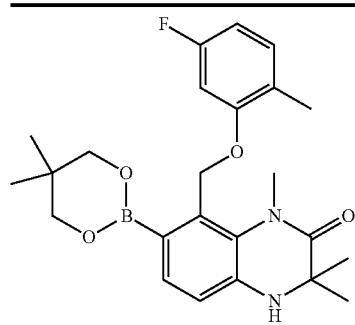

$^1$H-NMR (400 MHz, CDCl$_3$) δ 0.95 (s, 6H), 1.25 (s, 6H), 2.08 (s, 3H), 3.38 (s, 3H), 3.64 (s, 4H), 3.86 (s, 1H), 5.36 (s, 2H), 6.52 (td, J = 8.3, 2.4 Hz, 1H), 6.59 (dd, J = 11.2, 2.4 Hz, 1H), 6.69 (d, J = 7.8 Hz, 1H), 7.01 (t, J = 7.6 Hz, 1H), 7.47 (d, J = 7.8 Hz, 1H)

Reference Example 22

8-(5-Fluoro-2-methylphenoxymethyl)-7-(4,4,5,5-tetramethyl[1,3,2]dioxaborolan-2-yl)-1,3,3-trimethyl-3,4-dihydro-1H-quinoxalin-2-one (Reference Compound No. 22)

A mixture of 7-bromo-8-(5-fluoro-2-methylphenoxymethyl)-1,3,3-trimethyl-3,4-dihydro-1H-quinoxalin-2-one (Reference Compound No. 8-1, 101 mg, 0.248 mmol), bis(pinacolato)diboron (156 mg, 0.614 mmol), potassium acetate (75.5 mg, 0.769 mmol), 1,1'-bis(diphenylphosphino)ferrocene (7.2 mg, 0.013 mmol), and [1,1'-bis(diphenylphosphino)ferrocene]palladium(II)dichloride dichloromethane complex (1:1) (10.7 mg, 0.0131 mmol) was suspended in 1,4-dioxane (2 mL), and the reaction mixture was stirred at 80° C. overnight. After cooling down, ethyl acetate (15 mL) and water (15 mL) were added and partitioned. The organic layer was washed with saturated brine (15 mL), dried over anhydrous magnesium sulfate, and then the solvent was removed under reduced pressure. The obtained residue was purified by silica gel column chromatography (1st:hexane-ethyl acetate, 2nd:chloroform-methanol) to give the titled reference compound (87.9 mg) as a colorless amorphous product. (Yield 78%)

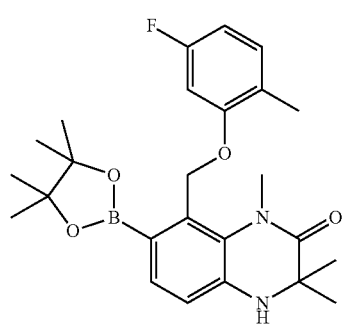

$^1$H-NMR (500 MHz, CDCl$_3$) δ 1.22 (s, 12H), 1.25 (s, 6H), 2.07 (s, 3H), 3.41 (s, 3H), 3.92 (s, 1H), 5.37 (s, 2H), 6.50-6.57 (m, 1H), 6.64 (dd, J = 11.0, 2.4 Hz, 1H), 6.70 (d, J = 7.6 Hz, 1H), 6.94-7.05 (m, 1H), 7.53 (d, J = 7.9 Hz, 1H)

Reference Example 23

2-Bromo-5-methoxymethoxyanisole (Reference Compound No. 23)

A mixture of 4-bromo-3-methoxyphenol (500 mg, 2.46 mmol), chlorodimethylether (281 μL, 3.70 mmol), and potassium carbonate (850 mg, 6.15 mmol) was suspended in anhydrous N,N-dimethylformamide (8 mL) and stirred at 50° C. for 1 hour. After cooling down, the reaction mixture was diluted with ethyl acetate (150 mL). The mixture was washed with water (150 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled reference compound (421 mg) as a colorless oil. (Yield 69%)

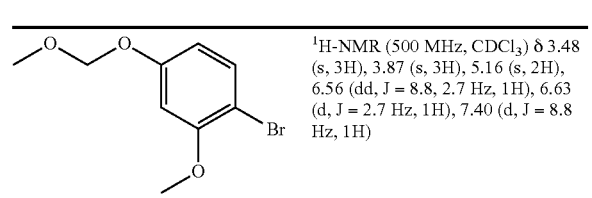

$^1$H-NMR (500 MHz, CDCl$_3$) δ 3.48 (s, 3H), 3.87 (s, 3H), 5.16 (s, 2H), 6.56 (dd, J = 8.8, 2.7 Hz, 1H), 6.63 (d, J = 2.7 Hz, 1H), 7.40 (d, J = 8.8 Hz, 1H)

Reference Example 24

8-Hydroxymethyl-7-[2-methoxy-4-(2-methylbenzoyloxy)phenyl]-3,3-dimethyl-3,4-dihydro-1H-quinoxalin-2-one (Reference Compound No. 24)

7-(4-Hydroxy-2-methoxyphenyl)-8-hydroxymethyl-3,3-dimethyl-3,4-dihydro-1H-quinoxalin-2-one (Reference Compound No. 3-5, 430 mg, 1.31 mmol) was dissolved in tetrahydrofuran (10 mL), and triethylamine (365 μL, 2.62 mmol) and 2-methylbenzoyl chloride (222 μL, 1.70 mmol) were added thereto successively. After the reaction mixture was stirred at the same temperature for 80 minutes, the reaction mixture was diluted with ethyl acetate (200 mL). The mixture was washed with water (100 mL) and saturated brine (100 mL) successively, dried over anhydrous magnesium sulfate, and then the solvent was removed under reduced pressure. The obtained residue was purified by silica gel column chromatography (hexane-ethyl acetate) to give the titled reference compound (362 mg) as a colorless solid. (Yield 62%)

Examples

Example 1

8-Benzoyloxymethyl-7-(2-methoxyphenyl)-3,3-dimethyl-3,4-dihydro-1H-quinoxalin-2-one (Compound No. 1-1)

8-Hydroxymethyl-7-(2-methoxyphenyl)-3,3-dimethyl-3,4-dihydro-1H-quinoxalin-2-one (Reference Compound No. 3-1, 54.2 mg, 0.17 mmol) was dissolved in tetrahydrofuran (1.5 mL) and triethylamine (73.0 μL, 0.52 mmol) and benzoyl chloride (30.0 μL, 0.26 mmol) were added thereto successively. The reaction mixture was stirred at room temperature

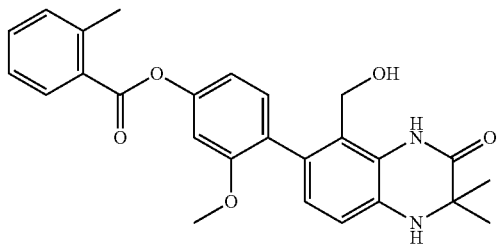 [SMILES: COc1cc(OC(=O)c2ccccc2C)ccc1-c1ccc2c(c1CO)NC(=O)C(C)(C)N2]

$^1$H-NMR (400 MHz, CDCl$_3$)
δ 1.40 (s, 3H), 1.50 (s, 3H), 2.06 (t, J = 4.8 Hz, 1H), 2.70 (s, 3H), 3.78 (s, 1H), 3.79 (s, 3H), 4.49 (d, J = 4.8 Hz, 2H), 6.70 (d, J = 8.1 Hz, 1H), 6.76 (d, J = 8.1 Hz, 1H), 6.84 (d, J = 2.2 Hz, 1H), 6.90 (dd, J = 8.2, 2.2 Hz, 1H), 7.22 (d, J = 8.2 Hz, 1H), 7.34 (d, J = 7.6 Hz, 1H), 7.35 (t, J = 7.6 Hz, 1H), 7.49-7.53 (m, 1H), 8.19 (d, J = 7.6 Hz, 1H), 8.59 (s, 1H)

Reference Example 25

5-Bromothiophene-2-carbonylchloride (Reference Compound No. 25)

A mixture of 5-bromothiophene-2-carboxylic acid (300 mg, 1.45 mmol), thionyl chloride (423 μL, 5.80 mmol), and N,N-dimethylformamide (1 drop) was dissolved in chloroform (3 mL), and refluxed for 1 hour. After cooling down, the reaction mixture was concentrated under reduced pressure to give the titled reference compound (324 mg) as a pale yellow solid. (Yield 99%)

for 24 hours. Ethyl acetate (30 mL) and water (30 mL) were added to the reaction mixture and partitioned. The organic layer was washed with water (30 mL) and saturated brine (30 mL) successively, dried over anhydrous magnesium sulfate, and then the solvent was removed under reduced pressure. The obtained residue was filtered with ethyl acetate to give the titled compound (54.1 mg) as a colorless solid. (Yield 76%)

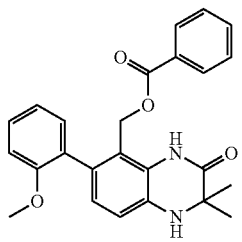

$^1$H-NMR (500 MHz, DMSO-d$_6$)
δ 1.25 (s, 3H), 1.30 (s, 3H), 3.60 (s, 3H), 4.97 (d, J = 12.5 Hz, 1H), 5.19 (d, J = 12.5 Hz, 1H), 6.20 (s, 1H), 6.66 (d, J = 7.9 Hz, 1H), 6.80 (d, J = 7.9 Hz, 1H), 6.94 (td, J = 7.5, 1.0 Hz, 1H), 7.03 (d, J = 8.2 Hz, 1H), 7.10 (dd, J = 7.5, 1.7 Hz, 1H), 7.31 (ddd, J = 8.2, 7.5, 1.7 Hz, 1H), 7.48 (t, J = 7.8 Hz, 2H), 7.61 (t, J = 7.8 Hz, 1H), 7.81 (d, J = 7.8 Hz, 2H), 9.90 (s, 1H)

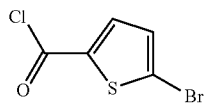

$^1$H-NMR (400 MHz, CDCl$_3$)
δ 7.19 (d, J = 4.2 Hz, 1H), 7.74 (d, J = 4.2 Hz, 1H)

Using any compounds among Reference Compounds No. 3-2, 3-3, 24, and 25, the following Compounds (No. 1-2~1-7) were obtained by a method similar to that of Compound No. 1-1.

| | |
|---|---|
| 8-Benzoyloxymethyl-7-(4-fluoro-2-methoxyphenyl)-3,3-dimethyl-3,4-dihydro-1H-quinoxalin-2-one (Compound No. 1-2) 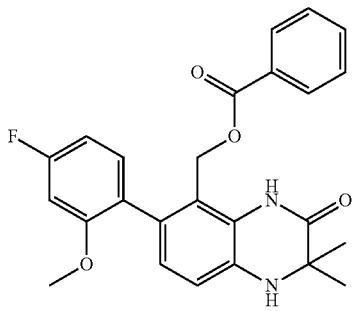 [SMILES: COc1cc(F)ccc1-c1ccc2c(c1COC(=O)c1ccccc1)NC(=O)C(C)(C)N2] | $^1$H-NMR (400 MHz, DMSO-$d_6$) δ 1.24 (s, 3H), 1.30 (s, 3H), 3.60 (s, 3H), 4.96 (d, J = 12.4 Hz, 1H), 5.17 (d, J = 12.4 Hz, 1H), 6.19 (s, 1H), 6.64 (d, J = 8.1 Hz, 1H), 6.74 (td, J = 8.4, 2.5 Hz, 1H), 6.78 (d, J = 8.1 Hz, 1H), 6.93 (dd, J = 11.5, 2.5 Hz, 1H), 7.11 (dd, J = 8.4, 7.1 Hz, 1H), 7.48 (t, J = 7.8 Hz, 2H), 7.62 (t, J = 7.8 Hz, 1H), 7.81 (d, J = 7.8 Hz, 2H), 9.92 (s, 1H) |
| 8-Benzoyloxymethyl-7-(5-fluoro-2-methoxyphenyl)-3,3-dimethyl-3,4-dihydro-1H-quinoxalin-2-one (Compound No. 1-3) 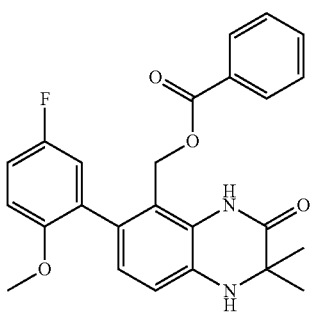 [SMILES: COc1ccc(F)cc1-c1ccc2c(c1COC(=O)c1ccccc1)NC(=O)C(C)(C)N2] | $^1$H-NMR (400 MHz, DMSO-$d_6$) δ 1.23 (s, 3H), 1.30 (s, 3H), 3.58 (s, 3H), 4.98 (d, J = 12.5 Hz, 1H), 5.21 (d, J = 12.5 Hz, 1H), 6.23 (s, 1H), 6.68 (d, J = 8.1 Hz, 1H), 6.79 (d, J = 8.1 Hz, 1H), 6.96 (dd, J = 9.0, 3.2 Hz, 1H), 7.02 (dd, J = 8.9, 4.6 Hz, 1H), 7.13 (td, J = 8.9, 3.2 Hz, 1H), 7.48 (t, J = 7.4 Hz, 2H), 7.62 (t, J = 7.4 Hz, 1H), 7.81 (d, J = 7.4 Hz, 2H), 9.94 (s, 1H) |
| 7-[2-Methoxy-4-(2-methylbenzoyloxy)phenyl]-8-(4-methoxybenzoyloxymethyl)-3,3-dimethyl-3,4-dihydro-1H-quinoxalin-2-one (Compound No. 1-4) 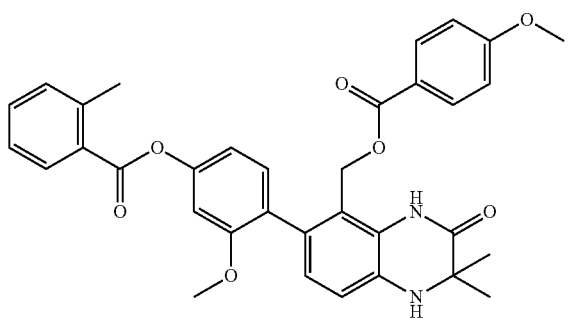 [SMILES: COc1ccc(C(=O)OCc2c(-c3ccc(OC(=O)c4ccccc4C)cc3OC)ccc3c2NC(=O)C(C)(C)N3)cc1] | $^1$H-NMR (400 MHz, CDCl$_3$) δ 1.46 (s, 6H), 2.71 (s, 3H), 3.69 (s, 3H), 3.80 (s, 1H), 3.85 (s, 3H), 5.02 (d, J = 12.8 Hz, 1H), 5.33 (d, J = 12.8 Hz, 1H), 6.74 (d, J = 8.2 Hz, 1H), 6.82 (d, J = 2.2 Hz, 1H), 6.83 (d, J = 8.2 Hz, 1H), 6.89 (d, J = 9.0 Hz, 2H), 6.90 (dd, J = 8.1, 2.2 Hz, 1H), 7.26 (d, J = 8.1 Hz, 1H), 7.35 (t, J = 8.0 Hz, 1H), 7.36 (d, J = 8.0 Hz, 1H), 7.48-7.52 (m, 1H), 7.93 (d, J = 9.0 Hz, 2H), 8.19 (d, J = 8.0 Hz, 1H), 8.65 (s, 1H) |
| 7-[2-Methoxy-4-(2-methylbenzoyloxy)phenyl]-8-(4-methylbenzoyloxymethyl)-3,3-dimethyl-3,4-dihydro-1H-quinoxalin-2-one (Compound No. 1-5) 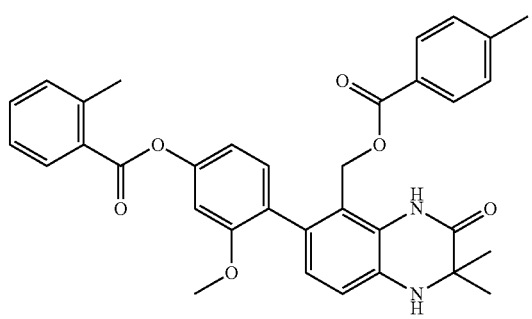 [SMILES: COc1cc(OC(=O)c2ccccc2C)ccc1-c1ccc2c(c1COC(=O)c1ccc(C)cc1)NC(=O)C(C)(C)N2] | $^1$H-NMR (400 MHz, CDCl$_3$) δ 1.45 (s, 6H), 2.39 (s, 3H), 2.71 (s, 3H), 3.68 (s, 3H), 3.81 (s, 1H), 5.03 (d, J = 12.8 Hz, 1H), 5.34 (d, J = 12.8 Hz, 1H), 6.75 (d, J = 8.2 Hz, 1H), 6.82 (d, J = 2.0 Hz, 1H), 6.83 (d, J = 8.2 Hz, 1H), 6.90 (dd, J = 8.2, 2.0 Hz, 1H), 7.21 (d, J = 8.2 Hz, 2H), 7.26 (d, J = 8.2 Hz, 1H), 7.34 (d, J = 7.9 Hz, 1H), 7.35 (t, J = 7.9 Hz, 1H), 7.49-7.52 (m, 1H), 7.87 (d, J = 8.2 Hz, 2H), 8.19 (d, J = 7.9 Hz, 1H), 8.59 (s, 1H) |

| | |
|---|---|
| 8-(3-Fluorobenzoyloxymethyl)-7-[2-methoxy-4-(2-methylbenzoyloxy)phenyl]-3,3-dimethyl-3,4-dihydro-1H-quinoxalin-2-one (Compound No. 1-6)<br>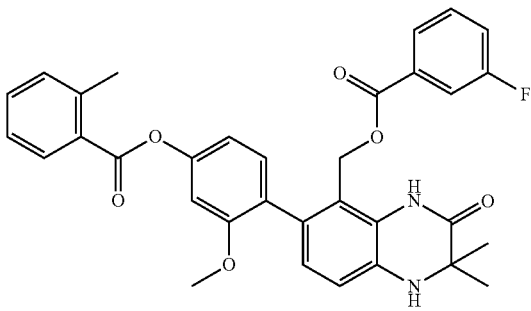 | $^1$H-NMR (500 MHz, CDCl$_3$)<br>δ 1.46 (s, 3H), 1.46 (s, 3H), 2.71 (s, 3H), 3.69 (s, 3H), 3.82 (s, 1H), 5.07 (d, J = 12.7 Hz, 1H), 5.35 (d, J = 12.7 Hz, 1H), 6.76 (d, J = 8.2 Hz, 1H), 6.83 (d, J = 2.1 Hz, 1H), 6.83 (d, J = 8.2 Hz, 1H), 6.91 (dd, J = 8.2, 2.1 Hz, 1H), 7.23-7.29 (m, 2H), 7.33-7.37 (m, 2H), 7.40 (td, J = 7.8, 5.6 Hz, 1H), 7.49-7.52 (m, 1H), 7.63-7.66 (m, 1H), 7.77 (d, J = 7.8 Hz, 1H), 8.19 (d, J = 7.6 Hz, 1H), 8.49 (s, 1H) |
| 8-(5-Bromothiophen-2-ylcarbonyloxymethyl)-7-[2-methoxy-4-(2-methylbenzoyloxy)phenyl]-3,3-dimethyl-3,4-dihydro-1H-quinoxalin-2-one (Compound No. 1-7)<br>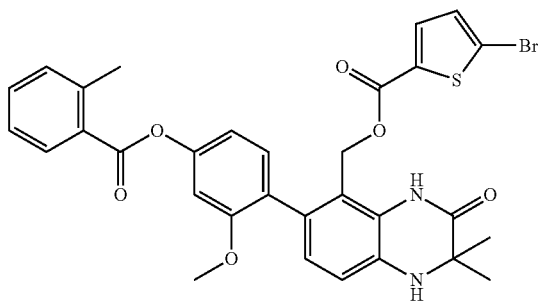 [SMILES: COc1cc(OC(=O)c2ccccc2C)ccc1-c1ccc2c(c1COC(=O)c1ccc(Br)s1)NC(=O)C(C)(C)N2] | $^1$H-NMR (400 MHz, CDCl$_3$)<br>δ 1.45 (s, 3H), 1.46 (s, 3H), 2.71 (s, 3H), 3.71 (s, 3H), 3.81 (s, 1H), 5.01 (d, J = 12.7 Hz, 1H), 5.30 (d, J = 12.7 Hz, 1H), 6.75 (d, J = 8.1 Hz, 1H), 6.82 (d, J = 8.1 Hz, 1H), 6.83 (d, J = 2.2 Hz, 1H), 6.91 (dd, J = 8.1, 2.2 Hz, 1H), 7.06 (d, J = 3.9 Hz, 1H), 7.25 (d, J = 8.1 Hz, 1H), 7.34 (d, J = 7.7 Hz, 1H), 7.35 (t, J = 7.7 Hz, 1H), 7.49-7.52 (m, 1H), 7.52 (d, J = 3.9 Hz, 1H), 8.19 (d, J = 7.7 Hz, 1H), 8.47 (s, 1H) |

Example 2

7-(5-Fluoro-2-methoxyphenyl)-8-(5-methylthiophen-2-ylcarbonyloxymethyl)-3,3-dimethyl-3,4-dihydro-1H-quinoxalin-2-one (Compound No. 2-1)

8-Chloromethyl-7-(5-fluoro-2-methoxyphenyl)-3,3-dimethyl-3,4-dihydro-1H-quinoxalin-2-one (Reference Compound No. 4-2, 50.9 mg, 0.14 mmol), 5-methyl-2-thiophenecarboxylic acid (62.5 mg, 0.44 mmol), and potassium carbonate (79.9 mg, 0.58 mmol) were suspended in anhydrous. N,N-dimethylformamide (1.5 mL) and stirred at 80° C. for 4.5 hours. Ethyl acetate (30 mL) and water (30 mL) were added to the reaction mixture and partitioned. The organic layer was washed with water (30 mL) and saturated brine (30 mL) successively, dried over anhydrous magnesium sulfate, and then the solvent was removed under reduced pressure. The obtained residue was purified by silica gel column chromatography (hexane-ethyl acetate) to give the titled compound (55.0 mg) as a colorless solid. (Yield 85%)

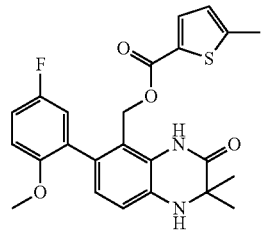 [SMILES: COc1ccc(F)cc1-c1ccc2c(c1COC(=O)c1ccc(C)s1)NC(=O)C(C)(C)N2]

$^1$H-NMR (400 MHz, DMSO-d$_6$)
δ 1.23 (s, 3H), 1.30 (s, 3H), 2.47 (s, 3H), 3.60 (s, 3H), 4.90 (d, J = 12.5 Hz, 1H), 5.17 (d, J = 12.5 Hz, 1H), 6.22 (s, 1H), 6.67 (d, J = 8.1 Hz, 1H), 6.78 (d, J = 8.1 Hz, 1H), 6.88 (d, J = 3.7 Hz, 1H), 6.94 (dd, J = 9.0, 3.2 Hz, 1H), 7.02 (dd, J = 8.9, 4.6 Hz, 1H), 7.14 (td, J = 8.9, 3.2 Hz, 1H), 7.46 (d, J = 3.7 Hz, 1H), 9.86 (s, 1H)

Using any compounds among Reference Compounds No. 4-1~4-3, 14-1, 14-2, and available compounds, the following Compounds (No. 2-2~2-19) were obtained by a method similar to that of Compound No. 2-1.

| Compound | NMR |
|---|---|
| 7-(5-Fluoro-2-methoxyphenyl)-8-(4-methylbenzoyloxymethyl)-3,3-dimethyl-3,4-dihydro-1H-quinoxalin-2-one (Compound No. 2-2) 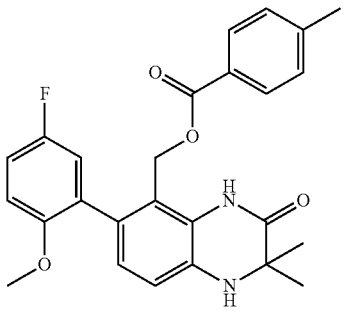 | 1H-NMR (400 MHz, DMSO-d$_6$) δ 1.23 (s, 3H), 1.30 (s, 3H), 2.35 (s, 3H), 3.58 (s, 3H), 4.95 (d, J = 12.5 Hz, 1H), 5.19 (d, J = 12.5 Hz, 1H), 6.23 (s, 1H), 6.67 (d, J = 8.1 Hz, 1H), 6.78 (d, J = 8.1 Hz, 1H), 6.95 (dd, J = 9.0, 3.2 Hz, 1H), 7.01 (dd, J = 9.0, 4.8 Hz, 1H), 7.13 (td, J = 9.0, 3.2 Hz, 1H), 7.27 (d, J = 8.1 Hz, 2H), 7.70 (d, J = 8.1 Hz, 2H), 9.92 (s, 1H) |
| 7-(5-Fluoro-2-methoxyphenyl)-8-(3-methylbenzoyloxymethyl)-3,3-dimethyl-3,4-dihydro-1H-quinoxalin-2-one (Compound No. 2-3) 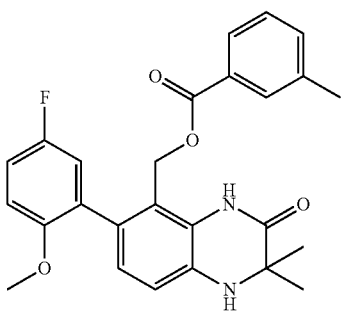 | $^1$H-NMR (500 MHz, DMSO-d$_6$) δ 1.23 (s, 3H), 1.31 (s, 3H), 2.32 (s, 3H), 3.59 (s, 3H), 4.97 (d, J = 12.5 Hz, 1H), 5.21 (d, J = 12.5 Hz, 1H), 6.23 (s, 1H), 6.68 (d, J = 8.1 Hz, 1H), 6.79 (d, J = 8.1 Hz, 1H), 6.96 (dd, J = 9.0, 3.2 Hz, 1H), 7.02 (dd, J = 8.8, 4.5 Hz, 1H), 7.13 (td, J = 8.8, 3.2 Hz, 1H), 7.36 (t, J = 7.8 Hz, 1H), 7.43 (d, J = 7.8 Hz, 1H), 7.60-7.61 (m, 2H), 9.94 (s, 1H) |
| 7-(5-Fluoro-2-methoxyphenyl)-8-(2-methylbenzoyloxymethyl)-3,3-dimethyl-3,4-dihydro-1H-quinoxalin-2-one (Compound No. 2-4) 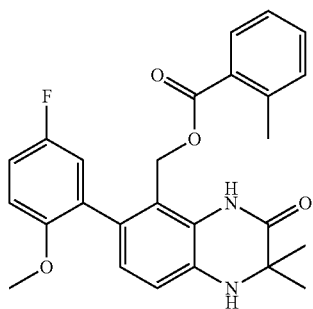 | $^1$H-NMR (400 MHz, CDCl$_3$) δ 1.45 (s, 6H), 2.55 (s, 3H), 3.65 (s, 3H), 3.82 (s, 1H), 4.99 (d, J = 12.8 Hz, 1H), 5.32 (d, J = 12.8 Hz, 1H), 6.74 (d, J = 8.1 Hz, 1H), 6.80 (d, J = 8.1 Hz, 1H), 6.86 (dd, J = 8.8, 4.4 Hz, 1H), 6.95 (dd, J = 8.8, 3.2 Hz, 1H), 7.04 (td, J = 8.8, 3.2 Hz, 1H), 7.20-7.23 (m, 2H), 7.37-7.41 (m, 1H), 7.84 (dd, J = 8.3, 1.4 Hz, 1H), 8.51 (s, 1H) |
| 7-(5-Fluoro-2-methoxyphenyl)-8-(thiophen-2-ylcarbonyloxymethyl)-3,3-dimethyl-3,4-dihydro-1H-quinoxalin-2-one (Compound No. 2-5) 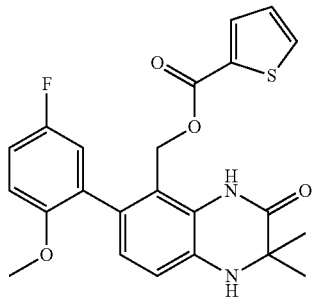 | $^1$H-NMR (500 MHz, DMSO-d$_6$) δ 1.23 (s, 3H), 1.30 (s, 3H), 3.60 (s, 3H), 4.93 (d, J = 12.5 Hz, 1H), 5.20 (d, J = 12.5 Hz, 1H), 6.22 (s, 1H), 6.67 (d, J = 8.2 Hz, 1H), 6.79 (d, J = 8.2 Hz, 1H), 6.95 (dd, J = 9.1, 3.2 Hz, 1H), 7.03 (dd, J = 8.9, 4.6 Hz, 1H), 7.14 (td, J = 8.9, 3.2 Hz, 1H), 7.17 (dd, J = 4.9, 3.7 Hz, 1H), 7.65 (dd, J = 3.7, 1.3 Hz, 1H), 7.90 (dd, J = 4.9, 1.3 Hz, 1H), 9.89 (s, 1H) |

| Compound | NMR |
|---|---|
| 7-(5-Fluoro-2-methoxyphenyl)-8-(4-methoxybenzoyloxymethyl)-3,3-dimethyl-3,4-dihydro-1H-quinoxalin-2-one (Compound No. 2-6)<br>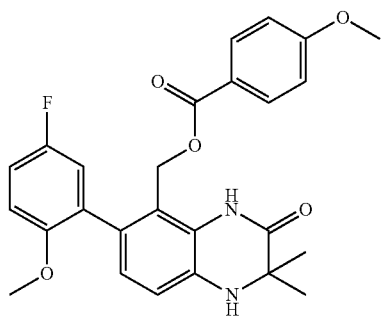 | $^1$H-NMR (400 MHz, DMSO-d$_6$) δ 1.23 (s, 3H), 1.30 (s, 3H), 3.58 (s, 3H), 3.81 (s, 3H), 4.94 (d, J = 12.6 Hz, 1H), 5.18 (d, J = 12.6 Hz, 1H), 6.22 (s, 1H), 6.67 (d, J = 8.1 Hz, 1H), 6.78 (d, J = 8.1 Hz, 1H), 6.95 (dd, J = 9.0, 3.2 Hz, 1H), 7.00 (d, J = 9.0 Hz, 2H), 7.00-7.03 (m, 1H), 7.13 (td, J = 8.6, 3.2 Hz, 1H), 7.76 (d, J = 9.0 Hz, 2H), 9.90 (s, 1H) |
| 7-(4-Fluoro-2-methoxyphenyl)-8-(4-methoxybenzoyloxymethyl)-1,3,3-trimethyl-3,4-dihydro-1H-quinoxalin-2-one (Compound No. 2-7)<br>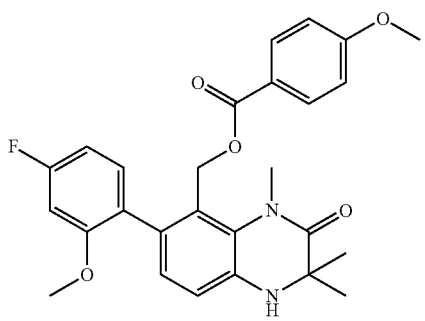 [SMILES: COc1ccc(C(=O)OCc2c(-c3ccc(F)cc3OC)ccc3c2N(C)C(=O)C(C)(C)N3)cc1] | $^1$H-NMR (400 MHz, CDCl$_3$) δ 1.20 (s, 3H), 1.42 (s, 3H), 3.47 (s, 3H), 3.74 (s, 3H), 3.79 (s, 1H), 3.83 (s, 3H), 5.14 (d, J = 13.4 Hz, 1H), 5.28 (d, J = 13.4 Hz, 1H), 6.63-6.68 (m, 1H), 6.64 (d, J = 9.3 Hz, 1H), 6.76 (d, J = 7.8 Hz, 1H), 6.84 (d, J = 9.0 Hz, 2H), 6.82-6.86 (m, 1H), 7.21 (t, J = 7.5 Hz, 1H), 7.78 (d, J = 9.0 Hz, 2H) |
| 7-(4-Fluoro-2-methoxyphenyl)-8-(thiophen-2-ylcarbonyloxymethyl)-1,3,3-trimethyl-3,4-dihydro-1H-quinoxalin-2-one (Compound No. 2-8)<br>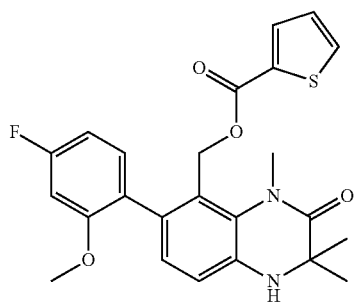 [SMILES: COc1cc(F)ccc1-c1ccc2c(c1COC(=O)c1cccs1)N(C)C(=O)C(C)(C)N2] | $^1$H-NMR (400 MHz, CDCl$_3$) δ 1.20 (s, 3H), 1.42 (s, 3H), 3.46 (s, 3H), 3.75 (s, 3H), 3.79 (s, 1H), 5.14 (d, J = 13.3 Hz, 1H), 5.28 (d, J = 13.3 Hz, 1H), 6.65-6.69 (m, 2H), 6.76 (d, J = 8.1 Hz, 1H), 6.85 (d, J = 8.1 Hz, 1H), 7.04 (dd, J = 5.0, 3.8 Hz, 1H), 7.20 (dd, J = 8.5, 6.5 Hz, 1H), 7.50 (dd, J = 5.0, 1.2 Hz, 1H), 7.63 (dd, J = 3.8, 1.2 Hz, 1H) |
| 7-(4-Fluoro-2-methoxyphenyl)-8-(5-methylthiophen-2-ylcarbonyloxymethyl)-1,3,3-trimethyl-3,4-dihydro-1H-quinoxalin-2-one (Compound No. 2-9)<br>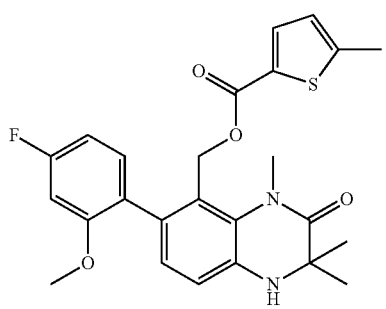 [SMILES: COc1cc(F)ccc1-c1ccc2c(c1COC(=O)c1ccc(C)s1)N(C)C(=O)C(C)(C)N2] | $^1$H-NMR (500 MHz, DMSO-d$_6$) δ 1.02 (s, 3H), 1.24 (s, 3H), 2.46 (s, 3H), 3.30 (s, 3H), 3.72 (s, 3H), 5.04 (d, J = 13.4 Hz, 1H), 5.21 (d, J = 13.4 Hz, 1H), 6.22 (s, 1H), 6.76 (d, J = 7.9 Hz, 1H), 6.78 (td, J = 8.4, 2.4 Hz, 1H), 6.83 (d, J = 7.9 Hz, 1H), 6.87 (d, J = 3.7 Hz, 1H), 6.96 (dd, J = 11.3, 2.4 Hz, 1H), 7.23 (dd, J = 8.4, 7.2 Hz, 1H), 7.38 (d, J = 3.7 Hz, 1H) |

| Compound | NMR |
|---|---|
| 7-(5-Chloro-2-methoxyphenyl)-8-(4-methoxybenzoyloxymethyl)-1,3,3-trimethyl-3,4-dihydro-1H-quinoxalin-2-one (Compound No. 2-10)<br />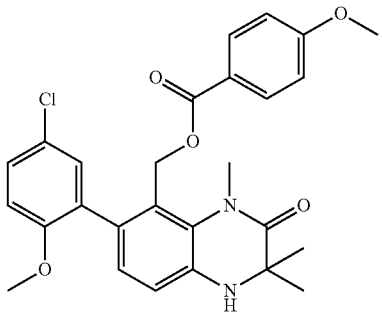 [SMILES: COc1ccc(C(=O)OCc2c(-c3cc(Cl)ccc3OC)ccc3c2N(C)C(=O)C(C)(C)N3)cc1] | $^1$H-NMR (400 MHz, DMSO-d$_6$) δ 1.02 (s, 3H), 1.25 (s, 3H), 3.32 (s, 3H), 3.71 (s, 3H), 3.80 (s, 3H), 5.09 (d, J = 13.4 Hz, 1H), 5.25 (d, J = 13.4 Hz, 1H), 6.28 (s, 1H), 6.81 (d, J = 8.1 Hz, 1H), 6.84 (d, J = 8.1 Hz, 1H), 6.96 (dt, J = 9.0, 2.5 Hz, 2H), 7.07 (d, J = 8.9 Hz, 1H), 7.26 (d, J = 2.7 Hz, 1H), 7.36 (dd, J = 8.9, 2.7 Hz, 1H), 7.66 (dt, J = 9.0, 2.5 Hz, 2H) |
| 7-(5-Chloro-2-methoxyphenyl)-8-(thiophen-2-ylcarbonyloxymethyl)-1,3,3-trimethyl-3,4-dihydro-1H-quinoxalin-2-one (Compound No. 2-11)<br />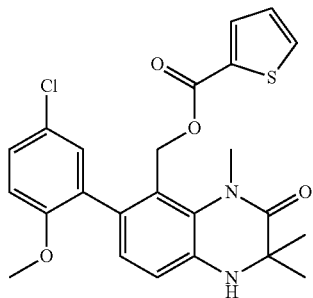 [SMILES: COc1ccc(Cl)cc1-c1ccc2c(c1COC(=O)c1cccs1)N(C)C(=O)C(C)(C)N2] | $^1$H-NMR (400 MHz, CDCl$_3$) δ 1.23 (s, 3H), 1.42 (s, 3H), 3.45 (s, 3H), 3.75 (s, 3H), 3.82 (s, 1H), 5.14 (d, J = 13.3 Hz, 1H), 5.30 (d, J = 13.3 Hz, 1H), 6.77 (d, J = 8.1 Hz, 1H), 6.83-6.87 (m, 1H), 6.86 (d, J = 8.1 Hz, 1H), 7.04 (dd, J = 5.0, 3.7 Hz, 1H), 7.23-7.29 (m, 2H), 7.51 (dd, J = 5.0, 1.2 Hz, 1H), 7.63 (dd, J = 3.7, 1.2 Hz, 1H) |
| 7-(5-Chloro-2-methoxyphenyl)-8-(5-methylthiophen-2-ylcarbonyloxymethyl)-1,3,3-trimethyl-3,4-dihydro-1H-quinoxalin-2-one (Compound No. 2-12)<br />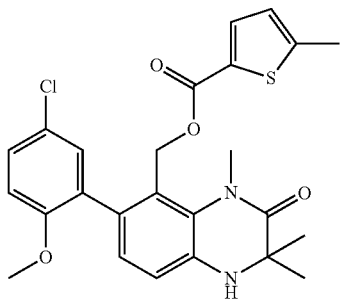 | $^1$H-NMR (400 MHz, CDCl$_3$) δ 1.24 (s, 3H), 1.41 (s, 3H), 2.48 (s, 3H), 3.44 (s, 3H), 3.75 (s, 3H), 3.81 (s, 1H), 5.09 (d, J = 13.2 Hz, 1H), 5.27 (d, J = 13.2 Hz, 1H), 6.70 (d, J = 3.8 Hz, 1H), 6.76 (d, J = 8.0 Hz, 1H), 6.83-6.87 (m, 1H), 6.86 (d, J = 8.0 Hz, 1H), 7.23-7.26 (m, 2H), 7.43 (d, J = 3.8 Hz, 1H) |
| 7-(2-Methoxy-4-methoxymethoxyphenyl)-8-(5-methylthiophen-2-ylcarbonyloxymethyl)-3,3-dimethyl-3,4-dihydro-1H-quinoxalin-2-one (Compound No. 2-13)<br />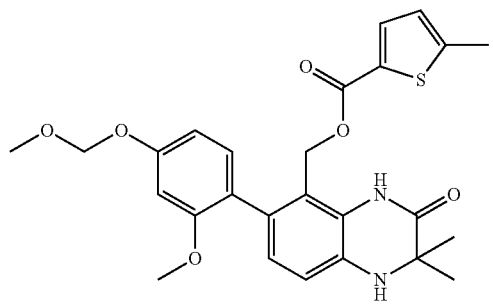 | $^1$H-NMR(500 MHz, CDCl$_3$) δ 1.44 (s, 6H), 2.51 (s, 3H), 3.53 (s, 3H), 3.68 (s, 3H), 3.76 (s, 1H), 4.98 (d, J = 12.5 Hz, 1H), 5.22 (d, J = 6.7 Hz, 1H), 5.23 (d, J = 6.7 Hz, 1H), 5.26 (d, J = 12.5 Hz, 1H), 6.64 (d, J = 2.3 Hz, 1H), 6.71 (dd, J = 8.2, 2.3 Hz, 1H), 6.72 (d, J = 8.1 Hz, 1H), 6.74 (d, J = 3.7 Hz, 1H), 6.79 (d, J = 8.1 Hz, 1H), 7.11 (d, J = 8.2 Hz, 1H), 7.58 (d, J = 3.7 Hz, 1H), 8.48 (s, 1H) |

| Compound | NMR |
|---|---|
| 7-(5-Chloro-2-methoxyphenyl)-8-(5-chlorothiophen-2-ylcarbonyloxymethyl)-1,3,3-trimethyl-3,4-dihydro-1H-quinoxalin-2-one (Compound No. 2-14) 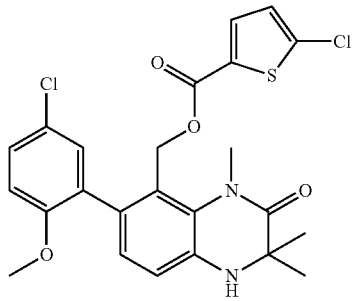 [SMILES: COc1ccc(Cl)cc1-c1ccc2c(c1COC(=O)c1ccc(Cl)s1)N(C)C(=O)C(C)(C)N2] | $^1$H-NMR (500 MHz, CDCl$_3$) δ 1.25 (s, 3H), 1.42 (s, 3H), 3.43 (s, 3H), 3.75 (s, 3H), 3.83 (s, 1H), 5.12 (d, J = 13.1 Hz, 1H), 5.28 (d, J = 13.1 Hz, 1H), 6.77 (d, J = 8.3 Hz, 1H), 6.85 (d, J = 8.3 Hz, 1H), 6.86 (d, J = 7.6 Hz, 1H), 6.87 (d, J = 4.0 Hz, 1H), 7.22-7.27 (m, 2H), 7.40 (d, J = 4.0 Hz, 1H) |
| 7-(5-Chloro-2-methoxyphenyl)-8-(5-ethylthiophen-2-ylcarbonyloxymethyl)-1,3,3-trimethyl-3,4-dihydro-1H-quinoxalin-2-one (Compound No. 2-15) 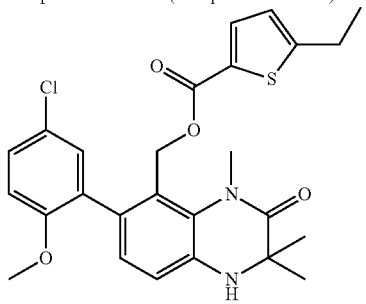 | $^1$H-NMR (400 MHz, CDCl$_3$) δ 1.25 (s, 3H), 1.29 (t, J = 7.6 Hz, 3H), 1.41 (s, 3H), 2.83 (q, J = 7.6 Hz, 2H), 3.44 (s, 3H), 3.75 (s, 3H), 3.81 (s, 1H), 5.09 (d, J = 13.2 Hz, 1H), 5.28 (d, J = 13.2 Hz, 1H), 6.74 (d, J = 3.7 Hz, 1H), 6.76 (d, J = 8.1 Hz, 1H), 6.84 (d, J = 9.5 Hz, 1H), 6.86 (d, J = 8.1 Hz, 1H), 7.23-7.26 (m, 2H), 7.46 (d, J = 3.7 Hz, 1H) |
| 8-(5-Bromothiophen-2-ylcarbonyloxymethyl)-7-(4-fluoro-2-methoxyphenyl)-1,3,3-trimethyl-3,4-dihydro-1H-quinoxalin-2-one (Compound No. 2-16) 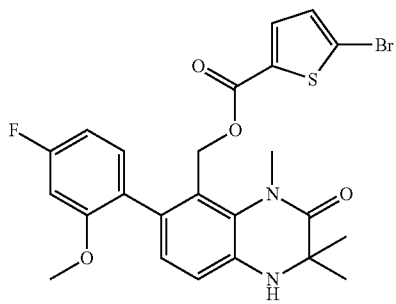 [SMILES: COc1cc(F)ccc1-c1ccc2c(c1COC(=O)c1ccc(Br)s1)N(C)C(=O)C(C)(C)N2] | $^1$H-NMR (400 MHz, CDCl$_3$) δ 1.23 (s, 3H), 1.42 (s, 3H), 3.44 (s, 3H), 3.75 (s, 3H), 3.80 (s, 1H), 5.11 (d, J = 13.2 Hz, 1H), 5.27 (d, J = 13.2 Hz, 1H), 6.64-6.70 (m, 2H), 6.76 (d, J = 8.1 Hz, 1H), 6.84 (d, J = 8.1 Hz, 1H), 7.01 (d, J = 3.9 Hz, 1H), 7.17-7.21 (m, 1H), 7.37 (d, J = 3.9 Hz, 1H) |
| 8-(4-Chlorobenzoyloxymethyl)-7-(5-chloro-2-methoxyphenyl)-1,3,3-trimethyl-3,4-dihydro-1H-quinoxalin-2-one (Compound No. 2-17) 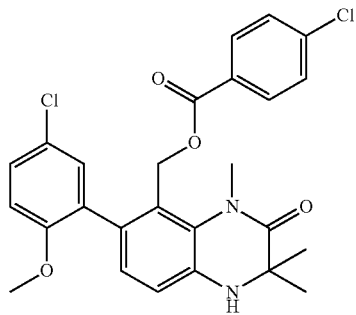 [SMILES: COc1ccc(Cl)cc1-c1ccc2c(c1COC(=O)c1ccc(Cl)cc1)N(C)C(=O)C(C)(C)N2] | $^1$H-NMR (500 MHz, CDCl$_3$) δ 1.23 (s, 3H), 1.41 (s, 3H), 3.44 (s, 3H), 3.74 (s, 3H), 3.82 (s, 1H), 5.16 (d, J = 13.3 Hz, 1H), 5.34 (d, J = 13.3 Hz, 1H), 6.77 (d, J = 8.0 Hz, 1H), 6.83 (d, J = 9.4 Hz, 1H), 6.87 (d, J = 8.0 Hz, 1H), 7.22-7.26 (m, 2H), 7.35 (d, J = 8.9 Hz, 2H), 7.75 (d, J = 8.9 Hz, 2H) |

7-(5-Chloro-2-methoxyphenyl)-8-(5-methoxyfuran-2-ylcarbonyloxymethyl)-1,3,3-trimethyl-3,4-dihydro-1H-quinoxalin-2-one (Compound No. 2-18)

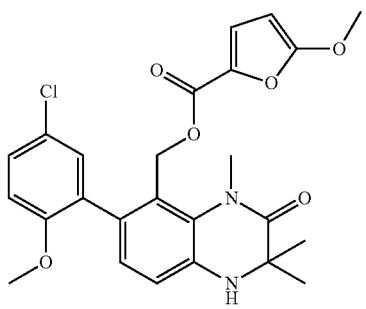 [SMILES: COc1ccc(C(=O)OCc2c(-c3cc(Cl)ccc3OC)ccc3c2N(C)C(=O)C(C)(C)N3)o1]

$^1$H-NMR (500 MHz, CDCl$_3$)
δ 1.25 (s, 3H), 1.40 (s, 3H), 3.43 (s, 3H), 3.75 (s, 3H), 3.80 (s, 1H), 3.90 (s, 3H), 5.07 (d, J = 13.3 Hz, 1H), 5.23 (d, J = 13.3 Hz, 1H), 5.26 (d, J = 3.7 Hz, 1H), 6.75 (d, J = 7.9 Hz, 1H), 6.82-6.75 (m, 1H), 6.84 (d, J = 7.9 Hz, 1H), 6.93 (d, J = 3.7 Hz, 1H), 7.24-7.26 (m, 2H)

7-(4-Fluoro-2-methoxyphenyl)-8-(5-methylthiophen-2-ylcarbonyloxymethyl)-3,3-dimethyl-3,4-dihydro-1H-quinoxalin-2-one (Compound No. 2-19)

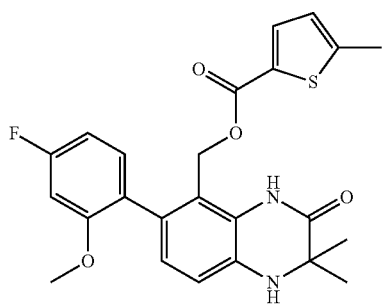 [SMILES: COc1cc(F)ccc1-c1ccc2c(c1COC(=O)c1ccc(C)s1)NC(=O)C(C)(C)N2]

$^1$H-NMR (400 MHz, DMSO-d$_6$)
δ 1.24 (s, 3H), 1.30 (s, 3H), 2.48 (s, 3H), 3.63 (s, 3H), 4.88 (d, J = 12.5 Hz, 1H), 5.13 (d, J = 12.5 Hz, 1H), 6.19 (s, 1H), 6.63 (d, J = 8.1 Hz, 1H), 6.77 (td, J = 8.4, 2.4 Hz, 1H), 6.78 (d, J = 8.1 Hz, 1H), 6.89 (d, J = 3.8 Hz, 1H), 6.94 (dd, J = 11.5, 2.4 Hz, 1H), 7.10 (dd, J = 8.4, 7.1 Hz, 1H), 7.47 (d, J = 3.8 Hz, 1H), 9.84 (s, 1H)

Example 3

7-(4-Fluoro-2-methoxyphenyl)-8-phenoxymethyl-3,3-dimethyl-3,4-dihydro-1H-quinoxalin-2-one (Compound No. 3-1)

A mixture of 8-chloromethyl-7-(4-fluoro-2-methoxyphenyl)-3,3-dimethyl-3,4-dihydro-1H-quinoxalin-2-one (Reference Compound No. 4-1, 47.1 mg, 0.14 mmol), phenol (37.5 mg, 0.40 mmol), and potassium carbonate (73.0 mg, 0.53 mmol) was suspended in anhydrous N,N-dimethylformamide (1.5 mL) and stirred at 80° C. for 19 hours. After cooling down, ethyl acetate (30 mL) and water (30 mL) were added to the reaction mixture and partitioned. The organic layer was washed with water (30 mL) and saturated brine (30 mL) successively, dried over anhydrous magnesium sulfate, and then the solvent was removed under reduced pressure. The obtained residue was purified by silica gel column chromatography (hexane-ethyl acetate) to give the titled compound (35.7 mg) as a pale yellow solid. (Yield 67%)

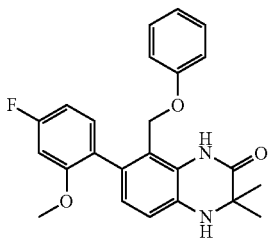 [SMILES: COc1cc(F)ccc1-c1ccc2c(c1COc1ccccc1)NC(=O)C(C)(C)N2]

$^1$H-NMR (400 MHz, DMSO-d$_6$)
δ 1.18 (s, 3H), 1.27 (s, 3H), 3.68 (s, 3H), 4.62 (d, J = 11.5 Hz, 1H), 5.11 (d, J = 11.5 Hz, 1H), 6.14 (s, 1H), 6.63 (d, J = 8.1 Hz, 1H), 6.74 (d, J = 8.1 Hz, 1H), 6.71-6.77 (m, 3H), 6.87 (t, J = 7.3 Hz, 1H), 6.93 (dd, J = 11.4, 2.6 Hz, 1H), 7.12 (dd, J = 8.3, 7.1 Hz, 1H), 7.19 (dd, J = 8.5, 7.3 Hz, 2H), 9.50 (s, 1H)

Using any compounds among Reference Compounds No. 4-2, 14-1, 14-2, and available compounds, the following Compounds (No. 3-2~3-19) were obtained by a method similar to that of Compound No. 3-1.

| Compound | NMR |
|---|---|
| 7-(5-Fluoro-2-methoxyphenyl)-8-phenoxymethyl-3,3-dimethyl-3,4-dihydro-1H-quinoxalin-2-one (Compound No. 3-2)<br />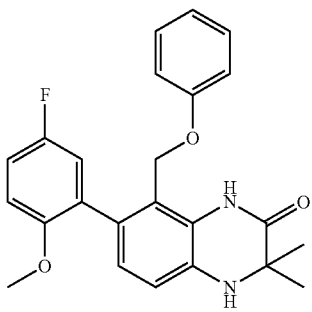 [SMILES: COc1ccc(F)cc1-c1ccc2c(c1COc1ccccc1)NC(=O)C(C)(C)N2] | $^1$H-NMR (400 MHz, DMSO-$d_6$) δ 1.19 (s, 3H), 1.28 (s, 3H), 3.65 (s, 3H), 4.62 (d, J = 11.5 Hz, 1H), 5.15 (d, J = 11.5 Hz, 1H), 6.18 (s, 1H), 6.67 (d, J = 8.1 Hz, 1H), 6.73 (d, J = 8.8 Hz, 2H), 6.75 (d, J = 8.1 Hz, 1H), 6.87 (t, J = 7.3 Hz, 1H), 6.94 (dd, J = 9.3, 3.2 Hz, 1H), 7.01 (dd, J = 8.9, 4.9 Hz, 1H), 7.11 (td, J = 8.9, 3.2 Hz, 1H), 7.19 (dd, J = 8.8, 7.3 Hz, 2H), 9.56 (s, 1H) |
| 7-(5-Fluoro-2-methoxyphenyl)-8-(3-fluorophenoxymethyl)-3,3-dimethyl-3,4-dihydro-1H-quinoxalin-2-one (Compound No. 3-3)<br />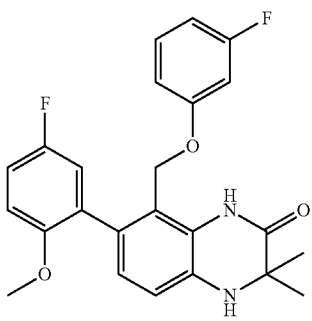 [SMILES: COc1ccc(F)cc1-c1ccc2c(c1COc1cccc(F)c1)NC(=O)C(C)(C)N2] | $^1$H-NMR (500 MHz, DMSO-$d_6$) δ 1.19 (s, 3H), 1.28 (s, 3H), 3.64 (s, 3H), 4.63 (d, J = 11.6 Hz, 1H), 5.15 (d, J = 11.6 Hz, 1H), 6.19 (s, 1H), 6.56-6.59 (m, 2H), 6.67 (d, J = 8.2 Hz, 1H), 6.68-6.72 (m, 1H), 6.76 (d, J = 8.2 Hz, 1H), 6.93 (dd, J = 9.2, 3.1 Hz, 1H), 7.01 (dd, J = 8.8, 4.7 Hz, 1H), 7.11 (td, J = 8.8, 3.1 Hz, 1H), 7.19-7.24 (m, 1H), 9.66 (s, 1H) |
| 7-(5-Fluoro-2-methoxyphenyl)-8-(4-methylphenoxymethyl)-3,3-dimethyl-3,4-dihydro-1H-quinoxalin-2-one (Compound No. 3-4)<br />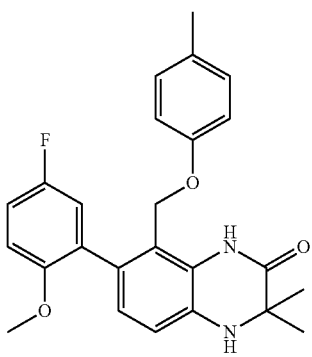 [SMILES: COc1ccc(F)cc1-c1ccc2c(c1COc1ccc(C)cc1)NC(=O)C(C)(C)N2] | $^1$H-NMR (400 MHz, DMSO-$d_6$) δ 1.18 (s, 3H), 1.28 (s, 3H), 2.18 (s, 3H), 3.64 (s, 3H), 4.58 (d, J = 11.7 Hz, 1H), 5.12 (d, J = 11.7 Hz, 1H), 6.17 (s, 1H), 6.61 (d, J = 8.7 Hz, 2H), 6.66 (d, J = 8.1 Hz, 1H), 6.74 (d, J = 8.1 Hz, 1H), 6.93 (dd, J = 9.3, 3.2 Hz, 1H), 6.98 (d, J = 8.7 Hz, 2H), 7.01 (dd, J = 9.0, 4.9 Hz, 1H), 7.11 (td, J = 9.0, 3.2 Hz, 1H), 9.48 (s, 1H) |

| Compound | ¹H-NMR |
|---|---|
| 7-(5-Fluoro-2-methoxyphenyl)-8-(3-methylphenoxymethyl)-3,3-dimethyl-3,4-dihydro-1H-quinoxalin-2-one (Compound No. 3-5) 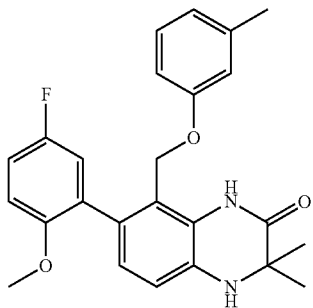 [SMILES: COc1ccc(F)cc1-c1ccc2c(c1COc1cccc(C)c1)NC(=O)C(C)(C)N2] | ¹H-NMR (400 MHz, DMSO-d₆) δ 1.18 (s, 3H), 1.28 (s, 3H), 2.19 (s, 3H), 3.66 (s, 3H), 4.61 (d, J = 11.9 Hz, 1H), 5.16 (d, J = 11.9 Hz, 1H), 6.17 (s, 1H), 6.50-6.60 (m, 1H), 6.52 (s, 1H), 6.65-6.78 (m, 1H), 6.66 (d, J = 8.1 Hz, 1H), 6.74 (d, J = 8.1 Hz, 1H), 6.94 (dd, J = 9.2, 3.2 Hz, 1H), 7.01-7.08 (m, 2H), 7.13 (td, J = 8.7, 3.2 Hz, 1H), 9.49 (s, 1H) |
| 7-(5-Fluoro-2-methoxyphenyl)-8-(2-methylphenoxymethyl)-3,3-dimethyl-3,4-dihydro-1H-quinoxalin-2-one (Compound No. 3-6) 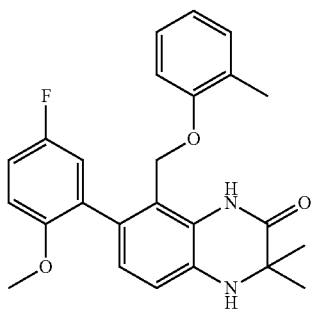 [SMILES: COc1ccc(F)cc1-c1ccc2c(c1COc1ccccc1C)NC(=O)C(C)(C)N2] | ¹H-NMR (400 MHz, DMSO-d₆) δ 1.17 (s, 3H), 1.29 (s, 3H), 2.02 (s, 3H), 3.66 (s, 3H), 4.67 (d, J = 11.7 Hz, 1H), 5.17 (d, J = 11.7 Hz, 1H), 6.19 (s, 1H), 6.61 (d, J = 7.8 Hz, 1H), 6.68 (d, J = 8.1 Hz, 1H), 6.74-6.78 (m, 1H), 6.76 (d, J = 8.1 Hz, 1H), 6.96 (dd, J = 9.0, 3.2 Hz, 1H), 6.99-7.09 (m, 3H), 7.13 (td, J = 8.7, 3.2 Hz, 1H), 9.61 (s, 1H) |
| 7-(4-Fluoro-2-methoxyphenyl)-8-(2-methyl-5-nitrophenoxymethyl)-1,3,3-trimethyl-3,4-dihydro-1H-quinoxalin-2-one (Compound No. 3-7) 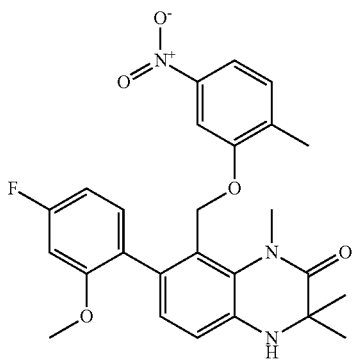 [SMILES: COc1cc(F)ccc1-c1ccc2c(c1COc1cc([N+](=O)[O-])ccc1C)N(C)C(=O)C(C)(C)N2] | ¹H-NMR (400 MHz, DMSO-d₆) δ 0.53 (s, 3H), 1.18 (s, 3H), 2.09 (s, 3H), 3.37 (s, 3H), 3.83 (s, 3H), 4.89 (d, J = 14.2 Hz, 1H), 5.47 (d, J = 14.2 Hz, 1H), 6.13 (s, 1H), 6.78 (d, J = 8.1 Hz, 1H), 6.82 (d, J = 8.1 Hz, 1H), 6.92 (td, J = 8.4, 2.4 Hz, 1H), 6.97 (d, J = 2.2 Hz, 1H), 7.03 (dd, J = 11.5, 2.4 Hz, 1H), 7.29 (d, J = 8.2 Hz, 1H), 7.42 (dd, J = 8.4, 7.0 Hz, 1H), 7.60 (dd, J = 8.2, 2.2 Hz, 1H) |

| | |
|---|---|
| 7-(5-Chloro-2-methoxyphenyl)-8-(2-methyl-5-nitrophenoxymethyl)-1,3,3-trimethyl-3,4-dihydro-1H-quinoxalin-2-one (Compound No. 3-8)<br>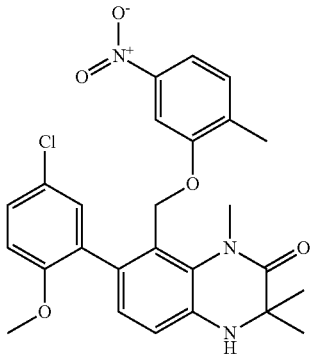 [SMILES: COc1ccc(Cl)cc1-c1ccc2c(c1COc1cc([N+](=O)[O-])ccc1C)N(C)C(=O)C(C)(C)N2] | $^1$H-NMR (400 MHz, DMSO-d$_6$) δ 0.54 (s, 3H), 1.18 (s, 3H), 2.09 (s, 3H), 3.37 (s, 3H), 3.81 (s, 3H), 4.88 (d, J = 14.2 Hz, 1H), 5.48 (d, J = 14.2 Hz, 1H), 6.19 (s, 1H), 6.79 (d, J = 8.1 Hz, 1H), 6.86 (d, J = 8.1 Hz, 1H), 6.99 (d, J = 2.4 Hz, 1H), 7.13 (d, J = 9.7 Hz, 1H), 7.30 (d, J = 8.2 Hz, 1H), 7.43 (dd, J = 9.7, 2.4 Hz, 1H), 7.43 (d, J = 2.3 Hz, 1H), 7.61 (dd, J = 8.2, 2.3 Hz, 1H) |
| 7-(5-Chloro-2-methoxyphenyl)-8-(2,5-dimethylphenoxymethyl)-1,3,3-trimethyl-3,4-dihydro-1H-quinoxalin-2-one (Compound No. 3-9)<br>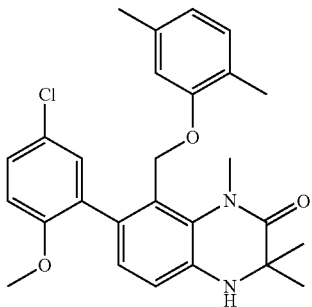 [SMILES: COc1ccc(Cl)cc1-c1ccc2c(c1COc1cc(C)ccc1C)N(C)C(=O)C(C)(C)N2] | $^1$H-NMR (500 MHz, DMSO-d$_6$) δ 0.80 (s, 3H), 1.16 (s, 3H), 1.91 (s, 3H), 2.10 (s, 3H), 3.32 (s, 3H), 3.80 (s, 3H), 4.72 (d, J = 13.8 Hz, 1H), 5.19 (d, J = 13.8 Hz, 1H), 6.13 (s, 1H), 6.16 (s, 1H), 6.49 (d, J = 7.6 Hz, 1H), 6.79 (d, J = 7.9 Hz, 1H), 6.82 (d, J = 7.9 Hz, 1H), 6.86 (d, J = 7.6 Hz, 1H), 7.14 (d, J = 9.0 Hz, 1H), 7.31 (d, J = 2.7 Hz, 1H), 7.42 (d, J = 9.0, 2.7 Hz, 1H) |
| 7-(5-Chloro-2-methoxyphenyl)-8-[2-(2-hydroxyethyl)phenoxymethyl]-1,3,3-trimethyl-3,4-dihydro-1H-quinoxalin-2-one (Compound No. 3-10)<br>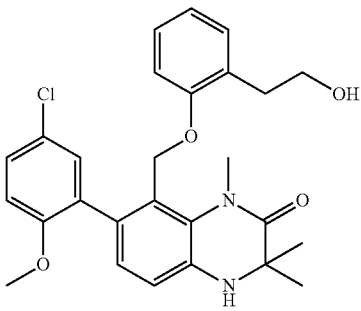 [SMILES: COc1ccc(Cl)cc1-c1ccc2c(c1COc1ccccc1CCO)N(C)C(=O)C(C)(C)N2] | $^1$H-NMR (500 MHz, CDCl$_3$) δ 1.13 (s, 3H), 1.39 (s, 3H), 2.01 (t, J = 6.0 Hz, 1H), 2.67-2.71 (m, 1H), 2.76-2.80 (m, 1H), 3.42 (s, 3H), 3.68-3.72 (m, 2H), 3.79 (s, 4H), 4.83 (d, J = 12.8 Hz, 1H), 5.14 (d, J = 12.8 Hz, 1H), 6.47 (d, J = 7.7 Hz, 1H), 6.76 (d, J = 8.1 Hz, 1H), 6.81 (t, J = 7.7 Hz, 1H), 6.89 (d, J = 8.1 Hz, 1H), 6.89 (d, J = 8.7 Hz, 1H), 7.03 (t, J = 7.7 Hz, 1H), 7.08 (d, J = 7.7 Hz, 1H), 7.28 (d, J = 2.7 Hz, 1H), 7.30 (d, J = 8.7, 2.7 Hz, 1H) |

| | |
|---|---|
| 7-(5-Chloro-2-methoxyphenyl)-8-(3-trifluoromethylphenoxymethyl)-1,3,3-trimethyl-3,4-dihydro-1H-quinoxalin-2-one (Compound No. 3-11)<br>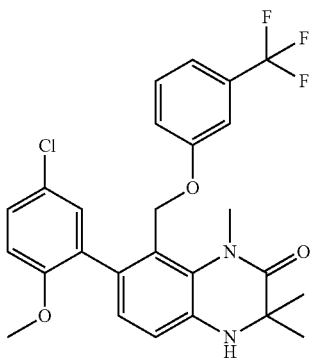 [SMILES: COc1ccc(Cl)cc1-c1ccc2c(c1COc1cccc(C(F)(F)F)c1)N(C)C(=O)C(C)(C)N2] | $^1$H-NMR (500 MHz, CDCl$_3$) δ 0.90 (s, 3H), 1.29 (s, 3H), 3.51 (s, 3H), 3.73 (s, 1H), 3.79 (s, 3H), 4.84 (d, J = 13.3 Hz, 1H), 5.23 (d, J = 13.3 Hz, 1H), 6.71 (br s, 1H), 6.72 (d, J = 8.3 Hz, 1H), 6.78 (dd, J = 8.1, 2.4 Hz, 1H), 6.86-6.88 (m, 1H), 6.87 (d, J = 8.3 Hz, 1H), 7.06 (d, J = 7.6 Hz, 1H), 7.21 (t, J = 8.1 Hz, 1H), 7.27-7.30 (m, 2H) |
| 7-(5-Chloro-2-methoxyphenyl)-8-(4-phenylphenoxymethyl)-1,3,3-trimethyl-3,4-dihydro-1H-quinoxalin-2-one (Compound No. 3-12)<br>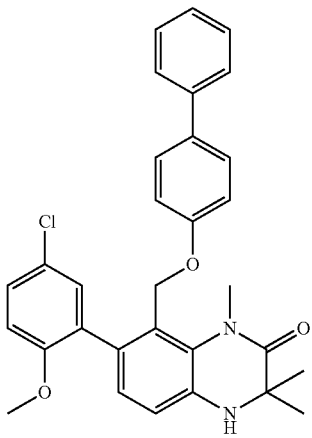 [SMILES: COc1ccc(Cl)cc1-c1ccc2c(c1COc1ccc(-c3ccccc3)cc1)N(C)C(=O)C(C)(C)N2] | $^1$H-NMR (400 MHz, CDCl$_3$) δ 1.02 (s, 3H), 1.30 (s, 3H), 3.51 (s, 3H), 3.74 (s, 1H), 3.80 (s, 3H), 4.82 (d, J = 12.9 Hz, 1H), 5.18 (d, J = 12.9 Hz, 1H), 6.65 (d, J = 8.7 Hz, 2H), 6.72 (d, J = 7.8 Hz, 1H), 6.87 (d, J = 7.8 Hz, 1H), 6.88 (d, J = 8.7 Hz, 1H), 7.26-7.39 (m, 7H), 7.44-7.49 (m, 2H) |
| 7-(5-Chloro-2-methoxyphenyl)-8-(2-methoxyphenoxymethyl)-1,3,3-trimethyl-3,4-dihydro-1H-quinoxalin-2-one (Compound No. 3-13)<br>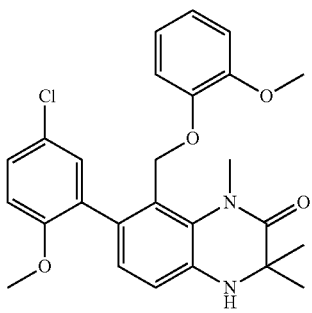 [SMILES: COc1ccccc1OCc1c(-c2cc(Cl)ccc2OC)ccc2c1N(C)C(=O)C(C)(C)N2] | $^1$H-NMR (400 MHz, CDCl$_3$) δ 1.06 (s, 3H), 1.30 (s, 3H), 3.52 (s, 3H), 3.72 (s, 1H), 3.74 (s, 3H), 3.77 (s, 3H), 4.80 (d, J = 12.7 Hz, 1H), 5.21 (d, J = 12.7 Hz, 1H), 6.40 (dd, J = 8.0, 1.3 Hz, 1H), 6.65-6.69 (m, 1H), 6.71 (d, J = 8.0 Hz, 1H), 6.75-6.80 (m, 2H), 6.83 (d, J = 8.0 Hz, 1H), 6.85 (d, J = 8.8 Hz, 1H), 7.25-7.30 (m, 2H) |

| Compound | NMR |
|---|---|
| 7-(5-Chloro-2-methoxyphenyl)-8-(3-methoxycarbonylphenoxymethyl)-1,3,3-trimethyl-3,4-dihydro-1H-quinoxalin-2-one (Compound No. 3-14)<br>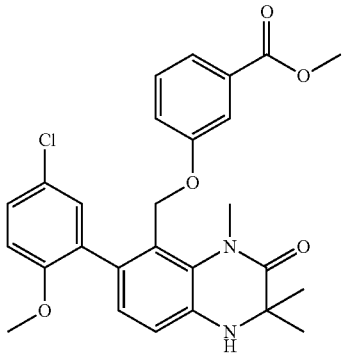 [SMILES: COC(=O)c1cccc(OCc2c(-c3cc(Cl)ccc3OC)ccc3c2N(C)C(=O)C(C)(C)N3)c1] | $^1$H-NMR (500 MHz, CDCl$_3$) δ 0.89 (s, 3H), 1.34 (s, 3H), 3.50 (s, 3H), 3.73 (s, 1H), 3.78 (s, 3H), 3.90 (s, 3H), 4.82 (d, J = 13.0 Hz, 1H), 5.23 (d, J = 13.0 Hz, 1H), 6.72 (d, J = 8.0 Hz, 1H), 6.84 (ddd, J = 8.0, 2.5, 1.2 Hz, 1H), 6.85 (d, J = 8.7 Hz, 1H), 6.86 (d, J = 8.0 Hz, 1H), 7.14 (dd, J = 2.5, 1.2 Hz, 1H), 7.18 (t, J = 8.0 Hz, 1H), 7.27 (dd, J = 8.7, 2.6 Hz, 1H), 7.37 (d, J = 2.6 Hz, 1H), 7.51 (dt, J = 8.0, 1.2 Hz, 1H) |
| 8-(5-Chloro-2-methylphenoxymethyl)-7-(4-fluoro-2-methoxyphenyl)-1,3,3-trimethyl-3,4-dihydro-1H-quinoxalin-2-one (Compound No. 3-15)<br>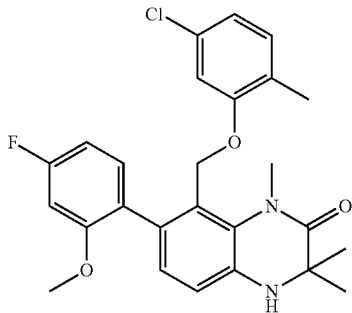 | $^1$H-NMR (500 MHz, CDCl$_3$) δ 0.90 (s, 3H), 1.32 (s, 3H), 2.02 (s, 3H), 3.46 (s, 3H), 3.72 (s, 1H), 3.82 (s, 3H), 4.80 (d, J = 13.6 Hz, 1H), 5.21 (d, J = 13.6 Hz, 1H), 6.26 (d, J = 1.8 Hz, 1H), 6.68 (dd, J = 7.9, 1.8 Hz, 1H), 6.71-6.73 (m, 1H), 6.72 (d, J = 8.1 Hz, 1H), 6.77 (td, J = 8.2, 2.4 Hz, 1H), 6.86 (d, J = 8.1 Hz, 1H), 6.89 (d, J = 7.9 Hz, 1H), 7.30 (dd, J = 8.2, 6.7 Hz, 1H) |
| 7-(4-Fluoro-2-methoxyphenyl)-8-(2-methoxy-5-nitrophenoxymethyl)-1,3,3-trimethyl-3,4-dihydro-1H-quinoxalin-2-one (Compound No. 3-16)<br>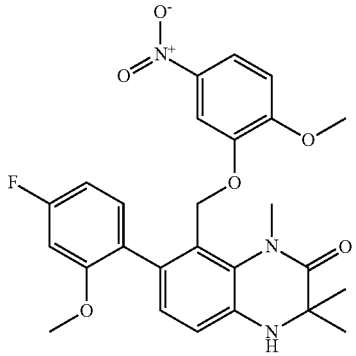 [SMILES: COc1ccc([N+](=O)[O-])cc1OCc1c(-c2ccc(F)cc2OC)ccc2c1N(C)C(=O)C(C)(C)N2] | $^1$H-NMR (400 MHz, DMSO-d$_6$) δ 0.70 (s, 3H), 1.15 (s, 3H), 3.36 (s, 3H), 3.78 (s, 3H), 3.79 (s, 3H), 4.81 (d, J = 13.6 Hz, 1H), 5.39 (d, J = 13.6 Hz, 1H), 6.11 (s, 1H), 6.78 (s, 2H), 6.84 (t d, J = 8.4, 2.5 Hz, 1H), 6.98 (d, J = 11.5, 2.5 Hz, 1H), 7.04 (d, J = 9.0 Hz, 1H), 7.10 (d, J = 2.7 Hz, 1H), 7.34 (dd, J = 8.4, 7.1 Hz, 1H), 7.76 (dd, J = 9.0, 2.7 Hz, 1H) |

| Compound | NMR |
|---|---|
| 8-(2-Allylphenoxymethyl)-7-(4-fluoro-2-methoxyphenyl)-1,3,3-trimethyl-3,4-dihydro-1H-quinoxalin-2-one (Compound No. 3-17) 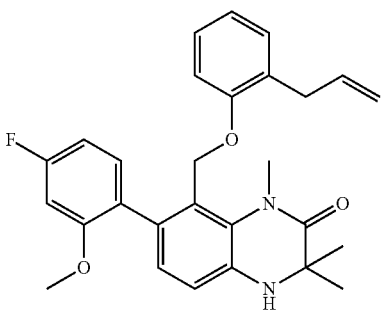 [SMILES: C=CCc1ccccc1OCc1c(-c2ccc(F)cc2OC)ccc2c1N(C)C(=O)C(C)(C)N2] | $^1$H-NMR (500 MHz, CDCl$_3$) δ 1.05 (s, 3H), 1.33 (s, 3H), 3.19 (dd, J = 15.4, 6.7 Hz, 1H), 3.26 (dd, J = 15.4, 6.7 Hz, 1H), 3.44 (s, 3H), 3.73 (s, 1H), 3.79 (s, 3H), 4.79 (d, J = 12.8 Hz, 1H), 4.95-4.99 (m, 2H), 5.14 (d, J = 12.8 Hz, 1H), 5.87 (ddt, J = 16.8, 10.4, 6.7 Hz, 1H), 6.40 (dd, J = 7.7, 1.2 Hz, 1H), 6.68 (dd, J = 10.4, 2.5 Hz, 1H), 6.72 (dd, J = 8.2, 2.5 Hz, 1H), 6.73 (d, J = 7.9 Hz, 1H), 6.77 (td, J = 7.7, 1.3 Hz, 1H), 6.85 (d, J = 7.9 Hz, 1H), 6.97 (td, J = 7.7, 1.2 Hz, 1H), 7.03 (dd, J = 7.7, 1.3 Hz, 1H), 7.25 (dd, J = 8.2, 7.0 Hz, 1H) |
| 8-(3-Acetylphenoxymethyl)-7-(4-fluoro-2-methoxyphenyl)-1,3,3-trimethyl-3,4-dihydro-1H-quinoxalin-2-one (Compound No. 3-18) 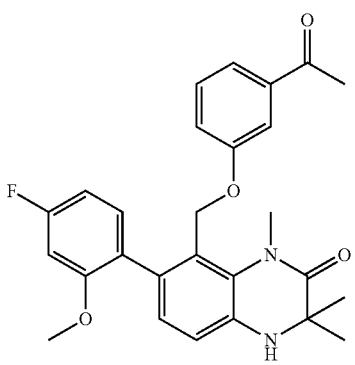 [SMILES: COc1cc(F)ccc1-c1ccc2c(c1COc1cccc(C(C)=O)c1)N(C)C(=O)C(C)(C)N2] | $^1$H-NMR (500 MHz, DMSO-d$_6$) δ 0.78 (s, 3H), 1.12 (s, 3H), 2.46 (s, 3H), 3.35 (s, 3H), 3.78 (s, 3H), 4.78 (d, J = 13.1 Hz, 1H), 5.22 (d, J = 13.1 Hz, 1H), 6.11 (s, 1H), 6.78 (s, 2H), 6.81 (td, J = 8.3, 2.5 Hz, 1H), 6.82 (dd, J = 8.2, 2.6 Hz, 1H), 6.97 (dd, J = 11.3, 2.5 Hz, 1H), 7.02-7.03 (m, 1H), 7.27 (t, J = 8.2 Hz, 1H), 7.35 (dd, J = 8.3, 7.0 Hz, 1H), 7.41-7.43 (m, 1H) |
| 8-(3-Cyanophenoxymethyl)-7-(4-fluoro-2-methoxyphenyl)-1,3,3-trimethyl-3,4-dihydro-1H-quinoxalin-2-one (Compound No. 3-19) 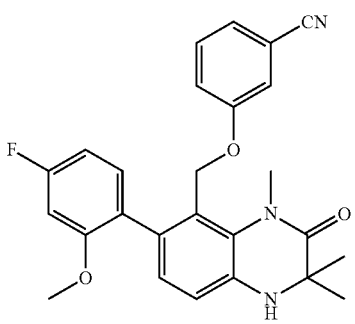 [SMILES: COc1cc(F)ccc1-c1ccc2c(c1COc1cccc(C#N)c1)N(C)C(=O)C(C)(C)N2] | $^1$H-NMR (500 MHz, DMSO-d$_6$) δ 0.90 (s, 3H), 1.04 (s, 3H), 3.33 (s, 3H), 3.79 (s, 3H), 4.83 (d, J = 13.4 Hz, 1H), 5.17 (d, J = 13.4 Hz, 1H), 6.15 (s, 1H), 6.77-6.82 (m, 3H), 6.89-6.91 (m, 1H), 6.94-6.95 (m, 1H), 6.98 (dd, J = 11.3, 2.4 Hz, 1H), 7.24-7.28 (m, 2H), 7.32-7.35 (m, 1H) |

Example 4

7-(5-Fluoro-2-methoxyphenyl)-8-(4-methylphenylaminomethyl)-3,3-dimethyl-3,4-dihydro-1H-quinoxalin-2-one (Compound No. 4-1)

A mixture of 8-chloromethyl-7-(5-fluoro-2-methoxyphenyl)-3,3-dimethyl-3,4-dihydro-1H-quinoxalin-2-one (Reference Compound No. 4-2, 50.7 mg, 0.15 mmol), 4-methylaniline (19.3 mg, 0.18 mmol), and potassium carbonate (60.6 mg, 0.44 mmol) was suspended in anhydrous N,N-dimethylformamide (1 mL) and stirred at 80° C. overnight. After cooling down, ethyl acetate (30 mL) and water (30 mL) were added and partitioned. The organic layer was washed with water (30 mL) and saturated brine (30 mL) successively, dried over anhydrous magnesium sulfate, and then the solvent was removed under reduced pressure. The obtained residue was purified by silica gel column chromatography (hexane-ethyl acetate) to give the titled compound (48.2 mg) as a pale yellow solid. (Yield 80%)

| | 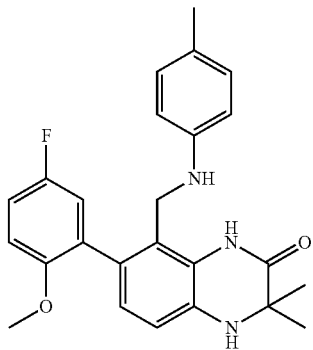 | ¹H-NMR (400 MHz, CDCl₃) δ 1.38 (s, 3H), 1.49 (s, 3H), 2.25 (s, 3H), 3.65 (s, 4H), 3.78 (s, 1H), 3.84 (d, J = 12.7 Hz, 1H), 4.07 (dd, J = 10.9, 7.0 Hz, 1H), 6.59 (d, J = 8.1 Hz, 2H), 6.70 (d, J = 8.1 Hz, 1H), 6.75 (dd, J = 9.5, 3.9 Hz, 1H), 6.75 (d, J = 8.1 Hz, 1H), 6.89-6.98 (m, 2H), 7.00 (d, J = 8.1 Hz, 2H), 8.96 (s, 1H) |
|---|---|---|

Using any compounds among Reference Compounds No. 4-2, 14-1, 14-2, and available compounds, the following Compounds (No. 4-2~4-11) were obtained by a method similar to that of Compound No. 4-1.

| Compound | Structure | ¹H-NMR |
|---|---|---|
| 7-(5-Fluoro-2-methoxyphenyl)-8-phenylaminomethyl-3,3-dimethyl-3,4-dihydro-1H-quinoxalin-2-one (Compound No. 4-2) | 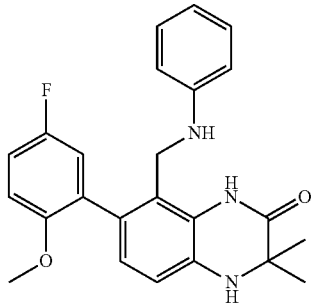 [SMILES: COc1ccc(F)cc1-c1ccc2c(c1CNc1ccccc1)NC(=O)C(C)(C)N2] | ¹H-NMR (500 MHz, DMSO-d₆) δ 1.21 (s, 3H), 1.26 (s, 3H), 3.67 (s, 3H), 3.84 (dd, J = 13.0, 4.9 Hz, 1H), 4.05 (dd, J = 13.0, 4.9 Hz, 1H), 5.52 (t, J = 4.9 Hz, 1H), 6.13 (s, 1H), 6.55 (d, J = 8.6 Hz, 2H), 6.56 (t, J = 8.2 Hz, 1H), 6.66 (d, J = 8.1 Hz, 1H), 6.71 (d, J = 8.1 Hz, 1H), 6.99-7.04 (m, 4H), 7.11 (td, J = 8.6, 3.3 Hz, 1H), 9.28 (s, 1H) |
| 7-(5-Fluoro-2-methoxyphenyl)-8-(3-methylphenylaminomethyl)-3,3-dimethyl-3,4-dihydro-1H-quinoxalin-2-one (Compound No. 4-3) | 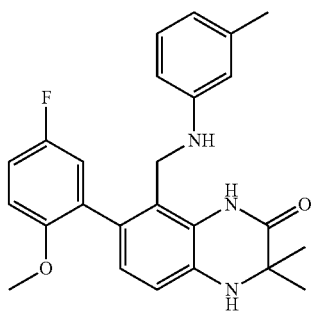 [SMILES: COc1ccc(F)cc1-c1ccc2c(c1CNc1cccc(C)c1)NC(=O)C(C)(C)N2] | ¹H-NMR (500 MHz, CDCl₃) δ 1.38 (s, 3H), 1.49 (s, 3H), 2.27 (s, 3H), 3.66 (s, 3H), 3.72 (d, J = 11.9 Hz, 1H), 3.79 (s, 1H), 3.86 (d, J = 11.9 Hz, 1H), 4.06-4.12 (m, 1H), 6.48 (d, J = 7.6 Hz, 1H), 6.49 (s, 1H), 6.63 (d, J = 7.6 Hz, 1H), 6.70 (d, J = 8.2 Hz, 1H), 6.73-6.79 (m, 1H), 6.75 (d, J = 8.2 Hz, 1H), 6.91 (dd, J = 8.7, 3.2 Hz, 1H), 6.96 (td, J = 8.7, 3.2 Hz, 1H), 7.07 (t, J = 7.6 Hz, 1H), 8.85 (s, 1H) |
| 7-(5-Fluoro-2-methoxyphenyl)-8-(2-methylphenylaminomethyl)-3,3-dimethyl-3,4-dihydro-1H-quinoxalin-2-one (Compound No. 4-4) | 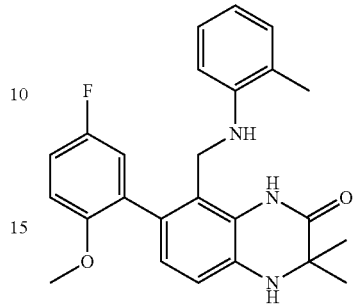 | ¹H-NMR (500 MHz, CDCl₃) δ 1.38 (s, 3H), 1.50 (s, 3H), 2.15 (s, 3H), 3.58 (d, J = 5.2 Hz, 1H), 3.61 (s, 3H), 3.80 (br s, 1H), 3.91 (d, J = 12.2 Hz, 1H), 4.08-4.11 (m, 1H), 6.64 (d, J = 7.9 Hz, 1H), 6.72 (d, J = 7.9 Hz, 1H), 6.76-6.79 (m, 3H), 6.92 (dd, J = 8.7, 3.2 Hz, 1H), 6.97 (td, J = 8.4, 3.2 Hz, 1H), 7.09 (d, J = 7.3 Hz, 1H), 7.12 (t, J = 7.9 Hz, 1H), 8.86 (s, 1H) |
| 7-(4-Fluoro-2-methoxyphenyl)-8-(2-methoxy-5-methylphenylaminomethyl)-1,3,3-trimethyl-3,4-dihydro-1H-quinoxalin-2-one (Compound No. 4-5) | 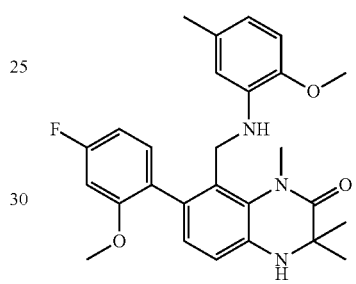 | ¹H-NMR (400 MHz, CDCl₃) δ 1.18 (s, 3H), 1.43 (s, 3H), 2.17 (s, 3H), 3.47 (s, 3H), 3.70 (s, 3H), 3.73 (s, 1H), 3.78 (s, 3H), 4.07 (br s, 2H), 4.44 (br s, 1H), 6.14 (d, J = 1.5 Hz, 1H), 6.36 (dd, J = 8.1, 1.5 Hz, 1H), 6.55 (d, J = 8.1 Hz, 1H), 6.62-6.71 (m, 2H), 6.69 (d, J = 7.9 Hz, 1H), 6.77 (d, J = 7.9 Hz, 1H), 7.12 (dd, J = 8.3, 6.8 Hz, 1H) |
| 7-(5-Chloro-2-methoxyphenyl)-8-(2-methoxy-5-methylphenylaminomethyl)-1,3,3-trimethyl-3,4-dihydro-1H-quinoxalin-2-one (Compound No. 4-6) | 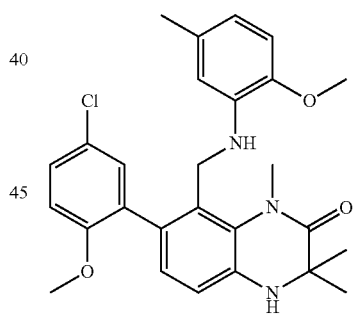 | ¹H-NMR (500 MHz, CDCl₃) δ 1.18 (s, 3H), 1.43 (s, 3H), 2.17 (s, 3H), 3.48 (s, 3H), 3.71 (s, 3H), 3.75 (s, 1H), 3.77 (s, 3H), 4.10-4.14 (m, 2H), 4.42-4.44 (m, 1H), 6.14 (d, J = 1.5 Hz, 1H), 6.36 (dd, J = 8.0, 1.5 Hz, 1H), 6.55 (d, J = 8.0 Hz, 1H), 6.69 (d, J = 8.0 Hz, 1H), 6.78 (d, J = 8.0 Hz, 1H), 6.82 (d, J = 8.9 Hz, 1H), 7.17 (d, J = 2.8 Hz, 1H), 7.25 (dd, J = 8.9, 2.8 Hz, 1H) |
| 7-(5-Chloro-2-methoxyphenyl)-8-(5-fluoro-2-methylphenylaminomethyl)-1,3,3-trimethyl-3,4-dihydro-1H-quinoxalin-2-one (Compound No. 4-7) | 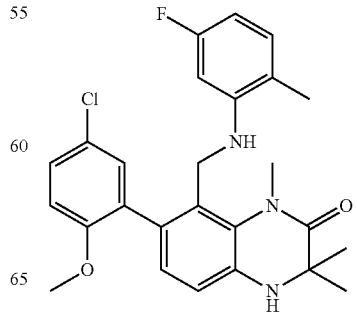 | ¹H-NMR (400 MHz, CDCl₃) δ 1.22 (s, 3H), 1.40 (s, 3H), 1.85 (s, 3H), 3.42 (s, 3H), 3.73-3.80 (m, 2H), 3.77 (s, 3H), 4.10-4.22 (m, 2H), 6.03 (d, J = 11.5, 2.5 Hz, 1H), 6.24 (td, J = 8.3, 2.5, 1H), 6.72 (d, J = 8.1 Hz, 1H), 6.77 (d, J = 8.1 Hz, 1H), 6.84-6.88 (m, 1H), 6.87 (d, J = 8.8 Hz, 1H), 7.18 (d, J = 2.7 Hz, 1H), 7.29 (d, J = 8.8, 2.7 Hz, 1H) |

| Compound | ¹H-NMR |
|---|---|
| 7-(5-Chloro-2-methoxyphenyl)-8-(2-methoxyphenylaminomethyl)-1,3,3-trimethyl-3,4-dihydro-1H-quinoxalin-2-one (Compound No. 4-8) 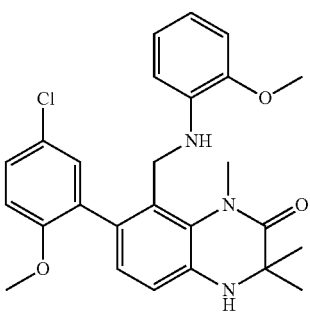 [SMILES: COc1ccccc1NCc1c(-c2cc(Cl)ccc2OC)ccc2c1N(C)C(=O)C(C)(C)N2] | ¹H-NMR (500 MHz, CDCl₃) δ 1.21 (s, 3H), 1.42 (s, 3H), 3.46 (s, 3H), 3.74 (s, 3H), 3.75 (s, 1H), 3.77 (s, 3H), 4.11-4.14 (m, 2H), 4.43 (br s, 1H), 6.32 (dd, J = 7.8, 1.5 Hz, 1H), 6.57 (td, J = 7.8, 1.5 Hz, 1H), 6.66 (dd, J = 7.8, 1.5 Hz, 1H), 6.69 (d, J = 8.0 Hz, 1H), 6.72 (td, J = 7.8, 1.5 Hz, 1H), 6.78 (d, J = 8.0 Hz, 1H), 6.82 (d, J = 8.9 Hz, 1H), 7.16 (d, J = 2.7 Hz, 1H), 7.24 (dd, J = 8.9, 2.7 Hz, 1H) |
| 7-(5-Chloro-2-methoxyphenyl)-8-(2,5-dimethylphenylaminomethyl)-1,3,3-trimethyl-3,4-dihydro-1H-quinoxalin-2-one (Compound No. 4-9) 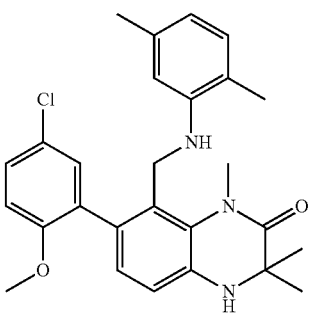 [SMILES: COc1ccc(Cl)cc1-c1ccc2c(c1CNc1cc(C)ccc1C)N(C)C(=O)C(C)(C)N2] | ¹H-NMR (400 MHz, CDCl₃) δ 1.20 (s, 3H), 1.43 (s, 3H), 1.88 (s, 3H), 2.21 (s, 3H), 3.46 (s, 3H), 3.69 (s, 1H), 3.77 (s, 3H), 4.10-4.19 (m, 2H), 6.19 (s, 1H), 6.40 (d, J = 7.3 Hz, 1H), 6.71 (d, J = 7.8 Hz, 1H), 6.80 (d, J = 7.8 Hz, 1H), 6.82-6.85 (m, 1H), 6.86 (d, J = 8.8 Hz, 1H), 7.20 (d, J = 2.5 Hz, 1H), 7.27 (dd, J = 8.8, 2.5 Hz, 1H) |
| 7-(5-Chloro-2-methoxyphenyl)-8-(2-isopropylphenylaminomethyl)-1,3,3-trimethyl-3,4-dihydro-1H-quinoxalin-2-one (Compound No. 4-10) 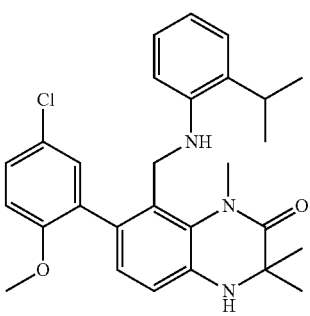 [SMILES: COc1ccc(Cl)cc1-c1ccc2c(c1CNc1ccccc1C(C)C)N(C)C(=O)C(C)(C)N2] | ¹H-NMR (400 MHz, CDCl₃) δ 1.21 (d, J = 6.8 Hz, 3H), 1.15 (d, J = 6.8 Hz, 3H), 1.26 (s, 3H), 1.41 (s, 3H), 2.49-2.56 (m, 1H), 3.45 (s, 3H), 3.76 (s, 3H), 3.80 (s, 1H), 3.81 (br s, 1H), 4.15-4.22 (m, 2H), 6.43 (dd, J = 7.4, 1.3 Hz, 1H), 6.68 (td, J = 7.4, 1.3 Hz, 1H), 6.72 (d, J = 7.9 Hz, 1H), 6.81 (d, J = 7.9 Hz, 1H), 6.85 (d, J = 8.7 Hz, 1H), 7.01 (td, J = 7.4, 1.3 Hz, 1H), 7.06 (dd, J = 7.4, 1.3 Hz, 1H), 7.20 (d, J = 2.7 Hz, 1H), 7.26 (d, J = 8.7, 2.7 Hz, 1H) |
| 7-(4-Fluoro-2-methoxyphenyl)-8-(2-methoxyphenylaminomethyl)-1,3,3-trimethyl-3,4-dihydro-1H-quinoxalin-2-one (Compound No. 4-11) 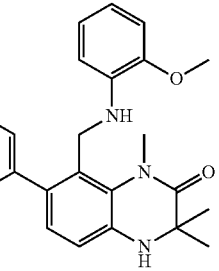 | ¹H-NMR (500 MHz, CDCl₃) δ 1.18 (s, 3H), 1.42 (s, 3H), 3.46 (s, 3H), 3.73 (s, 3H), 3.76 (s, 1H), 3.77 (s, 3H), 4.10 (d, J = 5.2 Hz, 2H), 4.45 (t, J = 5.2 Hz, 1H), 6.32 (dd, J = 7.7, 1.4 Hz, 1H), 6.57 (td, J = 7.7, 1.4 Hz, 1H), 6.62-6.69 (m, 3H), 6.69 (d, J = 7.9 Hz, 1H), 6.73 (td, J = 7.7, 1.4 Hz, 1H), 6.78 (d, J = 7.9 Hz, 1H), 7.12 (dd, J = 8.4, 6.9 Hz, 1H) |

Example 5

8-Benzoyloxymethyl 7-(5-fluoro-2-methoxyphenyl)-1,3,3-trimethyl-3,4-dihydro-1H-quinoxalin-2-one (Compound No. 5-1)

A mixture of 8-benzoyloxymethyl-7-(5-fluoro-2-methoxyphenyl)-3,3-dimethyl-3,4-dihydro-1H-quinoxalin-2-one (Compound No. 1-3, 42.9 mg, 0.099 mmol), methyliodide (30.7 μL, 0.49 mmol), and cessium carbonate (89.0 mg, 0.27 mmol) was suspended in anhydrous N,N-dimethylformamide (1 mL) and stirred at room temperature for 1.5 hours. The reaction mixture was diluted with ethyl acetate (100 mL). The mixture was washed with water (100 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled compound (35.0 mg) as a colorless amorphous product. (Yield 79%)

¹H-NMR (400 MHz, CDCl₃) δ 1.21 (s, 3H), 1.42 (s, 3H), 3.47 (s, 3H), 3.72 (s, 3H), 3.82 (br s, 1H), 5.20 (d, J = 13.3 Hz, 1H), 5.36 (d, J = 13.3 Hz, 1H), 6.77 (d, J = 8.1 Hz, 1H), 6.83 (dd, J = 8.8, 4.4 Hz, 1H), 6.88 (d, J = 8.1 Hz, 1H), 6.96-7.02 (m, 2H), 7.36 (t, J = 7.7 Hz, 2H), 7.49-7.53 (m, 1H), 7.81-7.84 (m, 2H)

Using any compounds among Reference Compounds No. 1-4~1-7, 2-1~2-6, 2-13, 3-1~3-6, 4-1~4-4, 22, and available compounds, the following Compounds (No. 5-2~5-25) were obtained by a method similar to that of Compound No. 5-1.

7-(5-Fluoro-2-methoxyphenyl)-8-(5-methylthiophen-2-ylcarbonyloxymethyl)-1,3,3-trimethyl-3,4-dihydro-1H-quinoxalin-2-one (Compound No. 5-2)

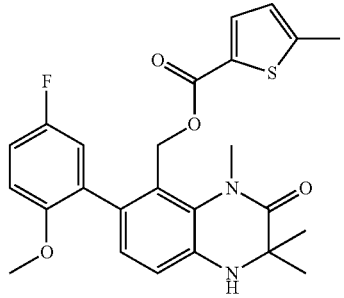 [SMILES: COc1ccc(F)cc1-c1ccc2c(c1COC(=O)c1ccc(C)s1)N(C)C(=O)C(C)(C)N2]

$^1$H-NMR (500 MHz, DMSO-d$_6$) δ 1.02 (s, 3H), 1.25 (s, 3H), 2.45 (s, 3H), 3.31 (s, 3H), 3.69 (s, 3H), 5.08 (d, J = 13.4 Hz, 1H), 5.24 (d, J = 13.4 Hz, 1H), 6.26 (s, 1H), 6.80 (d, J = 7.9 Hz, 1H), 6.84 (d, J = 7.9 Hz, 1H), 6.86 (d, J = 3.7 Hz, 1H), 7.05 (dd, J = 8.8, 4.6 Hz, 1H), 7.07 (dd, J = 8.9, 3.3 Hz, 1H), 7.16 (td, J = 8.8, 3.3 Hz, 1H), 7.38 (d, J = 3.7 Hz, 1H)

7-(5-Fluoro-2-methoxyphenyl)-8-(4-methylbenzoyloxymethyl)-1,3,3-trimethyl-3,4-dihydro-1H-quinoxalin-2-one (Compound No. 5-3)

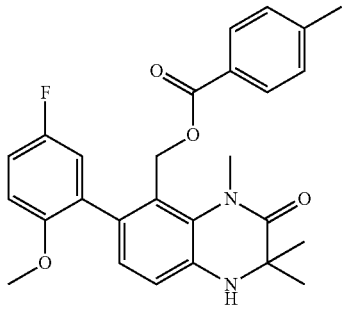 [SMILES: COc1ccc(F)cc1-c1ccc2c(c1COC(=O)c1ccc(C)cc1)N(C)C(=O)C(C)(C)N2]

$^1$H-NMR (500 MHz, DMSO-d$_6$) δ 1.01 (s, 3H), 1.25 (s, 3H), 2.34 (s, 3H), 3.30 (s, 3H), 3.69 (s, 3H), 5.13 (d, J = 13.4 Hz, 1H), 5.28 (d, J = 13.4 Hz, 1H), 6.27 (s, 1H), 6.82 (d, J = 7.9 Hz, 1H), 6.84 (d, J = 7.9 Hz, 1H), 7.04 (dd, J = 8.9, 4.6 Hz, 1H), 7.09 (dd, J = 9.0, 3.2 Hz, 1H), 7.15 (td, J = 8.9, 3.2 Hz, 1H), 7.24 (d, J = 8.2 Hz, 2H), 7.60 (d, J = 8.2 Hz, 2H)

7-(5-Fluoro-2-methoxyphenyl)-8-(3-methylbenzoyloxymethyl)-1,3,3-trimethyl-3,4-dihydro-1H-quinoxalin-2-one (Compound No. 5-4)

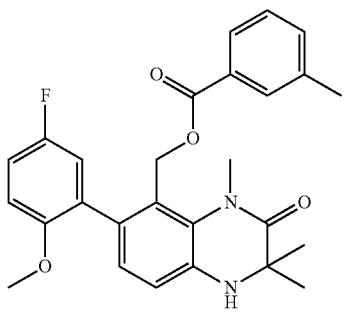 [SMILES: COc1ccc(F)cc1-c1ccc2c(c1COC(=O)c1cccc(C)c1)N(C)C(=O)C(C)(C)N2]

$^1$H-NMR (400 MHz, CDCl$_3$) δ 1.23 (s, 3H), 1.43 (s, 3H), 2.34 (s, 3H), 3.46 (s, 3H), 3.73 (s, 3H), 3.82 (s, 1H), 5.18 (d, J = 13.4 Hz, 1H), 5.35 (d, J = 13.4 Hz, 1H), 6.77 (d, J = 8.1 Hz, 1H), 6.83 (dd, J = 8.7, 4.5 Hz, 1H), 6.88 (d, J = 8.1 Hz, 1H), 6.96-7.02 (m, 2H), 7.23-7.32 (m, 2H), 7.62-7.64 (m, 2H)

7-(5-Fluoro-2-methoxyphenyl)-8-(2-methylbenzoyloxymethyl)-1,3,3-trimethyl-3,4-dihydro-1H-quinoxalin-2-one (Compound No. 5-5)

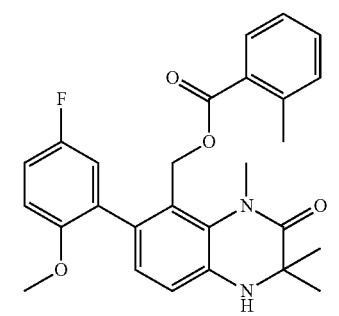 [SMILES: COc1ccc(F)cc1-c1ccc2c(c1COC(=O)c1ccccc1C)N(C)C(=O)C(C)(C)N2]

$^1$H-NMR (400 MHz, CDCl$_3$) δ 1.26 (s, 3H), 1.42 (s, 3H), 2.48 (s, 3H), 3.46 (s, 3H), 3.71 (s, 3H), 3.82 (s, 1H), 5.13 (d, J = 13.3 Hz, 1H), 5.34 (d, J = 13.3 Hz, 1H), 6.77 (d, J = 8.0 Hz, 1H), 6.83-6.88 (m, 1H), 6.87 (d, J = 8.0 Hz, 1H), 6.98-7.01 (m, 1H), 6.99 (d, J = 8.1 Hz, 1H), 7.13-7.19 (m, 2H), 7.35 (td, J = 8.6, 1.5 Hz, 1H), 7.66 (dd, J = 8.0, 1.2 Hz, 1H)

| Compound | NMR |
|---|---|
| 7-(5-Fluoro-2-methoxyphenyl)-8-(thiophen-2-ylcarbonyloxymethyl)-1,3,3-trimethyl-3,4-dihydro-1H-quinoxalin-2-one (Compound No. 5-6) 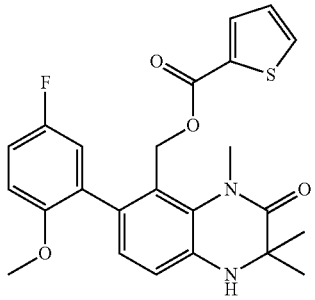 [SMILES: COc1ccc(F)cc1-c1ccc2c(c1COC(=O)c1cccs1)N(C)C(=O)C(C)(C)N2] | ¹H-NMR (400 MHz, CDCl₃) δ 1.20 (s, 3H), 1.42 (s, 3H), 3.46 (s, 3H), 3.74 (s, 3H), 3.82 (s, 1H), 5.17 (d, J = 13.3 Hz, 1H), 5.33 (d, J = 13.3 Hz, 1H), 6.77 (d, J = 8.0 Hz, 1H), 6.85 (dd, J = 8.6, 4.4 Hz, 1H), 6.87 (d, J = 8.0 Hz, 1H), 6.98-7.05 (m, 3H), 7.50 (dd, J = 4.9, 1.2 Hz, 1H), 7.63 (dd, J = 3.6, 1.2 Hz, 1H) |
| 7-(5-Fluoro-2-methoxyphenyl)-8-(4-methoxybenzoyloxymethyl)-1,3,3-trimethyl-3,4-dihydro-1H-quinoxalin-2-one (Compound No. 5-7) 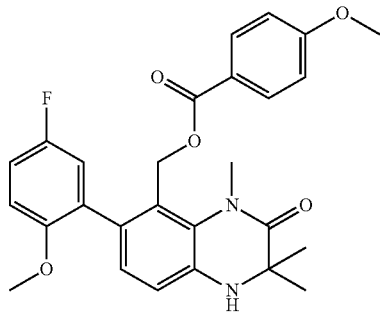 [SMILES: COc1ccc(C(=O)OCc2c(-c3cc(F)ccc3OC)ccc3c2N(C)C(=O)C(C)(C)N3)cc1] | ¹H-NMR (500 MHz, DMSO-d₆) δ 1.02 (s, 3H), 1.25 (s, 3H), 3.32 (s, 3H), 3.69 (s, 3H), 3.80 (s, 3H), 5.11 (d, J = 13.3 Hz, 1H), 5.26 (d, J = 13.3 Hz, 1H), 6.26 (s, 1H), 6.81 (d, J = 8.2 Hz, 1H), 6.84 (d, J = 8.2 Hz, 1H), 6.95 (d, J = 8.7 Hz, 2H), 7.04 (dd, J = 8.8, 4.7 Hz, 1H), 7.09 (dd, J = 9.2, 3.1 Hz, 1H), 7.15 (td, J = 8.8, 3.1 Hz, 1H), 7.66 (d, J = 8.7 Hz, 2H) |
| 7-(4-Fluoro-2-methoxyphenyl)-8-phenoxymethyl-1,3,3-trimethyl-3,4-dihydro-1H-quinoxalin-2-one (Compound No. 5-8) 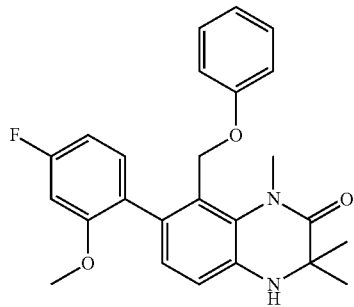 [SMILES: COc1cc(F)ccc1-c1ccc2c(c1COc1ccccc1)N(C)C(=O)C(C)(C)N2] | ¹H-NMR (400 MHz, DMSO-d₆) δ 0.87 (s, 3H), 1.09 (s, 3H), 3.32 (s, 3H), 3.79 (s, 3H), 4.71 (d, J = 13.1 Hz, 1H), 5.10 (d, J = 13.1 Hz, 1H), 6.11 (s, 1H), 6.53-6.56 (m, 2H), 6.76 (d, J = 8.1 Hz, 1H), 6.78-6.83 (m, 2H), 6.81 (td, J = 8.3, 2.4 Hz, 1H), 6.98 (dd, J = 11.5, 2.4 Hz, 1H), 7.11 (dd, J = 8.5, 7.3 Hz, 2H), 7.28 (dd, J = 8.4, 7.0 Hz, 1H) |
| 7-(5-Fluoro-2-methoxyphenyl)-8-phenoxymethyl-1,3,3-trimethyl-3,4-dihydro-1H-quinoxalin-2-one (Compound No. 5-9) 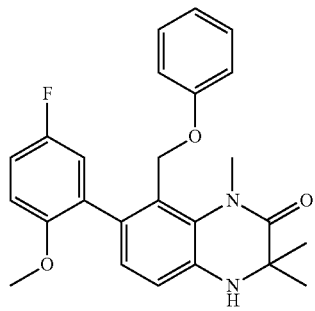 [SMILES: COc1ccc(F)cc1-c1ccc2c(c1COc1ccccc1)N(C)C(=O)C(C)(C)N2] | ¹H-NMR (400 MHz, CDCl₃) δ 1.00 (s, 3H), 1.31 (s, 3H), 3.49 (s, 3H), 3.72 (br s, 1H), 3.77 (s, 3H), 4.80 (d, J = 12.9 Hz, 1H), 5.15 (d, J = 12.9 Hz, 1H), 6.57-6.59 (m, 2H), 6.71 (d, J = 7.9 Hz, 1H), 6.79-6.83 (m, 1H), 6.86 (dd, J = 8.9, 4.5 Hz, 1H), 6.86 (d, J = 7.9 Hz, 1H), 6.99-7.13 (m, 4H) |

| Compound | NMR |
|---|---|
| 7-(5-Fluoro-2-methoxyphenyl)-8-(3-fluorophenoxymethyl)-1,3,3-trimethyl-3,4-dihydro-1H-quinoxalin-2-one (Compound No. 5-10) 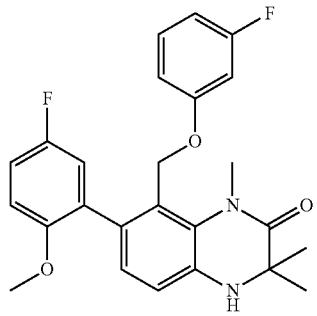 [SMILES: COc1ccc(F)cc1-c1ccc2c(c1COc1cccc(F)c1)N(C)C(=O)C(C)(C)N2] | ¹H-NMR (400 MHz, DMSO-d₆) δ 0.95 (s, 3H), 1.06 (s, 3H), 3.30 (s, 3H), 3.74 (s, 3H), 4.79 (d, J = 12.6 Hz, 1H), 5.13 (d, J = 12.6 Hz, 1H), 6.19 (s, 1H), 6.37-6.43 (m, 2H), 6.63 (td, J = 8.4, 2.0 Hz, 1H), 6.80 (d, J = 8.1 Hz, 1H), 6.82 (d, J = 8.1 Hz, 1H), 7.05-7.18 (m, 4H) |
| 7-(5-Fluoro-2-methoxyphenyl)-8-(4-methylphenoxymethyl)-1,3,3-trimethyl-3,4-dihydro-1H-quinoxalin-2-one (Compound No. 5-11) 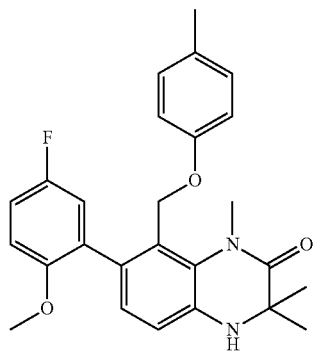 [SMILES: COc1ccc(F)cc1-c1ccc2c(c1COc1ccc(C)cc1)N(C)C(=O)C(C)(C)N2] | ¹H-NMR (500 MHz, DMSO-d₆) δ 0.94 (s, 3H), 1.10 (s, 3H), 2.13 (s, 3H), 3.32 (s, 3H), 3.74 (s, 3H), 4.69 (d, J = 13.1 Hz, 1H), 5.07 (d, J = 13.1 Hz, 1H), 6.15 (s, 1H), 6.46 (d, J = 8.4 Hz, 2H), 6.78 (d, J = 8.4 Hz, 1H), 6.80 (d, J = 8.4 Hz, 1H), 6.92 (d, J = 8.4 Hz, 2H), 7.06 (dd, J = 8.8, 4.7 Hz, 1H), 7.10 (dd, J = 9.0, 3.2 Hz, 1H), 7.15 (td, J = 8.8, 3.2 Hz, 1H) |
| 7-(5-Fluoro-2-methoxyphenyl)-8-(3-methylphenoxymethyl)-1,3,3-trimethyl-3,4-dihydro-1H-quinoxalin-2-one (Compound No. 5-12) 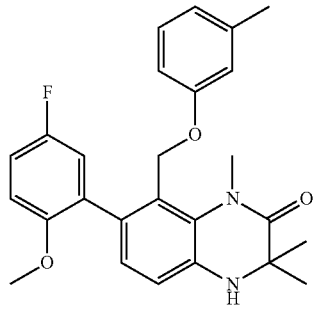 [SMILES: COc1ccc(F)cc1-c1ccc2c(c1COc1cccc(C)c1)N(C)C(=O)C(C)(C)N2] | ¹H-NMR (400 MHz, DMSO-d₆) δ 0.92 (s, 3H), 1.11 (s, 3H), 2.14 (s, 3H), 3.33 (s, 3H), 3.75 (s, 3H), 4.72 (d, J = 12.7 Hz, 1H), 5.11 (d, J = 12.7 Hz, 1H), 6.15 (s, 1H), 6.32-6.39 (m, 2H), 6.62 (d, J = 7.3 Hz, 1H), 6.79 (d, J = 8.1 Hz, 1H), 6.81 (d, J = 8.1 Hz, 1H), 6.99 (t, J = 7.8 Hz, 1H), 7.05-7.18 (m, 3H) |
| 7-(5-Fluoro-2-methoxyphenyl)-8-(2-methylphenoxymethyl)-1,3,3-trimethyl-3,4-dihydro-1H-quinoxalin-2-one (Compound No. 5-13) 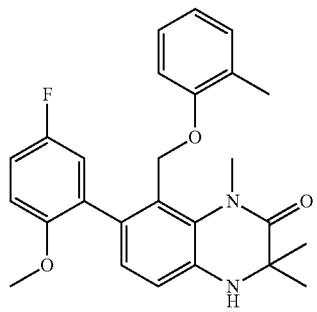 [SMILES: COc1ccc(F)cc1-c1ccc2c(c1COc1ccccc1C)N(C)C(=O)C(C)(C)N2] | ¹H-NMR (400 MHz, DMSO-d₆) δ 0.85 (s, 3H), 1.11 (s, 3H), 1.96 (s, 3H), 3.29 (s, 3H), 3.78 (s, 3H), 4.80 (d, J = 13.3 Hz, 1H), 5.17 (d, J = 13.3 Hz, 1H), 6.17 (s, 1H), 6.38 (d, J = 7.8 Hz, 1H), 6.69 (t, J = 7.1 Hz, 1H), 6.79 (d, J = 8.1 Hz, 1H), 6.83 (d, J = 8.1 Hz, 1H), 6.94 (t, J = 7.8 Hz, 1H), 7.00 (d, J = 7.1 Hz, 1H), 7.10 (dd, J = 9.0, 4.6 Hz, 1H), 7.13-7.23 (m, 2H) |

| Compound | NMR |
|---|---|
| 7-(5-Fluoro-2-methoxyphenyl)-8-phenylaminomethyl-1,3,3-trimethyl-3,4-dihydro-1H-quinoxalin-2-one (Compound No. 5-14) 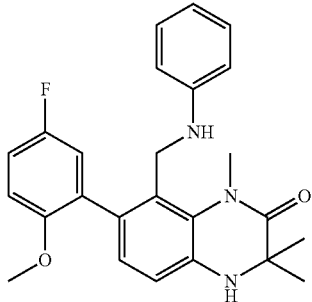 [SMILES: COc1ccc(F)cc1-c1ccc2c(c1CNc1ccccc1)N(C)C(=O)C(C)(C)N2] | ¹H-NMR (400 MHz, CDCl₃) δ 1.18 (s, 3H), 1.44 (s, 3H), 3.50 (s, 3H), 3.76 (br s, 1H), 3.80 (s, 3H), 4.02 (d, J = 12.0 Hz, 1H), 4.03 (br s, 1H), 4.16 (d, J = 12.0 Hz, 1H), 6.34 (d, J = 7.6 Hz, 2H), 6.62 (t, J = 7.3 Hz, 1H), 6.69 (d, J = 7.9 Hz, 1H), 6.79 (d, J = 7.9 Hz, 1H), 6.86 (dd, J = 9.0, 4.4 Hz, 1H), 6.90 (dd, J = 8.5, 3.2 Hz, 1H), 6.96-7.01 (m, 1H), 7.03-7.07 (m, 2H) |
| 7-(5-Fluoro-2-methoxyphenyl)-8-(4-methylphenylaminomethyl)-1,3,3-trimethyl-3,4-dihydro-1H-quinoxalin-2-one (Compound No. 5-15) 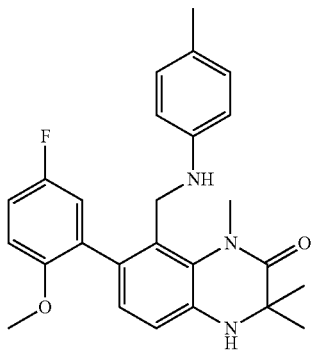 [SMILES: COc1ccc(F)cc1-c1ccc2c(c1CNc1ccc(C)cc1)N(C)C(=O)C(C)(C)N2] | ¹H-NHR (400 MHz, CDCl₃) δ 1.18 (s, 3H), 1.44 (s, 3H), 2.17 (s, 3H), 3.51 (s, 3H), 3.75 (s, 1H), 3.80 (s, 3H), 3.90 (br s, 1H), 3.98 (d, J = 12.5 Hz, 1H), 4.13 (d, J = 12.5 Hz, 1H), 6.27 (d, J = 8.3 Hz, 2H), 6.69 (d, J = 7.8 Hz, 1H), 6.78 (d, J = 7.8 Hz, 1H), 6.83-6.92 (m, 4H), 6.95-7.02 (m, 1H) |
| 7-(5-Fluoro-2-methoxyphenyl)-8-(3-methylphenylaminomethyl)-1,3,3-trimethyl-3,4-dihydro-1H-quinoxalin-2-one (Compound No. 5-16) 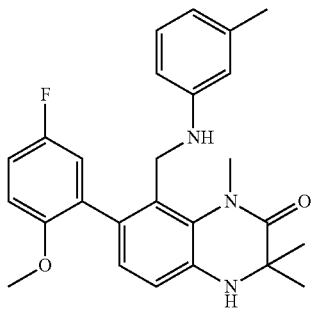 [SMILES: COc1ccc(F)cc1-c1ccc2c(c1CNc1cccc(C)c1)N(C)C(=O)C(C)(C)N2] | ¹H-NMR (400 MHz, CDCl₃) δ 1.18 (s, 3H), 1.45 (s, 3H), 2.19 (s, 3H), 3.51 (s, 3H), 3.75 (s, 1H), 3.80 (s, 3H), 3.95-4.04 (m, 2H), 4.10-4.19 (m, 1H), 6.16 (d, J = 7.3 Hz, 1H), 6.17 (s, 1H), 6.44 (d, J = 7.3 Hz, 1H), 6.69 (d, J = 8.1 Hz, 1H), 6.79 (d, J = 8.1 Hz, 1H), 6.84-7.01 (m, 4H) |
| 7-(5-Fluoro-2-methoxyphenyl)-8-(2-methylphenylaminomethyl)-1,3,3-trimethyl-3,4-dihydro-1H-quinoxalin-2-one (Compound No. 5-17) 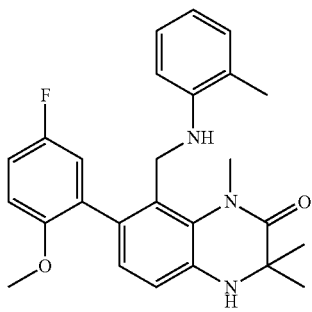 [SMILES: COc1ccc(F)cc1-c1ccc2c(c1CNc1ccccc1C)N(C)C(=O)C(C)(C)N2] | ¹H-NMR (400 MHz, CDCl₃) δ 1.21 (s, 3H), 1.43 (s, 3H), 1.92 (s, 3H), 3.45 (s, 3H), 3.73 (s, 1H), 3.75 (s, 3H), 3.78 (s, 1H), 4.18-4.19 (m, 2H), 6.36 (d, J = 7.8 Hz, 1H), 6.58 (t, J = 7.1 Hz, 1H), 6.71 (d, J = 7.9 Hz, 1H), 6.82 (d, J = 7.9 Hz, 1H), 6.86 (dd, J = 8.9, 4.5 Hz, 1H), 6.92-7.03 (m, 4H) |

| Compound | NMR |
|---|---|
| 1-Ethyl-7-(5-fluoro-2-methoxyphenyl)-8-(4-methylbenzoyloxymethyl)-3,3-dimethyl-3,4-dihydro-1H-quinoxalin-2-one (Compound No. 5-18)<br />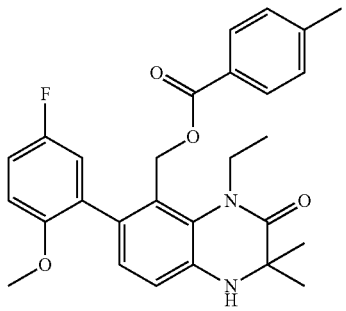 [SMILES: CCN1C(=O)C(C)(C)Nc2ccc(-c3cc(F)ccc3OC)c(COC(=O)c3ccc(C)cc3)c21] | $^1$H-NMR (500 MHz, DMSO-d$_6$) δ 0.96 (s, 3H), 1.01 (t, J = 7.0 Hz, 3H), 1.27 (s, 3H), 2.33 (s, 3H), 3.62 (dq, J = 7.0 Hz, 1H), 3.69 (s, 3H), 4.29 (dq, J = 7.0 Hz, 1H), 5.10 (d, J = 13.4 Hz, 1H), 5.17 (d, J = 13.4 Hz, 1H), 6.23 (s, 1H), 6.82 (d, J = 7.9 Hz, 1H), 6.85 (d, J = 7.9 Hz, 1H), 7.05 (dd, J = 8.9, 4.6 Hz, 1H), 7.10 (dd, J = 9.0, 3.2 Hz, 1H), 7.16 (td, J = 8.9, 3.2 Hz, 1H), 7.24 (d, J = 8.2 Hz, 2H), 7.59 (d, J = 8.2 Hz, 2H) |
| 1-(Propen-3-yl)-7-(5-fluoro-2-methoxyphenyl)-8-(4-methylbenzoyloxymethyl)-3,3-dimethyl-3,4-dihydro-1H-quinoxalin-2-one (Compound No. 5-19)<br />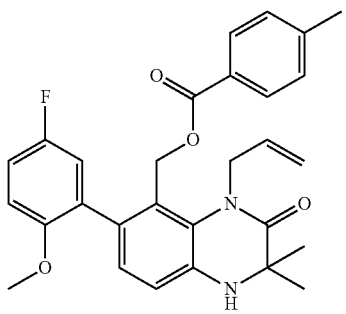 [SMILES: C=CCN1C(=O)C(C)(C)Nc2ccc(-c3cc(F)ccc3OC)c(COC(=O)c3ccc(C)cc3)c21] | $^1$H-NMR (400 MHz, DMSO-d$_6$) δ 1.03 (s, 3H), 1.27 (s, 3H), 2.34 (s, 3H), 3.64 (s, 3H), 4.27 (dd, J = 16.7, 5.4 Hz, 1H), 4.73-4.80 (m, 1H), 5.04 (dd, J = 10.6, 1.6 Hz, 1H), 5.08 (d, J = 13.7 Hz, 1H), 5.10 (dd, J = 17.3, 1.6 Hz, 1H), 5.18 (d, J = 13.7 Hz, 1H), 5.70 (ddt, J = 17.3, 10.6, 5.4 Hz, 1H), 6.31 (s, 1H), 6.81 (d, J = 8.1 Hz, 1H), 6.86 (d, J = 8.1 Hz, 1H), 7.02 (dd, J = 9.0, 4.6 Hz, 1H), 7.04 (dd, J = 9.2, 3.2 Hz, 1H), 7.13 (td, J = 9.0, 3.2 Hz, 1H), 7.25 (d, J = 8.0 Hz, 2H), 7.60 (d, J = 8.0 Hz, 2H) |
| 7-(2-Methoxy-4-methoxymethoxyphenyl)-8-(5-methylthiophen-2-ylcarbonyloxymethyl)-1,3,3-trimethyl-3,4-dihydro-1H-quinoxalin-2-one (Compound No. 5-20)<br />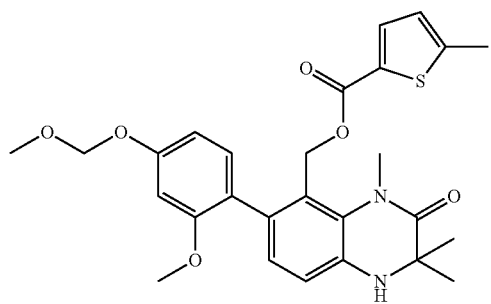 | $^1$H-NMR (400 MHz, CDCl$_3$) δ 1.20 (s, 3H), 1.42 (s, 3H), 2.47 (s, 3H), 3.44 (s, 3H), 3.51 (s, 3H), 3.75 (s, 4H), 5.13 (d, J = 13.4 Hz, 1H), 5.18 (d, J = 6.8 Hz, 1H), 5.21 (d, J = 6.8 Hz, 1H), 5.29 (d, J = 13.4 Hz, 1H), 6.63 (d, J = 2.4 Hz, 1H), 6.66 (dd, J = 8.3, 2.4 Hz, 1H), 6.69 (d, J = 3.6 Hz, 1H), 6.74 (d, J = 8.1 Hz, 1H), 6.86 (d, J = 8.1 Hz, 1H), 7.17 (d, J = 8.3 Hz, 1H), 7.43 (d, J = 3.6 Hz, 1H) |
| 7-[2-Methoxy-4-(2-methylbenzoyloxy)phenyl]-8-(4-methoxybenzoyloxymethyl)-1,3,3-trimethyl-3,4-dihydro-1H-quinoxalin-2-one (Compound No. 5-21)<br />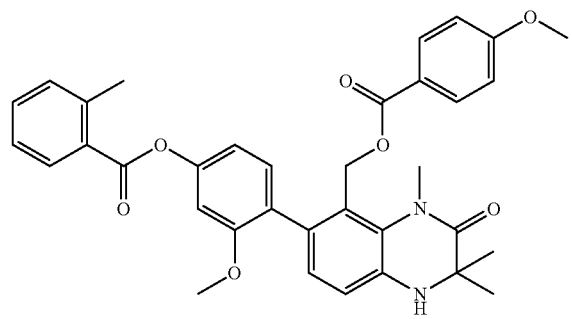 [SMILES: COc1ccc(C(=O)OCc2c(-c3ccc(OC(=O)c4ccccc4C)cc3OC)ccc3c2N(C)C(=O)C(C)(C)N3)cc1] | $^1$H-NMR (500 MHz, CDCl$_3$) δ 1.20 (s, 3H), 1.43 (s, 3H), 2.70 (s, 3H), 3.48 (s, 3H), 3.77 (s, 3H), 3.80 (s, 1H), 3.83 (s, 3H), 5.20 (d, J = 13.4 Hz, 1H), 5.35 (d, J = 13.4 Hz, 1H), 6.77 (d, J = 7.9 Hz, 1H), 6.80 (d, J = 2.1 Hz, 1H), 6.84 (dd, J = 8.2, 2.1 Hz, 1H), 6.84 (d, J = 8.7 Hz, 2H), 6.91 (d, J = 7.9 Hz, 1H), 7.32 (d, J = 8.2 Hz, 1H), 7.32-7.36 (m, 2H), 7.50 (t, J = 7.3 Hz, 1H), 7.80 (d, J = 8.7 Hz, 2H), 8.17 (d, J = 7.9 Hz, 1H) |

| Compound | ¹H-NMR |
|---|---|
| 7-[2-Methoxy-4-(2-methylbenzoyloxy)phenyl]-8-(2-methoxy-5-nitrophenoxymethyl)-1,3,3-trimethyl-3,4-dihydro-1H-quinoxalin-2-one (Compound No. 5-22) 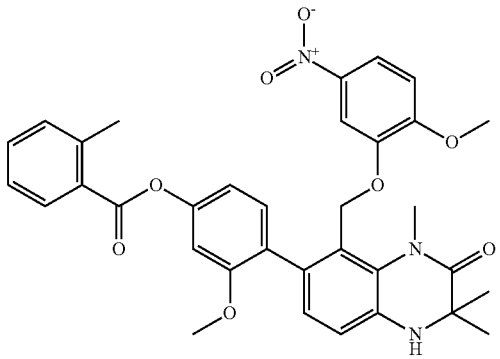 [SMILES: COc1ccc([N+](=O)[O-])cc1OCc1c(-c2ccc(OC(=O)c3ccccc3C)cc2OC)ccc2c1N(C)C(=O)C(C)(C)N2] | ¹H-NMR (400 MHz, CDCl₃) δ 0.72 (s, 3H), 1.34 (s, 3H), 2.70 (s, 3H), 3.54 (s, 3H), 3.69 (s, 1H), 3.85 (s, 3H), 3.86 (s, 3H), 5.02 (d, J = 13.8 Hz, 1H), 5.47 (d, J = 13.8 Hz, 1H), 6.72 (d, J = 7.9 Hz, 1H), 6.76 (d, J = 8.8 Hz, 1H), 6.86 (d, J = 2.2 Hz, 1H), 6.92 (d, J = 7.9 Hz, 1H), 6.97 (dd, J = 8.3, 2.2 Hz, 1H), 7.15 (d, J = 2.6 Hz, 1H), 7.34 (d, J = 7.6 Hz, 1H), 7.35 (t, J = 7.6 Hz, 1H), 7.48-7.52 (m, 1H), 7.53 (d, J = 8.3 Hz, 1H), 7.74 (dd, J = 8.8, 2.6 Hz, 1H), 8.19 (d, J = 7.6 Hz, 1H) |
| 7-[2-Methoxy-4-(2-methylbenzoyloxy)phenyl]-8-(4-methylbenzoyloxymethyl)-1,3,3-trimethyl-3,4-dihydro-1H-quinoxalin-2-one (Compound No. 5-23) 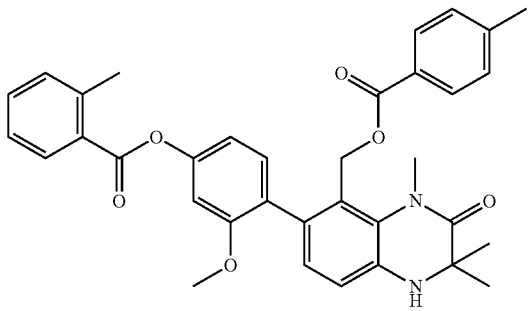 [SMILES: COc1cc(OC(=O)c2ccccc2C)ccc1-c1ccc2c(c1COC(=O)c1ccc(C)cc1)N(C)C(=O)C(C)(C)N2] | ¹H-NMR (400 MHz, CDCl₃) δ 1.20 (s, 3H), 1.43 (s, 3H), 2.36 (s, 3H), 2.69 (s, 3H), 3.47 (s, 3H), 3.76 (s, 3H), 3.80 (s, 1H), 5.19 (d, J = 13.2 Hz, 1H), 5.36 (d, J = 13.2 Hz, 1H), 6.77 (d, J = 8.1 Hz, 1H), 6.80 (d, J = 2.2 Hz, 1H), 6.84 (dd, J = 8.2, 2.2 Hz, 1H), 6.91 (d, J = 8.1 Hz, 1H), 7.16 (d, J = 8.1 Hz, 2H), 7.32 (d, J = 8.2 Hz, 1H), 7.33 (d, J = 7.7 Hz, 1H), 7.34 (t, J = 7.7 Hz, 1H), 7.48-7.52 (m, 1H), 7.74 (d, J = 8.1 Hz, 2H), 8.17 (d, J = 7.7 Hz, 1H) |
| 8-(3-Fluorobenzoyloxymethyl)-7-[2-methoxy-4-(2-methylbenzoyloxy)phenyl]-1,3,3-trimethyl-3,4-dihydro-1H-quinoxalin-2-one (Compound No. 5-24) 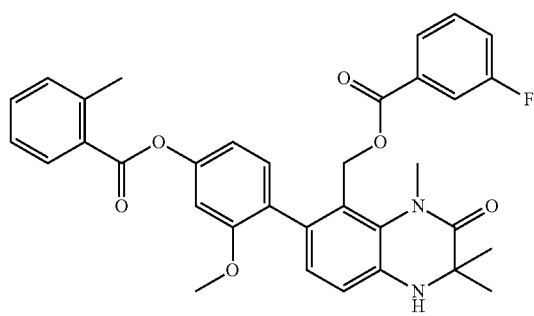 [SMILES: COc1cc(OC(=O)c2ccccc2C)ccc1-c1ccc2c(c1COC(=O)c1cccc(F)c1)N(C)C(=O)C(C)(C)N2] | ¹H-NMR (500 MHz, CDCl₃) δ 1.23 (s, 3H), 1.44 (s, 3H), 2.69 (s, 3H), 3.46 (s, 3H), 3.77 (s, 3H), 3.82 (s, 1H), 5.23 (d, J = 13.3 Hz, 1H), 5.39 (d, J = 13.3 Hz, 1H), 6.79 (d, J = 8.2 Hz, 1H), 6.80 (d, J = 2.4 Hz, 1H), 6.83 (dd, J = 8.2, 2.4 Hz, 1H), 6.92 (d, J = 8.2 Hz, 1H), 7.19-7.23 (m, 1H), 7.29 (d, J = 8.2 Hz, 1H), 7.32-7.37 (m, 3H), 7.48-7.53 (m, 2H), 7.64 (dt, J = 7.9, 1.2 Hz, 1H), 8.17 (d, J = 7.6 Hz, 1H) |
| 8-(5-Bromothiophen-2-ylcarbonyloxymethyl)-7-[2-methoxy-4-(2-methylbenzoyloxy)phenyl]-1,3,3-trimethyl-3,4-dihydro-1H-quinoxalin-2-one (Compound No. 5-25) 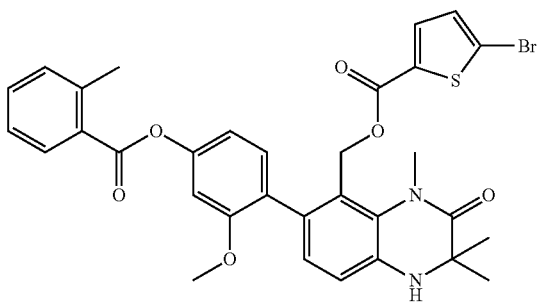 [SMILES: COc1cc(OC(=O)c2ccccc2C)ccc1-c1ccc2c(c1COC(=O)c1ccc(Br)s1)N(C)C(=O)C(C)(C)N2] | ¹H-NMR (500 MHz, CDCl₃) δ 1.23 (s, 3H), 1.43 (s, 3H), 2.70 (s, 3H), 3.45 (s, 3H), 3.78 (s, 3H), 3.81 (s, 1H), 5.17 (d, J = 13.3 Hz, 1H), 5.34 (d, J = 13.3 Hz, 1H), 6.78 (d, J = 7.9 Hz, 1H), 6.81 (d, J = 2.1 Hz, 1H), 6.85 (dd, J = 7.9, 2.1 Hz, 1H), 6.91 (d, J = 7.9 Hz, 1H), 7.01 (d, J = 4.0 Hz, 1H), 7.30 (d, J = 7.9 Hz, 1H), 7.33-7.36 (m, 2H), 7.38 (d, J = 4.0 Hz, 1H), 7.50 (td, J = 7.7, 1.4 Hz, 1H), 8.18 (d, J = 7.7 Hz, 1H) |

Example 6

8-(5-Fluoro-2-methylphenoxymethyl)-7-(2-methoxy-4-trifluoromethoxyphenyl)-1,3,3-trimethyl-3,4-dihydro-1H-quinoxalin-2-one (Compound No. 6-1)

A mixture of 7-bromo-8-(5-fluoro-2-methylphenoxymethyl)-1,3,3-trimethyl-3,4-dihydro-1H-quinoxalin-2-one (Reference Compound No. 8-1, 49.7 mg, 0.122 mmol), 2-methoxy-4-trifluoromethoxyphenylboronic acid (58.1 mg, 0.246 mmol), cessium carbonate (119 mg, 0.36 mmol) and bis(triphenylphosphin)palladium(II)dichloride (12.0 mg, 0.0171 mmol) was suspended in anhydrous N,N-dimethylformamide (0.5 ml) and stirred at 80° C. for 2 hours under argon atmosphere. After cooling down, ethyl acetate (100 mL) and water (100 mL) was added and partitioned. The organic layer was washed with saturated brine (50 mL), dried over anhydrous magnesium sulfate, and then the solvent was removed under reduced pressure. The obtained residue was purified by silica gel column chromatography (hexane-ethyl acetate) to give the titled compound (52.7 mg) as a colorless amorphous product. (Yield 58%)

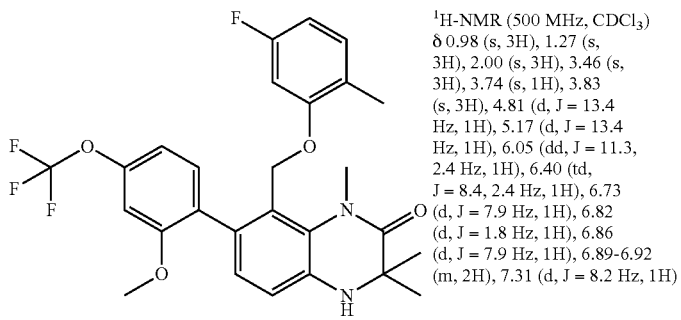

$^1$H-NMR (500 MHz, CDCl$_3$) δ 0.98 (s, 3H), 1.27 (s, 3H), 2.00 (s, 3H), 3.46 (s, 3H), 3.74 (s, 1H), 3.83 (s, 3H), 4.81 (d, J = 13.4 Hz, 1H), 5.17 (d, J = 13.4 Hz, 1H), 6.05 (dd, J = 11.3, 2.4 Hz, 1H), 6.40 (td, J = 8.4, 2.4 Hz, 1H), 6.73 (d, J = 7.9 Hz, 1H), 6.82 (d, J = 1.8 Hz, 1H), 6.86 (d, J = 7.9 Hz, 1H), 6.89-6.92 (m, 2H), 7.31 (d, J = 8.2 Hz, 1H)

Using any compounds among Reference Compounds No. 8-1~8-4, 17, 18-1~18-5, 20-1, 20-2, and available compounds, the following Compounds (No. 6-2~6-34 and 6-37~6-43) were obtained by a method similar to that of Compound No. 6-1. The following Compounds (No. 6-35 and 6-36) were obtained by a method similar to that of Reference Compound No. 20-1 using any compounds among Reference Compounds No. 19-2, 19-3, and available compounds followed by a method similar to that of Compound No. 6-1 using Reference Compound No. 8-1 and available compounds.

7-(4-Fluoro-2-methoxyphenyl)-8-(2-methylphenoxymethyl)-1,3,3-trimethyl-3,4-dihydro-1H-quinoxalin-2-one (Compound No. 6-2)

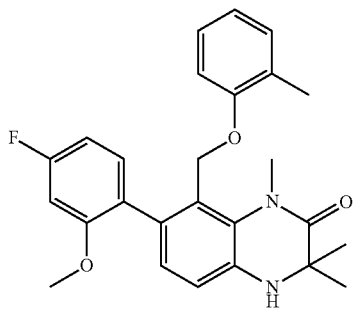

$^1$H-NMR (400 MHz, CDCl$_3$) δ 1.00 (s, 3H), 1.33 (s, 3 H), 2.07 (s, 3H), 3.44 (s, 3H), 3.72 (br s, 1H), 3.80 (s, 3H), 4.80 (d, J = 12.9 Hz, 1H), 5.16 (d, J = 12.9 Hz, 1H), 6.33 (d, J = 8.1 Hz, 1H), 6.68-6.75 (m, 3H), 6.72 (d, J = 8.1 Hz, 1H), 6.85 (d, J = 8.1 Hz, 1H), 6.93 (t, J = 7.9 Hz, 1H), 7.01 (d, J = 7.9 Hz, 1H), 7.24-7.28 (m, 1H)

| | |
|---|---|
| 8-(5-Fluoro-2-methylphenoxymethyl)-7-(2-fluorophenyl)-1,3,3-trimethyl-3,4-dihydro-1H-quinoxalin-2-one (Compound No. 6-3)<br>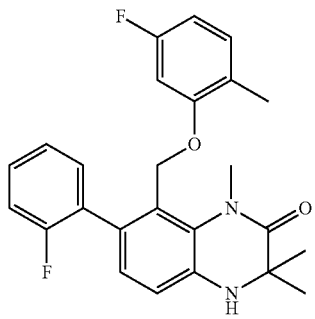 | $^1$H-NMR (400 MHz, CDCl$_3$) δ 1.06 (s, 3H), 1.32 (s, 3H), 2.02 (s, 3H), 3.45 (s, 3H), 3.80 (s, 1H), 4.87 (br s, 1H), 5.17 (br s, 1H), 6.10 (dd, J = 11.0, 2.4 Hz, 1H), 6.43 (td, J = 8.3, 2.4 Hz, 1H), 6.77 (d, J = 8.1 Hz, 1H), 6.88-7.00 (m, 1H), 6.94 (d, J = 8.1 Hz, 1H), 7.12-7.19 (m, 1H), 7.22 (td, J = 7.4, 1.2 Hz, 1H), 7.31-7.45 (m, 2H) |
| 7-(2-Chlorophenyl)-8-(5-fluoro-2-methylphenoxymethyl)-1,3,3-trimethyl-3,4-dihydro-1H-quinoxalin-2-one (Compound No. 6-4)<br>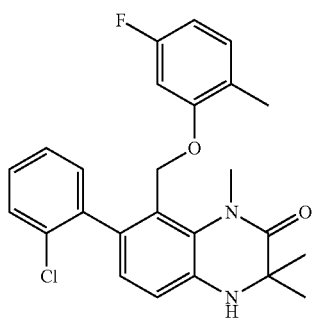 | $^1$H-NMR (400 MHz, CDCl$_3$) δ 1.09 (s, 3H), 1.34 (s, 3H), 2.03 (s, 3H), 3.43 (s, 3H), 3.80 (s, 1H), 4.71 (d, J = 12.5 Hz, 1H), 5.18 (d, J = 12.5 Hz, 1H), 6.14 (dd, J = 11.0, 2.4 Hz, 1H), 6.43 (td, J = 8.3, 2.4 Hz, 1H), 6.77 (d, J = 8.0 Hz, 1H), 6.86 (d, J = 8.0 Hz, 1H), 6.91-6.95 (m, 1H), 7.28-7.33 (m, 2H), 7.39-7.43 (m, 1H), 7.45-7.49 (m, 1H) |
| 8-(5-Fluoro-2-methylphenoxymethyl)-7-(2-methylphenyl)-1,3,3-trimethyl-3,4-dihydro-1H-quinoxalin-2-one (Compound No. 6-5)<br>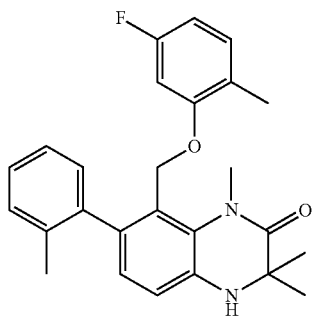 | $^1$H-NMR (400 MHz, CDCl$_3$) δ 1.20 (s, 3H), 1.28 (s, 3H), 2.04 (s, 3H), 2.15 (s, 3H), 3.42 (s, 3H), 3.76 (s, 1H), 4.74 (d, J = 12.0 Hz, 1H), 4.94 (d, J = 12.0 Hz, 1H), 6.14 (dd, J = 11.0, 2.4 Hz, 1H), 6.44 (td, J = 8.3, 2.4 Hz, 1H), 6.76 (d, J = 8.1 Hz, 1H), 6.84 (d, J = 8.1 Hz, 1H), 6.94 (t, J = 7.6 Hz, 1H), 7.16-7.29 (m, 4H) |

| | |
|---|---|
| 7-(2-Ethylphenyl)-8-{5-fluoro-2-methylphenoxymethyl)-1,3,3-trimethyl-3,4-dihydro-1H-quinoxalin-2-one (Compound No. 6-6)<br />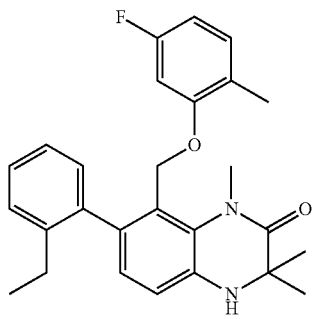 | ¹H-NMR (500 MHz, CDCl₃) δ 1.06 (t, J = 7.6 Hz, 3H), 1.21 (s, 3H), 1.30 (s, 3H), 2.04 (s, 3H), 2.42-2.55 (m, 2H), 3.40 (s, 3H), 3.76 (s, 1H), 4.72 (d, J = 11.9 Hz, 1H), 4.90 (d, J = 11.9 Hz, 1H), 6.14 (dd, J = 11.0, 2.4 Hz, 1H), 6.45 (td, J = 8.2, 2.4 Hz, 1H), 6.76 (d, J = 7.9 Hz, 1H), 6.85 (d, J = 7.9 Hz, 1H), 6.95 (t, J = 7.3 Hz, 1H), 7.17-7.24 (m, 2H), 7.28-7.32 (m, 2H) |
| 8-(5-Fluoro-2-methylphenoxymethyl)-7-(2-trifluoromethylphenyl)-1,3,3-trimethyl-3,4-dihydro-1H-quinoxalin-2-one (Compound No. 6-7)<br />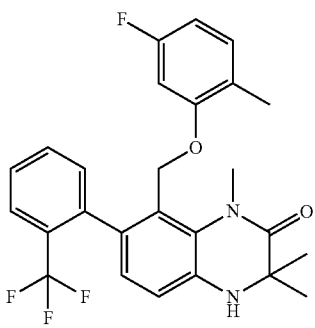 | ¹H-NMR (400 MHz, CDCl₃) δ 1.29 (s, 3H), 1.32 (s, 3H), 2.06 (s, 3H), 3.37 (s, 3H), 3.83 (s, 1H), 4.49 (d, J = 11.6 Hz, 1H), 4.88 (d, J = 11.6 Hz, 1H), 6.21 (dd, J = 10.9, 2.5 Hz, 1H), 6.48 (td, J = 8.3, 2.5 Hz, 1H), 6.76 (d, J = 8.1 Hz, 1H), 6.86 (d, J = 8.1 Hz, 1H), 6.98 (t, J = 7.5 Hz, 1H), 7.43-7.52 (m, 3H), 7.73 (d, J = 7.3 Hz, 1H) |
| 8-(5-Fluoro-2-methylphenoxymethyl)-7-(2-methoxyphenyl)-1,3,3-trimethyl-3,4-dihydro-1H-quinoxalin-2-one (Compound No. 6-8)<br />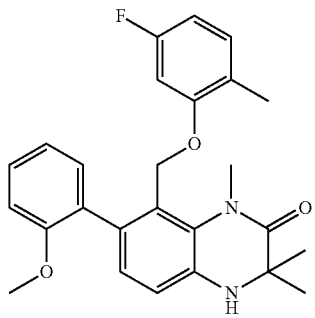 | ¹H-NMR (400 MHz, CDCl₃) δ 0.93 (s, 3H), 1.28 (s, 3H), 2.01 (s, 3H), 3.47 (s, 3H), 3.71 (s, 1H), 3.83 (s, 3H), 4.85 (d, J = 13.7 Hz, 1H), 5.23 (d, J = 13.7 Hz, 1H), 6.05 (dd, J = 11.2, 2.4 Hz, 1H), 6.38 (td, J = 8.3, 2.4 Hz, 1H), 6.72 (d, J = 8.0 Hz, 1H), 6.88 (td, J = 7.6, 0.7 Hz, 1H), 6.91 (d, J = 8.0 Hz, 1H), 6.99 (dd, J = 8.3, 0.7 Hz, 1H), 7.06 (td, J = 7.5, 1.1 Hz, 1H), 7.30-7.33 (m, 1H), 7.35-7.40 (m, 1H) |

| | |
|---|---|
| 8-(5-Fluoro-2-methylphenoxymethyl)-7-(2-trifluoromethoxyphenyl)-1,3,3-trimethyl-3,4-dihydro-1H-quinoxalin-2-one (Compound No. 6-9) 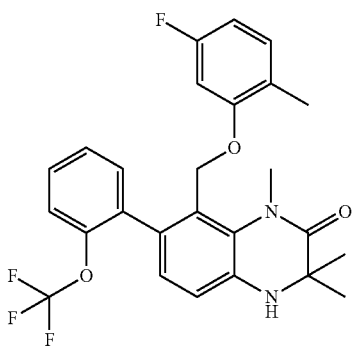 | ¹H-NMR (400 MHz, CDCl₃) δ 1.03 (s, 3H), 1.37 (s, 3H), 2.02 (s, 3H), 3.42 (s, 3H), 3.81 (s, 1H), 4.70 (d, J = 12.9 Hz, 1H), 5.18 (d, J = 12.9 Hz, 1H), 6.09 (dd, J = 11.0, 2.4 Hz, 1H), 6.43 (td, J = 8.3, 2.4 Hz, 1H), 6.77 (d, J = 8.1 Hz, 1H), 6.90 (d, J = 8.1 Hz, 1H), 6.93 (t, J = 7.5 Hz, 1H), 7.34-7.52 (m, 4H) |
| 8-(5-Fluoro-2-methylphenoxymethyl)-7-(2-methylthiophenyl)-1,3,3-trimethyl-3,4-dihydro-1H-quinoxalin-2-one (Compound No. 6-10) 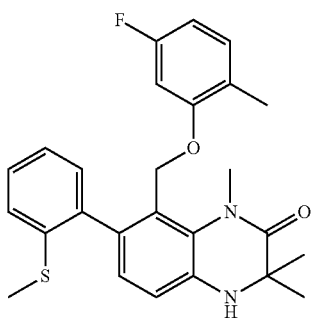 | ¹H-NMR (400 MHz, CDCl₃) δ 1.09 (s, 3H), 1.33 (s, 3H), 2.03 (s, 3H), 2.38 (s, 3H), 3.43 (s, 3H), 3.78 (s, 1H), 4.68 (d, J = 12.5 Hz, 1H), 5.20 (d, J = 12.5 Hz, 1H), 6.18 (dd, J = 11.2, 2.4 Hz, 1H), 6.43 (td, J = 8.3, 2.4 Hz, 1H), 6.77 (d, J = 8.1 Hz, 1H), 6.87 (d, J = 8.1 Hz, 1H), 6.91-6.95 (m, 1H), 7.15-7.29 (m, 3H), 7.33-7.37 (m, 1H) |
| 8-(5-Fluoro-2-methylphenoxymethyl)-7-(2-methoxycarbonylphenyl)-1,3,3-trimethyl-3,4-dihydro-1H-quinoxalin-2-one (Compound No. 6-11) 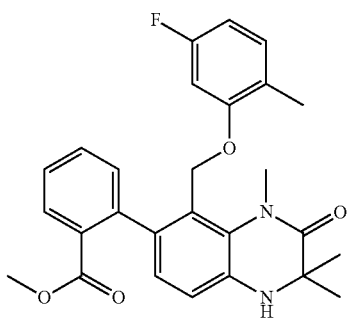 | ¹H-NMR (400 MHz, CDCl₃) δ 1.25 (s, 3H), 1.28 (s, 3H), 2.06 (s, 3H), 3.42 (s, 3H), 3.62 (s, 3H), 3.76 (s, 1H), 4.69 (d, J = 12.0 Hz, 1H), 4.97 (d, J = 12.0 Hz, 1H), 6.19 (dd, J = 10.9, 2.3 Hz, 1H), 6.46 (td, J = 8.3, 2.3 Hz, 1H), 6.73 (d, J = 8.1 Hz, 1H), 6.78 (d, J = 8.1 Hz, 1H), 6.96 (t, J = 7.7 Hz, 1H), 7.39-7.42 (m, 2H), 7.47-7.49 (m, 1H), 7.91 (dd, J = 7.9, 1.5 Hz, 1H) |

| | |
|---|---|
| 7-(4-Fluoro-2-methoxyphenyl)-8-(5-fluoro-2-methylphenoxymethyl)-1,3,3-trimethyl-3,4-dihydro-1H-quinoxalin-2-one (Compound No. 6-12)<br>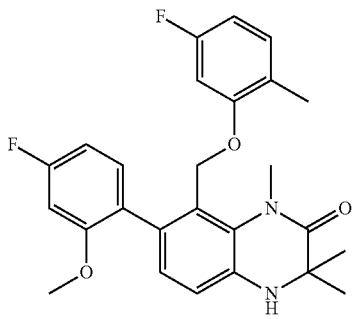 | $^1$H-NMR (500 MHz, CDCl$_3$) δ 0.96 (s, 3H), 1.27 (s, 3H), 2.01 (s, 3H), 3.46 (s, 3H), 3.72 (s, 1H), 3.81 (s, 3H), 4.81 (d, J = 13.4 Hz, 1H), 5.17 (d, J = 13.4 Hz, 1H), 6.05 (dd, J = 11.0, 2.5 Hz, 1H), 6.40 (td, J = 8.3, 2.5 Hz, 1H), 6.71-6.73 (m, 1H), 6.72 (d, J = 7.9 Hz, 1H), 6.76 (td, J = 7.9, 2.4 Hz, 1H), 6.86 (d, J = 7.9 Hz, 1H), 6.91 (t, J = 7.9 Hz, 1H), 7.24-7.27 (m, 1H) |
| 7-{5-Fluoro-2-methoxyphenyl)-8-(5-fluoro-2-methylphenoxymethyl)-1,3,3-trimethyl-3,4-dihydro-1H-quinoxalin-2-one (Compound No. 6-13)<br>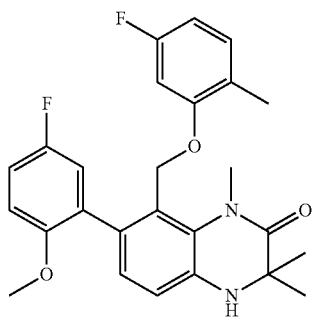 | $^1$H-NMR (400 MHz, CDCl$_3$) δ 1.01 (s, 3H), 1.29 (s, 3H), 2.01 (s, 3H), 3.44 (s, 3H), 3.75 (s, 1H), 3.79 (s, 3H), 4.82 (d, J = 13.3 Hz, 1H), 5.18 (d, J = 13.3 Hz, 1H), 6.10 (dd, J = 11.2, 2.4 Hz, 1H), 6.41 (td, J = 8.3, 2.4 Hz, 1H), 6.73 (d, J = 8.1 Hz, 1H), 6.88 (d, J = 8.1 Hz, 1H), 6.88-6.94 (m, 2H), 7.02-7.08 (m, 2H) |
| 7-(4-Chloro-2-methoxyphenyl)-8-(5-fluoro-2-methylphenoxymethyl)-1,3,3-trimethyl-3,4-dihydro-1H-quinoxalin-2-one (Compound No. 6-14)<br>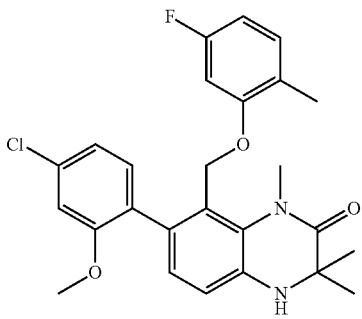 | $^1$H-NMR (500 MHz, CDCl$_3$) δ 0.96 (s, 3H), 1.28 (s, 3H), 2.01 (s, 3H), 3.45 (s, 3H), 3.73 (s, 1H), 3.82 (s, 3H), 4.80 (d, J = 13.4 Hz, 1H), 5.17 (d, J = 13.4 Hz, 1H), 6.05 (dd, J = 11.3, 2.4 Hz, 1H), 6.40 (td, J = 8.0, 2.4 Hz, 1H), 6.72 (d, J = 7.9 Hz, 1H), 6.85 (d, J = 7.9 Hz, 1H), 6.91 (t, J = 8.0 Hz, 1H), 6.97 (d, J = 1.8 Hz, 1H), 7.05 (dd, J = 8.1, 1.8 Hz, 1H), 7.24 (d, J = 8.1 Hz, 1H) |

| | |
|---|---|
| 7-(5-Chloro-2-methoxyphenyl)-8-(5-fluoro-2-methylphenoxy-methyl)-1,3,3-trimethyl-3,4-dihydro-1H-quinoxalin-2-one (Compound No. 6-15) 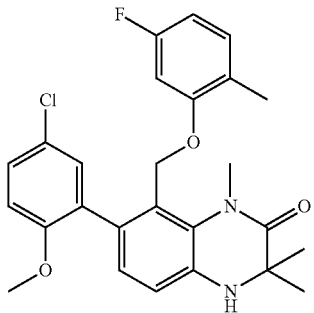 | $^1$H-NMR (500 MHz, CDCl$_3$) δ 1.05 (s, 3H), 1.28 (s, 3H), 2.02 (s, 3H), 3.44 (s, 3H), 3.76 (s, 1H), 3.80 (s, 3H), 4.80 (d, J = 13.1 Hz, 1H), 5.14 (d, J = 13.1 Hz, 1H), 6.11 (dd, J = 11.3, 2.4 Hz, 1H), 6.42 (td, J = 8.2, 2.4 Hz, 1H), 6.73 (d, J = 7.9 Hz, 1H), 6.87 (d, J = 7.9 Hz, 1H), 6.90 (d, J = 8.6 Hz, 1H), 6.92 (d, J = 8.6 Hz, 1H), 7.29-7.30 (m, 1H), 7.32 (d, J = 2.7 Hz, 1H) |
| 7-(2,4-Dimethoxyphenyl)-8-(5-fluoro-2-methylphenoxy-methyl)-1,3,3-trimethyl-3,4-dihydro-1H-quinoxalin-2-one (Compound No. 6-16) 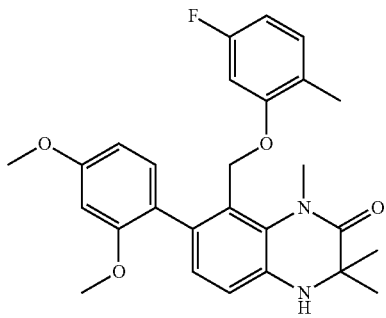 | $^1$H-NMR (500 MHz, CDCl$_3$) δ 0.90 (s, 3H), 1.28 (s, 3H), 2.01 (s, 3H), 3.47 (s, 3H), 3.68 (s, 1H), 3.81 (s, 3H), 3.87 (s, 3H), 4.86 (d, J = 13.6 Hz, 1H), 5.22 (d, J = 13.6 Hz, 1H), 6.04 (dd, J = 11.2, 2.4 Hz, 1H), 6.38 (td, J = 8.4, 2.4 Hz, 1H), 6.56 (d, J = 2.3 Hz, 1H), 6.60 (dd, J = 8.2, 2.3 Hz, 1H), 6.70 (d, J = 7.9 Hz, 1H), 6.87-6.90 (m, 1H), 6.88 (d, J = 7.9 Hz, 1H), 7.23 (d, J = 8.2 Hz, 1H) |
| 7-(2,5-Dimethoxyphenyl)-8-(5-fluoro-2-methylphenoxy-methyl)-1,3,3-trimethyl-3,4-dihydro-1H-quinoxalin-2-one (Compound No. 6-17) 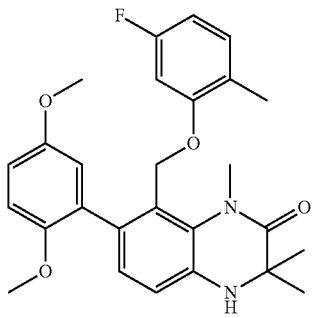 | $^1$H-NMR (400 MHz, CDCl$_3$) δ 0.91 (s, 3H), 1.31 (s, 3H), 2.01 (s, 3H), 3.47 (s, 3H), 3.72 (s, 1H), 3.76 (s, 3H), 3.81 (s, 3H), 4.87 (d, J = 13.7 Hz, 1H), 5.25 (d, J = 13.7 Hz, 1H), 6.09 (dd, J = 11.2, 2.4 Hz, 1H), 6.39 (td, J = 8.3, 2.4 Hz, 1H), 6.72 (d, J = 8.1 Hz, 1H), 6.87-6.92 (m, 5H) |

| | |
|---|---|
| 8-(5-Fluoro-2-methylphenoxymethyl)-7-(2-methoxy-5-methylphenyl)-1,3,3-trimethyl-3,4-dihydro-1H-quinoxalin-2-one (Compound No. 6-18)<br>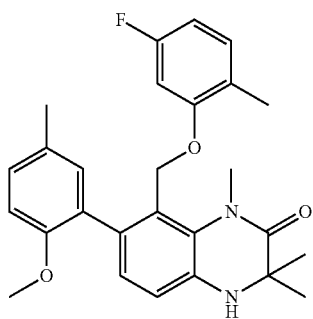 | $^1$H-NMR (400 MHz, CDCl$_3$) δ 0.93 (s, 3H), 1.29 (s, 3H), 2.01 (s, 3H), 2.33 (s, 3H), 3.47 (s, 3H), 3.70 (br s, 1H), 3.79 (s, 3H), 4.84 (d, J = 13.7 Hz, 1H), 5.22 (d, J = 13.7 Hz, 1H), 6.08 (dd, J = 11.2, 2.4 Hz, 1H), 6.39 (td, J = 8.3, 2.4 Hz, 1H), 6.72 (d, J = 8.0 Hz, 1H), 6.87-6.91 (m, 2H), 6.90 (d, J = 8.0 Hz, 1H), 7.13 (d, J = 2.3 Hz, 1H), 7.16 (dd, J = 8.3, 2.3 Hz, 1H) |
| 8-(5-Fluoro-2-methylphenoxymethyl)-7-(2-methoxy-5-trifluoromethylphenyl)-1,3,3-trimethyl-3,4-dihydro-1H-quinoxalin-2-one (Compound No. 6-19)<br>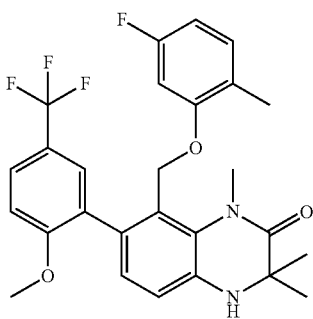 | $^1$H-NMR (500 MHz, CDCl$_3$) δ 1.09 (s, 3H), 1.28 (s, 3H), 1.99 (s, 3H), 3.45 (s, 3H), 3.78 (s, 1H), 3.88 (s, 3H), 4.77 (d, J = 12.8 Hz, 1H), 5.11 (d, J = 12.8 Hz, 1H), 6.09 (dd, J = 11.0, 2.4 Hz, 1H), 6.42 (td, J = 8.4, 2.4 Hz, 1H), 6.76 (d, J = 7.9 Hz, 1H), 6.89 (d, J = 7.9 Hz, 1H), 6.90-6.94 (m, 1H), 7.04 (d, J = 8.9 Hz, 1H), 7.56 (d, J = 2.1 Hz, 1H), 7.62 (dd, J = 8.9, 2.1 Hz, 1H) |
| 8-(5-Fluoro-2-methylphenoxymethyl)-7-(5-isopropyl-2-methoxyphenyl)-1,3,3-trimethyl-3,4-dihydro-1H-quinoxalin-2-one (Compound No. 6-20)<br>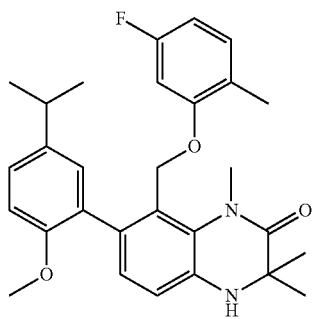 | $^1$H-NMR (400 MHz, CDCl$_3$) δ 0.88 (s, 3H), 1.26 (d, J = 6.9 Hz, 3H), 1.26 (d, J = 6.9 Hz, 3H), 1.30 (s, 3H), 2.01 (s, 3H), 2.91 (septet, J = 6.9 Hz, 1H), 3.49 (s, 3H), 3.70 (s, 1H), 3.81 (s, 3H), 4.86 (d, J = 13.8 Hz, 1H), 5.25 (d, J = 13.8 Hz, 1H), 6.04 (dd, J = 11.2, 2.4 Hz, 1H), 6.37 (td, J = 8.3, 2.4 Hz, 1H), 6.72 (d, J = 8.1 Hz, 1H), 6.86-6.90 (m, 1H), 6.92 (d, J = 8.3 Hz, 1H), 6.92 (d, J = 8.1 Hz, 1H), 7.19 (d, J = 2.4 Hz, 1H), 7.23 (dd, J = 8.3, 2.4 Hz, 1H) |

| | |
|---|---|
| 7-(5-tert-Butyl-2-methoxy-phenyl)-8-(5-fluoro-2-methyl-phenoxymethyl)-1,3(3-trimethyl-3,4-dihydro-1H-quinoxalin-2-one (Compound No. 6-21)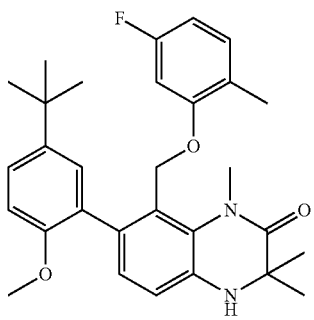 | $^1$H-NMR (400 MHz, CDCl$_3$) δ 0.84 (s, 3H), 1.31 (s, 3 H), 1.34 (s, 9H), 2.01 (s, 3H), 3.50 (s, 3H), 3.69 (s, 1H), 3.81 (s, 3H), 4.87 (d, J = 13.9 Hz, 1H), 5.27 (d, J = 13.9 Hz, 1H), 6.01 (dd, J = 11.2, 2.4 Hz, 1H), 6.36 (td, J = 8.3, 2.4 Hz, 1 H), 6.73 (d, J = 7.9 Hz, 1H), 6.85-6.90 (m, 1H), 6.92 (d, J = 7.9 Hz, 1H), 6.92 (d, J = 8.5 Hz, 1H), 7.36 (d, J = 2.4 Hz, 1H), 7.39 (dd, J = 8.5, 2.4 Hz, 1H) |
| 7-(3-Fluoro-2-methoxyphenyl)-8-(5-fluoro-2-methylphenoxy-methyl)-1,3,3-trimethyl-3,4-dihydro-1H-quinoxalin-2-one (Compound No. 6-22)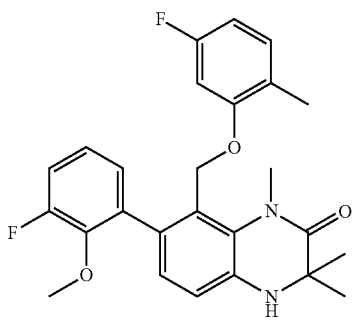 | $^1$H-NMR (400 MHz, CDCl$_3$) δ 0.96 (s, 3H), 1.37 (s, 3 H), 2.00 (s, 3H), 3.44 (s, 3H), 3.66 (d, J = 1.7 Hz, 3 H), 3.78 (br s, 1H), 4.80 (d, J = 13.3 Hz, 1H), 5.28 (d, J = 13.3 Hz, 1H), 6.09 (dd, J = 11.1, 2.4 Hz, 1H), 6.41 (td, J = 8.3, 2.4 Hz, 1H), 6.75 (d, J = 8.1 Hz, 1 H), 6.91 (t, J = 7.6 Hz, 1H), 6.91 (d, J = 8.1 Hz, 1H), 7.07-7.17 (m, 3H) |
| 7-(6-Fluoro-2-methoxyphenyl)-8-(5-fluoro-2-methylphenoxy-methyl)-1,3,3-trimethyl-3,4-dihydro-1H-quinoxalin-2-one (Compound No. 6-23)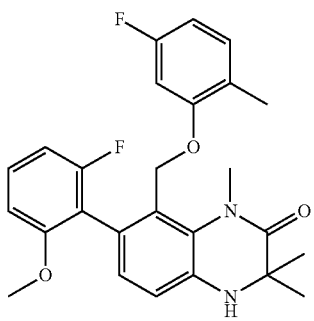 | $^1$H-NMR (500 MHz, CDCl$_3$) δ 1.06 (s, 3H), 1.17 (s, 3 H), 2.02 (s, 3H), 3.46 (s, 3H), 3.75 (br s, 1H), 3.82 (s, 3H), 5.02 (s, 2H), 6.15 (dd, J = 11.3, 2.5 Hz, 1H), 6.39 (td, J = 8.3, 2.5 Hz, 1H), 6.73 (d, J = 8.1 Hz, 1H), 6.78-6.83 (m, 2H), 6.88-6.91 (m, 1H), 6.91 (d, J = 8.1 Hz, 1H), 7.31 (td, J = 8.3, 6.6 Hz, 1H) |

| Compound | NMR |
|---|---|
| 7-(3,5-Difluoro-2-methoxy-phenyl)-8-(5-fluoro-2-methyl-phenoxymethyl)-1,3,3-trimethyl-3,4-dihydro-1H-quinoxalin-2-one (Compound No. 6-24) 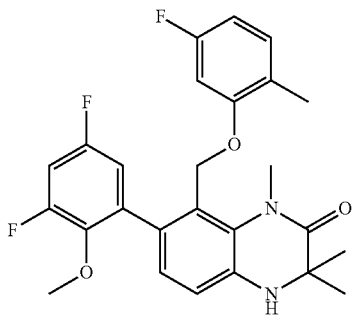 | ¹H-NMR (400 MHz, CDCl₃) δ 1.03 (s, 3H), 1.37 (s, 3 H), 2.00 (s, 3H), 3.42 (s, 3H), 3.59 (s, 3H), 3.83 (s, 1H), 4.76 (d, J = 13.2 Hz, 1H), 5.24 (d, J = 13.2 Hz, 1H), 6.15 (dd, J = 11.0, 2.4 Hz, 1H), 6.44 (td, J = 8.3, 2.4 Hz, 1H), 6.76 (d, J = 7.8 Hz, 1H), 6.87-6.95 (m, 4H) |
| 7-(3,4-Difluorophenyl)-8-(5-fluoro-2-methylphenoxy-methyl)-1,3,3-trimethyl-3,4-dihydro-1H-quinoxalin-2-one (Compound No. 6-25) 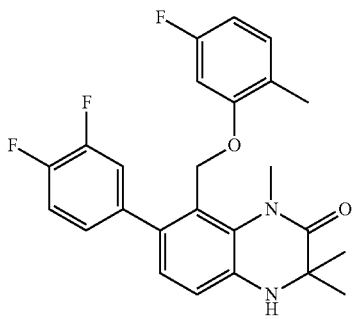 | ¹H-NMR (500 MHz, CDCl₃) δ 1.26 (s, 6H), 2.13 (s, 3 H), 3.45 (s, 3H), 3.80 (br s, 1H), 4.86 (s, 2H), 6.22 (dd, J = 11.0, 2.4 Hz, 1H), 6.51 (td, J = 8.2, 2.4 Hz, 1H), 6.78 (d, J = 8.1 Hz, 1H), 6.92 (d, J = 8.1 Hz, 1 H), 7.01 (t, J = 7.5 Hz, 1H), 7.11-7.18 (m, 2H), 7.24-7.29 (m, 1H) |
| 7-(5-Chloro-4-fluoro-2-methoxy-phenyl)-8-(5-fluoro-2-methylphenoxy-methyl)-1,3,3-trimethyl-3,4-dihydro-1H-quinoxalin-2-one (Compound No. 6-26) 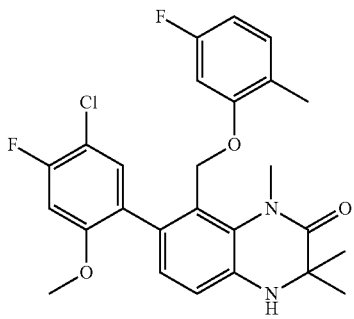 | ¹H-NMR (500 MHz, CDCl₃) δ 1.08 (s, 3H), 1.27 (s, 3 H), 2.02 (s, 3H), 3.43 (s, 3H), 3.77 (s, 1H), 3.80 (s, 3H), 4.76 (d, J = 13.0 Hz, 1H), 5.10 (d, J = 13.0 Hz, 1H), 6.12 (dd, J = 11.0, 2.4 Hz, 1H), 6.44 (td, J = 7.9, 2.4 Hz, 1H), 6.73 (d, J = 8.1 Hz, 1H), 6.79 (d, J = 10.7 Hz, 1H), 6.84 (d, J = 8.1 Hz, 1H), 6.94 (t, J = 7.9 Hz, 1H), 7.33 (d, J = 8.2 Hz, 1H) |

| | |
|---|---|
| 8-(5-Fluoro-2-methylphenoxymethyl)-7-(2-methoxy-5-nitrophenyl)-1,3,3-trimethyl-3,4-dihydro-1H-quinoxalin-2-one (Compound No. 6-27)<br>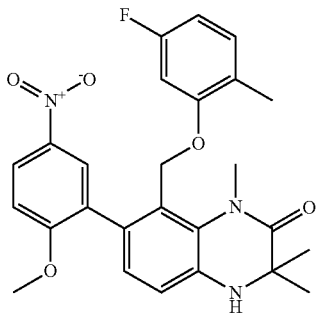 | $^1$H-NMR (400 MHz, CDCl$_3$) δ 1.18 (s, 3H), 1.27 (s, 3H), 2.01 (s, 3H), 3.43 (s, 3H), 3.84 (s, 1H), 3.93 (s, 3H), 4.73 (d, J = 12.7 Hz, 1H), 5.05 (d, J = 12.7 Hz, 1H), 6.12 (dd, J = 11.0, 2.4 Hz, 1H), 6.44 (td, J = 8.3, 2.4 Hz, 1H), 6.78 (d, J = 8.0 Hz, 1H), 6.88 (d, J = 8.0 Hz, 1H), 6.91-6.95 (m, 1H), 7.04 (d, J = 9.0 Hz, 1H), 8.21 (d, J = 2.8 Hz, 1H), 8.27 (dd, J = 9.0, 2.8 Hz, 1H) |
| 8-(5-Fluoro-2-methylphenoxymethyl)-7-(2-methoxy-4-nitrophenyl)-1,3,3-trimethyl-3,4-dihydro-1H-quinoxalin-2-one (Compound No. 6-28)<br>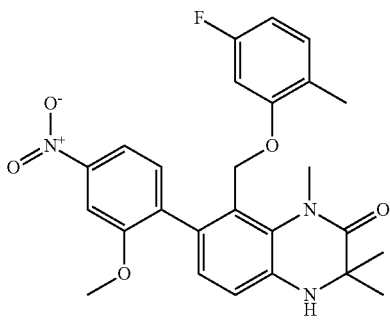 | $^1$H-NMR (400 MHz, CDCl$_3$) δ 1.05 (s, 3H), 1.31 (s, 3H), 1.99 (s, 3H), 3.45 (s, 3H), 3.85 (s, 1H), 3.93 (s, 3H), 4.75 (d, J = 13.2 Hz, 1H), 5.15 (d, J = 13.2 Hz, 1H), 6.05 (dd, J = 11.0, 2.4 Hz, 1H), 6.43 (td, J = 8.3, 2.4 Hz, 1H), 6.76 (d, J = 8.1 Hz, 1H), 6.86 (d, J = 8.1 Hz, 1H), 6.92 (t, J = 7.6 Hz, 1H), 7.47 (d, J = 8.2 Hz, 1H), 7.83 (d, J = 2.2 Hz, 1H), 7.93 (dd, J = 8.2, 2.2 Hz, 1H) |
| 7-(5-Cyano-2-methoxyphenyl)-8-(5-fluoro-2-methylphenoxymethyl)-1,3,3-trimethyl-3,4-dihydro-1H-quinoxalin-2-one (Compound No. 6-29)<br>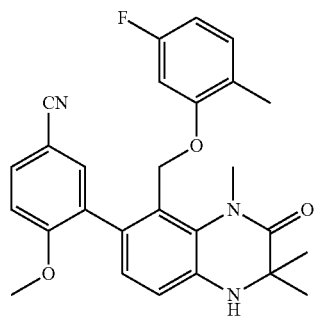 | $^1$H-NMR (400 MHz, CDCl$_3$) δ 1.13 (s, 3H), 1.27 (s, 3H), 2.02 (s, 3H), 3.43 (s, 3H), 3.82 (s, 1H), 3.88 (s, 3H), 4.72 (d, J = 12.8 Hz, 1H), 5.06 (d, J = 12.8 Hz, 1H), 6.10 (dd, J = 11.0, 2.4 Hz, 1H), 6.45 (td, J = 8.3, 2.4 Hz, 1H), 6.76 (d, J = 8.1 Hz, 1H), 6.84 (d, J = 8.1 Hz, 1H), 6.95 (t, J = 7.2 Hz, 1H), 7.02 (d, J = 8.5 Hz, 1H), 7.59 (d, J = 2.2 Hz, 1H), 7.66 (dd, J = 8.5, 2.2 Hz, 1H) |

| Compound | NMR |
|---|---|
| 7-(5-Acetyl-2-methoxyphenyl)-8-(5-fluoro-2-methylphenoxymethyl)-1,3,3-trimethyl-3,4-dihydro-1H-quinoxalin-2-one (Compound No. 6-30) 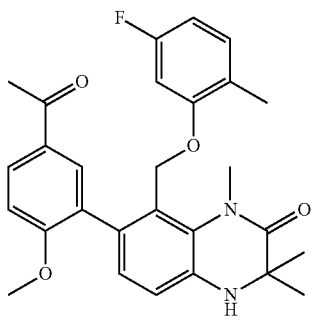 | $^1$H-NMR (400 MHz, CDCl$_3$) δ 1.03 (s, 3H), 1.29 (s, 3H), 2.00 (s, 3H), 2.58 (s, 3H), 3.46 (s, 3H), 3.77 (s, 1H), 3.90 (s, 3H), 4.79 (d, J = 13.2 Hz, 1H), 5.14 (d, J = 13.2 Hz, 1H), 6.07 (dd, J = 11.1, 2.5 Hz, 1H), 6.41 (td, J = 8.3, 2.5 Hz, 1H), 6.76 (d, J = 8.1 Hz, 1H), 6.88-6.93 (m, 1H), 6.89 (d, J = 8.1 Hz, 1H), 7.03 (d, J = 8.8 Hz, 1H), 7.92 (d, J = 2.3 Hz, 1H), 8.03 (dd, J = 8.8, 2.3 Hz, 1H) |
| 7-(4-Benzoyloxy-2-methoxyphenyl)-8-(5-fluoro-2-methylphenoxymethyl)-1,3,3-trimethyl-3,4-dihydro-1H-quinoxalin-2-one (Compound No. 6-31) 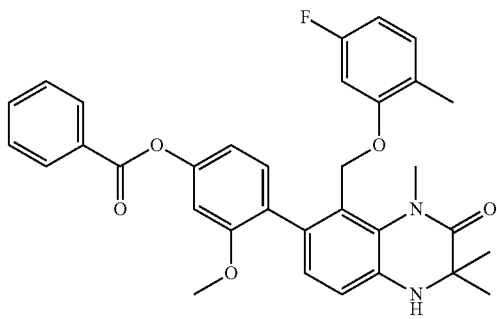 | $^1$H-NMR (400 MHz, CDCl$_3$) δ 0.95 (s, 3H), 1.28 (s, 3H), 2.03 (s, 3H), 3.47 (s, 3H), 3.73 (br s, 1H), 3.84 (s, 3H), 4.89 (d, J = 13.7 Hz, 1H), 5.23 (d, J = 13.7 Hz, 1H), 6.09 (dd, J = 11.0, 2.4 Hz, 1H), 6.40 (td, J = 8.3, 2.4 Hz, 1H), 6.73 (d, J = 8.1 Hz, 1H), 6.89-6.96 (m, 4H), 7.37 (d, J = 8.1 Hz, 1H), 7.52-7.56 (m, 2H), 7.64-7.69 (m, 1H), 8.22-8.25 (m, 2H) |
| 7-(5-Benzoyloxy-2-methoxyphenyl)-8-(S-fluoro-2-methylphenoxymethyl)-1,3,3-trimethyl-3,4-dihydro-1H-quinoxalin-2-one (Compound No. 6-32) 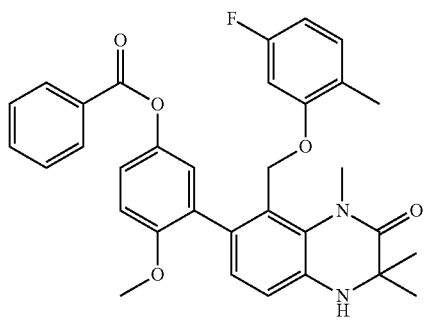 | $^1$H-NMR (500 MHz, CDCl$_3$) δ 1.03 (s, 3H), 1.25 (s, 3H), 2.01 (s, 3H), 3.45 (s, 3H), 3.77 (s, 1H), 3.84 (s, 3H), 4.90 (d, J = 13.4 Hz, 1H), 5.20 (d, J = 13.4 Hz, 1H), 6.17 (dd, J = 11.3, 2.4 Hz, 1H), 6.41 (td, J = 8.2, 2.4 Hz, 1H), 6.73 (d, J = 8.1 Hz, 1H), 6.90 (t, J = 7.3 Hz, 1H), 6.96 (d, J = 8.1 Hz, 1H), 7.02 (d, J = 8.8 Hz, 1H), 7.19 (d, J = 3.0 Hz, 1H), 7.23 (dd, J = 8.8, 3.0 Hz, 1H), 7.51 (t, J = 7.8 Hz, 2H), 7.64 (t, J = 7.8 Hz, 1H), 8.19 (d, J = 7.8 Hz, 2H) |

| | |
|---|---|
| 8-(5-Fluoro-2-methylphenoxymethyl)-7-(5-hydroxy-2-methoxyphenyl)-1,3,3-trimethyl-3,4-dihydro-1H-quinoxalin-2-one (Compound No. 6-33) 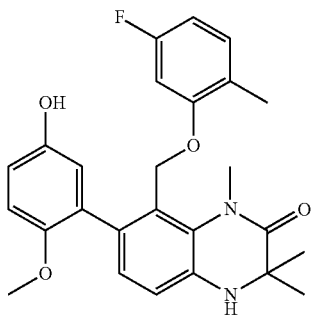 | $^1$H-NMR (500 MHz, CDCl$_3$) δ 0.93 (s, 3H), 1.29 (s, 3H), 2.01 (s, 3H), 3.45 (s, 3H), 3.73 (s, 1H), 3.75 (s, 3H), 4.87 (d, J = 13.7 Hz, 1H), 5.01 (s, 1H), 5.23 (d, J = 13.7 Hz, 1H), 6.10 (dd, J = 11.0, 2.4 Hz, 1H), 6.39 (td, J = 8.4, 2.4 Hz, 1H), 6.71 (d, J = 7.9 Hz, 1H), 6.83-6.86 (m, 3H), 6.89 (d, J = 7.9 Hz, 1H), 6.90 (t, J = 7.3 Hz, 1H) |
| 7-(4-Cyano-2-methoxyphenyl)-8-(5-fluoro-2-methylphenoxymethyl)-1,3,3-trimethyl-3,4-dihydro-1H-quinoxalin-2-one (Compound No. 6-34) 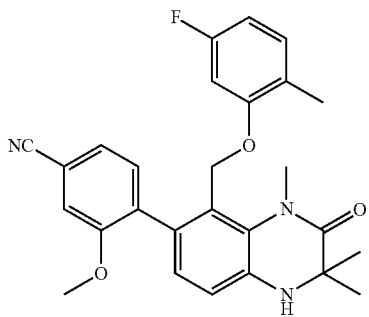 | $^1$H-NMR (500 MHz, CDCl$_3$) δ 1.03 (s, 3H), 1.30 (s, 3H), 1.99 (s, 3H), 3.45 (s, 3H), 3.81 (s, 1H), 3.86 (s, 3H), 4.75 (d, J = 13.1 Hz, 1H), 5.14 (d, J = 13.1 Hz, 1H), 6.04 (dd, J = 11.0, 2.4 Hz, 1H), 6.43 (td, J = 8.2, 2.4 Hz, 1H), 6.75 (d, J = 7.9 Hz, 1H), 6.84 (d, J = 7.9 Hz, 1H), 6.91-6.94 (m, 1H), 7.20 (d, J = 1.5 Hz, 1H), 7.35 (dd, J = 7.6, 1.5 Hz, 1H), 7.40 (d, J = 7.6 Hz, 1H) |
| 7-(4-Acetyl-2-methoxyphenyl)-8-(5-fluoro-2-methylphenoxymethyl)-1,3,3-trimethyl-3,4-dihydro-1H-quinoxalin-2-one (Compound No. 6-35) 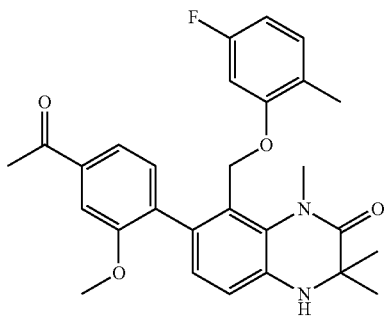 | $^1$H-NMR (400 MHz, CDCl$_3$) δ 0.96 (s, 3H), 1.31 (s, 3H), 2.00 (s, 3H), 2.66 (s, 3H), 3.46 (s, 3H), 3.77 (s, 1H), 3.90 (s, 3H), 4.79 (d, J = 13.5 Hz, 1H), 5.20 (d, J = 13.5 Hz, 1H), 6.03 (dd, J = 11.1, 2.4 Hz, 1H), 6.40 (td, J = 8.2, 2.4 Hz, 1H), 6.74 (d, J = 8.1 Hz, 1H), 6.89-6.92 (m, 1H), 6.89 (d, J = 8.1 Hz, 1H), 7.41 (d, J = 7.8 Hz, 1H), 7.60 (d, J = 1.6 Hz, 1H), 7.64 (dd, J = 7.8, 1.6 Hz, 1H) |

| | |
|---|---|
| 8-(5-Fluoro-2-methylphenoxymethyl)-7-(2-methoxy-4-methylphenyl)-1,3,3-trimethyl-3,4-dihydro-1H-quinoxalin-2-one (Compound No. 6-36) 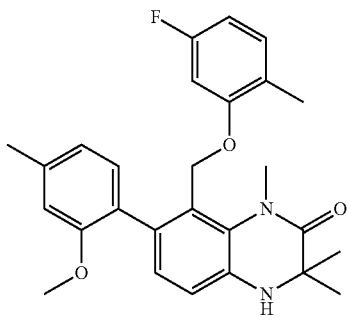 | $^1$H-NMR (500 MHz, CDCl$_3$) δ 0.90 (s, 3H), 1.28 (s, 3H), 2.01 (s, 3H), 2.43 (s, 3H), 3.46 (s, 3H), 3.68 (s, 1H), 3.81 (s, 3H), 4.86 (d, J = 13.7 Hz, 1H), 5.23 (d, J = 13.7 Hz, 1H), 6.05 (dd, J = 11.3, 2.4 Hz, 1H), 6.38 (td, J = 8.2, 2.4 Hz, 1H), 6.71 (d, J = 8.1 Hz, 1H), 6.80 (s, 1H), 6.87-6.90 (m, 2H), 6.89 (d, J = 8.1 Hz, 1H), 7.20 (d, J = 7.6 Hz, 1H) |
| 8-(5-Fluoro-2-methylphenoxymethyl)-7-(2-methoxy-5-methoxycarbonylphenyl)-1,3,3-trimethyl-3,4-dihydro-1H-quinoxalin-2-one (Compound No. 6-37) 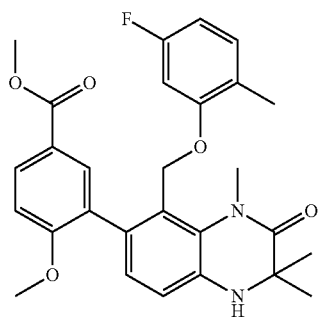 | $^1$H-NMR (400 MHz, CDCl$_3$) δ 1.08 (s, 3H), 1.24 (s, 3H), 2.01 (s, 3H), 3.45 (s, 3H), 3.81 (s, 1H), 3.88 (s, 3H), 3.89 (s, 3H), 4.80 (d, J = 13.1 Hz, 1H), 5.11 (d, J = 13.1 Hz, 1H), 6.09 (dd, J = 11.1, 2.4 Hz, 1H), 6.41 (td, J = 8.3, 2.4 Hz, 1H), 6.75 (d, J = 7.8 Hz, 1H), 6.89-6.92 (m, 1H), 6.90 (d, J = 7.8 Hz, 1H), 7.01 (d, J = 8.5 Hz, 1H), 7.99 (d, J = 2.2 Hz, 1H), 8.07 (dd, J = 8.5, 2.2 Hz, 1H) |
| 8-(2-Methoxyphenylaminomethyl)-7-(2-methoxy-5-trifluoromethylphenyl)-1,3,3-trimethyl-3,4-dihydro-1H-quinoxalin-2-one (Compound No. 6-38) 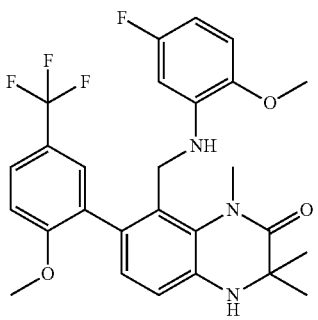 | $^1$H-NMR (400 MHz, CDCl$_3$) δ 1.22 (s, 3H), 1.43 (s, 3H), 3.47 (s, 3H), 3.71 (s, 3H), 3.78 (s, 1H), 3.84 (s, 3H), 4.09-4.11 (m, 2H), 4.39 (br s, 1H), 6.30 (dd, J = 7.8, 1.5 Hz, 1H), 6.57 (td, J = 7.8, 1.5 Hz, 1H), 6.65 (dd, J = 8.1, 1.5 Hz, 1H), 6.70-6.74 (m, 1H), 6.71 (d, J = 8.1 Hz, 1H), 6.80 (d, J = 8.1 Hz, 1H), 6.96 (d, J = 8.7 Hz, 1H), 7.45 (d, J = 2.0 Hz, 1H), 7.56 (dd, J = 8.7, 2.0 Hz, 1H) |

| | |
|---|---|
| 7-(2-Methoxy-4-methoxymethoxy-phenyl)-8-(2-methoxyphenyl-aminomethyl)-1,3,3-trimethyl-3,4-dihydro-1H-quinoxalin-2-one (Compound No. 6-39)<br>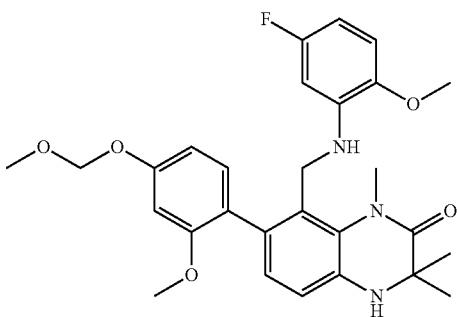 | $^1$H-NMR (500 MHz, CDCl$_3$) δ 1.16 (s, 3H), 1.42 (s, 3 H), 3.46 (s, 3H), 3.50 (s, 3H), 3.70 (s, 1H), 3.73 (s, 3H), 3.77 (s, 3H), 4.13 (d, J = 5.3 Hz, 2H), 4.52 (t, J = 5.3 Hz, 1H), 5.19 (s, 2H), 6.34 (dd, J = 7.6, 1.5 Hz, 1H), 6.56 (td, J = 7.6, 1.5 Hz, 1H), 6.61 (d, J = 2.4 Hz, 1H), 6.65-6.67 (m, 2H), 6.68 (d, J = 7.9 Hz, 1H), 6.72 (td, J = 7.6, 1.5 Hz, 1H), 6.80 (d, J = 7.9 Hz, 1H), 7.07 (d, J = 8.2 Hz, 1H) |
| 7-(2-Methoxy-5-methylphenyl)-8-(2-methoxyphenylaminomethyl)-1,3,3-trimethyl-3,4-dihydro-1H-quinoxalin-2-one (Compound No. 6-40)<br>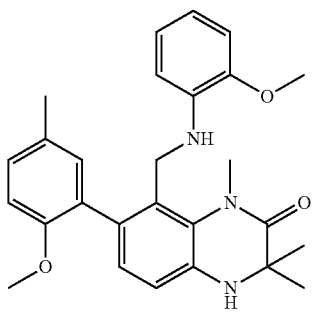 | $^1$H-NMR (400 MHz, CDCl$_3$) δ 1.19 (s, 3H), 1.42 (s, 3 H), 2.29 (s, 3H), 3.47 (s, 3H), 3.71 (s, 1H), 3.73 (s, 3H), 3.76 (s, 3H), 4.13 (br s, 2H), 4.52 (br s, 1H), 6.34 (dd, J = 7.8, 1.4 Hz, 1H), 6.56 (td, J = 7.8, 1.4 Hz, 1H), 6.66 (dd, J = 7.8, 1.4 Hz, 1H), 6.69 (d, J = 8.1 Hz, 1H), 6.72 (td, J = 7.8, 1.4 Hz, 1H), 6.80 (d, J = 8.2 Hz, 1H), 6.82 (d, J = 8.1 Hz, 1H), 6.99 (d, J = 2.0 Hz, 1H), 7.09 (dd, J = 8.2, 2.0 Hz, 1H) |
| 8-(5-Fluoro-2-methylphenyl-aminomethyl)-7-(2-methoxy-4-methoxymethoxyphenyl)-1,3,3-trimethyl-3,4-dihydro-1H-quinoxalin-2-one (Compound No. 6-41)<br>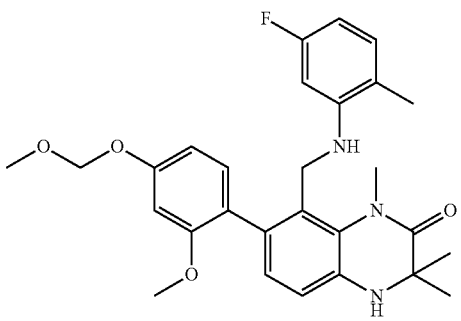 | $^1$H-NMR (400 MHz, CDCl$_3$) δ 1.17 (s, 3H), 1.40 (s, 3 H), 1.85 (s, 3H), 3.42 (s, 3H), 3.51 (s, 3H), 3.73 (s, 1H), 3.77 (s, 3H), 3.83 (br s, 1H), 4.13-4.23 (m, 2H), 5.20 (s, 2H), 6.03 (dd, J = 11.7, 2.5 Hz, 1H), 6.22 (td, J = 8.4, 2.5 Hz, 1H), 6.65 (d, J = 2.3 Hz, 1H), 6.70 (d, J = 7.8 Hz, 1H), 6.71 (dd, J = 8.3, 2.3 Hz, 1H), 6.81-6.85 (m, 1H), 6.83 (d, J = 7.8 Hz, 1H), 7.11 (d, J = 8.3 Hz, 1H) |

| | |
|---|---|
| 7-(2-Methoxy-5-methoxycarbonyl-phenyl)-8-(2-methoxyphenyl-aminomethyl)-1,3,3-trimethyl-3,4-dihydro-1H-quinoxalin-2-one (Compound No. 6-42) 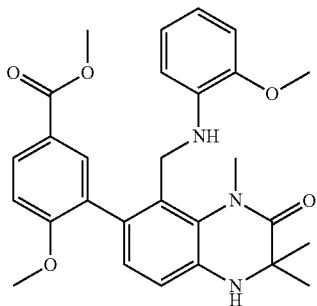 | $^1$H-NMR (400 MHz, CDCl$_3$) δ 1.20 (s, 3H, 1.43 (s, 3 H), 3.47 (s, 3H), 3.70 (s, 3H), 3.76 (s, 1H), 3.85 (s, 3H), 3.88 (s, 3H), 4.09 (d, J = 5.3 Hz, 2H), 4.41 (t, J = 5,3 Hz, 1H), 6.31 (dd, J = 7.7, 1.4 Hz, 1H), 6.56 (td, J = 7.7, 1.4 Hz, 1H), 6.64 (dd, J = 7.7, 1.5 Hz, 1H), 6.71 (d, J = 8.0 Hz, 1H), 6.71 (td, J = 7.7, 1.5 Hz, 1H), 6.81 (d, J = 8.0 Hz, 1H), 6.93 (d, J = 8.5 Hz, 1H), 7.88 (d, J = 2.2 Hz, 1H), 8.01 (dd, J = 8.5, 2.2 Hz, 1H) |
| 7-(2-Methoxy-5-nitrophenyl)-8-(2-methoxyphenylaminomethyl)-1,3,3-trimethyl-3,4-dihydro-1H-quinoxalin-2-one (Compound No. 6-43) 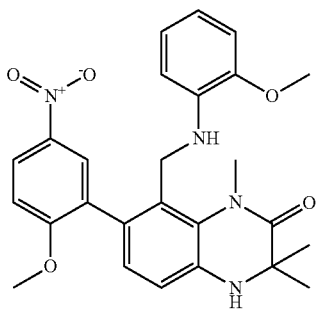 | $^1$H-NMR (500 MHz, CDCl$_3$) δ 1.25 (s, 3H), 1.43 (s, 3 H), 3.47 (s, 3H), 3.70 (s, 3H), 3.82 (s, 1H), 3.89 (s, 3H), 4.06 (d, J = 14.1 Hz, 1H), 4.13 (d, J = 14.1 Hz, 1H), 4.30 (br s, 1H), 6.28 (dd, J = 7.8, 1.4 Hz, 1H), 6.57 (td, J = 7.8, 1.4 Hz, 1H), 6.64 (dd, J = 7.8, 1.4 Hz, 1H), 6.70 (td, J = 7.8, 1.4 Hz, 1H), 6.73 (d, J = 7.9 Hz, 1H), 6.79 (d, J = 7.9 Hz, 1H), 6.94 (d, J = 9.2 Hz, 1H), 8.09 (d, J = 2.7 Hz, 1H), 8.20 (dd, J = 9.2, 2.7 Hz, 1H) |

Example 7

8-(5-Fluoro-2-methylphenoxymethyl)-7-(2-nitrophenyl)-1,3,3-trimethyl-3,4-dihydro-1H-quinoxalin-2-one (Compound No. 7-1)

A mixture of 7-(5,5-dimethyl[1,3,2]dioxaborinan-2-yl)-8-(5-fluoro-2-methylphenoxymethyl)-1,3,3-trimethyl-3,4-dihydro-1H-quinoxalin-2-one (Reference Compound No. 21, 68.2 mg, 0.155 mmol), 2-nitro-1-iodobenzene (79.0 mg, 0.317 mmol), sodium hydrogen carbonate (41.5 mg, 0.494 mmol) and tetrakis(triphenylphosphine)palladium (0) (19.0 mg, 0.0164 mmol) was suspended in mixed solvent of anhydrous N,N-dimethylformamide (0.5 ml) and water (0.5 mL), and stirred at 120° C. for 30 minutes by irradiated microwave. After cooling down, ethyl acetate (15 mL) and water (15 mL) were added and partitioned. The organic layer was washed with saturated brine (15 mL), dried over anhydrous magnesium sulfate, and then the solvent was removed under reduced pressure. The obtained residue was purified by silica gel column chromatography (hexane-ethyl acetate) to give the titled compound (42.6 mg) as a yellow solid. (Yield 61%)

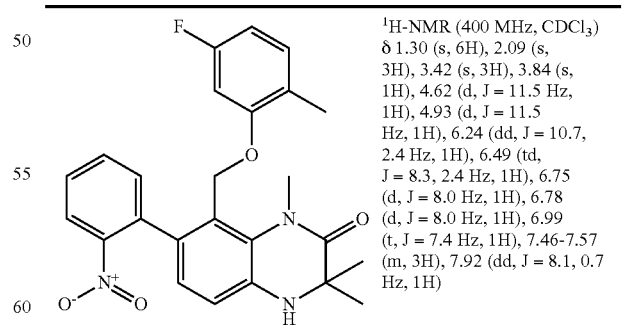

$^1$H-NMR (400 MHz, CDCl$_3$) δ 1.30 (s, 6H), 2.09 (s, 3H), 3.42 (s, 3H), 3.84 (s, 1H), 4.62 (d, J = 11.5 Hz, 1H), 4.93 (d, J = 11.5 Hz, 1H), 6.24 (dd, J = 10.7, 2.4 Hz, 1H), 6.49 (td, J = 8.3, 2.4 Hz, 1H), 6.75 (d, J = 8.0 Hz, 1H), 6.78 (d, J = 8.0 Hz, 1H), 6.99 (t, J = 7.4 Hz, 1H), 7.46-7.57 (m, 3H), 7.92 (dd, J = 8.1, 0.7 Hz, 1H)

Using any compounds among Reference Compounds No. 22 and available compounds, the following Compound (No. 7-2) was obtained by a method similar to that of Compound No. 7-1.

| Compound | Structure | ¹H-NMR |
|---|---|---|
| 7-(2-Cyanophenyl)-8-(5-fluoro-2-methylphenoxymethyl)-1,3,3-trimethyl-3,4-dihydro-1H-quinoxalin-2-one (Compound No. 7-2) | 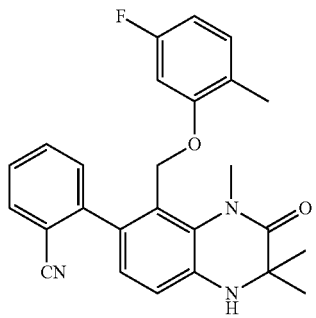 | ¹H-NMR (400 MHz, CDCl₃) δ 1.15 (s, 3H), 1.36 (s, 3H), 2.04 (s, 3H), 3.45 (s, 3H), 3.88 (s, 1H), 4.72 (d, J = 12.4 Hz, 1H), 5.21 (d, J = 12.4 Hz, 1H), 6.13 (dd, J = 11.0, 2.4 Hz, 1H), 6.46 (td, J = 8.3, 2.4 Hz, 1H), 6.80 (d, J = 8.1 Hz, 1H), 6.94 (d, J = 8.1 Hz, 1H), 6.96 (t, J = 7.6 Hz, 1H), 7.45 (td, J = 7.7, 1.4 Hz, 1H), 7.54 (dd, J = 7.7, 0.9 Hz, 1H), 7.61 (td, J = 7.7, 1.4 Hz, 1H), 7.75 (dd, J = 7.7, 0.9 Hz, 1H) |
| 7-(4-Amino-2-methoxyphenyl)-8-(5-fluoro-2-methylphenoxymethyl)-1,3,3-trimethyl-3,4-dihydro-1H-quinoxalin-2-one (Compound No.8-2) | 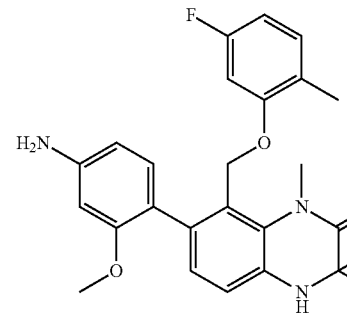 | ¹H-NMR (400 MHz, CDCl₃) δ 0.87 (s, 3H), 1.28 (s, 3H), 2.01 (s, 3H), 3.47 (s, 3H), 3.64 (s, 1H), 3.78 (s, 3H), 4.89 (d, J = 13.7 Hz, 1H), 5.23 (d, J = 13.7 Hz, 1H), 6.05 (dd, J = 11.2, 2.4 Hz, 1H), 6.33 (d, J = 2.2 Hz, 1H), 6.37 (td, J = 8.4, 2.4 Hz, 1H), 6.40 (dd, J = 8.0, 2.2 Hz, 1H), 6.68 (d, J = 8.1 Hz, 1H), 6.88 (d, J = 8.1 Hz, 1H), 6.88 (t, J = 7.6 Hz, 1H), 7.10 (d, J = 8.0 Hz, 1H) |

Example 8

7-(5-Amino-2-methoxyphenyl)-8-(5-fluoro-2-methylphenoxymethyl)-1,3,3-trimethyl-3,4-dihydro-1H-quinoxalin-2-one (Compound No. 8-1)

A mixture of 8-(5-fluoro-2-methylphenoxymethyl)-7-(2-methoxy-5-nitrophenyl)-1,3,3-trimethyl-3,4-dihydro-1H-quinoxalin-2-one (Compound No. 6-27, 18.8 mg, 0.0392 mmol) and tin chloride (II) (23.0 mg, 0.121 mmol) was suspended in mixed solvent of anhydrous N,N-dimethylformamide (0.25 ml) and anhydrous ethanol (0.5 mL), and stirred at 80° C. overnight. After cooling down, the reaction mixture was diluted with ethyl acetate (10 mL) and saturated aqueous sodium hydrogen carbonate solution was added thereto until the pH became 9. After the precipitate was filtered, the filtrate was washed with water (50 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled compound (8.2 mg) as a brown solid. (Yield 47%)

Example No. 9

8-(5-Fluoro-2-methylphenoxymethyl)-7-(5-hydroxymethyl-2-methoxyphenyl)-1,3,3-trimethyl-3,4-dihydro-1H-quinoxalin-2-one (Compound No. 9-1)

8-(5-Fluoro-2-methylphenoxymethyl)-7-(2-methoxy-5-methoxycarbonylphenyl)-1,3,3-trimethyl-3,4-dihydro-1H-quinoxalin-2-one (Compound No. 6-37, 50.2 mg, 0.102 mmol) was dissolved in anhydrous tetrahydrofuran (0.5 ml), and lithium aluminum hydride (6.8 mg, 0.18 mmol) was added thereto at 0° C. After the reaction mixture was stirred at same temperature for 30 minutes, ethyl acetate (1 mL) and water (1 mL) were added thereto successively. Moreover ethyl acetate (10 mL) and water (10 mL) were added and partitioned. The organic layer was washed with saturated brine (10 mL), dried over anhydrous magnesium sulfate, and then the solvent was removed under reduced pressure. The obtained residue was purified by silica gel column chromatography (hexane-ethyl acetate) to give the titled compound (29.8 mg) as a pale yellow solid. (Yield 47%)

| Structure | ¹H-NMR |
|---|---|
| 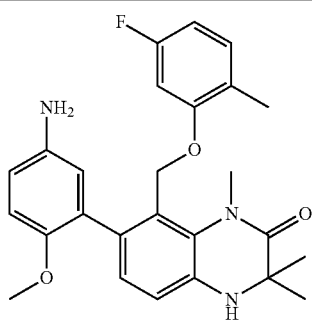 [SMILES: COc1ccc(N)cc1-c1ccc2c(c1COc1cc(F)ccc1C)N(C)C(=O)C(C)(C)N2] | ¹H-NMR (400 MHz, CDCl₃) δ 0.89 (s, 3H), 1.31 (s, 3H), 2.01 (s, 3H), 3.46 (s, 3H), 3.72 (s, 3H), 3.81 (s, 1H), 4.88 (d, J = 13.7 Hz, 1H), 5.26 (d, J = 13.7 Hz, 1H), 6.11 (dd, J = 11.4, 2.5 Hz, 1H), 6.39 (td, J = 8.3, 2.5 Hz, 1H), 6.70-6.73 (m, 3H), 6.82 (d, J = 8.8 Hz, 1H), 6.89 (t, J = 7.2 Hz, 1H), 6.90 (d, J = 7.8 Hz, 1H) |
| 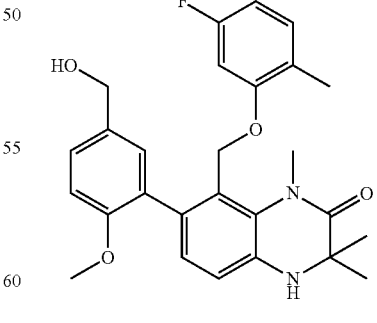 | ¹H-NMR (500 MHz, CDCl₃) δ 0.97 (s, 3H), 1.29 (s, 3H), 2.01 (s, 3H), 3.47 (s, 3H), 3.80 (br s, 1H), 3.83 (s, 3H), 4.66 (s, 2H), 4.81 (d, J = 13.3 Hz, 1H), 5.20 (d, J = 13.3 Hz, 1H), 6.07 (dd, J = 11.3, 2.4 Hz, 1H), 6.39 (td, J = 8.4, 2.4 Hz, 1H), 6.73 (d, J = 7.9 Hz, 1H), 6.89-6.91 (m, 1H), 6.91 (d, J = 7.9 Hz, 1H), 6.97 (d, J = 8.5 Hz, 1H), 7.32 (d, J = 2.2 Hz, 1H), 7.37 (dd, J = 8.5, 2.2 Hz, 1H) |

Using Compound No. 6-28, the following Compound (No. 8-2) was obtained by a method similar to that of Compound No. 8-1.

Using Compound No. 6-42, the following Compound (No. 9-2) was obtained by a method similar to that of Compound No. 9-1.

7-(5-hydroxymethyl-2-methoxy-phenyl)-8-(2-methoxyphenyl-aminomethyl)-1,3,3-trimethyl-3,4-dihydro-1H-quinoxalin-2-one (Compound No. 9-2)

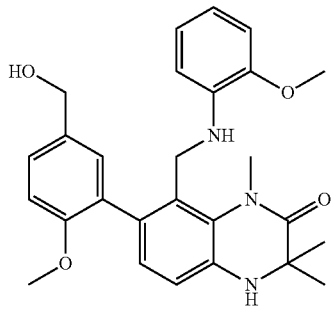

¹H-NMR (400 MHz, CDCl₃) δ 1.21 (s, 3H), 1.42 (s, 3H), 3.47 (s, 3H), 3.73 (s, 4H), 3.79 (s, 3H), 4.07 (d, J = 13.7 Hz, 1H), 4.13 (d, J = 13.7 Hz, 1H), 4.47 (br s, 1 H), 4.61 (d, J = 5.9 Hz, 2H), 6.32 (dd, J = 7.8, 1.5 Hz, 1H), 6.56 (td, J = 7.8, 1.5 Hz, 1H), 6.67 (dd, J = 7.8, 1.4 Hz, 1H), 6.70 (d, J = 7.8 Hz, 1H), 6.73 (td, J = 7.8, 1.4 Hz, 1H), 6.82 (d, J = 7.8 Hz, 1H), 6.89 (d, J = 8.3 Hz, 1H), 7.19 (d, J = 2.2 Hz, 1H), 7.29 (dd, J = 8.3, 2.2 Hz, 1H)

7-(5-Carboxy-2-methoxyphenyl)-8-(2-methoxyphenylaminomethyl)-1,3,3-trimethyl-3,4-dihydro-1H-quinoxalin-2-one (Compound No. 10-2)

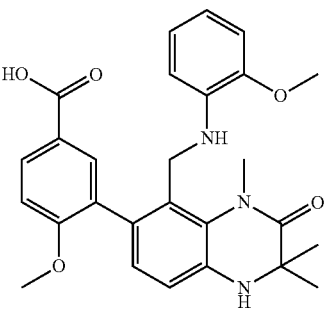

¹H-NMR (400 MHz, DMSO-d₆) δ 0.99 (s, 3H), 1.23 (s, 3 H), 3.31 (s, 3H), 3.64 (s, 3H), 3.83 (s, 3H), 4.05 (d, J = 4.9 Hz, 2H), 4.44 (t, J = 4.9 Hz, 1H), 6.15 (s, 1H), 6.23 (d, J = 7.8 Hz, 1H), 6.46 (t, J = 7.8 Hz, 1H), 6.57 (t, J = 7.8 Hz, 1H), 6.67 (d, J = 7.8 Hz, 1H), 6.73 (d, J = 8.0 Hz, 1H), 6.78 (d, J = 8.0 Hz, 1H), 7.16 (d, J = 8.7 Hz, 1H), 7.69 (d, J = 2.2 Hz, 1H), 7.93 (dd, J = 8.7, 2.2 Hz, 1H), 12.60 (br s, 1H)

Example 10

7-(5-Carboxy-2-methoxyphenyl)-8-(5-fluoro-2-methylphenoxymethyl)-1,3,3-trimethyl-3,4-dihydro-1H-quinoxalin-2-one (Compound No. 10-1)

8-(5-Fluoro-2-methylphenoxymethyl)-7-(2-methoxy-5-methoxycarbonylphenyl)-1,3,3-trimethyl-3,4-dihydro-1H-quinoxalin-2-one (Compound No. 6-37, 50.5 mg, 0.103 mmol) was dissolved in mixed solvent of tetrahydrofuran (1 mL) and methanol (1 mL), and 4N aqueous sodium hydroxide solution (0.5 mL) was added thereto and stirred at room temperature overnight. Ethyl acetate (15 mL) and 0.25N aqueous HCl solution (20 mL) were added to the reaction mixture and partitioned. The organic layer was washed with saturated brine (15 mL), dried over anhydrous magnesium sulfate, and then the solvent was removed under reduced pressure. The obtained residue was purified by silica gel column chromatography (hexane-ethyl acetate). The obtained materials were filtered with chloroform (3 mL) to give the titled compound (20.3 mg) as a pale yellow solid. (Yield 42%)

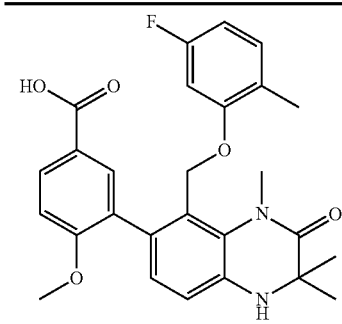

¹H-NMR (400 MHz, DMSO-d₆) δ 0.83 (s, 3H), 1.11 (s, 3H), 1.92 (s, 3H), 3.32 (s, 3H), 3.86 (s, 3H), 4.75 (d, J = 13.7 Hz, 1H), 5.20 (d, J = 13.7 Hz, 1H), 6.15-6.17 (m, 2H), 6.49 (t, J = 7.7 Hz, 1H), 6.83 (s, 2 H), 6.99 (t, J = 7.7 Hz, 1 H), 7.19 (d, J = 8.4 Hz, 1 H), 7.82 (s, 1H), 7.96 (d, J = 8.4 Hz, 1H), 12.6 (br s, 1H)

Using Compound No. 6-42, the following Compound (No. 10-2) was obtained by a method similar to that of Compound No. 10-1.

Example 11

8-(5-Fluoro-2-methylphenoxymethyl)-7-(4-hydroxy-2-methoxyphenyl)-1,3,3-trimethyl-3,4-dihydro-1H-quinoxalin-2-one (Compound No. 11)

7-(4-Benzoyloxy-2-methoxyphenyl)-8-(5-fluoro-2-methylphenoxymethyl)-1,3,3-trimethyl-3,4-dihydro-1H-quinoxalin-2-one (Compound No. 6-31, 422 mg, 0.761 mmol) was dissolved in mixed solvent of methanol (2 mL) and tetrahydrofuran (2 mL), and 4N aqueous sodium hydroxide solution (0.761 mL, 3.04 mmoL) was added thereto. After the reaction mixture was stirred at room temperature for 40 minutes, water (100 mL) and 1N aqueous HCl solution (4 mL) were added thereto. After the mixture was extracted with ethyl acetate (100 mL), the organic layer was washed with water (100 mL) and saturated brine (50 mL) successively, dried over anhydrous magnesium sulfate, and then the solvent was removed under reduced pressure. The obtained residue was filtered with a mixed solvent of hexane (10 mL) and ethyl acetate (10 mL) to give the titled compound (292 mg) as a colorless solid. (Yield 85%)

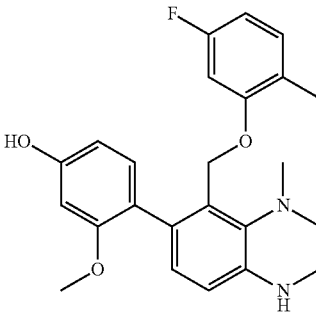

¹H-NMR (400 MHz, CDCl₃) δ 0.91 (s, 3H), 1.28 (s, 3H), 2.02 (s, 3H), 3.47 (s, 3H), 3.68 (br s, 1H), 3.80 (s, 3H), 4.85 (d, J = 13.4 Hz, 1H), 4.92 (s, 1H), 5.21 (d, J = 13.4 Hz, 1H), 6.05 (dd, J = 11.4, 2.5 Hz, 1H), 6.38 (td, J = 8.4, 2.5 Hz, 1H), 6.50-6.53 (m, 2H), 6.70 (d, J = 8.1 Hz, 1H), 6.87 (d, J = 8.1 Hz, 1H), 6.87-6.91 (m, 1H), 7.16 (d, J = 8.3 Hz, 1H)

Example 12

7-(2-Methoxy-4-methoxymethoxyphenyl)-8-[N-(2-(9-fluorenylmethoxycarbonyl)aminomethyl]-1,3,3-trimethyl-3,4-dihydro-1H-quinoxalin-2-one (Compound No. 12-1)

7-(2-Methoxy-4-methoxymethoxyphenyl)-8-(2-methoxyphenylaminomethyl)-1,3,3-trimethyl-3,4-dihydro-1H-quinoxalin-2-one (Compound No. 6-39, 104 mg, 0.212 mmol) and sodium hydrogen carbonate (22.0 mg, 0.262 mmol) were dissolved in mixed solvent of 1,4-dioxane (1.5 mL) and water (1 mL), and 9-fluorenylmethoxycarbonyl chloride (60.3 mg, 0.233 mmol) was added thereto. After the reaction mixture was stirred at room temperature for 30 minutes, the mixture was diluted with ethyl acetate (50 mL). The mixture was washed with water (50 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled compound (149 mg) as a colorless amorphous product. (Yield 99%)

Example 13

7-(4-Hydroxy-2-methoxyphenyl)-8-[N-(2-methoxyphenyl)-N-(9-fluorenylmethoxycarbonyl)aminomethyl]-1,3,3-trimethyl-3,4-dihydro-1H-quinoxalin-2-one (Compound No. 13-1)

7-(2-Methoxy-4-methoxymethoxyphenyl)-8-[N-(2-methoxyphenyl)-N-(9-fluorenylmethoxycarbonyl)aminomethyl]-1,3,3-trimethyl-3,4-dihydro-1H-quinoxalin-2-one (Compound No. 12-1, 137 mg, 0.192 mmol) was dissolved in 1,4-dioxane (1 mL) and 4N hydrochloride/1,4-dioxane solution (144 μL, 0.576 mmol) was added thereto. After the reaction mixture was stirred at room temperature for 2 hours, the mixture was diluted with ethyl acetate (100 mL). The mixture was washed with water (100 mL) and saturated brine (50 mL) successively, dried over anhydrous magnesium sulfate, and

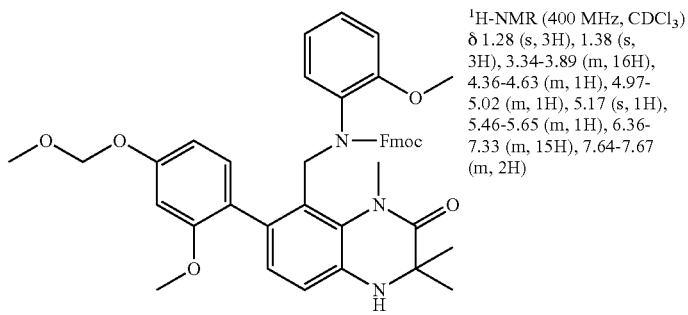

$^1$H-NMR (400 MHz, CDCl$_3$)
δ 1.28 (s, 3H), 1.38 (s, 3H), 3.34-3.89 (m, 16H), 4.36-4.63 (m, 1H), 4.97-5.02 (m, 1H), 5.17 (s, 1H), 5.46-5.65 (m, 1H), 6.36-7.33 (m, 15H), 7.64-7.67 (m, 2H)

Using any compounds among Compounds No. 6-41 and available compounds, the following Compound (No. 12-2) was obtained by a method similar to that of Compound No. 12-1.

then the solvent was removed under reduced pressure. The obtained residue was purified by silica gel column chromatography (hexane-ethyl acetate) to give the titled compound (71.6 mg) as a colorless solid. (Yield 56%)

8-[N-(5-Fluoro-2-methylphenyl)-N-(9-fluorenylmethoxycarbonyl)aminomethyl]-7-(2-methoxy-4-methoxymethoxyphenyl)-1,3,3-trimethyl-3,4-dihydro-1H-quinoxalin-2-one (Compound No. 12-2)

$^1$H-NMR (400 MHz, CDCl$_3$)
δ 1.26 (s, 3H), 1.41 (s, 3H), 1.87 (s, 3H), 3.36-4.27 (m, 13H), 4.66-5.21 (m, 4H), 6.07-7.64 (m, 16H)

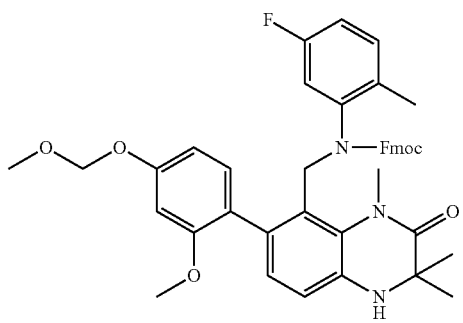

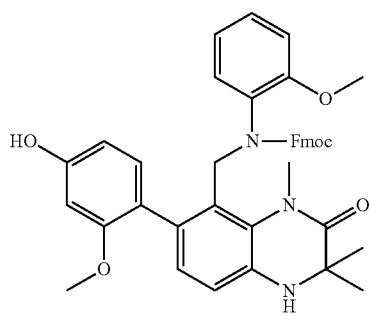

¹H-NMR (400 MHz, CDCl₃) δ 1.27 (s, 3H), 1.38 (s, 3 H), 3.32 (s, 3H), 3.49-4.15 (m, 10H), 4.39-4.59 (m, 1H), 5.23-5.90 (m, 2H), 6.29-7.33 (m, 15H), 7.62-7.66 (m, 2H)

Using Compounds No. 5-20 and 12-2, the following Compounds (No. 13-2 and 13-3) were obtained by a method similar to that of Compound No. 13-1.

7-(4-Hydroxy-2-methoxyphenyl)-8-(5-methylthiophen-2-yl carbonyloxymethyl)-1,3,3-trimethyl-3,4-dihydro-1H-quinoxalin-2-one (Compound No. 13-2)

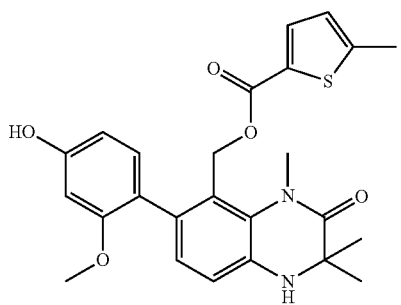

¹H-NMR (400 MHz, CDCl₃) δ 1.20 (s, 3H), 1.42 (s, 3 H), 2.47 (s, 3H), 3.45 (s, 3H), 3.73 (s, 3H), 3.76 (s, 1H), 5.14 (d, J = 13.3 Hz, 1H), 5.17 (s, 1H), 5.27 (d, J = 13.3 Hz, 1H), 6.42 (dd, J = 8.2, 2.3 Hz, 1H), 6.46 (d, J = 2.3 Hz, 1H), 6.69 (d, J = 3.9 Hz, 1H), 6.74 (d, J = 8.0 Hz, 1H), 6.86 (d, J = 8.0 Hz, 1H), 7.11 (d, J = 8.2 Hz, 1H), 7.45 (d, J = 3.9 Hz, 1H)

8-[N-(5-Fluoro-2-methylphenyl)-N-(9-fluorenylmethoxycarbonyl)aminomethyl]-1-(4-hydroxy-2-methoxyphenyl)-1,3,3-trimethyl-3,4-dihydro-1H-quinoxalin-2-one (Compound No. 13-3)

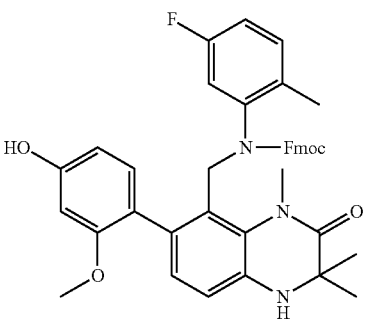

¹H-NMR (400 MHz, CDCl₃) δ 1.26 (s, 3H), 1.40 (s, 3 H), 1.89 (s, 3H), 3.33-4.54 (m, 10H), 5.15-5.58 (m, 3H), 6.04-7.64 (m, 16H)

Example 14

7-(4-Butyryloxy-2-methoxyphenyl)-8-(5-fluoro-2-methylphenoxymethyl)-1,3,3-trimethyl-3,4-dihydro-1H-quinoxalin-2-one (Compound No. 14-1)

8-(5-Fluoro-2-methylphenoxymethyl)-7-(4-hydroxy-2-methoxyphenyl)-1,3,3-trimethyl-3,4-dihydro-1H-quinoxalin-2-one (Compound No. 11, 25 mg, 0.055 mmol) was dissolved in tetrahydrofuran (1 mL), and triethylamine (20 μL, 0.14 mmol) and butyryl chloride (7.6 μL, 0.073 mmol) were added successively. After the reaction mixture was stirred at room temperature for 1 hour, the mixture was purified by silica gel column chromatography (hexane-ethyl acetate) to give the titled compound (27 mg) as a colorless amorphous product. (Yield 92%)

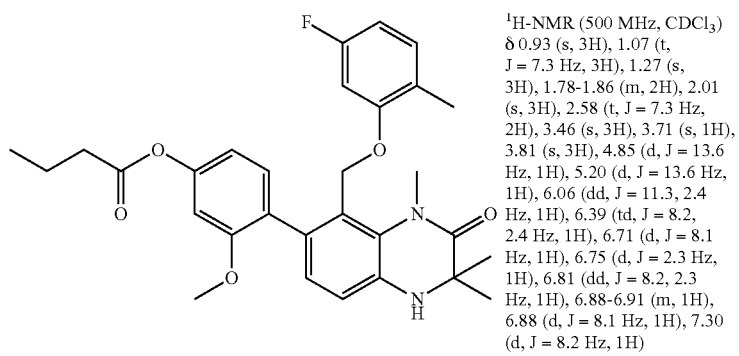

¹H-NMR (500 MHz, CDCl₃) δ 0.93 (s, 3H), 1.07 (t, J = 7.3 Hz, 3H), 1.27 (s, 3H), 1.78-1.86 (m, 2H), 2.01 (s, 3H), 2.58 (t, J = 7.3 Hz, 2H), 3.46 (s, 3H), 3.71 (s, 1H), 3.81 (s, 3H), 4.85 (d, J = 13.6 Hz, 1H), 5.20 (d, J = 13.6 Hz, 1H), 6.06 (dd, J = 11.3, 2.4 Hz, 1H), 6.39 (td, J = 8.2, 2.4 Hz, 1H), 6.71 (d, J = 8.1 Hz, 1H), 6.75 (d, J = 2.3 Hz, 1H), 6.81 (dd, J = 8.2, 2.3 Hz, 1H), 6.88-6.91 (m, 1H), 6.88 (d, J = 8.1 Hz, 1H), 7.30 (d, J = 8.2 Hz, 1H)

Using any compounds among Compounds No. 8-2, 11, 13-2, and available compounds, the following Compounds (No. 14-2~14-62) were obtained by a method similar to that of Compound No. 14-1.

8-(5-Fluoro-2-methylphenoxymethyl)-7-[2-methoxy-4-(2-methylbenzoyloxy)phenyl]-1,3,3-trimethyl-3,4-dihydro-1H-quinoxalin-2-one (Compound No. 14-2)

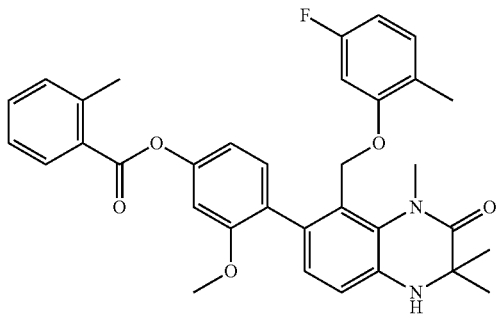

$^1$H-NMR (500 MHz, DMSO-$d_6$) δ 0.80 (s, 3H), 1.07 (s, 3H), 1.94 (s, 3H), 2.62 (s, 3H), 3.34 (s, 3H), 3.82 (s, 3H), 4.88 (d, J = 13.9 Hz, 1H), 5.25 (d, J = 13.9 Hz, 1H), 6.15 (dd, J = 11.6, 2.4 Hz, 1H), 6.15 (s, 1H), 6.50 (td, J = 8.5, 2.4 Hz, 1H), 6.82 (d, J = 8.1 Hz, 1H), 6.86 (d, J = 8.1 Hz, 1H), 7.00 (dd, J = 8.1, 2.1 Hz, 1H), 7.00-7.02 (m, 1H), 7.13 (d, J = 2.1 Hz, 1H), 7.34 (d, J = 8.1 Hz, 1H), 7.42 (d, J = 7.5 Hz, 1H), 7.43 (d, J = 7.5 Hz, 1H), 7.59 (td, J = 7.5, 1.4 Hz, 1H), 8.11-8.13 (m, 1H)

8-(5-Fluoro-2-methylphenoxymethyl)-7-[2-methoxy-4-(2-methoxybenzoyloxy)phenyl]-1,3,3-trimethyl-3,4-dihydro-1H-quinoxalin-2-one (Compound No. 14-3)

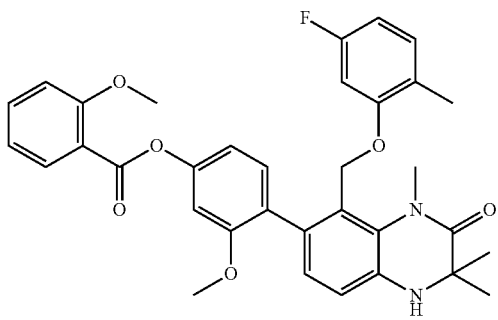

$^1$H-NMR (400 MHz, DMSO-$d_6$) δ 0.80 (s, 3H), 1.07 (s, 3H), 1.93 (s, 3H), 3.33 (s, 3H), 3.82 (s, 3H), 3.89 (s, 3H), 4.87 (d, J = 13.8 Hz, 1H), 5.24 (d, J = 13.8 Hz, 1H), 6.14 (dd, J = 11.2, 2.6 Hz, 1H), 6.15 (s, 1H), 6.50 (td, J = 8.4, 2.6 Hz, 1H), 6.81 (d, J = 8.1 Hz, 1H), 6.85 (d, J = 8.1 Hz, 1H), 6.95 (dd, J = 8.2, 2.2 Hz, 1H), 6.98-7.02 (m, 1H), 7.05 (d, J = 2.2 Hz, 1H), 7.12 (td, J = 7.4, 0.8 Hz, 1H), 7.25 (dd, J = 8.7, 0.8 Hz, 1H), 7.33 (d, J = 8.2 Hz, 1H), 7.66 (ddd, J = 8.7, 7.4, 1.7 Hz, 1H), 7.95 (dd, J = 7.4, 1.7 Hz, 1H)

7-[4-(2-Chlorobenzoyloxy)-2-methoxyphenyl]-8-(5-fluoro-2-methylphenoxymethyl)-1,3,3-trimethyl-3,4-dihydro-1H-quinoxalin-2-one (Compound No. 14-4)

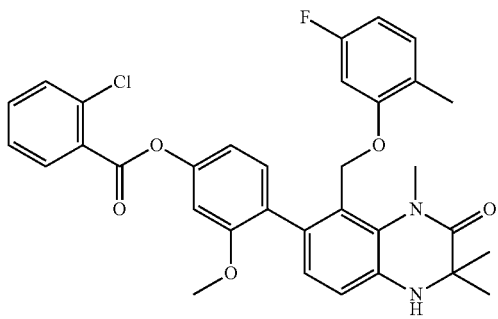

$^1$H-NMR (500 MHz, DMSO-$d_6$) δ 0.80 (s, 3H), 1.08 (s, 3H), 1.93 (s, 3H), 3.34 (s, 3H), 3.83 (s, 3H), 4.87 (d, J = 13.9 Hz, 1H), 5.24 (d, J = 13.9 Hz, 1H), 6.16 (dd, J = 11.6, 2.4 Hz, 1H), 6.16 (s, 1H), 6.50 (td, J = 8.2, 2.4 Hz, 1H), 6.82 (d, J = 7.9 Hz, 1H), 6.86 (d, J = 7.9 Hz, 1H), 6.98-7.03 (m, 2H), 7.14 (d, J = 2.1 Hz, 1H), 7.36 (d, J = 8.1 Hz, 1H), 7.56-7.60 (m, 1H), 7.69-7.70 (m, 2H), 8.13-8.15 (m, 1H)

| | |
|---|---|
| 7-[4-(3-Chlorobenzoyloxy)-2-methoxyphenyl]-8-(5-fluoro-2-methylphenoxymethyl)-1,3,3-trimethyl-3,4-dihydro-1H-quinoxalin-2-one (Compound No. 14-5) 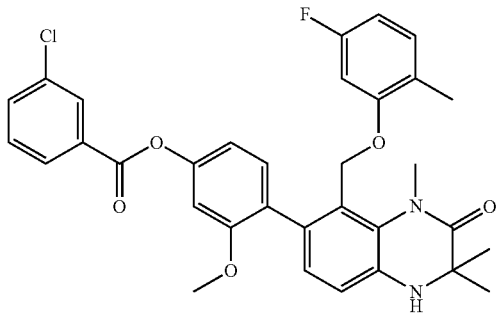 | $^1$H-NMR (400 MHz, DMSO-$d_6$) δ 0.81 (s, 3H), 1.08 (s, 3H), 1.93 (s, 3H), 3.33 (s, 3H), 3.81 (s, 3H), 4.86 (d, J = 13.8 Hz, 1H), 5.24 (d, J = 13.8 Hz, 1H), 6.15 (dd, J = 12.0, 2.5 Hz, 1H), 6.16 (s, 1H), 6.51 (td, J = 8.4, 2.5 Hz, 1H), 6.82 (d, J = 8.1 Hz, 1H), 6.86 (d, J = 8.1 Hz, 1H), 6.99-7.03 (m, 1H), 7.02 (dd, J = 8.0, 2.2 Hz, 1H), 7.17 (d, J = 2.2 Hz, 1H), 7.35 (d, J = 8.0 Hz, 1H), 7.68 (t, J = 8.0 Hz, 1H), 7.86 (ddd, J = 8.0, 2.2, 1.0 Hz, 1H), 8.10-8.13 (m, 1H), 8.14-8.18 (m, 1H) |
| 7-[4-(4-Chlorobenzoyloxy)-2-methoxyphenyl]-8-(5-fluoro-2-methylphenoxymethyl)-1,3,3-trimethyl-3,4-dihydro-1H-quinoxalin-2-one (Compound No. 14-6) 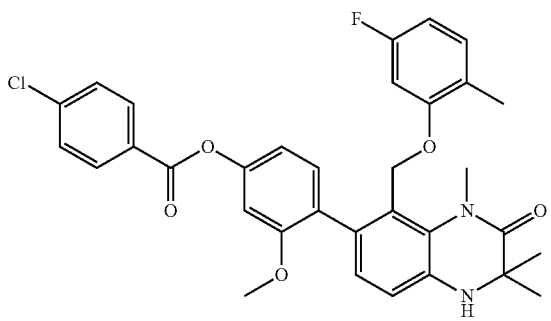 | $^1$H-NMR (400 MHz, DMSO-$d_6$) δ 0.86 (s, 3H), 1.07 (s, 3H), 1.93 (s, 3H), 3.33 (s, 3H), 3.81 (s, 3H), 4.87 (d, J = 13.7 Hz, 1H), 5.24 (d, J = 13.7 Hz, 1H), 6.15 (dd, J = 11.1, 2.6 Hz, 1H), 6.16 (s, 1H), 6.51 (td, J = 8.3, 2.6 Hz, 1H), 6.81 (d, J = 8.1 Hz, 1H), 6.86 (d, J = 8.1 Hz, 1H), 6.99-7.02 (m, 1H), 7.01 (dd, J = 8.2, 2.2 Hz, 1H), 7.14 (d, J = 2.2 Hz, 1H), 7.34 (d, J = 8.2 Hz, 1H), 7.71 (d, J = 8.8 Hz, 2H), 8.16 (d, J = 8.8 Hz, 2H) |
| 8-(5-Fluoro-2-methylphenoxymethyl)-7-[2-methoxy-4-(2-trifluoromethylbenzoyloxy)phenyl]-1,3,3-trimethyl-3,4-dihydro-1H-quinoxalin-2-one (Compound No. 14-7) 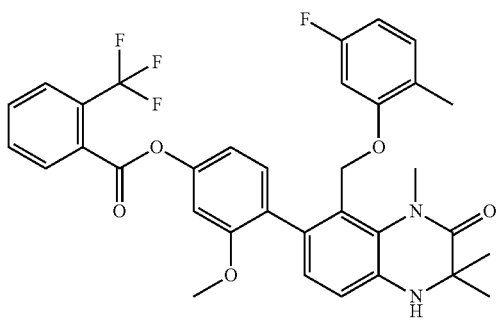 | $^1$H-NMR (400 MHz, CDCl$_3$) δ 0.94 (s, 3H), 1.27 (s, 3H), 2.02 (s, 3H), 3.47 (s, 3H), 3.73 (s, 1H), 3.85 (s, 3H), 4.89 (d, J = 13.7 Hz, 1H), 5.23 (d, J = 13.7 Hz, 1H), 6.08 (dd, J = 11.1, 2.4 Hz, 1H), 6.40 (td, J = 8.3, 2.4 Hz, 1H), 6.73 (d, J = 8.1 Hz, 1H), 6.88-6.92 (m, 2H), 6.90 (d, J = 8.1 Hz, 1H), 6.98 (dd, J = 8.2, 2.2 Hz, 1H), 7.37 (d, J = 8.2 Hz, 1H), 7.71-7.73 (m, 2H), 7.85-7.87 (m, 1H), 8.01-8.04 (m, 1H) |
| 8-(5-Fluoro-2-methylphenoxymethyl)-7-[2-methoxy-4-(pyridin-2-ylcarbonyloxy)phenyl]-1,3,3-trimethyl-3,4-dihydro-1H-quinoxalin-2-one (Compound No. 14-8) 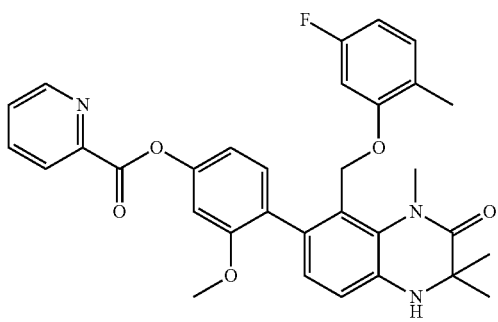 | $^1$H-NMR (500 MHz, CDCl$_3$) δ 0.97 (s, 3H), 1.27 (s, 3H), 2.02 (s, 3H), 3.47 (s, 3H), 3.73 (s, 1H), 3.83 (s, 3H), 4.87 (d, J = 13.4 Hz, 1H), 5.21 (d, J = 13.4 Hz, 1H), 6.09 (dd, J = 11.3, 2.4 Hz, 1H), 6.40 (td, J = 8.2, 2.4 Hz, 1H), 6.74 (d, J = 7.9 Hz, 1H), 6.89-6.92 (m, 1H), 6.93 (d, J = 7.9 Hz, 1H), 6.94 (d, J = 2.1 Hz, 1H), 7.00 (dd, J = 8.2, 2.1 Hz, 1H), 7.37 (d, J = 8.2 Hz, 1H), 7.59 (ddd, J = 7.8, 4.8, 1.1 Hz, 1H), 7.95 (td, J = 7.8, 1.8 Hz, 1H), 8.31 (dt, J = 7.8, 1.1 Hz, 1H), 8.87 (ddd, J = 4.8, 1.8, 1.1 Hz, 1H) |

| | |
|---|---|
| 8-(5-Fluoro-2-methylphenoxymethyl)-7-[2-methoxy-4-(pyridin-3-ylcarbonyloxy)phenyl]-1,3,3-trimethyl-3,4-dihydro-1H-quinoxalin-2-one (Compound No. 14-9)<br>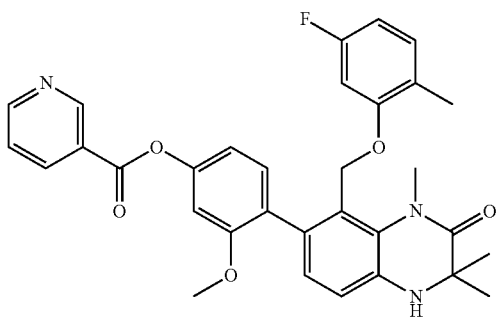 | $^1$H-NMR (400 MHz, CDCl$_3$) δ 0.96 (s, 3H), 1.28 (s, 3H), 2.03 (s, 3H), 3.47 (s, 3H), 3.74 (s, 1H), 3.85 (s, 3H), 4.88 (d, J = 13.5 Hz, 1H), 5.23 (d, J = 13.5 Hz, 1H), 6.09 (dd, J = 11.2, 2.5 Hz, 1H), 6.41 (td, J = 8.2, 2.5 Hz, 1H), 6.74 (d, J = 8.1 Hz, 1H), 6.90-6.93 (m, 1H), 6.90 (d, J = 2.3 Hz, 1H), 6.92 (d, J = 8.1 Hz, 1H), 6.96 (dd, J = 8.2, 2.3 Hz, 1H), 7.38 (d, J = 8.2 Hz, 1H), 7.50 (ddd, J = 8.0, 4.8, 0.9 Hz, 1H), 8.49 (dt, J = 8.0, 2.0 Hz, 1H), 8.88 (dd, J = 4.8, 2.0 Hz, 1H), 9.43 (dd, J = 2.0, 0.9 Hz, 1H) |
| 8-(5-Fluoro-2-methylphenoxymethyl)-7-[2-methoxy-4-(pyridin-4-ylcarbonyloxy)phenyl]-1,3,3-trimethyl-3,4-dihydro-1H-quinoxalin-2-one (Compound No. 14-10)<br>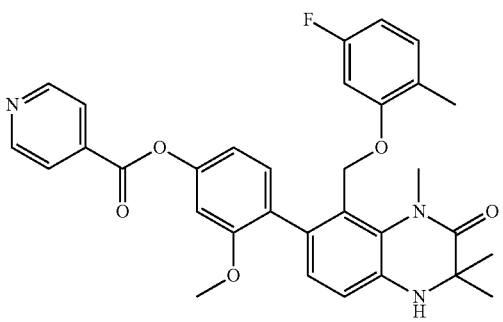 | $^1$H-NMR (400 MHz, CDCl$_3$) δ 0.96 (s, 3H), 1.28 (s, 3H), 2.03 (s, 3H), 3.47 (s, 3H), 3.75 (s, 1H), 3.84 (s, 3H), 4.87 (d, J = 13.5 Hz, 1H), 5.22 (d, J = 13.5 Hz, 1H), 6.09 (dd, J = 11.2, 2.4 Hz, 1H), 6.41 (td, J = 8.3, 2.4 Hz, 1H), 6.74 (d, J = 7.8 Hz, 1H), 6.89 (d, J = 2.3 Hz, 1H), 6.90-6.93 (m, 1H), 6.92 (d, J = 7.8 Hz, 1H), 6.95 (dd, J = 8.1, 2.3 Hz, 1H), 7.38 (d, J = 8.1 Hz, 1H), 8.04 (dd, J = 4.3, 1.6 Hz, 2H), 8.89 (dd, J = 4.3, 1.6 Hz, 2H) |
| 8-(5-Fluoro-2-methylphenoxymethyl)-7-[4-(furan-3-ylcarbonyloxy)-2-methoxyphenyl]-1,3,3-trimethyl-3,4-dihydro-1H-quinoxalin-2-one (Compound No. 14-11)<br>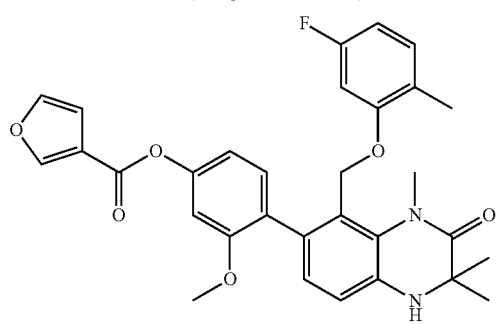 | $^1$H-NMR (500 MHz, CDCl$_3$) δ 0.95 (s, 3H), 1.27 (s, 3H), 2.02 (s, 3H), 3.47 (s, 3H), 3.73 (s, 1H), 3.83 (s, 3H), 4.87 (d, J = 13.4 Hz, 1H), 5.22 (d, J = 13.4 Hz, 1H), 6.08 (dd, J = 11.0, 2.4 Hz, 1H), 6.40 (td, J = 8.2, 2.4 Hz, 1H), 6.73 (d, J = 8.2 Hz, 1H), 6.85 (d, J = 2.1 Hz, 1H), 6.89-6.92 (m, 4H), 7.34 (d, J = 3.2 Hz, 1H), 7.53 (t, J = 1.7 Hz, 1H), 8.23 (dd, J = 1.7, 0.6 Hz, 1H) |
| 7-(4-Cyclohexylcarbonyloxy-2-methoxyphenyl)-8-(5-fluoro-2-methylphenoxymethyl)-1,3,3-trimethyl-3,4-dihydro-1H-quinoxalin-2-one (Compound No. 14-12)<br>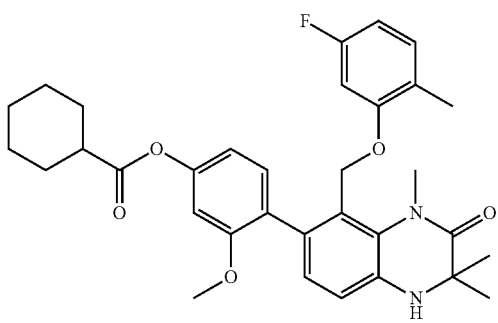 [SMILES: CCCC(=O)Oc1ccc(-c2ccc3c(c2COc2cc(F)ccc2C)N(C)C(=O)C(C)(C)N3)c(OC)c1] | $^1$H-NMR (400 MHz, CDCl$_3$) δ 0.93 (s, 3H), 1.27 (s, 3H), 1.31-1.44 (m, 3H), 1.60-1.73 (m, 3H), 1.83-1.87 (m, 2H), 2.01 (s, 3H), 2.08-2.11 (m, 2H), 2.59 (tt, J = 11.2, 3.7 Hz, 1H), 3.46 (s, 3H), 3.71 (s, 1H), 3.81 (s, 3H), 4.85 (d, J = 13.6 Hz, 1H), 5.21 (d, J = 13.6 Hz, 1H), 6.05 (dd, J = 11.1, 2.5 Hz, 1H), 6.39 (td, J = 8.3, 2.5 Hz, 1H), 6.71 (d, J = 8.2 Hz, 1H), 6.73 (d, J = 2.2 Hz, 1H), 6.79 (dd, J = 8.2, 2.2 Hz, 1H), 6.88 (d, J = 8.1 Hz, 1H), 6.87-6.91 (m, 1H), 7.30 (d, J = 8.1 Hz, 1H) |

| | |
|---|---|
| 8-(5-Fluoro-2-methylphenoxymethyl)-7-(2-methoxy-4-phenylacetoxyphenyl)-1,3,3-trimethyl-3,4-dihydro-1H-quinoxalin-2-one (Compound No. 14-13)<br>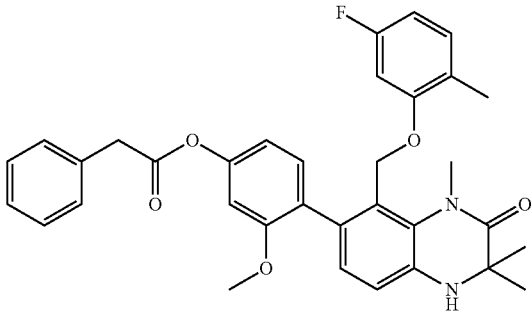 | $^1$H-NMR (400 MHz, CDCl$_3$) δ 0.93 (s, 3H), 1.26 (s, 3H), 2.00 (s, 3H), 3.45 (s, 3H), 3.71 (s, 1H), 3.79 (s, 3H), 3.90 (s, 2H), 4.82 (d, J = 13.7 Hz, 1H), 5.19 (d, J = 13.7 Hz, 1H), 6.04 (dd, J = 11.2, 2.4 Hz, 1H), 6.38 (td, J = 8.3, 2.4 Hz, 1H), 6.70 (d, J = 8.2 Hz, 1H), 6.73 (d, J = 2.2 Hz, 1H), 6.79 (dd, J = 8.2, 2.2 Hz, 1H), 6.86 (d, J = 8.2 Hz, 1H), 6.88-6.91 (m, 1H), 7.29 (d, J = 8.2 Hz, 1H), 7.30-7.43 (m, 5H) |
| 8-(5-Fluoro-2-methylphenoxymethyl)-7-[2-methoxy-4-(3-phenylpropionyloxy)phenyl]-1,3,3-trimethyl-3,4-dihydro-1H-quinoxalin-2-one (Compound No. 14-14)<br>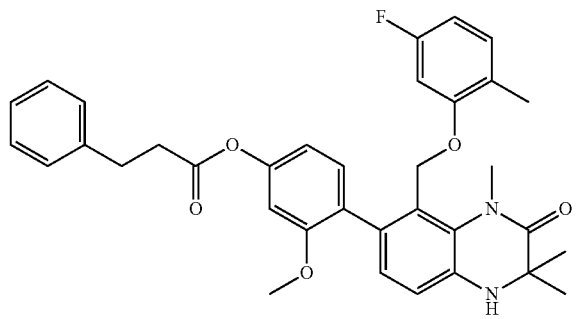 | $^1$H-NMR (500 MHz, CDCl$_3$) δ 0.94 (s, 3H), 1.26 (s, 3H), 2.01 (s, 3H), 2.93 (t, J = 7.6 Hz, 2H), 3.11 (t, J = 7.6 Hz, 2H), 3.46 (s, 3H), 3.71 (s, 1H), 3.78 (s, 3H), 4.84 (d, J = 13.7 Hz, 1H), 5.19 (d, J = 13.7 Hz, 1H), 6.05 (dd, J = 11.3, 2.4 Hz, 1H), 6.39 (td, J = 8.2, 2.4 Hz, 1H), 6.62 (d, J = 2.4 Hz, 1H), 6.71 (d, J = 7.9 Hz, 1H), 6.74 (dd, J = 8.1, 2.4 Hz, 1H), 6.87 (d, J = 7.9 Hz, 1H), 6.83-6.91 (m, 1H), 7.24-7.36 (m, 6H) |
| 8-(5-Fluoro-2-methylphenoxymethyl)-7-[4-(furan-2-ylcarbonyloxy)-2-methoxyphenyl]-1,3,3-trimethyl-3,4-dihydro-1H-quinoxalin-2-one (Compound No. 14-15)<br>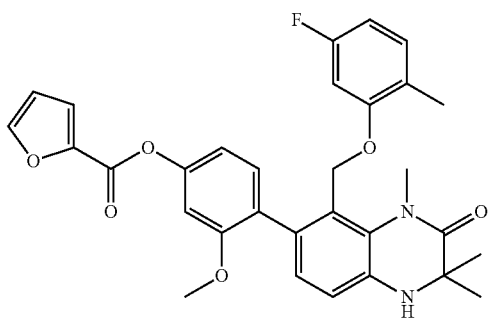 | $^1$H-NMR (500 MHz, DMSO-d$_6$) δ 0.81 (s, 3H), 1.07 (s, 3H), 1.93 (s, 3H), 3.33 (s, 3H), 3.80 (s, 3H), 4.86 (d, J = 14.0 Hz, 1H), 5.23 (d, J = 14.0 Hz, 1H), 6.15 (dd, J = 11.1, 2.4 Hz, 1H), 6.15 (s, 1H), 6.50 (td, J = 8.3, 2.4 Hz, 1H), 6.81 (d, J = 8.1 Hz, 1H), 6.82 (dd, J = 3.7, 1.7 Hz, 1H), 6.85 (d, J = 8.1 Hz, 1H), 6.97 (dd, J = 8.3, 2.1 Hz, 1H), 6.99-7.02 (m, 1H), 7.10 (d, J = 2.1 Hz, 1H), 7.33 (d, J = 8.3 Hz, 1H), 7.59 (dd, J = 3.7, 0.8 Hz, 1H), 8.13 (dd, J = 1.7, 0.8 Hz, 1H) |
| 7-(4-Acetoxy-2-methoxyphenyl)-8-(5-(fluoro-2-methylphenoxymethyl)-1,3,3-trimethyl-3,4-dihydro-1H-quinoxalin-2-one (Compound No. 14-16)<br>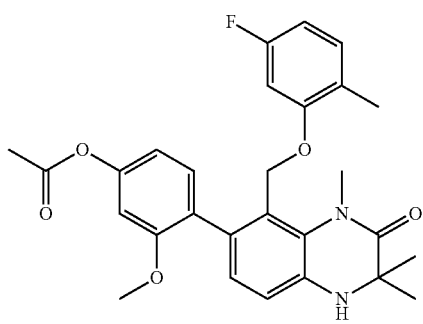 | $^1$H-NMR (400 MHz, DMSO-d$_6$) δ 0.86 (s, 3H), 1.07 (s, 3H), 1.92 (s, 3H), 2.29 (s, 3H), 3.32 (s, 3H), 3.78 (s, 3H), 4.83 (d, J = 14.0 Hz, 1H), 5.21 (d, J = 14.0 Hz, 1H), 6.12 (dd, J = 11.5, 2.5 Hz, 1H), 6.14 (s, 1H), 6.49 (td, J = 8.3, 2.5 Hz, 1H), 6.79 (d, J = 8.0 Hz, 1H), 6.82 (d, J = 8.0 Hz, 1H), 6.83 (dd, J = 8.2, 2.2 Hz, 1H), 6.93 (d, J = 2.2 Hz, 1H), 6.98-7.01 (m, 1H), 7.27 (d, J = 8.2 Hz, 1H) |

| | |
|---|---|
| 7-(4-Benzoylamino-2-methoxyphenyl)-8-(5-(fluoro-2-methylphenoxymethyl)-1,3,3-trimethyl-3,4-dihydro-1H-quinoxalin-2-one (Compound No. 14-17)<br>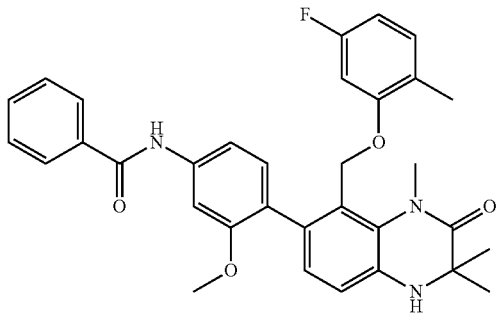 | $^1$H-NMR (400 MHz, CDCl$_3$) δ 0.92 (s, 3H), 1.29 (s, 3H), 2.02 (s, 3H), 3.48 (s, 3H), 3.72 (s, 1H), 3.89 (s, 3H), 4.87 (d, J = 13.6 Hz, 1H), 5.25 (d, J = 13.6 Hz, 1H), 6.06 (dd, J = 11.2, 2.4 Hz, 1H), 6.39 (td, J = 8.3, 2.4 Hz, 1H), 6.73 (d, J = 8.1 Hz, 1H), 6.88-6.91 (m, 1H), 6.90 (d, J = 8.1 Hz, 1H), 7.07 (dd, J = 8.1, 2.0 Hz, 1H), 7.31 (d, J = 8.1 Hz, 1H), 7.50-7.61 (m, 3H), 7.77 (d, J = 2.0 Hz, 1H), 7.89-7.92 (m, 3H) |
| 7-(4-Acetylamino-2-methoxyphenyl)-8-(5-(fluoro-2-methylphenoxymethyl)-1,3,3-trimethyl-3,4-dihydro-1H-quinoxalin-2-one (Compound No. 14-18)<br>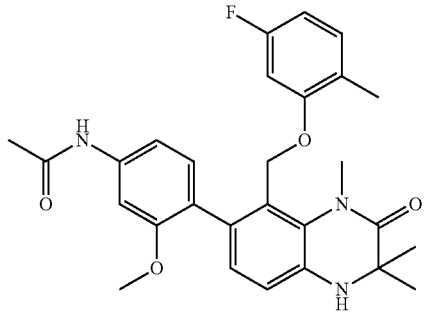 | $^1$H-NMR (400 MHz, CDCl$_3$) δ 0.91 (s, 3H), 1.29 (s, 3H), 2.01 (s, 3H), 2.22 (s, 3H), 3.46 (s, 3H), 3.70 (s, 1H), 3.84 (s, 3H), 4.84 (d, J = 13.4 Hz, 1H), 5.22 (d, J = 13.4 Hz, 1H), 6.04 (dd, J = 11.2, 2.5 Hz, 1H), 6.38 (td, J = 8.2, 2.5 Hz, 1H), 6.71 (d, J = 8.1 Hz, 1H), 6.87 (d, J = 8.1 Hz, 1H), 6.87-6.91 (m, 1H), 6.92 (dd, J = 8.2, 1.8 Hz, 1H), 7.24 (d, J = 8.2 Hz, 1H), 7.58 (d, J = 1.8 Hz, 1H) |
| 8-(5-Fluoro-2-methylphenoxymethyl)-7-[2-methoxy-4-(pyridin-2-ylcarbonylamino)phenyl]-1,3,3-trimethyl-3,4-dihydro-1H-quinoxalin-2-one (Compound No. 14-19)<br>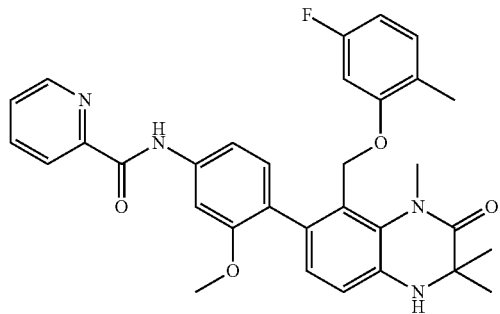 | $^1$H-NMR (400 MHz, CDCl$_3$) δ 0.92 (s, 3H), 1.29 (s, 3H), 2.02 (s, 3H), 3.48 (s, 3H), 3.71 (s, 1H), 3.91 (s, 3H), 4.88 (d, J = 13.7 Hz, 1H), 5.25 (d, J = 13.7 Hz, 1H), 6.07 (dd, J = 11.2, 2.4 Hz, 1H), 6.38 (td, J = 8.2, 2.4 Hz, 1H), 6.73 (d, J = 8.1 Hz, 1H), 6.87-6.91 (m, 1H), 6.92 (d, J = 8.1 Hz, 1H), 7.25 (dd, J = 8.2, 2.2 Hz, 1H), 7.33 (d, J = 8.2 Hz, 1H), 7.52 (ddd, J = 7.7, 4.7, 1.1 Hz, 1H), 7.85 (d, J = 2.2 Hz, 1H), 7.94 (td, J = 7.7, 1.7 Hz, 1H), 8.32 (dt, J = 7.7, 1.1 Hz, 1H), 8.65 (ddd, J = 4.7, 1.7, 1.1 Hz, 1H), 10.16 (s, 1H) |
| 8-(5-Fluoro-2-methylphenoxymethyl)-7-[2-methoxy-4-(pyridin-3-ylcarbonylamino)phenyl]-1,3,3-trimethyl-3,4-dihydro-1H-quinoxalin-2-one (Compound No. 14-20)<br>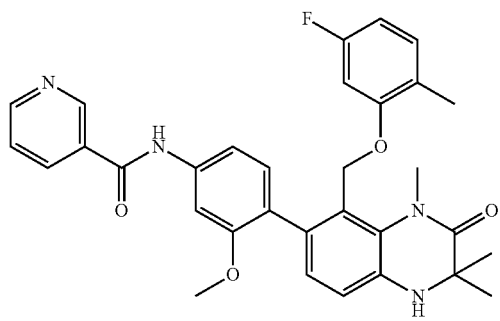 | $^1$H-NMR (400 MHz, CDCl$_3$) δ 0.94 (s, 3H), 1.30 (s, 3H), 2.02 (s, 3H), 3.47 (s, 3H), 3.73 (s, 1H), 3.89 (s, 3H), 4.86 (d, J = 13.6 Hz, 1H), 5.24 (d, J = 13.6 Hz, 1H), 6.07 (dd, J = 11.2, 2.4 Hz, 1H), 6.39 (td, J = 8.3, 2.4 Hz, 1H), 6.73 (d, J = 8.1 Hz, 1H), 6.89-6.92 (m, 1H), 6.90 (d, J = 8.1 Hz, 1H), 7.10 (dd, J = 8.1, 1.9 Hz, 1H), 7.33 (d, J = 8.1 Hz, 1H), 7.49 (ddd, J = 7.9, 4.8, 1.5 Hz, 1H), 7.71 (d, J = 1.9 Hz, 1H), 7.91 (s, 1H), 8.24 (dt, J = 7.9, 1.5 Hz, 1H), 8.82 (dd, J = 4.8, 1.5 Hz, 1H), 9.13 (d, J = 1.5 Hz, 1H) |

8-(5-Fluoro-2-methylphenoxymethyl)-7-[2-methoxy-4-(pyridin-4-ylcarbonylamino)phenyl]-1,3,3-trimethyl-3,4-dihydro-1H-quinoxalin-2-one (Compound No. 14-21)

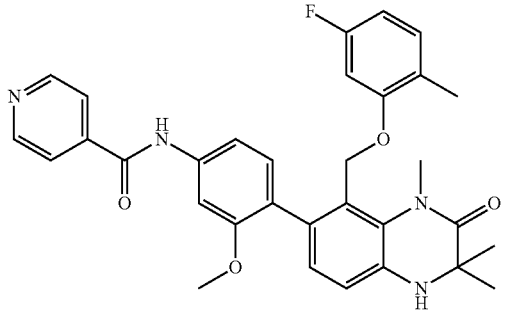

¹H-NMR (400 MHz, CDCl₃) δ 0.94 (s, 3H), 1.30 (s, 3H), 2.02 (s, 3H), 3.47 (s, 3H), 3.73 (s, 1H), 3.89 (s, 3H), 4.85 (d, J = 13.6 Hz, 1H), 5.23 (d, J = 13.6 Hz, 1H), 6.06 (dd, J = 11.2, 2.4 Hz, 1H), 6.40 (td, J = 8.2, 2.4 Hz, 1H), 6.73 (d, J = 8.1 Hz, 1H), 6.90 (d, J = 8.1 Hz, 1H), 6.89-6.92 (m, 1H), 7.09 (dd, J = 8.3, 2.1 Hz, 1H), 7.33 (d, J = 8.3 Hz, 1H), 7.71 (d, J = 2.1 Hz, 1H), 7.74 (dd, J = 4.4 Hz, 2H), 7.95 (s, 1H), 8.84 (dd, J = 4.4 Hz, 2H)

7-[4-(2-Chlorobenzoylamino)-2-methoxyphenyl]-8-(5-fluoro-2-methylphenoxymethyl)-1,3,3-trimethyl-3,4-dihydro-1H-quinoxalin-2-one (Compound No. 14-22)

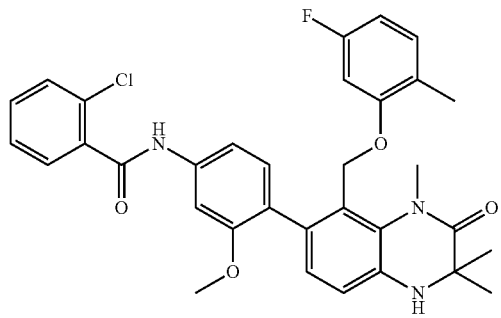

¹H-NMR (400 MHz, CDCl₃) δ 0.92 (s, 3H), 1.29 (s, 3H), 2.02 (s, 3H), 3.47 (s, 3H), 3.71 (s, 1H), 3.89 (s, 3H), 4.87 (d, J = 14.0 Hz, 1H), 5.25 (d, J = 14.0 Hz, 1H), 6.07 (dd, J = 10.9, 2.4 Hz, 1H), 6.39 (td, J = 8.4, 2.4 Hz, 1H), 6.72 (d, J = 8.1 Hz, 1H), 6.88-6.92 (m, 1H), 6.90 (d, J = 8.1 Hz, 1H), 7.06 (dd, J = 8.2, 1.9 Hz, 1H), 7.31 (d, J = 8.2 Hz, 1H), 7.39-7.52 (m, 2H), 7.43 (td, J = 7.6, 2.0 Hz, 1H), 7.74 (d, J = 1.9 Hz, 1H), 7.81 (dd, J = 7.6, 2.0 Hz, 1H), 7.97 (br s, 1H)

8-(5-Fluoro-2-methylphenoxymethyl)-7-[2-methoxy-4-(4-methoxybenzoylamino)phenyl]-1,3,3-trimethyl-3,4-dihydro-1H-quinoxalin-2-one (Compound No. 14-23)

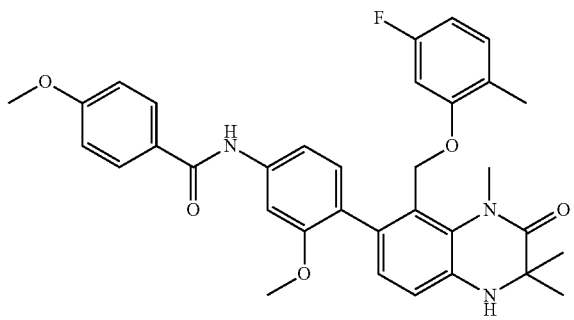

¹H-NMR (400 MHz, CDCl₃) δ 0.92 (s, 3H), 1.29 (s, 3H), 2.02 (s, 3H), 3.47 (s, 3H), 3.71 (s, 1H), 3.88 (s, 3H), 3.89 (s, 3H), 4.87 (d, J = 13.8 Hz, 1H), 5.24 (d, J = 13.8 Hz, 1H), 6.06 (dd, J = 11.2, 2.4 Hz, 1H), 6.38 (td, J = 8.2, 2.4 Hz, 1H), 6.72 (d, J = 8.0 Hz, 1H), 6.88-6.91 (m, 1H), 6.90 (d, J = 8.0 Hz, 1H), 7.01 (d, J = 8.8 Hz, 2H), 7.04 (dd, J = 8.1, 2.1 Hz, 1H), 7.30 (d, J = 8.1 Hz, 1H), 7.76 (d, J = 2.1 Hz, 1H), 7.83 (s, 1H), 7.87 (d, J = 8.8 Hz, 2H)

8-(5-Fluoro-2-methylphenoxymethyl)-7-(4-isobutyryloxy-2-methoxyphenyl)-1,3,3-trimethyl-3,4-dihydro-1H-quinoxalin-2-one (Compound No. 14-24)

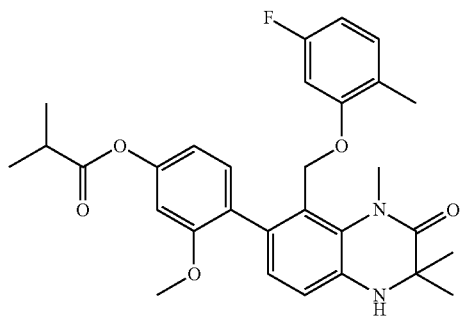

¹H-NMR (500 MHz, CDCl₃) δ 0.93 (s, 3H), 1.27 (s, 3H), 1.35 (d, J = 7.0 Hz, 6H), 2.01 (s, 3H), 2.84 (sept, J = 7.0 Hz, 1H), 3.46 (s, 3H), 3.71 (s, 1H), 3.82 (s, 3H), 4.85 (d, J = 13.7 Hz, 1H), 5.21 (d, J = 13.7 Hz, 1H), 6.06 (dd, J = 11.0, 2.4 Hz, 1H), 6.39 (td, J = 8.4, 2.4 Hz, 1H), 6.71 (d, J = 8.1 Hz, 1H), 6.74 (d, J = 2.2 Hz, 1H), 6.80 (dd, J = 8.2, 2.2 Hz, 1H), 6.88-6.91 (m, 1H), 6.89 (d, J = 8.1 Hz, 1H), 7.31 (d, J = 8.2 Hz, 1H)

| | |
|---|---|
| 8-(5-Fluoro-2-methylphenoxymethyl)-7-[2-methoxy-4-(thiophen-3-ylcarbonyloxy)phenyl]-1,3,3-trimethyl-3,4-dihydro-1H-quinoxalin-2-one (Compound No. 14-25)<br>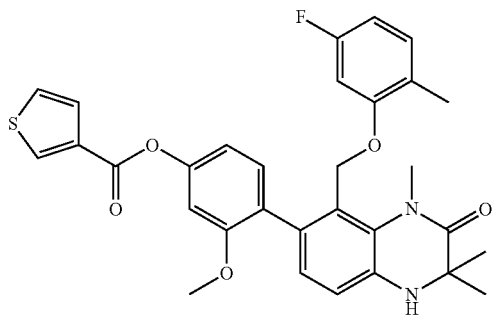 | $^1$H-NMR (500 MHz, CDCl$_3$) δ 0.95 (s, 3H), 1.27 (s, 3H), 2.02 (s, 3H), 3.47 (s, 3H), 3.72 (s, 1H), 3.83 (s, 3H), 4.88 (d, J = 13.4 Hz, 1H), 5.23 (d, J = 13.4 Hz, 1H), 6.08 (dd, J = 11.3, 2.4 Hz, 1H), 6.40 (td, J = 8.2, 2.4 Hz, 1H), 6.73 (d, J = 7.9 Hz, 1H), 6.88 (d, J = 2.1 Hz, 1H), 6.89-6.92 (m, 1H), 6.91 (d, J = 7.9 Hz, 1H), 6.93 (dd, J = 8.3, 2.1 Hz, 1H), 7.35 (d, J = 8.3 Hz, 1H), 7.41 (dd, J = 5.0, 3.1 Hz, 1H), 7.69 (dd, J = 5.0, 1.2 Hz, 1H), 8.35 (dd, J = 3.1, 1.2 Hz, 1H) |
| 8-(5-Fluoro-2-methylphenoxymethyl)-7-(2-methoxy-4-pivaloyloxyphenyl)-1,3,3-trimethyl-3,4-dihydro-1H-quinoxalin-2-one (Compound No. 14-26)<br>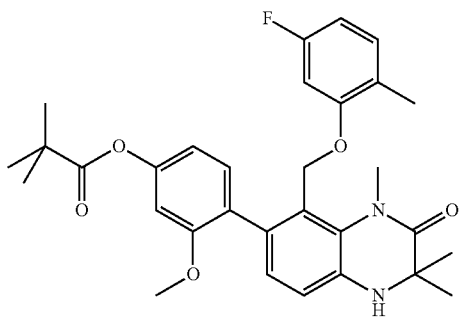 | $^1$H-NMR (400 MHz, CDCl$_3$) δ 0.93 (s, 3H), 1.27 (s, 3H), 1.39 (s, 9H), 2.01 (s, 3H), 3.46 (s, 3H), 3.71 (br s, 1H), 3.82 (s, 3H), 4.85 (d, J = 13.7 Hz, 1H), 5.21 (d, J = 13.7 Hz, 1H), 6.06 (dd, J = 11.2, 2.4 Hz, 1H), 6.39 (td, J = 8.3, 2.4 Hz, 1H), 6.71 (d, J = 8.1 Hz, 1H), 6.72 (d, J = 2.1 Hz, 1H), 6.79 (dd, J = 3.3, 2.1 Hz, 1H), 6.87-6.92 (m, 1H), 6.88 (d, J = 8.1 Hz, 1H), 7.31 (d, J = 8.3 Hz, 1H) |
| 7-[4-(2-Fluorobenzoyloxy)-2-methoxyphenyl]-8-(5-fluoro-2-methylphenoxymethyl)-1,3,3-trimethyl-3,4-dihydro-1H-quinoxalin-2-one (Compound No. 14-27)<br>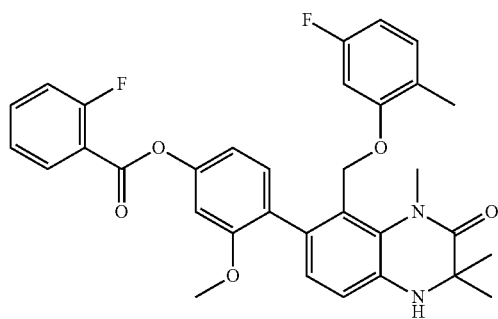 | $^1$H-NMR (500 MHz, CDCl$_3$) δ 0.95 (s, 3H), 1.27 (s, 3H), 2.02 (s, 3H), 3.47 (s, 3H), 3.73 (br s, 1H), 3.84 (s, 3H), 4.88 (d, J = 13.7 Hz, 1H), 5.23 (d, J = 13.7 Hz, 1H), 6.08 (dd, J = 11.0, 2.4 Hz, 1H), 6.40 (td, J = 8.2, 2.4 Hz, 1H), 6.73 (d, J = 8.1 Hz, 1H), 6.89-6.92 (m, 1H), 6.91 (d, J = 2.2 Hz, 1H), 6.92 (d, J = 8.1 Hz, 1H), 6.97 (dd, J = 8.2, 2.2 Hz, 1H), 7.22-7.26 (m, 1H), 7.31 (td, J = 7.6, 0.9 Hz, 1H), 7.37 (d, J = 8.2 Hz, 1H), 7.61-7.65 (m, 1H), 8.14 (td, J = 7.6, 1.8 Hz, 1H) |
| 7-[4-(3-Fluorobenzoyloxy)-2-methoxyphenyl]-8-(5-fluoro-2-methylphenoxymethyl)-1,3,3-trimethyl-3,4-dihydro-1H-quinoxalin-2-one (Compound No. 14-28)<br>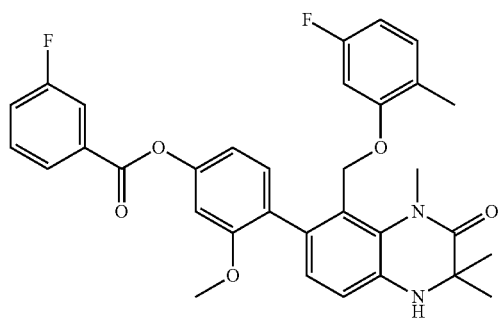 | $^1$H-NMR (400 MHz, CDCl$_3$) δ 0.96 (s, 3H), 1.28 (s, 3H), 2.03 (s, 3H), 3.48 (s, 3H), 3.64-3.85 (m, 1H), 3.84 (s, 3H), 4.88 (d, J = 13.6 Hz, 1H), 5.23 (d, J = 13.6 Hz, 1H), 6.09 (dd, J = 11.2, 2.4 Hz, 1H), 6.41 (td, J = 8.3, 2.4 Hz, 1H), 6.74 (d, J = 8.0 Hz, 1H), 6.88-6.94 (m, 1H), 6.89 (d, J = 2.4 Hz, 1H), 6.92 (d, J = 8.0 Hz, 1H), 6.95 (dd, J = 8.3, 2.4 Hz, 1H), 7.37 (tdd, J = 8.2, 2.7, 1.2 Hz, 1H), 7.37 (d, J = 8.3 Hz, 1H), 7.52 (td, J = 8.2, 5.5 Hz, 1H), 7.90-7.93 (m, 1H), 8.02-8.05 (m, 1H) |

| | |
|---|---|
| 8-(5-Fluoro-2-methylphenoxymethyl)-7-[2-methoxy-4-(3-methoxybenzoyloxy)phenyl]-1,3,3-trimethyl-3,4-dihydro-1H-quinoxalin-2-one (Compound No. 14-29)<br>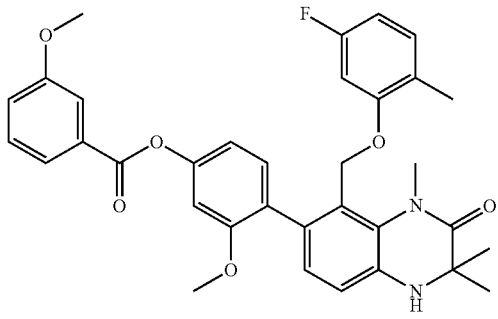 | $^1$H-NMR (400 MHz, CDCl$_3$) δ 0.96 (s, 3H), 1.28 (s, 3H), 2.03 (s, 3H), 3.48 (s, 3H), 3.73 (s, 1H), 3.84 (s, 3H), 3.91 (s, 3H), 4.89 (d, J = 13.6 Hz, 1H), 5.24 (d, J = 13.6 Hz, 1H), 6.09 (dd, J = 11.2, 2.4 Hz, 1H), 6.40 (td, J = 8.3, 2.4 Hz, 1H), 6.74 (d, J = 8.1 Hz, 1H), 6.89-6.96 (m, 1H), 6.89 (d, J = 2.3 Hz, 1H), 6.93 (d, J = 8.1 Hz, 1H), 6.95 (dd, J = 8.2, 2.3 Hz, 1H), 7.21 (dt, J = 8.1, 1.3 Hz, 1H), 7.37 (d, J = 8.2 Hz, 1H), 7.45 (t, J = 8.1 Hz, 1H), 7.73-7.74 (m, 1H), 7.83-7.85 (m, 1H) |
| 8-(5-Fluoro-2-methylphenoxymethyl)-7-[2-methoxy-4-(4-methoxybenzoyloxy)phenyl]-1,3,3-trimethyl-3,4-dihydro-1H-quinoxalin-2-one (Compound No. 14-30)<br>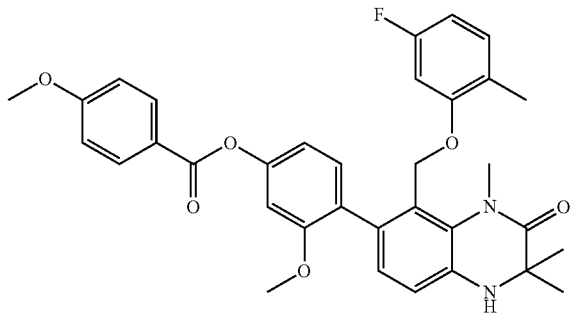 | $^1$H-NMR (400 MHz, CDCl$_3$) δ 0.94 (s, 3H), 1.28 (s, 3H), 2.03 (s, 3H), 3.47 (s, 3H), 3.73 (s, 1H), 3.83 (s, 3H), 3.91 (s, 3H), 4.89 (d, J = 13.6 Hz, 1H), 5.23 (d, J = 13.6 Hz, 1H), 6.09 (dd, J = 11.2, 2.4 Hz, 1H), 6.40 (td, J = 8.3, 2.4 Hz, 1H), 6.73 (d, J = 8.1 Hz, 1H), 6.88-6.95 (m, 1H), 6.88 (d, J = 2.2 Hz, 1H), 6.92 (d, J = 8.1 Hz, 1H), 6.93 (dd, J = 8.2, 2.2 Hz, 1H), 7.01 (dt, J = 9.5, 2.4 Hz, 2H), 7.36 (d, J = 8.2 Hz, 1H), 8.18 (dt, J = 9.5, 2.4 Hz, 2H) |
| 8-(5-Fluoro-2-methylphenoxymethyl)-7-[2-methoxy-4-(4-nitrobenzoyloxy)phenyl]-1,3,3-trimethyl-3,4-dihydro-1H-quinoxalin-2-one (Compound No. 14-31)<br>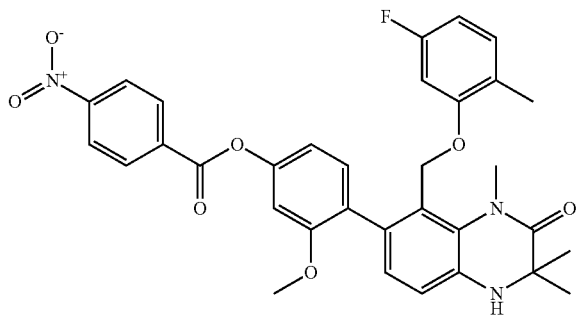 | $^1$H-NMR (500 MHz, CDCl$_3$) δ 0.97 (s, 3H), 1.28 (s, 3H), 2.03 (s, 3H), 3.47 (s, 3H), 3.75 (s, 1H), 3.85 (s, 3H), 4.87 (d, J = 13.4 Hz, 1H), 5.22 (d, J = 13.4 Hz, 1H), 6.09 (dd, J = 11.2, 2.4 Hz, 1H), 6.41 (td, J = 8.3, 2.4 Hz, 1H), 6.74 (d, J = 8.1 Hz, 1H), 6.90 (d, J = 2.4 Hz, 1H), 6.91-6.93 (m, 1H), 6.92 (d, J = 8.1 Hz, 1H), 6.96 (dd, J = 8.0, 2.4 Hz, 1H), 7.39 (d, J = 8.0 Hz, 1H), 8.37-8.43 (m, 4H) |
| 8-(5-Fluoro-2-methylphenoxymethyl)-7-(2-methoxy-4-propionyloxyphenyl)-1,3,3-trimethyl-3,4-dihydro-1H-quinoxalin-2-one (Compound No. 14-32)<br>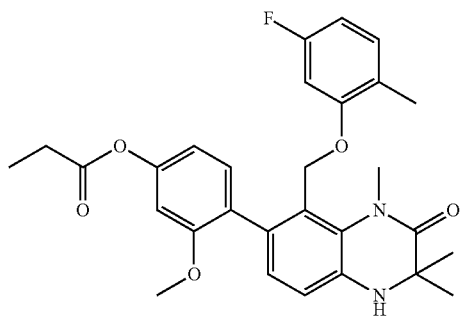 | $^1$H-NMR (400 MHz, CDCl$_3$) δ 0.94 (s, 3H), 1.27 (s, 3H), 1.30 (t, J = 7.6 Hz, 3H), 2.01 (s, 3H), 2.63 (q, J = 7.6 Hz, 2H), 3.46 (s, 3H), 3.71 (s, 1H), 3.81 (s, 3H), 4.85 (d, J = 13.7 Hz, 1H), 5.20 (d, J = 13.7 Hz, 1H), 6.06 (dd, J = 11.1, 2.4 Hz, 1H), 6.39 (td, J = 8.3, 2.4 Hz, 1H), 6.71 (d, J = 8.0 Hz, 1H), 6.75 (d, J = 2.1 Hz, 1H), 6.81 (dd, J = 8.1, 2.1 Hz, 1H), 6.88-6.92 (m, 1H), 6.89 (d, J = 8.0 Hz, 1H), 7.30 (d, J = 8.1 Hz, 1H) |

7-(4-Acryloyloxy-2-methoxyphenyl)-8-(5-fluoro-2-methylphenoxymethyl)-1,3,3-trimethyl-3,4-dihydro-1H-quinoxalin-2-one (Compound No. 14-33)

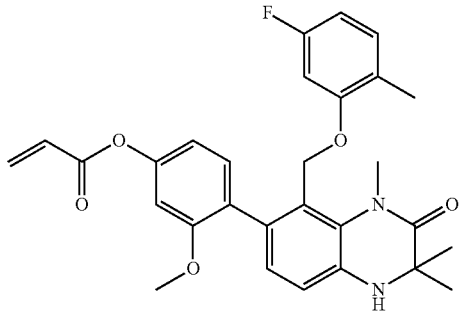

¹H-NMR (500 MHz, CDCl₃) δ 0.94 (s, 3H), 1.27 (s, 3H), 2.02 (s, 3H), 3.46 (s, 3H), 3.72 (s, 1H), 3.82 (s, 3H), 4.86 (d, J = 13.6 Hz, 1H), 5.21 (d, J = 13.6 Hz, 1H), 6.05 (dd, J = 10.5, 1.2 Hz, 1H), 6.07 (dd, J = 11.2, 2.4 Hz, 1H), 6.35 (dd, J = 17.3, 10.5 Hz, 1H), 6.39 (td, J = 8.4, 2.4 Hz, 1H), 6.65 (dd, J = 17.3, 1.2 Hz, 1H), 6.72 (d, J = 8.1 Hz, 1H), 6.80 (d, J = 2.1 Hz, 1H), 6.89 (dd, J = 8.1, 2.1 Hz, 1H), 6.89-6.91 (m, 1H), 6.89 (d, J = 8.1 Hz, 1H), 7.32 (d, J = 8.1 Hz, 1H)

8-(5-Fluoro-2-methylphenoxymethyl)-7-[2-methoxy-4-(thiophen-2-ylcarbonyloxy)phenyl]-1,3,3-trimethyl-3,4-dihydro-1H-quinoxalin-2-one (Compound No. 14-34)

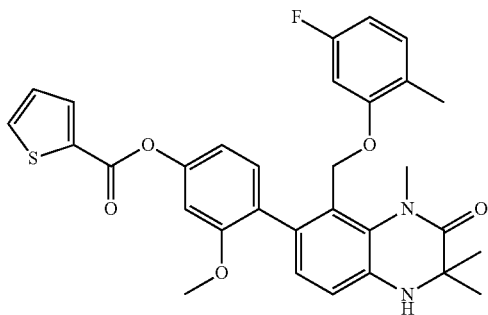

¹H-NMR (500 MHz, CDCl₃) δ 0.95 (s, 3H), 1.27 (s, 3H), 2.02 (s, 3H), 3.47 (s, 3H), 3.73 (s, 1H), 3.84 (s, 3H), 4.87 (d, J = 13.6 Hz, 1H), 5.22 (d, J = 13.6 Hz, 1H), 6.08 (dd, J = 11.3, 2.4 Hz, 1H), 6.40 (td, J = 8.2, 2.4 Hz, 1H), 6.73 (d, J = 8.1 Hz, 1H), 6.89-6.90 (m, 1H), 6.90 (d, J = 2.1 Hz, 1H), 6.91 (d, J = 8.1 Hz, 1H), 6.95 (dd, J = 8.1, 2.1 Hz, 1H), 7.19-7.21 (m, 1H), 7.35 (d, J = 8.1 Hz, 1H), 7.70 (d, J = 4.9 Hz, 1H), 8.01 (d, J = 3.7 Hz, 1H)

8-(5-Fluoro-2-methylphenoxymethyl)-7-(2-methoxy-4-methoxycarbonyloxyphenyl)-1,3,3-trimethyl-3,4-dihydro-1H-quinoxalin-2-one (Compound No. 14-35)

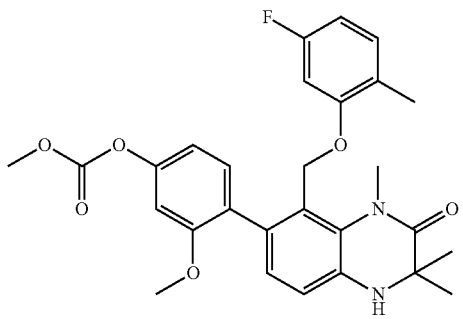

¹H-NMR (400 MHz, CDCl₃) δ 0.94 (s, 3H), 1.27 (s, 3H), 2.01 (s, 3H), 3.46 (s, 3H), 3.73 (s, 1H), 3.82 (s, 3H), 3.94 (s, 3H), 4.84 (d, J = 13.5 Hz, 1H), 5.20 (d, J = 13.5 Hz, 1H), 6.05 (dd, J = 11.2, 2.4 Hz, 1H), 6.39 (td, J = 8.3, 2.4 Hz, 1H), 6.72 (d, J = 8.1 Hz, 1H), 6.84 (d, J = 2.2 Hz, 1H), 6.87-6.92 (m, 3H), 7.31 (d, J = 8.3 Hz, 1H)

8-(5-Fluoro-2-methylphenoxymethyl)-7-(2-methoxy-4-phenoxycarbonyloxyphenyl)-1,3,3-trimethyl-3,4-dihydro-1H-quinoxalin-2-one (Compound No. 14-36)

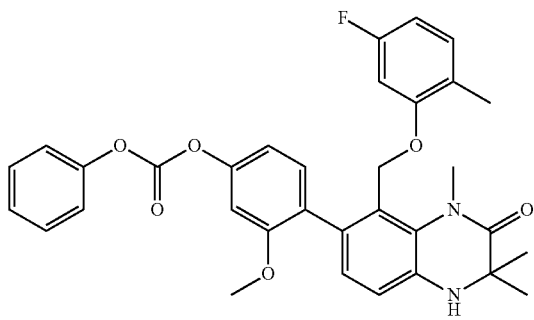

¹H-NMR (400 MHz, CDCl₃) δ 0.96 (s, 3H), 1.27 (s, 3H), 2.01 (s, 3H), 3.46 (s, 3H), 3.73 (s, 1H), 3.84 (s, 3H), 4.85 (d, J = 13.6 Hz, 1H), 5.20 (d, J = 13.6 Hz, 1H), 6.06 (dd, J = 11.2, 2.4 Hz, 1H), 6.39 (td, J = 8.3, 2.4 Hz, 1H), 6.73 (d, J = 7.9 Hz, 1H), 6.89 (d, J = 7.9 Hz, 1H), 6.88-6.92 (m, 1H), 6.95 (d, J = 2.3 Hz, 1H), 7.00 (dd, J = 8.2, 2.3 Hz, 1H), 7.28-7.32 (m, 3H), 7.34 (d, J = 8.2 Hz, 1H) 7.41-7.46 (m, 2H)

8-(5-Fluoro-2-methylphenoxymethyl)-7-(2-methoxy-4-phenoxycarbonylaminophenyl)-1,3,3-trimethyl-3,4-dihydro-1H-quinoxalin-2-one (Compound No. 14-37)

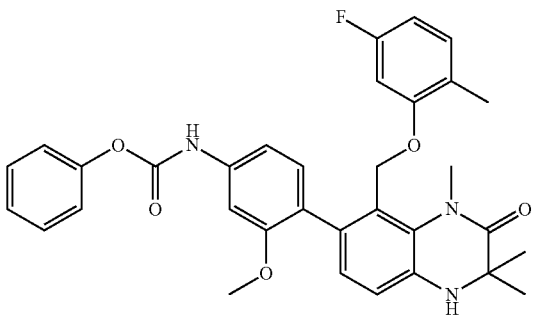

$^1$H-NMR (400 MHz, CDCl$_3$) δ 0.92 (s, 3H), 1.29 (s, 3H), 2.02 (s, 3H), 3.47 (s, 3H), 3.71 (s, 1H), 3.83 (s, 3H), 4.85 (d, J = 13.7 Hz, 1H), 5.22 (d, J = 13.7 Hz, 1H), 6.05 (dd, J = 11.2, 2.4 Hz, 1H), 6.39 (td, J = 8.3, 2.4 Hz, 1H), 6.71 (d, J = 8.1 Hz, 1H), 6.89 (d, J = 8.1 Hz, 1H), 6.89-6.91 (m, 2H), 7.10 (br s, 1H), 7.21 (dd, J = 8.5, 1.2 Hz, 2H), 7.25-7.28 (m, 2H), 7.40-7.44 (m, 2H), 7.52 (br s, 1H)

7-[4-(2-Chlorobenzoyloxy)-2-methoxyphenyl]-8-(5-methylthiophen-2-ylcarbonyloxymethyl)-1,3,3-trimethyl-3,4-dihydro-1H-quinoxalin-2-one (Compound No. 14-38)

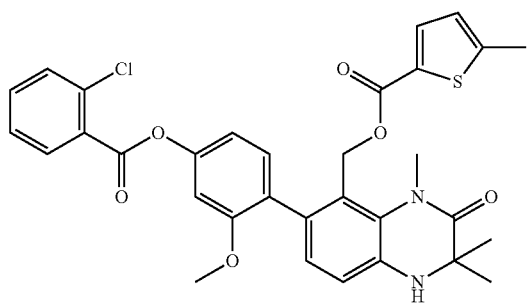

$^1$H-NMR (400 MHz, CDCl$_3$) δ 1.21 (s, 3H), 1.42 (s, 3H), 2.47 (s, 3H), 3.46 (s, H), 2.47 (s, 3H), 3.46 (s, 3H), 3.78 (s, 4H), 5.13 (d, J = 13.2 Hz, 1H), 5.31 (d, J = 13.2 Hz, 1H), 6.70 (d, J = 3.7 Hz, 1H), 6.77 (d, J = 8.0 Hz, 1H), 6.85 (d, J = 2.3 Hz, 1H), 6.89 (dd, J = 8.2, 2.3 Hz, 1H), 6.89 (d, J = 8.0 Hz, 1H), 7.33 (d, J = 8.2 Hz, 1H), 7.39-7.43 (m, 1H), 7.45 (d, J = 3.7 Hz, 1H), 7.49-7.56 (m, 2H), 8.07 (ddd, J = 7.8, 1.7, 0.5 Hz, 1H)

7-(4-Benzoyloxy-2-methoxyphenyl)-8-(5-methylthiophen-2-ylcarbonyloxymethyl)-1,3,3-trimethyl-3,4-dihydro-1H-quinoxalin-2-one (Compound No. 14-39)

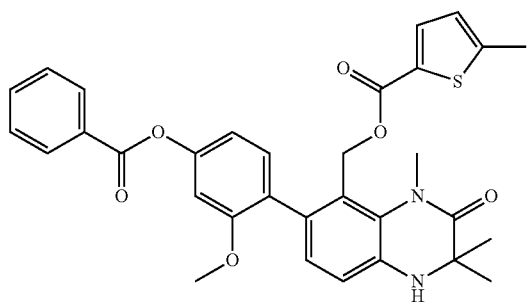

$^1$H-NMR (500 MHz, CDCl$_3$) δ 1.22 (s, 3H), 1.42 (s, 3H), 2.47 (s, 3H), 3.46 (s, 3H), 3.77 (s, 3H), 3.79 (s, 1H), 5.14 (d, J = 13.3 Hz, 1H), 5.31 (d, J = 13.3 Hz, 1H), 6.70 (d, J = 3.7 Hz, 1H), 6.77 (d, J = 7.9 Hz, 1H), 6.83 (d, J = 2.3 Hz, 1H), 6.86 (dd, J = 8.1, 2.3 Hz, 1H), 6.91 (d, J = 7.9 Hz, 1H), 7.32 (d, J = 8.1 Hz, 1H), 7.45 (d, J = 3.7 Hz, 1H), 7.53 (t, J = 7.8 Hz, 2H), 7.66 (t, J = 7.8 Hz, 1H), 8.22 (d, J = 7.8 Hz, 2H)

7-[2-Methoxy-4-(pyridin-4-ylcarbonyloxy)phenyl]-8-(5-methylthiophen-2-ylcarbonyloxymethyl)-1,3,3-trimethyl-3,4-dihydro-1H-quinoxalin-2-one (Compound No. 14-40)

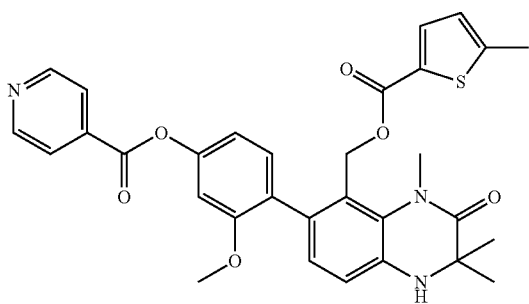

$^1$H-NMR (500 MHz, CDCl$_3$) δ 1.22 (s, 3H), 1.42 (s, 3H), 2.47 (s, 3H), 3.46 (s, 3H), 3.77 (s, 3H), 3.82 (s, 1H), 5.13 (d, J = 13.3 Hz, 1H), 5.30 (d, J = 13.3 Hz, 1H), 6.70 (d, J = 3.8 Hz, 1H), 6.78 (d, J = 7.9 Hz, 1H), 6.82 (d, J = 2.4 Hz, 1H), 6.87 (dd, J = 8.2, 2.4 Hz, 1H), 6.90 (d, J = 7.9 Hz, 1H), 7.34 (d, J = 8.2 Hz, 1H), 7.45 (d, J = 3.8 Hz, 1H), 8.02 (dd, J = 4.4, 1.6 Hz, 2H), 8.88 (dd, J = 4.4, 1.6 Hz, 2H)

| Compound | Structure | ¹H-NMR |
|---|---|---|
| 7-[4-(Furan-2-ylcarbonyloxy)-2-methoxyphenyl]-8-(5-methylthiophen-2-ylcarbonyloxymethyl)-1,3,3-trimethyl-3,4-dihydro-1H-quinoxalin-2-one (Compound No. 14-41) | 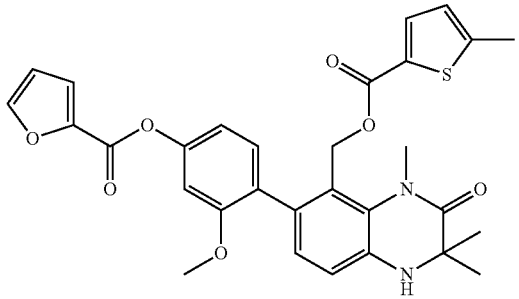 | ¹H-NMR (500 MHz, CDCl₃) δ 1.22 (s, 3H), 1.42 (s, 3H), 2.47 (s, 3H), 3.45 (s, 3H), 3.76 (s, 3H), 3.79 (s, 1H), 5.11 (d, J = 13.4 Hz, 1H), 5.30 (d, J = 13.4 Hz, 1H), 6.61 (d, J = 3.5 Hz, 1H), 6.70 (dd, J = 3.8 Hz, 1H), 6.76 (d, J = 7.9 Hz, 1H), 6.82 (d, J = 2.3 Hz, 1H), 6.86 (dd, J = 8.2, 2.3 Hz, 1H), 6.89 (d, J = 7.9 Hz, 1H), 7.31 (d, J = 8.2 Hz, 1H), 7.40 (dd, J = 3.5, 0.9 Hz, 1H), 7.44 (d, J = 3.8 Hz, 1H), 7.69 (dd, J = 1.7, 0.9 Hz, 1H) |
| 7-[2-Methoxy-4-(thiophen-3-ylcarbonyloxy)phenyl]-8-(5-methylthiophen-2-ylcarbonyloxymethyl)-1,3,3-trimethyl-3,4-dihydro-1H-quinoxalin-2-one (Compound No. 14-42) | 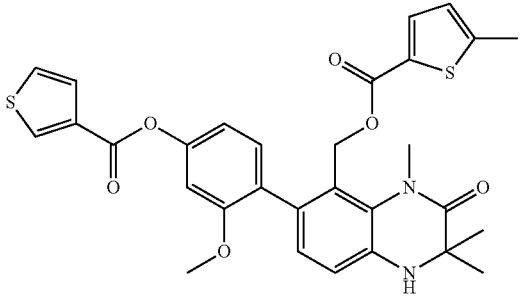 | ¹H-NMR (500 MHz, CDCl₃) δ 1.22 (s, 3H), 1.42 (s, 3H), 2.47 (s, 3H), 3.46 (s, 3H), 3.76 (s, 3H), 3.77 (s, 1H), 5.13 (d, J = 13.4 Hz, 1H), 5.30 (d, J = 13.4 Hz, 1H), 6.70 (d, J = 3.6 Hz, 1H), 6.77 (d, J = 7.9 Hz, 1H), 6.81 (d, J = 2.1 Hz, 1H), 6.84 (dd, J = 8.3, 2.1 Hz, 1H), 6.90 (d, J = 7.9 Hz, 1H), 7.31 (d, J = 8.3 Hz, 1H), 7.40 (dd, J = 5.3, 3.1 Hz, 1H), 7.45 (d, J = 3.6 Hz, 1H), 7.68 (dd, J = 5.3, 0.9 Hz, 1H), 8.33 (dd, J = 3.1, 0.9 Hz, 1H) |
| 7-[4-(Furan-3-ylcarbonyloxy)-2-methoxyphenyl]-8-(5-methylthiophen-2-ylcarbonyloxymethyl)-1,3,3-trimethyl-3,4-dihydro-1H-quinoxalin-2-one (Compound No. 14-43) | 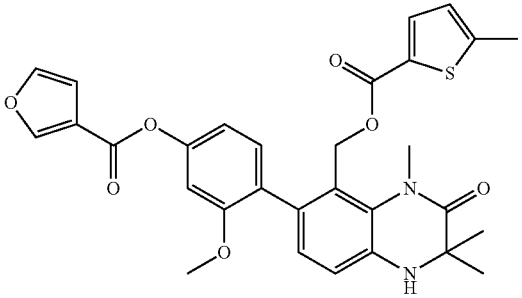 | ¹H-NMR (500 MHz, CDCl₃) δ 1.22 (s, 3H), 1.42 (s, 3H), 2.47 (s, 3H), 3.46 (s, 3H), 3.76 (s, 3H), 3.79 (s, 1H), 5.12 (d, J = 13.3 Hz, 1H), 5.30 (d, J = 13.3 Hz, 1H), 6.70 (d, J = 3.7 Hz, 1H), 6.77 (d, J = 7.9 Hz, 1H), 6.79 (d, J = 2.1 Hz, 1H), 6.82 (dd, J = 8.1, 2.1 Hz, 1H), 6.89-6.90 (m, 1H), 6.90 (d, J = 7.9 Hz, 1H), 7.30 (d, J = 8.1 Hz, 1H), 7.45 (d, J = 3.7 Hz, 1H), 7.51-7.52 (m, 1H), 8.21-8.22 (m, 1H) |
| 7-[4-(2-Fluorobenzoyloxy)-2-methoxyphenyl]-8-(5-methylthiophen-2-ylcarbonyloxymethyl)-1,3,3-trimethyl-3,4-dihydro-1H-quinoxalin-2-one (Compound No. 14-44) | 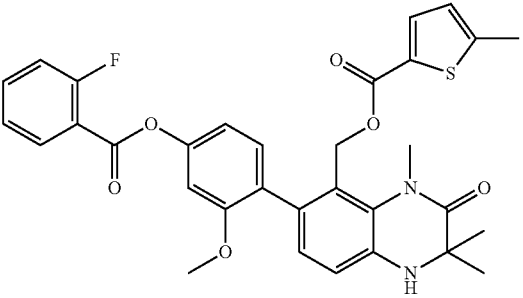 | ¹H-NMR (500 MHz, CDCl₃) δ 1.21 (s, 3H), 1.42 (s, 3H), 2.47 (s, 3H), 3.46 (s, 3H), 3.77 (s, 3H), 3.80 (s, 1H), 5.13 (d, J = 13.3 Hz, 1H), 5.31 (d, J = 13.3 Hz, 1H), 6.70 (d, J = 3.7 Hz, 1H), 6.77 (d, J = 8.1 Hz, 1H), 6.84 (d, J = 2.4 Hz, 1H), 6.88 (dd, J = 8.5, 2.4 Hz, 1H), 6.90 (d, J = 8.1 Hz, 1H), 7.21-7.26 (m, 1H), 7.30 (t, J = 7.6 Hz, 1H), 7.32 (d, J = 8.5 Hz, 1H), 7.45 (d, J = 3.7 Hz, 1H), 7.60-7.64 (m, 1H), 8.12 (td, J = 7.6, 1.7 Hz, 1H) |

| Compound | NMR |
|---|---|
| 7-[4-(4-Chlorobenzoyloxy)-2-methoxyphenyl]-8-(5-methylthiophen-2-ylcarbonyloxymethyl)-1,3,3-trimethyl-3,4-dihydro-1H-quinoxalin-2-one (Compound No. 14-45) 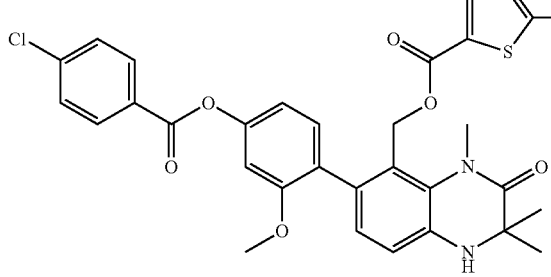 | $^1$H-NMR (500 MHz, CDCl$_3$) δ 1.22 (s, 3H), 1.42 (s, 3H), 2.47 (s, 3H), 3.46 (s, 3H), 3.77 (s, 3H), 3.80 (s, 1H), 5.13 (d, J = 13.4 Hz, 1H), 5.30 (d, J = 13.4 Hz, 1H), 6.70 (d, J = 3.7 Hz, 1H), 6.77 (d, J = 7.9 Hz, 1H), 6.81 (d, J = 2.2 Hz, 1H), 6.85 (dd, J = 8.2, 2.2 Hz, 1H), 6.90 (d, J = 7.9 Hz, 1H), 7.32 (d, J = 8.2 Hz, 1H), 7.45 (d, J = 3.7 Hz, 1H), 7.51 (d, J = 8.6 Hz, 2H), 8.15 (d, J = 8.6 Hz, 2H) |
| 7-[2-Methoxy-4-(2-methylbenzoyloxy)phenyl]-8-(5-methylthiophen-2-ylcarbonyloxymethyl)-1,3,3-trimethyl-3,4-dihydro-1H-quinoxalin-2-one (Compound No. 14-46) 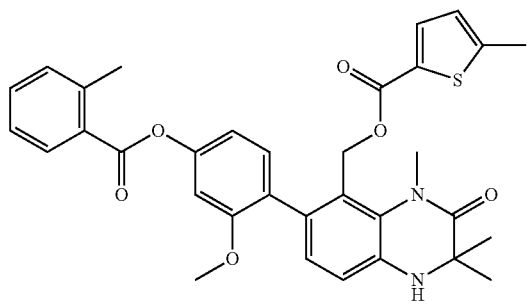 | $^1$H-NMR (400 MHz, CDCl$_3$) δ 1.21 (s, 3H), 1.42 (s, 3H), 2.47 (s, 3H), 2.70 (s, 3H), 3.46 (s, 3H), 3.77 (s, 3H), 3.80 (s, 1H), 5.14 (d, J = 13.3 Hz, 1H), 5.31 (d, J = 13.3 Hz, 1H), 6.70 (d, J = 3.7 Hz, 1H), 6.77 (d, J = 8.1 Hz, 1H), 6.81 (d, J = 2.2 Hz, 1H), 6.85 (dd, J = 8.2, 2.2 Hz, 1H), 6.90 (d, J = 8.1 Hz, 1H), 7.32-7.36 (m, 2H), 7.33 (d, J = 8.2 Hz, 1H), 7.45 (d, J = 3.7 Hz, 1H), 7.50 (td, J = 7.9, 1.5 Hz, 1H), 8.18 (d, J = 7.9 Hz, 1H) |
| 7-[2-Methoxy-4-(pyridin-3-ylcarbonyloxy)phenyl]-8-(5-methylthiophen-2-ylcarbonyloxymethyl)-1,3,3-trimethyl-3,4-dihydro-1H-quinoxalin-2-one (Compound No. 14-47) 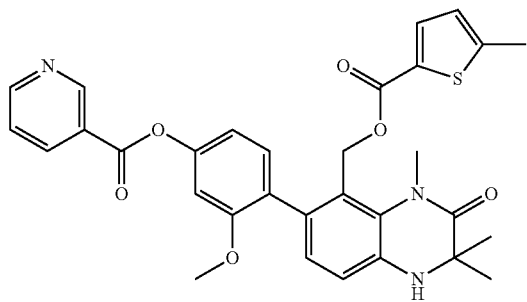 | $^1$H-NMR (400 MHz, CDCl$_3$) δ 1.22 (s, 3H), 1.42 (s, 3H), 2.48 (s, 3H), 3.46 (s, 3H), 3.78 (s, 3H), 3.81 (s, 1H), 5.13 (d, J = 13.3 Hz, 1H), 5.30 (d, J = 13.3 Hz, 1H), 6.70 (d, J = 3.6 Hz, 1H), 6.78 (d, J = 8.1 Hz, 1H), 6.83 (d, J = 2.2 Hz, 1H), 6.87 (dd, J = 8.2, 2.2 Hz, 1H), 6.91 (d, J = 8.1 Hz, 1H), 7.34 (d, J = 8.2 Hz, 1H), 7.45 (d, J = 3.6 Hz, 1H), 7.49 (ddd, J = 8.0, 4.9, 0.9 Hz, 1H), 8.47 (dt, J = 8.0, 1.9 Hz, 1H), 8.87 (dd, J = 4.9, 1.9 Hz, 1H), 9.42 (dd, J = 1.9, 0.9 Hz, 1H) |
| 7-[2-Methoxy-4-(2-methoxybenzoyloxy)phenyl]-8-(5-methylthiophen-2-ylcarbonyloxymethyl)-1,3,3-trimethyl-3,4-dihydro-1H-quinoxalin-2-one (Compound No. 14-48) 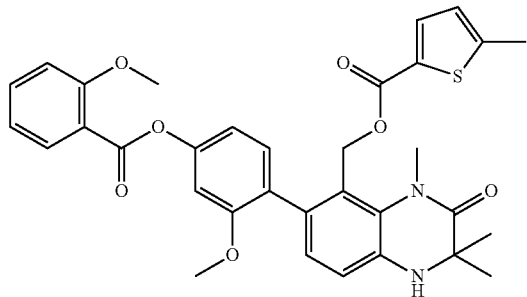 | $^1$H-NMR (500 MHz, CDCl$_3$) δ 1.21 (s, 3H), 1.42 (s, 3H), 2.47 (s, 3H), 3.46 (s, 3H), 3.77 (s, 3H), 3.79 (s, 1H), 3.96 (s, 3H), 5.13 (d, J = 13.4 Hz, 1H), 5.31 (d, J = 13.4 Hz, 1H), 6.70 (d, J = 3.7 Hz, 1H), 6.77 (d, J = 7.9 Hz, 1H), 6.84 (d, J = 2.2 Hz, 1H), 6.87 (dd, J = 8.2, 2.2 Hz, 1H), 6.90 (d, J = 7.9 Hz, 1H), 7.05-7.08 (m, 2H), 7.31 (d, J = 8.2 Hz, 1H), 7.45 (d, J = 3.7 Hz, 1H), 7.56 (ddd, J = 8.7, 6.9, 1.8 Hz, 1H), 8.04 (dd, J = 7.8, 1.8 Hz, 1H) |

| Compound | NMR |
|---|---|
| 7-(4-Butyryloxy-2-methoxyphenyl)-8-(5-methylthiophen-2-ylcarbonyloxymethyl)-1,3,3-trimethyl-3,4-dihydro-1H-quinoxalin-2-one (Compound No. 14-49) 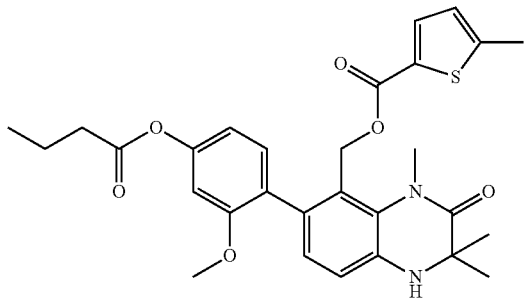 | $^1$H-NMR (500 MHz, CDCl$_3$) δ 1.06 (t, J = 7.5 Hz, 3H), 1.20 (s, 3H), 1.42 (s, 3H), 1.80 (qt, J = 7.5, 7.4 Hz, 2H), 2.47 (s, 3H), 2.56 (t, J = 7.4 Hz, 2H), 3.44 (s, 3H), 3.74 (s, 3H), 3.78 (s, 1H), 5.10 (d, J = 13.4 Hz, 1H), 5.28 (d, J = 13.4 Hz, 1H), 6.68 (d, J = 2.1 Hz, 1H), 6.69 (d, J = 3.7 Hz, 1H), 6.72 (dd, J = 8.1, 2.1 Hz, 1H), 6.75 (d, J = 8.1 Hz, 1H), 6.87 (d, J = 8.1 Hz, 1H), 7.26 (d, J = 8.1 Hz, 1H), 7.43 (d, J = 3.7 Hz, 1H) |
| 7-(4-Isobutyryloxy-2-methoxyphenyl)-8-(5-methylthiophen-2-ylcarbonyloxymethyl)-1,3,3-trimethyl-3,4-dihydro-1H-quinoxalin-2-one (Compound No. 14-50) 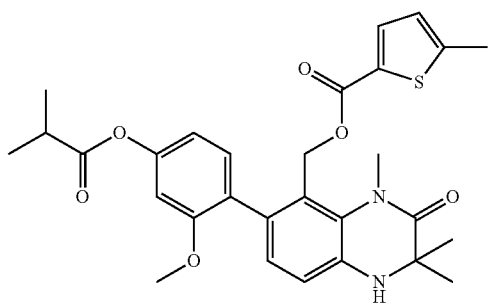 | $^1$H-NMR (500 MHz, CDCl$_3$) δ 1.20 (s, 3H), 1.33 (d, J = 7.0 Hz, 6H), 1.42 (s, 3H), 2.47 (s, 3H), 2.79-2.84 (m, 1H), 3.45 (s, 3H), 3.75 (s, 3H), 3.78 (s, 1H), 5.10 (d, J = 13.4 Hz, 1H), 5.28 (d, J = 13.4 Hz, 1H), 6.68 (d, J = 2.1 Hz, 1H), 6.69 (d, J = 3.7 Hz, 1H), 6.72 (dd, J = 8.2, 2.1 Hz, 1H), 6.75 (d, J = 7.9 Hz, 1H), 6.87 (d, J = 7.9 Hz, 1H), 7.26 (d, J = 8.2 Hz, 1H), 7.43 (d, J = 3.7 Hz, 1H) |
| 7-(2-Methoxy-4-phenylacetoxyphenyl)-8-(5-methylthiophen-2-ylcarbonyloxymethyl)-1,3,3-trimethyl-3,4-dihydro-1H-quinoxalin-2-one (Compound No. 14-51) 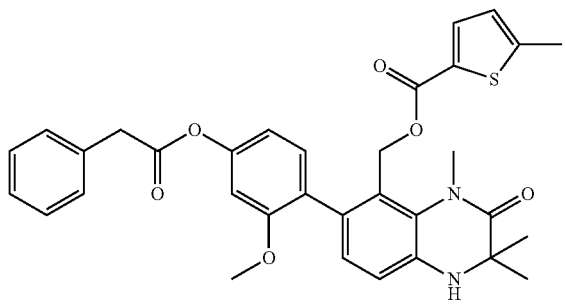 | $^1$H-NMR (500 MHz, CDCl$_3$) δ 1.20 (s, 3H), 1.41 (s, 3H), 2.46 (s, 3H), 3.44 (s, 3H), 3.72 (s, 3H), 3.77 (s, 1H), 3.88 (s, 2H), 5.08 (d, J = 13.3 Hz, 1H), 5.27 (d, J = 13.3 Hz, 1H), 6.67 (d, J = 2.3 Hz, 1H), 6.68 (d, J = 3.7 Hz, 1H), 6.71 (dd, J = 8.1, 2.3 Hz, 1H), 6.74 (d, J = 8.1 Hz, 1H), 6.85 (d, J = 8.1 Hz, 1H), 7.24 (d, J = 8.1 Hz, 1H), 7.29-7.34 (m, 1H), 7.37-7.47 (m, 5H) |
| 7-(4-Cyclohexylcarbonyloxy-2-methoxyphenyl)-8-(5-methylthiophen-2-ylcarbonyloxymethyl)-1,3,3-trimethyl-3,4-dihydro-1H-quinoxalin-2-one (Compound No. 14-52) 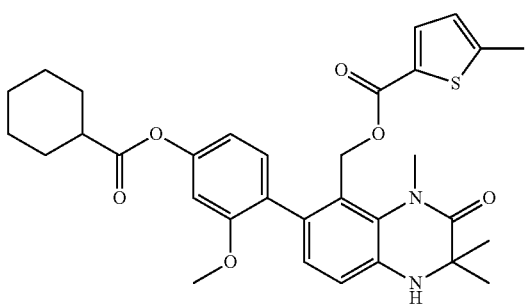 | $^1$H-NMR (500 MHz, CDCl$_3$) δ 1.20 (s, 3H), 1.29-1.39 (m, 3H), 1.42 (s, 3H), 1.57-1.72 (m, 3H), 1.82-1.85 (m, 2H), 2.05-2.09 (m, 2H), 2.47 (s, 3H), 2.55-2.60 (m, 1H), 3.41 (s, 3H), 3.74 (s, 3H), 3.78 (s, 1H), 5.10 (d, J = 13.3 Hz, 1H), 5.28 (d, J = 13.3 Hz, 1H), 6.67 (d, J = 2.2 Hz, 1H), 6.69 (d, J = 3.8 Hz, 1H), 6.71 (dd, J = 8.1, 2.2 Hz, 1H), 6.75 (d, J = 8.1 Hz, 1H), 6.87 (d, J = 8.1 Hz, 1H) 7.25-7.26 (m, 1H), 7.43 (d, J = 3.8 Hz, 1H) |

| | |
|---|---|
| 7-[2-Methoxy-4-(4-methoxybenzoyloxy)phenyl]-8-(5-methylthiophen-2-ylcarbonyloxymethyl)-1,3,3-trimethyl-3,4-dihydro-1H-quinoxalin-2-one (Compound No. 14-53)<br>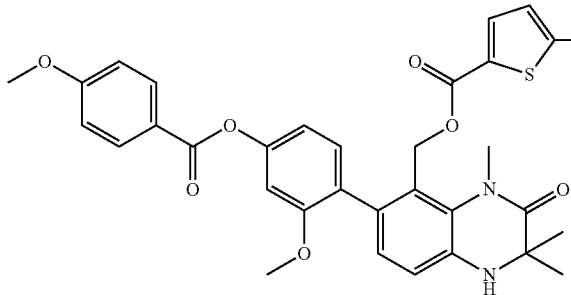 | ¹H-NMR (400 MHz, CDCl₃) δ 1.22 (s, 3H), 1.42 (s, 3H), 2.47 (s, 3H), 3.46 (s, 3H), 3.76 (s, 3H), 3.78 (s, 1H), 3.91 (s, 3H), 5.13 (d, J = 13.3 Hz, 1H), 5.31 (d, J = 13.3 Hz, 1H), 6.70 (d, J = 3.7 Hz, 1H), 6.77 (d, J = 8.1 Hz, 1H), 6.81 (d, J = 2.1 Hz, 1H), 6.84 (dd, J = 8.1, 2.1 Hz, 1H), 6.91 (d, J = 8.1 Hz, 1H) 7.00 (d, J = 8.9 Hz, 2H), 7.31 (d, J = 8.1 Hz, 1H), 7.45 (d, J = 3.7 Hz, 1H), 8.17 (d, J = 8.9 Hz, 2H) |
| 7-[2-Methoxy-4-(thiophen-2-ylcarbonyloxy)phenyl]-8-(5-methylthiophen-2-ylcarbonyloxymethyl)-1,3,3-trimethyl-3,4-dihydro-1H-quinoxalin-2-one (Compound No. 14-54)<br>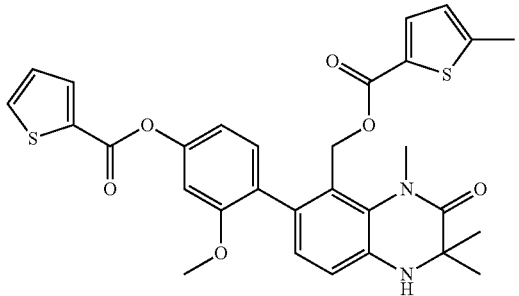 | ¹H-NMR (500 MHz, CDCl₃) δ 1.22 (s, 3H), 1.42 (s, 3H), 2.47 (s, 3H), 3.47 (s, 3H), 3.77 (s, 3H), 3.80 (s, 1H), 5.13 (d, J = 13.1 Hz, 1H), 5.30 (d, J = 13.1 Hz, 1H), 6.70 (d, J = 3.7 Hz, 1H), 6.77 (d, J = 7.9 Hz, 1H), 6.83 (d, J = 2.1 Hz, 1H), 6.86 (dd, J = 8.3, 2.1 Hz, 1H), 6.90 (d, J = 7.9 Hz, 1H) 7.20 (dd, J = 4.9, 3.7 Hz, 1H), 7.31 (d, J = 8.3 Hz, 1H), 7.45 (d, J = 3.7 Hz, 1H), 7.68 (dd, J = 4.9, 1.2 Hz, 1H), 8.00 (dd, J = 3.7, 1.2 Hz, 1H) |
| 7-(2-Methoxy-4-methoxycarbonyloxyphenyl)-8-(5-methylthiophen-2-ylcarbonyloxymethyl)-1,3,3-trimethyl-3,4-dihydro-1H-quinoxalin-2-one (Compound No. 14-55)<br>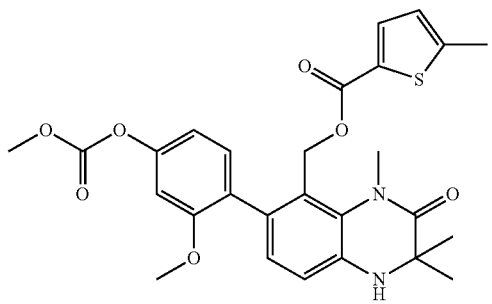 | ¹H-NMR (400 MHz, CDCl₃) δ 1.21 (s, 3H), 1.41 (s, 3H), 2.47 (s, 3H), 3.45 (s, 3H), 3.75 (s, 3H), 3.79 (s, 1H), 3.92 (s, 3H), 5.09 (d, J = 13.3 Hz, 1H), 5.28 (d, J = 13.3 Hz, 1H), 6.69 (d, J = 3.8 Hz, 1H), 6.75 (d, J = 8.1 Hz, 1H), 6.77 (d, J = 2.2 Hz, 1H), 6.82 (dd, J = 8.2, 2.2 Hz, 1H), 6.86 (d, J = 8.1 Hz, 1H), 7.27 (d, J = 8.2 Hz, 1H), 7.43 (d, J = 3.8 Hz, 1H) |
| 7-(2-Methoxy-4-phenoxycarbonyloxyphenyl)-8-(5-methylthiophen-2-ylcarbonyloxymethyl)-1,3,3-trimethyl-3,4-dihydro-1H-quinoxalin-2-one (Compound No. 14-56)<br>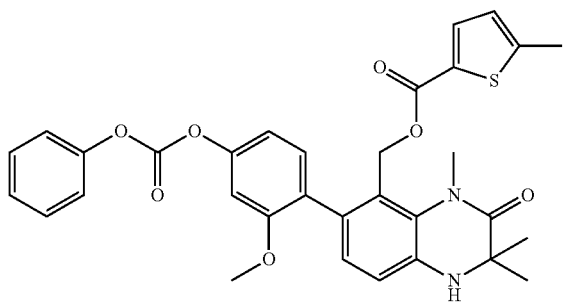 | ¹H-NMR (400 MHz, CDCl₃) δ 1.21 (s, 3H), 1.41 (s, 3H), 2.47 (s, 3H), 3.45 (s, 3H), 3.76 (s, 3H), 3.80 (s, 1H), 5.11 (d, J = 13.3 Hz, 1H), 5.29 (d, J = 13.3 Hz, 1H), 6.69 (d, J = 3.8 Hz, 1H), 6.76 (d, J = 8.1 Hz, 1H), 6.87 (d, J = 8.1 Hz, 1H), 6.89 (d, J = 2.2 Hz, 1H), 6.92 (dd, J = 8.2, 2.2 Hz, 1H), 7.27-7.31 (m, 4H), 7.40-7.45 (m, 3H) |

| | |
|---|---|
| 8-(5-Fluoro-2-methylphenoxymethyl)-7-[4-(furan-2-ylcarbonylamino)-2-methoxyphenyl]-1,3,3-trimethyl-3,4-dihydro-1H-quinoxalin-2-one (Compound No. 14-57)<br>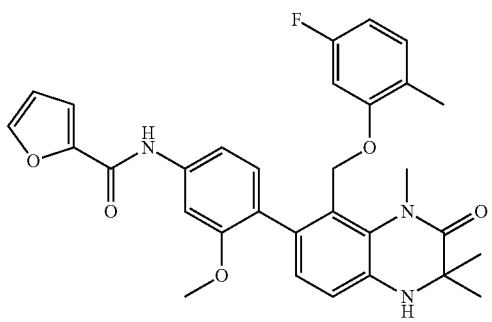 | ¹H-NMR (400 MHz, CDCl₃) δ 0.92 (s, 3H), 1.29 (s, 3H), 2.02 (s, 3H), 3.47 (s, 3H), 3.71 (s, 1H), 3.88 (s, 3H), 4.86 (d, J = 13.6 Hz, 1H), 5.24 (d, J = 13.6 Hz, 1H), 6.06 (dd, J = 11.2, 2.4 Hz, 1H), 6.38 (td, J = 8.3, 2.4 Hz, 1H), 6.59 (dd, J = 3.5, 1.8 Hz, 1H), 6.72 (d, J = 8.1 Hz, 1H), 6.87-6.91 (m, 1H), 6.90 (d, J = 8.1 Hz, 1H), 7.07 (dd, J = 8.3, 2.1 Hz, 1H), 7.27 (dd, J = 3.5, 0.9 Hz, 1H), 7.30 (d, J = 8.3 Hz, 1H), 7.55 (dd, J = 1.8, 0.9 Hz, 1H), 7.75 (d, J = 2.1 Hz, 1H), 8.17 (s, 1H) |
| 8-(5-Fluoro-2-methylphenoxymethyl)-7-[2-methoxy-4-(2-methylbenzoylamino)phenyl]-1,3,3-trimethyl-3,4-dihydro-1H-quinoxalin-2-one (Compound No. 14-58)<br>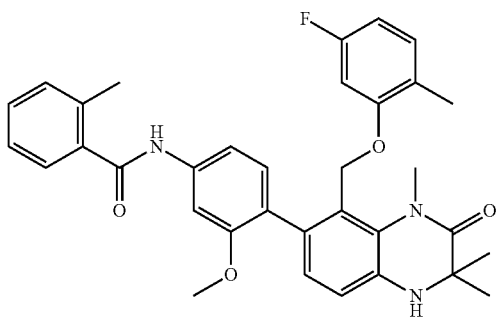 | ¹H-NMR (500 MHz, CDCl₃) δ 0.92 (s, 3H), 1.29 (s, 3H), 2.02 (s, 3H), 2.55 (s, 3H), 3.47 (s, 3H), 3.71 (s, 1H), 3.88 (s, 3H), 4.87 (d, J = 13.6 Hz, 1H), 5.24 (d, J = 13.6 Hz, 1H), 6.07 (dd, J = 11.2, 2.4 Hz, 1H), 6.39 (td, J = 8.2, 2.4 Hz, 1H), 6.72 (d, J = 7.9 Hz, 1H), 6.89-6.92 (m, 1H), 6.89 (d, J = 7.9 Hz, 1H), 7.02 (d, J = 7.3 Hz, 1H), 7.29 (t, J = 7.6 Hz, 1H), 7.30 (d, J = 7.6 Hz, 1H), 7.30 (d, J = 7.3 Hz, 1H), 7.38-7.41 (m, 1H), 7.52 (d, J = 7.6 Hz, 1H), 7.55 (s, 1H), 7.72 (s, 1H) |
| 7-[4-(2-Fluorobenzoylamino)-2-methoxyphenyl]-8-(5-fluoro-2-methylphenoxymethyl)-1,3,3-trimethyl-3,4-dihydro-1H-quinoxalin-2-one (Compound No. 14-59)<br>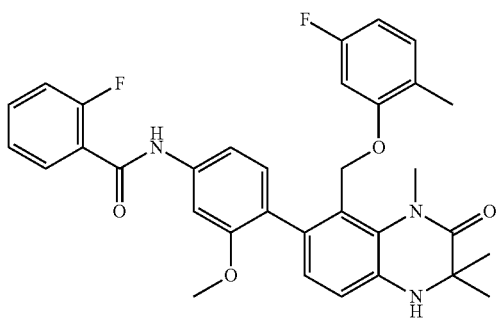 | ¹H-NMR (500 MHz, CDCl₃) δ 0.92 (s, 3H), 1.29 (s, 3H), 2.02 (s, 3H), 3.48 (s, 3H), 3.71 (s, 1H), 3.89 (s, 3H), 4.87 (d, J = 13.7 Hz, 1H), 5.24 (d, J = 13.7 Hz, 1H), 6.07 (dd, J = 11.0, 2.4 Hz, 1H), 6.39 (td, J = 8.2, 2.4 Hz, 1H), 6.72 (d, J = 7.9 Hz, 1H), 6.88-6.91 (m, 1H), 6.90 (d, J = 7.9 Hz, 1H), 7.10 (dd, J = 8.0, 2.1 Hz, 1H), 7.22 (dd, J = 11.9, 7.9 Hz, 1H), 7.31 (d, J = 8.0 Hz, 1H), 7.33-7.37 (m, 1H), 7.53-7.58 (m, 1H), 7.76 (d, J = 2.1 Hz, 1H), 8.19-8.22 (m, 1H), 8.55-8.58 (m, 1H) |

| | |
|---|---|
| 8-(5-Fluoro-2-methylphenoxymethyl)-7-[2-methoxy-4-(2-methoxybenzoylamino)phenyl]-1,3,3-trimethyl-3,4-dihydro-1H-quinoxalin-2-one (Compound No. 14-60) 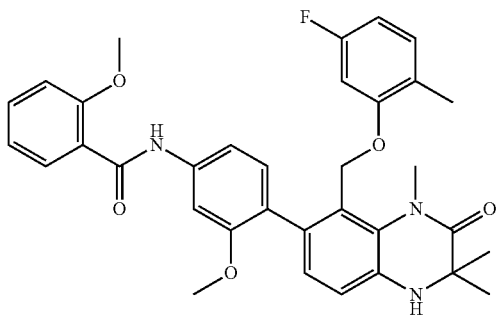 | $^1$H-NMR (500 MHz, CDCl$_3$) δ 0.89 (s, 3H), 1.30 (s, 3H), 2.02 (s, 3H), 3.48 (s, 3H), 3.70 (s, 1H), 3.90 (s, 3H), 4.10 (s, 3H), 4.89 (d, J = 13.7 Hz, 1H), 5.27 (d, J = 13.7 Hz, 1H), 6.06 (dd, J = 11.3, 2.4 Hz, 1H), 6.38 (td, J = 8.2, 2.4 Hz, 1H), 6.72 (d, J = 7.9 Hz, 1H), 6.88-6.90 (m, 1H), 6.91 (d, J = 7.9 Hz, 1H), 7.00 (dd, J = 8.0, 1.9 Hz, 1H), 7.07 (d, J = 7.9 Hz, 1H), 7.15-7.18 (m, 1H), 7.29 (d, J = 8.0 Hz, 1H), 7.53 (ddd, J = 8.6, 7.3, 1.7 Hz, 1H), 7.91 (d, J = 1.9 Hz, 1H), 8.31 (dd, J = 7.3, 1.7 Hz, 1H), 9.94 (s, 1H) |
| 8-(5-Fluoro-2-methylphenoxymethyl)-7-[2-methoxy-4-(2-trifluoromethylbenzoylamino)phenyl]-1,3,3-trimethyl-3,4-dihydro-1H-quinoxalin-2-one (Compound No. 14-61) 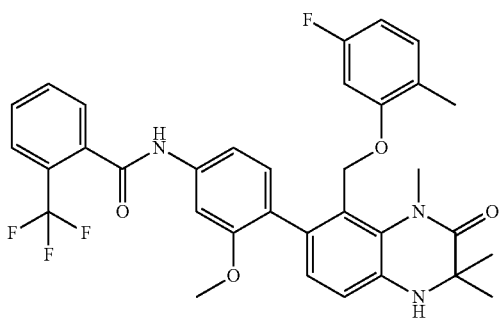 | $^1$H-NMR (500 MHz, CDCl$_3$) δ 0.92 (s, 3H), 1.29 (s, 3H), 2.02 (s, 3H), 3.47 (s, 3H), 3.71 (s, 1H), 3.88 (s, 3H), 4.88 (d, J = 13.4 Hz, 1H), 5.24 (d, J = 13.4 Hz, 1H), 6.07 (dd, J = 11.3, 2.4 Hz, 1H), 6.39 (td, J = 8.4, 2.4 Hz, 1H), 6.72 (d, J = 7.9 Hz, 1H), 6.88-6.91 (m, 1H), 6.89 (d, J = 7.9 Hz, 1H), 7.02 (dd, J = 8.0, 1.9 Hz, 1H), 7.30 (d, J = 8.0 Hz, 1H), 7.54 (s, 1H), 7.61-7.64 (m, 1H), 7.66 (d, J = 1.9 Hz, 1H), 7.68-7.71 (m, 2H), 7.79 (d, J = 7.6 Hz, 1H) |
| 8-(5-Fluoro-2-methylphenoxymethyl)-7-[2-methoxy-4-(2-nitrobenzoylamino)phenyl]-1,3,3-trimethyl-3,4-dihydro-1H-quinoxalin-2-one (Compound No. 14-62) 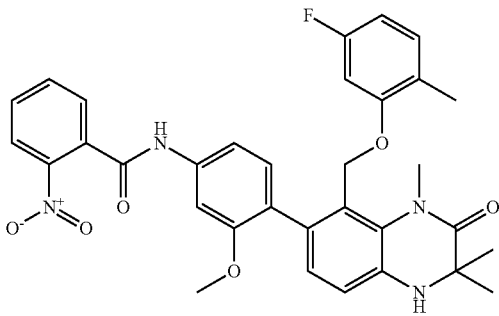 | $^1$H-NMR (400 MHz, CDCl$_3$) δ 0.93 (s, 3H), 1.29 (s, 3H), 2.03 (s, 3H), 3.48 (s, 3H), 3.73 (s, 1H), 3.88 (s, 3H), 4.88 (d, J = 13.7 Hz, 1H), 5.25 (d, J = 13.7 Hz, 1H), 6.08 (dd, J = 11.0, 2.3 Hz, 1H), 6.40 (td, J = 8.3, 2.3 Hz, 1H), 6.73 (d, J = 8.1 Hz, 1H), 6.89-6.93 (m, 1H), 6.90 (d, J = 8.1 Hz, 1H), 7.04 (dd, J = 8.1, 1.7 Hz, 1H), 7.31 (d, J = 8.1 Hz, 1H), 7.62 (s, 1H), 7.65-7.70 (m, 3H), 7.77 (t, J = 7.6 Hz, 1H), 8.17 (d, J = 8.0 Hz, 1H) |

Example 15

8-(5-Fluoro-2-methylphenoxymethyl)-7-[2-methoxy-4-(3-methoxycarbonylbenzoyloxy)phenyl]-1,3,3-trimethyl-3,4-dihydro-1H-quinoxalin-2-one (Compound No. 15-1)

A mixture of 8-(5-fluoro-2-methylphenoxymethyl)-7-(4-hydroxy-2-methoxyphenyl)-1,3,3-trimethyl-3,4-dihydro-1H-quinoxalin-2-one (Compound No. 11, 25.3 mg, 0.0562 mmol), monomethyl isophthalate (20.5 mg, 0.114 mmol), N,N-diisopropylethylamine (38.8 μL, 0.223 mmol) and O-(7-azabenzotriazol-1-yl)-N,N,N,N-tetramethyluronium hexafluorophosphate (43.4 mg, 0.114 mmol) was dissolved in anhydrous N,N-dimethylformamide (0.5 mL) and the reaction mixture was stirred at room temperature overnight. The mixture was diluted with ethyl acetate (15 mL). The mixture was washed with water (15 mL) and saturated brine (15 mL) successively, dried over anhydrous magnesium sulfate, and then the solvent was removed under reduced pressure. The obtained residue was purified by silica gel column chromatography (hexane-ethyl acetate) to give the titled compound (22.0 mg) as a colorless solid. (Yield 64%)

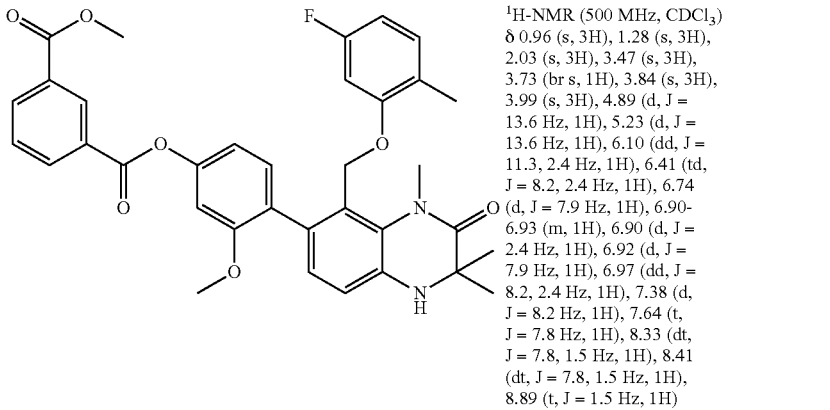

¹H-NMR (500 MHz, CDCl₃) δ 0.96 (s, 3H), 1.28 (s, 3H), 2.03 (s, 3H), 3.47 (s, 3H), 3.73 (br s, 1H), 3.84 (s, 3H), 3.99 (s, 3H), 4.89 (d, J = 13.6 Hz, 1H), 5.23 (d, J = 13.6 Hz, 1H), 6.10 (dd, J = 11.3, 2.4 Hz, 1H), 6.41 (td, J = 8.2, 2.4 Hz, 1H), 6.74 (d, J = 7.9 Hz, 1H), 6.90-6.93 (m, 1H), 6.90 (d, J = 2.4 Hz, 1H), 6.92 (d, J = 7.9 Hz, 1H), 6.97 (dd, J = 8.2, 2.4 Hz, 1H), 7.38 (d, J = 8.2 Hz, 1H), 7.64 (t, J = 7.8 Hz, 1H), 8.33 (dt, J = 7.8, 1.5 Hz, 1H), 8.41 (dt, J = 7.8, 1.5 Hz, 1H), 8.89 (t, J = 1.5 Hz, 1H)

Using any compounds among Compounds No. 8-2, 11, 13-2 and available compounds, the following Compounds (No. 15-2~15-32) were obtained by a method similar to that of Compound No. 15-1.

8-(5-Fluoro-2-methylphenoxymethyl)-7-[2-methoxy-4-(2-methylpyridin-3-ylcarbonyloxy)phenyl]-1,3,3-trimethyl-3,4-dihydro-1H-quinoxalin-2-one (Compound No. 15-2)

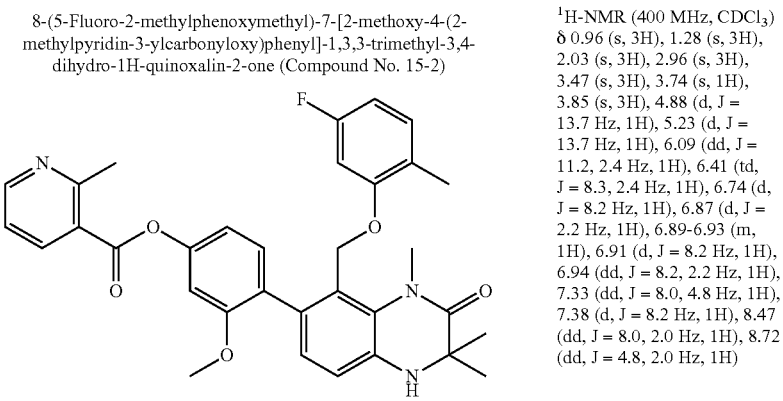

¹H-NMR (400 MHz, CDCl₃) δ 0.96 (s, 3H), 1.28 (s, 3H), 2.03 (s, 3H), 2.96 (s, 3H), 3.47 (s, 3H), 3.74 (s, 1H), 3.85 (s, 3H), 4.88 (d, J = 13.7 Hz, 1H), 5.23 (d, J = 13.7 Hz, 1H), 6.09 (dd, J = 11.2, 2.4 Hz, 1H), 6.41 (td, J = 8.3, 2.4 Hz, 1H), 6.74 (d, J = 8.2 Hz, 1H), 6.87 (d, J = 2.2 Hz, 1H), 6.89-6.93 (m, 1H), 6.91 (d, J = 8.2 Hz, 1H), 6.94 (dd, J = 8.2, 2.2 Hz, 1H), 7.33 (dd, J = 8.0, 4.8 Hz, 1H), 7.38 (d, J = 8.2 Hz, 1H), 8.47 (dd, J = 8.0, 2.0 Hz, 1H), 8.72 (dd, J = 4.8, 2.0 Hz, 1H)

8-(5-Fluoro-2-methylphenoxymethyl)-7-[2-methoxy-4-(3-methylfuran-2-ylcarbonyloxy)phenyl]-1,3,3-trimethyl-3,4-dihydro-1H-quinoxalin-2-one (Compound No. 15-3)

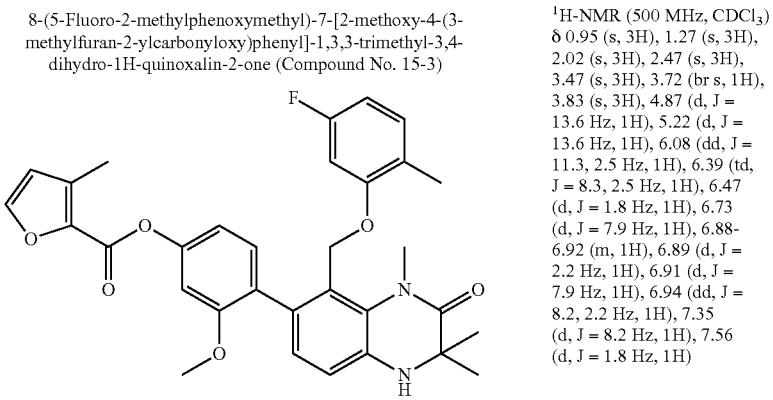

¹H-NMR (500 MHz, CDCl₃) δ 0.95 (s, 3H), 1.27 (s, 3H), 2.02 (s, 3H), 2.47 (s, 3H), 3.47 (s, 3H), 3.72 (br s, 1H), 3.83 (s, 3H), 4.87 (d, J = 13.6 Hz, 1H), 5.22 (d, J = 13.6 Hz, 1H), 6.08 (dd, J = 11.3, 2.5 Hz, 1H), 6.39 (td, J = 8.3, 2.5 Hz, 1H), 6.47 (d, J = 1.8 Hz, 1H), 6.73 (d, J = 7.9 Hz, 1H), 6.88-6.92 (m, 1H), 6.89 (d, J = 2.2 Hz, 1H), 6.91 (d, J = 7.9 Hz, 1H), 6.94 (dd, J = 8.2, 2.2 Hz, 1H), 7.35 (d, J = 8.2 Hz, 1H), 7.56 (d, J = 1.8 Hz, 1H)

| Compound | ¹H-NMR |
|---|---|
| 7-[4-(2-Acetoxybenzoyloxy)-2-methoxyphenyl]-8-(5-fluoro-2-methylphenoxymethyl)-1,3,3-trimethyl-3,4-dihydro-1H-quinoxalin-2-one (Compound No. 15-4)<br>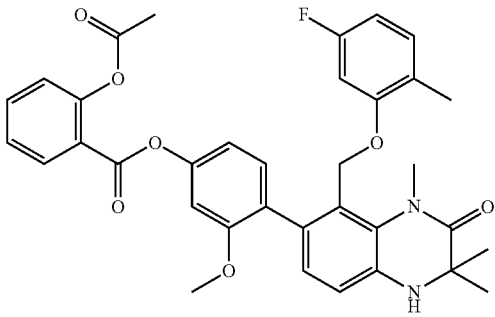 | ¹H-NMR (500 MHz, CDCl₃) δ 0.96 (s, 3H), 1.27 (s, 3H), 2.02 (s, 3H), 2.34 (s, 3H), 3.47 (s, 3H), 3.73 (br s, 1H), 3.83 (s, 3H), 4.87 (d, J = 13.4 Hz, 1H), 5.22 (d, J = 13.4 Hz, 1H), 6.08 (dd, J = 11.3, 2.5 Hz, 1H), 6.40 (td, J = 8.3, 2.5 Hz, 1H), 6.73 (d, J = 8.1 Hz, 1H), 6.83 (d, J = 2.4 Hz, 1H), 6.89-6.92 (m, 1H), 6.90 (dd, J = 7.6, 2.4 Hz, 1H), 6.91 (d, J = 8.1 Hz, 1H), 7.20 (d, J = 7.5 Hz, 1H), 7.35 (d, J = 7.6 Hz, 1H), 7.42 (t, J = 7.5 Hz, 1H), 7.67 (td, J = 7.5, 1.6 Hz, 1H), 8.26 (dd, J = 7.5, 1.6 Hz, 1H) |
| 8-(5-Fluoro-2-methylphenoxymethyl)-7-[2-methoxy-4-(thiazol-4-ylcarbonyloxy)phenyl]-1,3,3-trimethyl-3,4-dihydro-1H-quinoxalin-2-one (Compound No. 15-5)<br>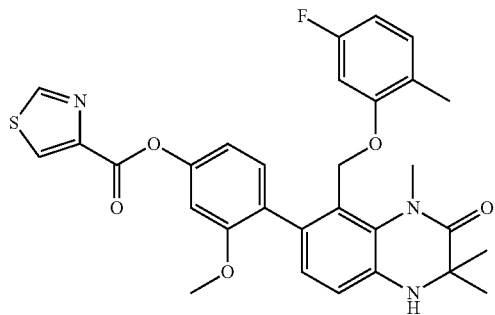 | ¹H-NMR (500 MHz, CDCl₃) δ 0.97 (s, 3H), 1.27 (s, 3H), 2.02 (s, 3H), 3.47 (s, 3H), 3.75 (br s, 1H), 3.83 (s, 3H), 4.87 (d, J = 13.4 Hz, 1H), 5.21 (d, J = 13.4 Hz, 1H), 6.09 (dd, J = 11.3, 2.4 Hz, 1H), 6.40 (td, J = 8.4, 2.4 Hz, 1H), 6.73 (d, J = 8.1 Hz, 1H), 6.89-6.92 (m, 1H), 6.92 (d, J = 8.1 Hz, 1H), 6.92 (d, J = 2.3 Hz, 1H), 6.98 (dd, J = 8.1, 2.3 Hz, 1H), 7.36 (d, J = 8.1 Hz, 1H), 8.48 (d, J = 2.0 Hz, 1H), 8.96 (d, J = 2.0 Hz, 1H) |
| 8-(5-Fluoro-2-methylphenoxymethyl)-7-[2-methoxy-4-(2-methylthiobenzoyloxy)phenyl]-1,3,3-trimethyl-3,4-dihydro-1H-quinoxalin-2-one (Compound No. 15-6)<br>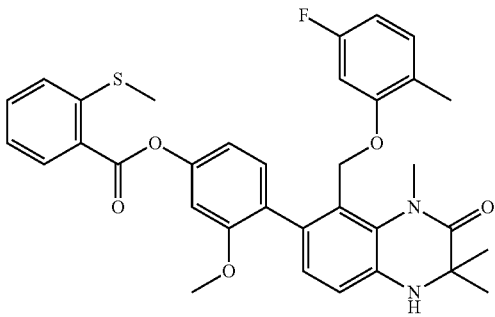 | ¹H-NMR (500 MHz, CDCl₃) δ 0.94 (s, 3H), 1.27 (s, 3H), 2.02 (s, 3H), 2.50 (s, 3H), 3.47 (s, 3H), 3.72 (br s, 1H), 3.84 (s, 3H), 4.89 (d, J = 13.4 Hz, 1H), 5.23 (d, J = 13.4 Hz, 1H), 6.08 (dd, J = 11.0, 2.4 Hz, 1H), 6.39 (td, J = 8.2, 2.4 Hz, 1H), 6.73 (d, J = 7.8 Hz, 1H), 6.89-6.92 (m, 1H), 6.90 (d, J = 2.4 Hz, 1H), 6.91 (d, J = 7.8 Hz, 1H), 6.96 (dd, J = 8.2, 2.4 Hz, 1H), 7.24-7.28 (m, 1H), 7.36 (d, J = 8.2 Hz, 1H), 7.36 (d, J = 7.9 Hz, 1H), 7.58 (t, J = 7.9 Hz, 1H), 8.28 (dd, J = 7.9, 1.7 Hz, 1H) |
| 8-(5-Fluoro-2-methylphenoxymethyl)-7-[2-methoxy-4-(5-methylfuran-2-ylcarbonyloxy)phenyl]-1,3,3-trimethyl-3,4-dihydro-1H-quinoxalin-2-one (Compound No. 15-7)<br>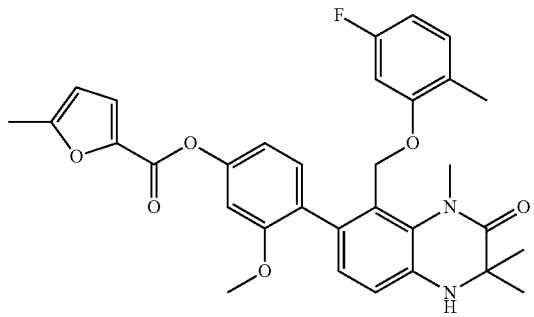 | ¹H-NMR (400 MHz, CDCl₃) δ 0.95 (s, 3H), 1.27 (s, 3H), 2.02 (s, 3H), 2.46 (s, 3H), 3.46 (s, 3H), 3.72 (br s, 1H), 3.82 (s, 3H), 4.87 (d, J = 13.7 Hz, 1H), 5.21 (d, J = 13.7 Hz, 1H), 6.08 (dd, J = 11.2, 2.4 Hz, 1H), 6.23 (d, J = 3.4 Hz, 1H), 6.40 (td, J = 8.3, 2.4 Hz, 1H), 6.73 (d, J = 8.0 Hz, 1H), 6.88 (t, J = 2.7 Hz, 1H), 6.88-6.92 (m, 1H), 6.91 (d, J = 8.0 Hz, 1H), 6.93 (dd, J = 8.3, 2.7 Hz, 1H), 7.33 (d, J = 3.4 Hz, 1H), 7.34 (d, J = 8.3 Hz, 1H) |

8-(5-Fluoro-2-methylphenoxymethyl)-7-[2-methoxy-4-(thiazol-5-ylcarbonyloxy)phenyl]-1,3,3-trimethyl-3,4-dihydro-1H-quinoxalin-2-one (Compound No. 15-8)

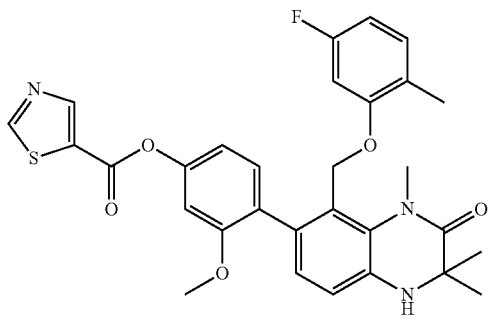

$^1$H-NMR (500 MHz, CDCl$_3$) δ 0.97 (s, 3H), 1.28 (s, 3H), 2.02 (s, 3H), 3.47 (s, 3H), 3.74 (br s, 1H), 3.84 (s, 3H), 4.86 (d, J = 13.4 Hz, 1H), 5.21 (d, J = 13.4 Hz, 1H), 6.08 (dd, J = 11.0, 2.5 Hz, 1H), 6.40 (td, J = 8.4, 2.5 Hz, 1H), 6.73 (d, J = 7.9 Hz, 1H), 6.89 (d, J = 2.1 Hz, 1H), 6.90-6.92 (m, 1H), 6.91 (d, J = 7.9 Hz, 1H), 6.95 (dd, J = 8.2, 2.1 Hz, 1H), 7.37 (d, J = 8.2 Hz, 1H), 8.72 (d, J = 0.6 Hz, 1H), 9.07 (d, J = 0.6 Hz, 1H)

8-(5-Fluoro-2-methylphenoxymethyl)-7-[2-methoxy-4-(6-methylpyridin-3-ylcarbonyloxy)phenyl]-1,3,3-trimethyl-3,4-dihydro-1H-quinoxalin-2-one (Compound No. 15-9)

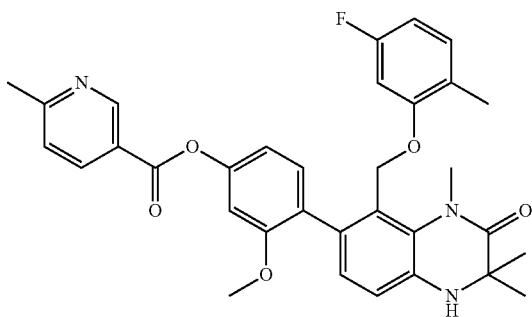

$^1$H-NMR (400 MHz, CDCl$_3$) δ 0.96 (s, 3H), 1.28 (s, 3H), 2.02 (s, 3H), 2.69 (s, 3H), 3.47 (s, 3H), 3.78 (s, 1H), 3.83 (s, 3H), 4.88 (d, J = 13.4 Hz, 1H), 5.23 (d, J = 13.4 Hz, 1H), 6.09 (dd, J = 11.2, 2.4 Hz, 1H), 6.40 (td, J = 8.3, 2.4 Hz, 1H), 6.74 (d, J = 8.0 Hz, 1H), 6.89 (d, J = 2.3 Hz, 1H), 6.89-6.93 (m, 1H), 6.92 (d, J = 8.0 Hz, 1H), 6.95 (dd, J = 8.2, 2.3 Hz, 1H), 7.34 (d, J = 8.1 Hz, 1H), 7.37 (d, J = 8.2 Hz, 1H), 8.35 (dd, J = 8.1, 1.9 Hz, 1H), 9.30 (d, J = 1.9 Hz, 1H)

8-(5-Fluoro-2-methylphenoxymethyl)-7-[2-methoxy-4-(pyrimidin-5-ylcarbonyloxy)phenyl]-1,3,3-trimethyl-3,4-dihydro-1H-quinoxalin-2-one (Compound No. 15-10)

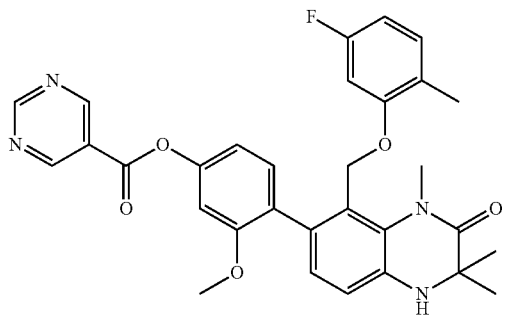

$^1$H-NMR (400 MHz, CDCl$_3$) δ 0.97 (s, 3H), 1.28 (s, 3H), 2.03 (s, 3H), 3.47 (s, 3H), 3.75 (s, 1H), 3.85 (s, 3H), 4.87 (d, J = 13.4 Hz, 1H), 5.21 (d, J = 13.4 Hz, 1H), 6.09 (dd, J = 11.2, 2.4 Hz, 1H), 6.41 (td, J = 8.3, 2.4 Hz, 1H), 6.74 (d, J = 8.1 Hz, 1H), 6.89 (d, J = 2.2 Hz, 1H), 6.90-6.93 (m, 1H), 6.91 (d, J = 8.1 Hz, 1H), 6.96 (dd, J = 8.3, 2.2 Hz, 1H), 7.39 (d, J = 8.3 Hz, 1H), 9.47 (s, 1H), 9.48 (s, 2H)

8-(5-Fluoro-2-methylphenoxymethyl)-7-[2-methoxy-4-(oxazol-4-ylcarbonyloxy)phenyl]-1,3,3-trimethyl-3,4-dihydro-1H-quinoxalin-2-one (Compound No. 15-11)

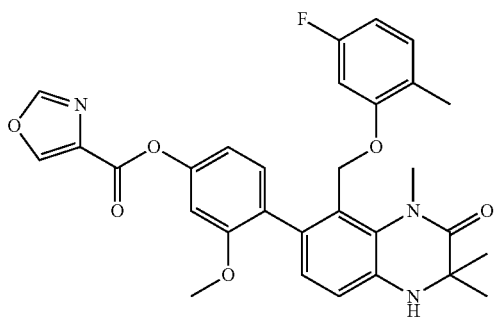

$^1$H-NMR (400 MHZ, CDCl$_3$) δ 0.96 (s, 3H), 1.27 (s, 3H), 2.02 (s, 3H), 3.47 (s, 3H), 3.74 (s, 1H), 3.82 (s, 3H), 4.86 (d, J = 13.5 Hz, 1H), 5.21 (d, J = 13.5 Hz, 1H), 6.08 (dd, J = 11.3, 2.4 Hz, 1H), 6.40 (td, J = 8.4, 2.4 Hz, 1H), 6.73 (d, J = 8.1 Hz, 1H), 6.89 (d, J = 2.2 Hz, 1H), 6.89-6.92 (m, 1H), 6.91 (d, J = 8.1 Hz, 1H), 6.95 (dd, J = 8.2, 2.2 Hz, 1H), 7.35 (d, J = 8.2 Hz, 1H), 8.04 (d, J = 1.0 Hz, 1H), 8.48 (d, J = 1.0 Hz, 1H)

| | |
|---|---|
| 7-[4-(4-Acetylbenzoyloxy)-2-methoxyphenyl]-8-(5-fluoro-2-methylphenoxymethyl)-1,3,3-trimethyl-3,4-dihydro-1H-quinoxalin-2-one (Compound No. 15-12)<br>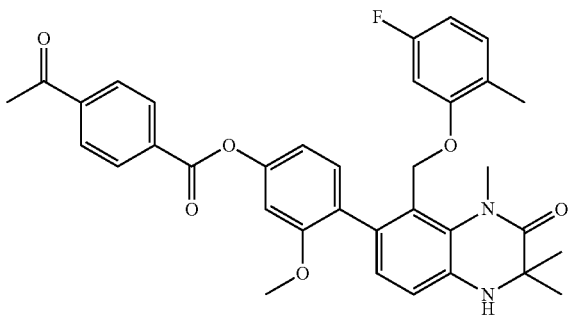 | $^1$H-NMR (500 MHz, CDCl$_3$) δ 0.96 (s, 3H), 1.28 (s, 3H), 2.03 (s, 3H), 2.69 (s, 3H), 3.47 (s, 3H), 3.84 (s, 3H), 4.88 (d, J = 13.6 Hz, 1H), 5.23 (d, J = 13.6 Hz, 1H), 6.09 (dd, J = 11.0, 2.4 Hz, 1H), 6.40 (td, J = 8.4, 2.4 Hz, 1H), 6.74 (d, J = 7.9 Hz, 1H), 6.90 (d, J = 2.3 Hz, 1H), 6.90-6.93 (m, 1H), 6.92 (d, J = 7.9 Hz, 1H), 6.96 (dd, J = 8.2, 2.3 Hz, 1H), 7.37 (d, J = 8.2 Hz, 1H), 8.10 (d, J = 8.2 Hz, 2H), 8.32 (d, J = 8.2 Hz, 2H) |
| 7-[4-(3-Acetylbenzoyloxy)-2-methoxyphenyl]-8-(5-fluoro-2-methylphenoxymethyl)-1,3,3-trimethyl-3,4-dihydro-1H-quinoxalin-2-one (Compound No. 15-13)<br>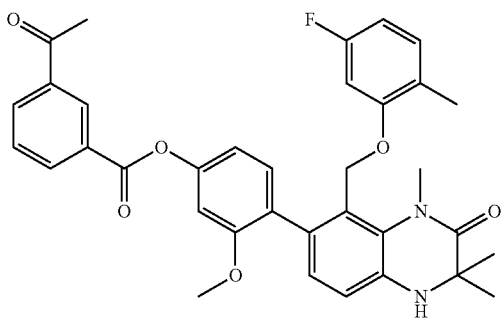 [SMILES: COC(=O)c1cccc(C(=O)Oc2ccc(-c3ccc4c(c3COc3cc(F)ccc3C)N(C)C(=O)C(C)(C)N4)c(OC)c2)c1] | $^1$H-NMR (500 MHz, CDCl$_3$) δ 0.96 (s, 3H), 1.28 (s, 3H), 2.03 (s, 3H), 2.67 (s, 1H), 2.71 (s, 3H), 3.47 (s, 3H), 3.85 (s, 3H), 4.89 (d, J = 13.5 Hz, 1H), 5.23 (d, J = 13.5 Hz, 1H), 6.09 (d, J = 11.5, 2.4 Hz, 1H), 6.41 (td, J = 8.3, 2.4 Hz, 1H), 6.74 (d, J = 7.9 Hz, 1H), 6.90 (d, J = 2.1 Hz, 1H), 6.90-6.93 (m, 1H), 6.93 (d, J = 7.9 Hz, 1H), 6.97 (dd, J = 8.1, 2.1 Hz, 1H), 7.37 (d, J = 8.1 Hz, 1H), 7.67 (t, J = 7.8 Hz, 1H), 8.26 (d, J = 7.8 Hz, 1H), 8.43 (d, J = 7.8 Hz, 1H), 8.78 (s, 1H) |
| 8-(5-Fluoro-2-methylphenoxymethyl)-7-[2-methoxy-4-(4-methylpyridin-3-ylcarbonyloxy)phenyl]-1,3,3-trimethyl-3,4-dihydro-1H-quinoxalin-2-one (Compound No. 15-14)<br>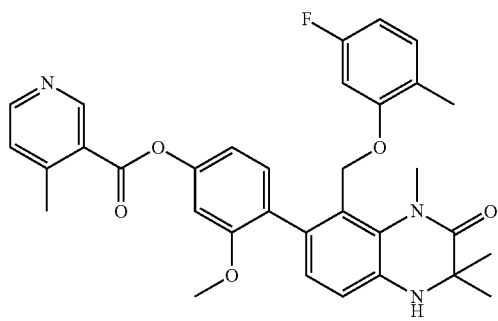 | $^1$H-NMR (500 MHz, CDCl$_3$) δ 0.95 (s, 3H), 1.28 (s, 3H), 2.03 (s, 3H), 2.73 (s, 3H), 3.47 (s, 3H), 3.76 (s, 1H), 3.85 (s, 3H), 4.89 (d, J = 13.4 Hz, 1H), 5.23 (d, J = 13.4 Hz, 1H), 6.09 (dd, J = 11.3, 2.4 Hz, 1H), 6.40 (td, J = 8.3, 2.4 Hz, 1H), 6.73 (d, J = 7.9 Hz, 1H), 6.89 (d, J = 2.2 Hz, 1H), 6.91 (d, J = 7.9 Hz, 1H), 6.66-6.92 (m, 1H), 6.95 (dd, J = 8.2, 2.2 Hz, 1H), 7.28 (d, J = 5.2 Hz, 1H), 7.38 (d, J = 8.2 Hz, 1H), 8.66 (d, J = 5.2 Hz, 1H), 9.35 (s, 1H) |
| 7-[4-(5-Bromofuran-2-ylcarbonyloxy)-2-methoxyphenyl]-8-(5-fluoro-2-methylphenoxymethyl)-1,3,3-trimethyl-3,4-dihydro-1H-quinoxalin-2-one (Compound No. 15-15)<br>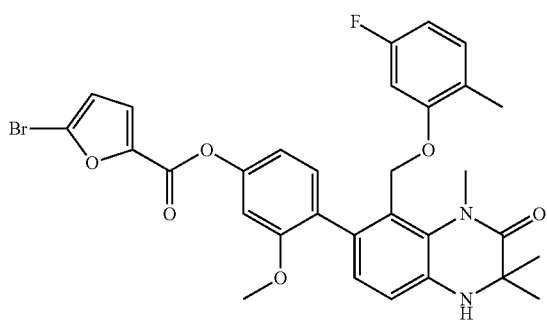 | $^1$H-NMR (400 MHz, CDCl$_3$) δ 0.96 (s, 3H), 1.27 (s, 3H), 2.02 (s, 3H), 3.46 (s, 3H), 3.73 (s, 1H), 3.83 (s, 3H), 4.86 (d, J = 13.7 Hz, 1H), 5.20 (d, J = 13.7 Hz, 1H), 6.07 (dd, J = 11.2, 2.4 Hz, 1H), 6.40 (td, J = 8.3, 2.4 Hz, 1H), 6.57 (d, J = 3.7 Hz, 1H), 6.73 (d, J = 8.1 Hz, 1H), 6.87 (d, J = 2.2 Hz, 1H), 6.88-6.92 (m, 1H), 6.90 (d, J = 8.1 Hz, 1H), 6.93 (dd, J = 8.3, 2.2 Hz, 1H), 7.35 (d, J = 8.3 Hz, 1H), 7.36 (d, J = 3.7 Hz, 1H) |

| | |
|---|---|
| 7-[4-(5-Chlorothiophen-2-ylcarbonyloxy)-2-methoxyphenyl]-8-(5-fluoro-2-methylphenoxymethyl)-1,3,3-trimethyl-3,4-dihydro-1H-quinoxalin-2-one (Compound No. 15-16)<br />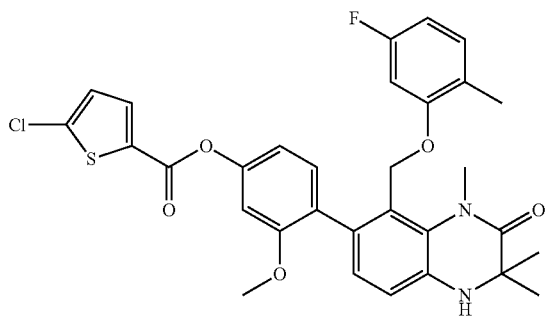 | ¹H-NMR (400 MHz, CDCl₃) δ 0.95 (s, 3H), 1.28 (s, 3H), 2.02 (s, 3H), 3.47 (s, 3H), 3.83 (s, 3H), 4.86 (d, J = 13.5 Hz, 1H), 5.21 (d, J = 13.5 Hz, 1H), 6.08 (dd, J = 11.2, 2.4 Hz, 1H), 6.40 (td, J = 8.3, 2.4 Hz, 1H), 6.73 (d, J = 8.1 Hz, 1H), 6.87 (d, J = 2.2 Hz, 1H), 6.88-6.93 (m, 1H), 6.90 (d, J = 8.1 Hz, 1H), 6.92 (dd, J = 8.2, 2.2 Hz, 1H), 7.04 (d, J = 4.2 Hz, 1H), 7.35 (d, J = 8.2 Hz, 1H), 7.80 (d, J = 4.2 Hz, 1H) |
| 7-[4-(3-Chlorothiophen-2-ylcarbonyloxy)-2-methoxyphenyl]-8-(5-fluoro-2-methylphenoxymethyl)-1,3,3-trimethyl-3,4-dihydro-1H-quinoxalin-2-one (Compound No. 15-17)<br />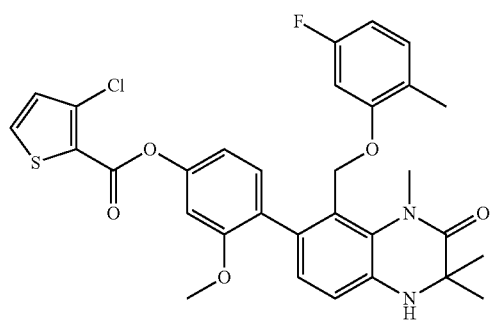 | ¹H-NMR (400 MHz, CDCl₃) δ 0.95 (s, 3H), 1.28 (s, 3H), 2.02 (s, 3H), 3.47 (s, 3H), 3.84 (s, 3H), 4.86 (d, J = 13.7 Hz, 1H), 5.22 (d, J = 13.7 Hz, 1H), 6.08 (dd, J = 11.1, 2.4 Hz, 1H), 6.40 (td, J = 8.3, 2.4 Hz, 1H), 6.73 (d, J = 8.1 Hz, 1H), 6.88-6.92 (m, 3H), 6.96 (dd, J = 8.2, 2.2 Hz, 1H), 7.12 (d, J = 5.3 Hz, 1H), 7.36 (d, J = 8.2 Hz, 1H), 7.61 (d, J = 5.3 Hz, 1H) |
| 8-(5-Fluoro-2-methylphenoxymethyl)-7-[2-methoxy-4-(5-methylthiophen-2-ylcarbonyloxy)phenyl]-1,3,3-trimethyl-3,4-dihydro-1H-quinoxalin-2-one (Compound No. 15-18)<br />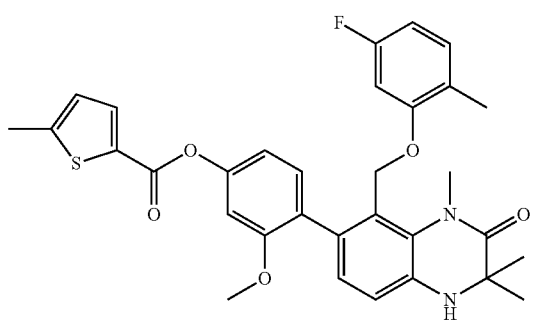 | ¹H-NMR (400 MHz, CDCl₃) δ 0.94 (s, 3H), 1.27 (s, 3H), 2.02 (s, 3H), 2.59 (s, 3H), 3.47 (s, 3H), 3.72 (s, 1H), 3.83 (s, 3H), 4.87 (d, J = 13.6 Hz, 1H), 5.22 (d, J = 13.6 Hz, 1H), 6.08 (dd, J = 11.2, 2.4 Hz, 1H), 6.39 (td, J = 8.4, 2.4 Hz, 1H), 6.72 (d, J = 8.1 Hz, 1H), 6.86-6.92 (m, 4H), 6.93 (dd, J = 8.4, 2.6 Hz, 1H), 7.34 (d, J = 8.4 Hz, 1H), 7.82 (d, J = 3.9 Hz, 1.1H) |
| 7-[4-(3-Chloro-4-methylthiophen-2-ylcarbonyloxy)-2-methoxyphenyl]-8-(5-fluoro-2-methylphenoxymethyl)-1,3,3-trimethyl-3,4-dihydro-1H-quinoxalin-2-one (Compound No. 15-19)<br />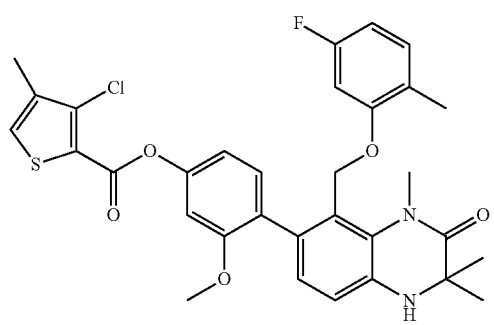 | ¹H-NMR (400 MHz, CDCl₃) δ 0.94 (s, 3H), 1.28 (s, 3H), 2.02 (s, 3H), 2.30 (s, 3H), 3.47 (s, 3H), 3.73 (s, 1H), 3.84 (s, 3H), 4.87 (d, J = 13.7 Hz, 1H), 5.22 (d, J = 13.7 Hz, 1H), 6.07 (dd, J = 11.0, 2.4 Hz, 1H), 6.40 (td, J = 8.3, 2.4 Hz, 1H), 6.73 (d, J = 8.1 Hz, 1H), 6.88-6.92 (m, 1H), 6.90 (d, J = 8.1 Hz, 1H), 6.91 (d, J = 2.2 Hz, 1H), 6.95 (dd, J = 8.3, 2.2 Hz, 1H), 7.33 (s, 1H), 7.35 (d, J = 8.3 Hz, 1H) |

| | |
|---|---|
| 7-[4-(2-Chloropyridin-4-ylcarbonyloxy)-2-methoxyphenyl]-8-(5-fluoro-2-methylphenoxymethyl)-1,3,3-trimethyl-3,4-dihydro-1H-quinoxalin-2-one (Compound No. 15-20) 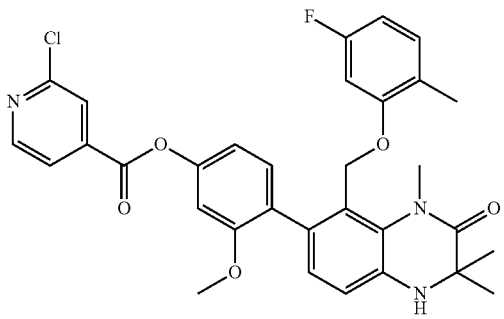 | $^1$H-NMR (400 MHz, CDCl$_3$) δ 0.97 (s, 3H), 1.28 (s, 3H), 2.02 (s, 3H), 3.47 (s, 3H), 3.75 (s, 1H), 3.84 (s, 3H), 4.86 (d, J = 13.6 Hz, 1H), 5.21 (d, J = 13.6 Hz, 1H), 6.08 (dd, J = 11.2, 2.4 Hz, 1H), 6.41 (td, J = 8.3, 2.4 Hz, 1H), 6.74 (d, J = 8.1 Hz, 1H), 6.87 (d, J = 2.2 Hz, 1H), 6.90-6.93 (m, 1H), 6.91 (d, J = 8.1 Hz, 1H), 6.94 (dd, J = 8.3, 2.2 Hz, 1H), 7.38 (d, J = 8.3 Hz, 1H), 7.96 (dd, J = 5.1, 1.3 Hz, 1H), 8.08 (dd, J = 1.3, 0.7 Hz, 1H), 8.65 (dd, J = 5.1, 0.7 Hz, 1H) |
| 7-[4-(6-Chloropyridin-3-ylcarbonyloxy)-2-methoxyphenyl]-8-(5-fluoro-2-methylphenoxymethyl)-1,3,3-trimethyl-3,4-dihydro-1H-quinoxalin-2-one (Compound No. 15-21) 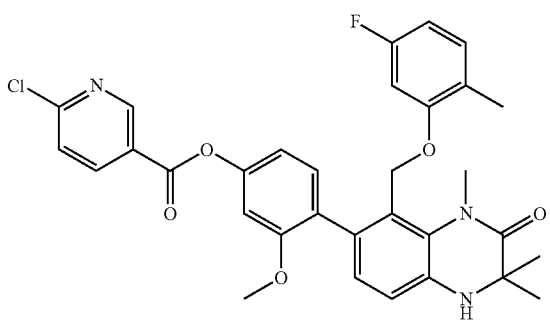 | $^1$H-NMR (500 MHz, CDCl$_3$) δ 0.97 (s, 3H), 1.28 (s, 3H), 2.02 (s, 3H), 3.47 (s, 3H), 3.74 (s, 1H), 3.84 (s, 3H), 4.87 (d, J = 13.4 Hz, 1H), 5.22 (d, J = 13.4 Hz, 1H), 6.09 (dd, J = 11.3, 2.4 Hz, 1H), 6.41 (td, J = 8.4, 2.4, 1H), 6.74 (d, J = 7.7 Hz, 1H), 6.88 (d, J = 2.1 Hz, 1H), 6.90-6.93 (m, 1H), 6.91 (d, J = 7.7 Hz, 1H), 6.94 (dd, J = 8.2, 2.1 Hz, 1H), 7.38 (d, J = 8.2 Hz, 1H), 7.52 (dd, J = 8.3, 0.6 Hz, 1H), 8.42 (dd, J = 8.3, 2.4 Hz, 1H), 9.20 (dd, J = 2.4, 0.6 Hz, 1H) |
| 8-(5-Fluoro-2-methylphenoxymethyl)-7-[2-methoxy-4-(2-methoxypyridin-3-ylcarbonyloxy)phenyl]-1,3,3-trimethyl-3,4-dihydro-1H-quinoxalin-2-one (Compound No. 15-22) 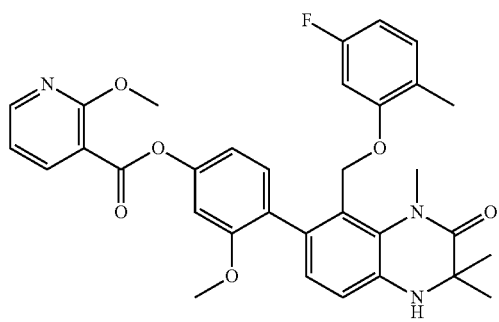 | $^1$H-NMR (500 MHz, CDCl$_3$) δ 0.95 (s, 3H), 1.27 (s, 3H), 2.02 (s, 3H), 3.47 (s, 3H), 3.72 (s, 1H), 3.80 (s, 3H), 4.11 (s, 3H), 4.88 (d, J = 13.6 Hz, 1H), 5.22 (d, J = 13.6 Hz, 1H), 5.22 (d, J = 13.6 Hz, 1H), 6.08 (dd, J = 11.3, 2.4 Hz, 1H), 6.40 (td, J = 8.4, 2.4 Hz, 1H), 6.73 (d, J = 8.1 Hz, 1H), 6.89-6.92 (m, 1H), 6.90 (d, J = 2.1 Hz, 1H), 6.91 (d, J = 8.1 Hz, 1H), 6.94 (dd, J = 8.2, 2.1 Hz, 1H), 7.04 (dd, J = 7.6, 5.0 Hz, 1H), 7.36 (d, J = 8.2 Hz, 1H), 8.40 (dd, J = 7.6, 2.1 Hz, 1H), 8.41 (dd, J = 5.0, 2.1 Hz, 1H) |

| Compound | ¹H-NMR |
|---|---|
| 8-(5-Fluoro-2-methylphenoxymethyl)-7-[2-methoxy-4-(2-methylthiobenzoylamino)phenyl]-1,3,3-trimethyl-3,4-dihydro-1H-quinoxalin-2-one (Compound No. 15-23)<br>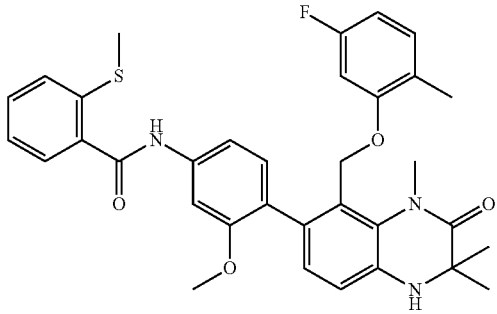 | ¹H-NMR (500 MHz, CDCl₃) δ 0.91 (s, 3H), 1.29 (s, 3H), 2.02 (s, 3H), 2.53 (s, 3H), 3.48 (s, 3H), 3.71 (s, 1H), 3.89 (s, 3H), 4.88 (d, J = 13.8 Hz, 1H), 5.25 (d, J = 13.8 Hz, 1H), 6.07 (dd, J = 11.2, 2.5 Hz, 1H), 6.39 (td, J = 8.3, 2.5, 1H), 6.72 (d, J = 7.9 Hz, 1H), 6.88-6.91 (m, 1H), 6.90 (d, J = 7.9 Hz, 1H), 7.05 (dd, J = 8.0, 2.1 Hz, 1H), 7.26-7.32 (m, 1H), 7.30 (d, J = 8.0 Hz, 1H), 7.42 (dd, J = 8.0, 1.4 Hz, 1H), 7.46 (td, J = 7.3, 1.4 Hz, 1H), 7.76-7.78 (m, 2H), 8.45 (s, 1H) |
| 7-[2-Methoxy-4-(2-methylthiobenzoyloxy)phenyl]-8-(5-methylthiophen-2-ylcarbonyloxymethyl)-1,3,3-trimethyl-3,4-dihydro-1H-quinoxalin-2-one (Compound No. 15-24)<br>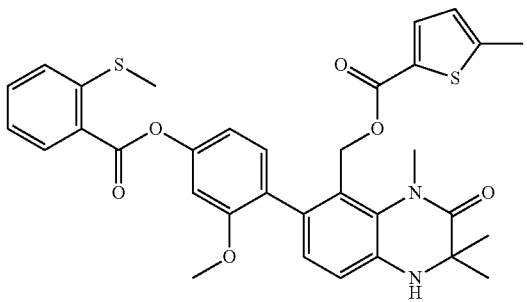 | ¹H-NMR (500 MHz, CDCl₃) δ 1.21 (s, 3H), 1.42 (s, 3H), 2.47 (s, 3H), 2.49 (s, 3H), 3.46 (s, 3H), 3.74 (s, 1H), 3.77 (s, 3H), 5.13 (d, J = 13.4 Hz, 1H), 5.31 (d, J = 13.4 Hz, 1H), 6.70 (d, J = 3.8 Hz, 1H), 6.77 (d, J = 7.9 Hz, 1H), 6.84 (d, J = 2.2 Hz, 1H), 6.87 (dd, J = 8.1, 2.2 Hz, 1H), 6.90 (d, J = 7.9 Hz, 1H), 7.23-7.27 (m, 1H), 7.32 (d, J = 8.1 Hz, 1H), 7.35 (d, J = 7.9 Hz, 1H), 7.45 (d, J = 3.8 Hz, 1H), 8.33 (t, J = 7.9 Hz, 1H), 8.26 (d, J = 7.9 Hz, 1H) |
| 7-[2-Methoxy-4-(3-methoxycarbonylbenzoyloxy)phenyl]-8-(5-methylthiophen-2-ylcarbonyloxymethyl)-1,3,3-trimethyl-3,4-dihydro-1H-quinoxalin-2-one (Compound No. 15-25)<br>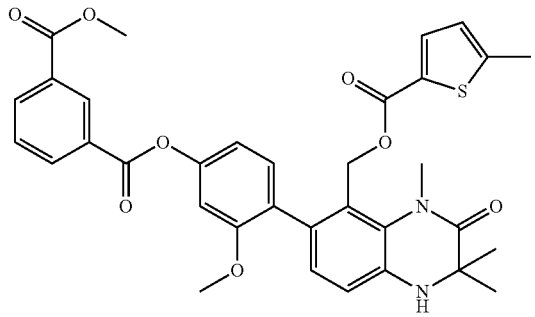 | ¹H-NMR (500 MHz, CDCl₃) δ 1.22 (s, 3H), 1.42 (s, 3H), 2.47 (s, 3H), 3.46 (s, 3H), 3.77 (s, 3H), 3.96 (s, 1H), 3.99 (s, 3H), 5.14 (d, J = 12.8 Hz, 1H), 5.31 (d, J = 12.8 Hz, 1H), 6.70 (d, J = 3.7 Hz, 1H), 6.78 (d, J = 7.9 Hz, 1H), 6.84 (d, J = 2.1 Hz, 1H), 6.88 (dd, J = 8.3, 2.1 Hz, 1H), 6.91 (d, J = 7.9 Hz, 1H), 7.33 (d, J = 8.3 Hz, 1H), 7.46 (d, J = 3.7 Hz, 1H), 7.63 (t, J = 7.8 Hz, 1H), 8.33 (d, J = 7.8 Hz, 1H), 8.40 (d, J = 7.8 Hz, 1H), 8.87 (s, 1H) |
| 7-[2-Methoxy-4-(3-methylfuran-2-ylcarbonyloxy)phenyl]-8-(5-methylthiophen-2-ylcarbonyloxymethyl)-1,3,3-trimethyl-3,4-dihydro-1H-quinoxalin-2-one (Compound No. 15-26)<br>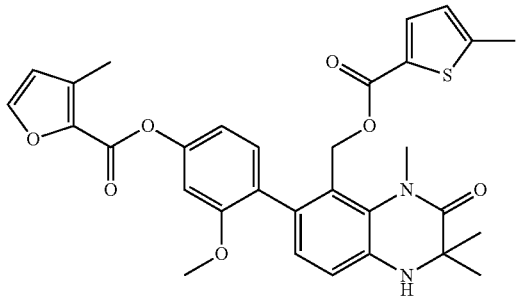 | ¹H-NMR (400 MHz, CDCl₃) δ 1.21 (s, 3H), 1.42 (s, 3H), 2.46 (s, 3H), 2.47 (s, 3H), 3.45 (s, 3H), 3.76 (s, 3H), 3.79 (s, 1H), 5.12 (d, J = 13.3 Hz, 1H), 5.30 (d, J = 13.3 Hz, 1H), 6.46 (d, J = 1.6 Hz, 1H), 6.69 (d, J = 3.7 Hz, 1H), 6.76 (d, J = 8.1 Hz, 1H), 6.82 (d, J = 2.2 Hz, 1H), 6.86 (dd, J = 8.3, 2.2 Hz, 1H), 6.90 (d, J = 8.1 Hz, 1H), 7.31 (d, J = 8.3 Hz, 1H), 7.44 (d, J = 3.7 Hz, 1H), 7.56 (d, J = 1.6 Hz, 1H) |

| | |
|---|---|
| 7-[2-Methoxy-4-(thiazol-4-ylcarbonyloxy)phenyl]-8-(5-methylthiophen-2-ylcarbonyloxymethyl)-1,3,3-trimethyl-3,4-dihydro-1H-quinoxalin-2-one (Compound No. 15-27)<br />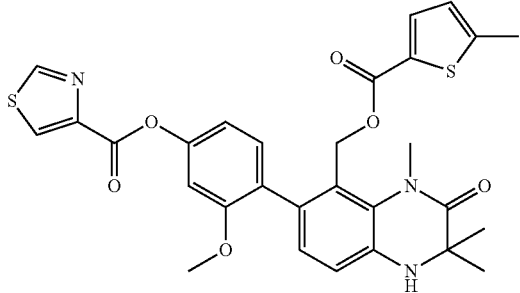 | $^1$H-NMR (400 MHz, CDCl$_3$) δ 1.22 (s, 3H), 1.42 (s, 3H), 2.47 (s, 3H), 3.46 (s, 3H), 3.76 (s, 3H), 3.80 (s, 1H), 5.11 (d, J = 13.4 Hz, 1H), 5.30 (d, J = 13.4 Hz, 1H), 6.70 (d, J = 3.6 Hz, 1H), 6.77 (d, J = 8.1 Hz, 1H), 6.86 (d, J = 1.8 Hz, 1H), 6.90 (dd, J = 8.1, 1.8 Hz, 1H), 6.90 (d, J = 8.1 Hz, 1H), 7.32 (d, J = 8.1 Hz, 1H), 7.45 (d, J = 3.6 Hz, 1H), 8.46 (d, J = 2.0 Hz, 1H), 8.95 (d, J = 2.0 Hz, 1H) |
| 7-[2-Methoxy-4-(thiazol-5-ylcarbonyloxy)phenyl]-8-(5-methylthiophen-2-ylcarbonyloxymethyl)-1,3,3-trimethyl-3,4-dihydro-1H-quinoxalin-2-one (Compound No. 15-28)<br />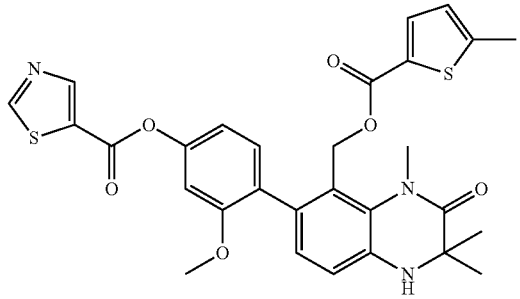 | $^1$H-NMR (400 MHz, CDCl$_3$) δ 1.22 (s, 3H), 1.42 (s, 3H), 2.48 (s, 3H), 3.46 (s, 3H), 3.77 (s, 3H), 3.81 (s, 1H), 5.15 (d, J = 13.2 Hz, 1H), 5.30 (d, J = 13.2 Hz, 1H), 6.71 (d, J = 3.8 Hz, 1H), 6.77 (d, J = 7.9 Hz, 1H), 6.82 (d, J = 2.2 Hz, 1H), 6.87 (dd, J = 8.3, 2.2 Hz, 1H), 6.90 (d, J = 7.9 Hz, 1H), 7.33 (d, J = 8.3 Hz, 1H), 7.45 (d, J = 3.8 Hz, 1H), 8.71 (d, J = 0.6 Hz, 1H), 9.06 (d, J = 0.6 Hz, 1H) |
| 7-[2-Methoxy-4-(2-methylpyridin-3-ylcarbonyloxy)phenyl]-8-(5-methylthiophen-2-ylcarbonyloxymethyl)-1,3,3-trimethyl-3,4-dihydro-1H-quinoxalin-2-one (Compound No. 15-29)<br />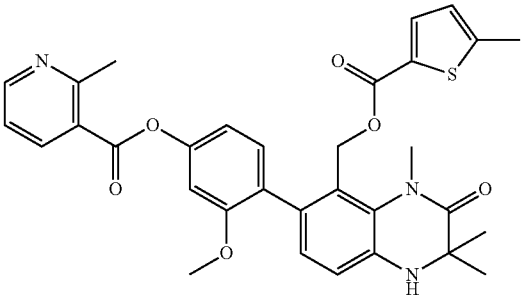 | $^1$H-NMR (500 MHz, CDCl$_3$) δ 1.22 (s, 3H), 1.42 (s, 3H), 2.47 (s, 3H), 2.94 (s, 3H), 3.46 (s, 3H), 3.77 (s, 3H), 3.80 (s, 1H), 5.14 (d, J = 13.4 Hz, 1H), 5.30 (d, J = 13.4 Hz, 1H), 6.70 (d, J = 3.8 Hz, 1H), 6.77 (d, J = 8.1 Hz, 1H), 6.81 (d, J = 2.1 Hz, 1H), 6.85 (dd, J = 8.3, 2.1 Hz, 1H), 6.90 (d, J = 8.1 Hz, 1H), 7.31-7.33 (m, 1H), 7.34 (d, J = 8.3 Hz, 1H), 7.45 (d, J = 3.8 Hz, 1H), 8.45 (dd, J = 1.9, 1.8 Hz, 1H), 8.71 (dd, J = 4.9, 1.8 Hz, 1H) |
| 7-[4-(3-Acetylbenzoyloxy)-2-methoxyphenyl]-8-(5-methylthiophen-2-ylcarbonyloxymethyl)-1,3,3-trimethyl-3,4-dihydro-1H-quinoxalin-2-one (Compound No. 15-30)<br />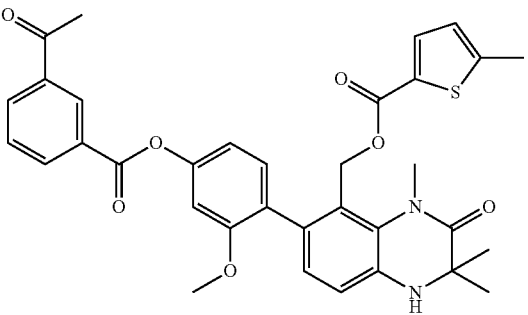 | $^1$H-NMR (500 MHz, CDCl$_3$) δ 1.22 (s, 3H), 1.42 (s, 3H), 2.47 (s, 3H), 2.71 (s, 3H), 3.47 (s, 3H), 3.78 (s, 3H), 5.14 (d, J = 13.1 Hz, 1H), 5.31 (d, J = 13.1 Hz, 1H), 6.70 (d, J = 3.7 Hz, 1H), 6.78 (d, J = 7.9 Hz, 1H), 6.84 (d, J = 2.1 Hz, 1H), 6.88 (dd, J = 8.1, 2.1 Hz, 1H), 6.91 (d, J = 7.9 Hz, 1H) 7.34 (d, J = 8.1 Hz, 1H), 7.46 (d, J = 3.7 Hz, 1H), 7.65 (t, J = 7.8 Hz, 1H), 8.25 (dt, J = 7.8, 1.6 Hz, 1H), 8.41 (dt, J = 7.8, 1.6 Hz, 1H), 8.77 (t, J = 1.6 Hz, 1H) |

| | |
|---|---|
| 7-(4-tert-Butoxycarbonylaminoacetylamino-2-methoxyphenyl)-8-(5-fluoro-2-methylphenoxymethyl)-1,3,3-trimethyl-3,4-dihydro-1H-quinoxalin-2-one (Compound No. 15-31)<br/>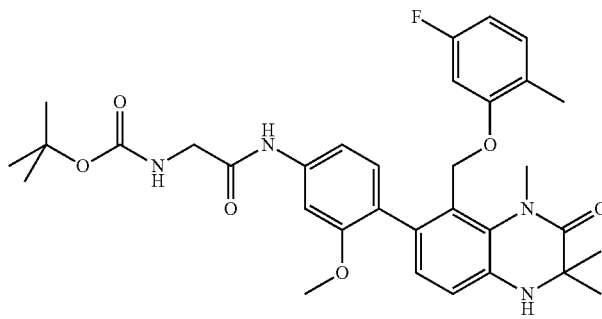 | ¹H-NMR (400 MHz, CDCl₃) δ 0.91 (s, 3H), 1.28 (s, 3H), 1.50 (s, 9H), 2.01 (s, 3H), 3.46 (s, 3H), 3.70 (s, 1H), 3.84 (s, 3H), 3.95 (d, J = 6.1 Hz, 2H), 4.83 (d, J = 13.8 Hz, 1H), 5.20 (br s, 1H), 5.21 (d, J = 13.8 Hz, 1H), 6.04 (dd, J = 11.2, 2.4 Hz, 1H), 6.38 (td, J = 8.3, 2.4 Hz, 1H), 6.71 (d, J = 8.1 Hz, 1H), 6.87 (d, J = 8.1 Hz, 1H), 6.87-6.91 (m, 1H), 6.97 (dd, J = 7.5, 1.9 Hz, 1H), 7.25 (d, J = 7.5 Hz, 1H), 7.54 (d, J = 1.9 Hz, 1H), 8.22 (br s, 1H) |
| 7-[4-(3-Chlorothiophen-2-ylcarbonyloxy)-2-methoxyphenyl]-8-(5-methylthiophen-2-ylcarbonyloxymethyl)-1,3,3-trimethyl-3,4-dihydro-1H-quinoxalin-2-one (Compound No. 15-32)<br/>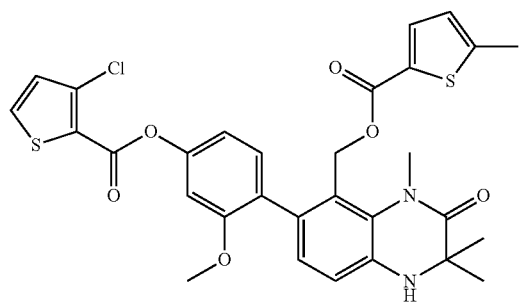 | ¹H-NMR (500 MHz, CDCl₃) δ 1.21 (s, 3H), 1.42 (s, 3H), 2.47 (s, 3H), 3.46 (s, 3H), 3.77 (s, 3H), 3.78 (br s, 1H), 5.12 (d, J = 13.4 Hz, 1H), 5.30 (d, J = 13.4 Hz, 1H), 6.70 (d, J = 3.9 Hz, 1H), 6.77 (d, J = 7.9 Hz, 1H), 6.85 (dd, J = 9.2, 2.8 Hz, 1H), 6.88 (t, J = 2.8 Hz, 1H), 6.89 (d, J = 7.9 Hz, 1H), 7.11 (d, J = 5.2 Hz, 1H), 7.31 (d, J = 9.2 Hz, 1H), 7.44 (d, J = 3.9 Hz, 1H), 7.60 (d, J = 5.2 Hz, 1H) |

Example 16

8-(5-Fluoro-2-methylphenoxymethyl)-7-[2-methoxy-4-[N-methyl-N-(pyridin-4-ylcarbonyl)amino]phenyl]-1,3,3-trimethyl-3,4-dihydro-1H-quinoxalin-2-one (Compound No. 16-1)

A mixture of 8-(5-fluoro-2-methylphenoxymethyl)-7-[2-methoxy-4-(pyridin-4-ylcarbonylamino)phenyl]-1,3,3-trimethyl-3,4-dihydro-1H-quinoxalin-2-one (Compound No. 14-21, 13.9 mg, 0.0251 mmol), cessium carbonate (41.7 mg, 0.128 mmol), and methyl iodide (4.7 μL, 0.075 mmol) was suspended in anhydrous N,N-dimethylformamide (0.5 ml) and stirred for 3 hours at room temperature. The mixture was diluted with ethyl acetate (10 mL). The mixture was washed with water (10 mL) and saturated brine (10 mL) successively, dried over anhydrous magnesium sulfate, and then the solvent was removed under reduced pressure. The obtained residue was purified by silica gel column chromatography (hexane-ethyl acetate) to give the titled compound (4.6 mg) as a yellow amorphous product. (Yield 32%)

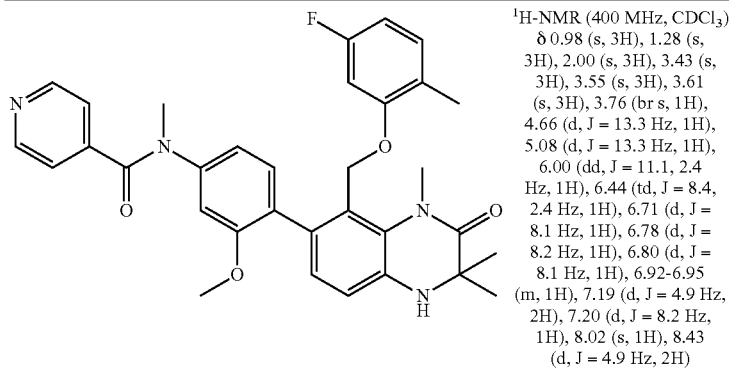

¹H-NMR (400 MHz, CDCl₃) δ 0.98 (s, 3H), 1.28 (s, 3H), 2.00 (s, 3H), 3.43 (s, 3H), 3.55 (s, 3H), 3.61 (s, 3H), 3.76 (br s, 1H), 4.66 (d, J = 13.3 Hz, 1H), 5.08 (d, J = 13.3 Hz, 1H), 6.00 (dd, J = 11.1, 2.4 Hz, 1H), 6.44 (td, J = 8.4, 2.4 Hz, 1H), 6.71 (d, J = 8.1 Hz, 1H), 6.78 (d, J = 8.2 Hz, 1H), 6.80 (d, J = 8.1 Hz, 1H), 6.92-6.95 (m, 1H), 7.19 (d, J = 4.9 Hz, 2H), 7.20 (d, J = 8.2 Hz, 1H), 8.02 (s, 1H), 8.43 (d, J = 4.9 Hz, 2H)

Using any compounds among Compounds No. 14-17~14-20 and available compounds, the following Compounds (No. 16-2~16-5) were obtained by a method similar to that of Compound No. 16-1.

7-[4-(N-Benzoyl-N-methylamino)-2-methoxyphenyl]-8-(5-fluoro-2-methylphenoxymethyl)-1,3,3-trimethyl-3,4-dihydro-1H-quinoxalin-2-one (Compound No. 16-2)

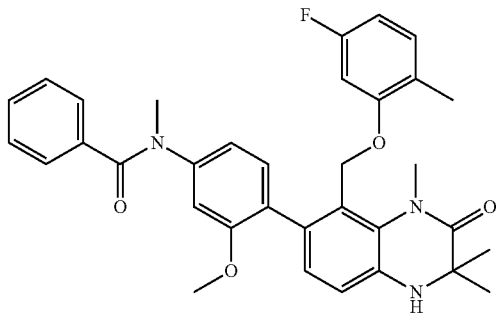

$^1$H-NMR (400 MHz, DMSO-d$_6$) δ 0.83 (s, 3H), 1.09 (s, 3H), 1.90 (s, 3H), 3.26 (s, 3H), 3.45 (s, 3H), 3.58 (s, 3H), 4.64 (d, J = 13.3 Hz, 1H), 5.06 (d, J = 13.3 Hz, 1H), 6.03 (dd, J = 11.5, 2.4 Hz, 1H), 6.14 (s, 1H), 6.54 (td, J = 8.4, 2.4 Hz, 1H), 6.74 (d, J = 8.1 Hz, 1H), 6.78 (d, J = 8.1 Hz, 1H), 6.83 (dd, J = 7.8, 2.0 Hz, 1H), 6.87 (d, J = 2.0 Hz, 1H), 7.01-7.04 (m, 1H), 7.10 (d, J = 7.8 Hz, 1H), 7.11 (t, J = 7.2 Hz, 2H), 7.18 (t, J = 7.2 Hz, 1H), 7.28 (d, J = 7.2 Hz, 2H)

7-[4-(N-Acetyl-N-methylamino)-2-methoxyphenyl]-8-(5-fluoro-2-methylphenoxymethyl)-1,3,3-trimethyl-3,4-dihydro-1H-quinoxalin-2-one (Compound No. 16-3)

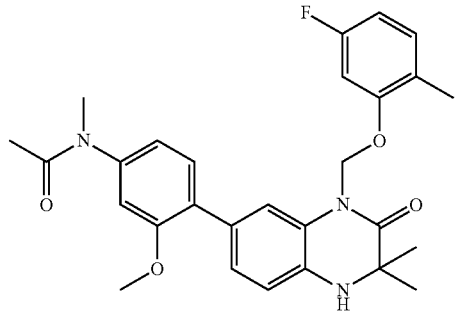

$^1$H-NMR (400 MHz, CDCl$_3$) δ 1.01 (s, 3H), 1.29 (s, 3H), 1.89 (s, 3H), 2.01 (s, 3H), 3.31 (s, 3H), 3.48 (s, 3H), 3.78 (br s, 1H), 3.82 (s, 3H), 4.80 (d, J = 13.2 Hz, 1H), 5.17 (d, J = 13.2 Hz, 1H), 6.06 (dd, J = 11.1, 2.5 Hz, 1H), 6.40 (td, J = 8.3, 2.5 Hz, 1H), 6.75 (d, J = 8.1 Hz, 1H), 6.77 (s, 1H), 6.86 (dd, J = 8.0, 1.8 Hz, 1H), 6.89 (d, J = 8.1 Hz, 1H), 6.89-6.93 (m, 1H), 7.32 (d, J = 8.0 Hz, 1H)

8-(5-Fluoro-2-methylphenoxymethyl)-7-[2-methoxy-4-[N-methyl-N-(pyridin-2-ylcarbonyl)amino]phenyl]-1,3,3-trimethyl-3,4-dihydro-1H-quinoxalin-2-one (Compound No. 16-4)

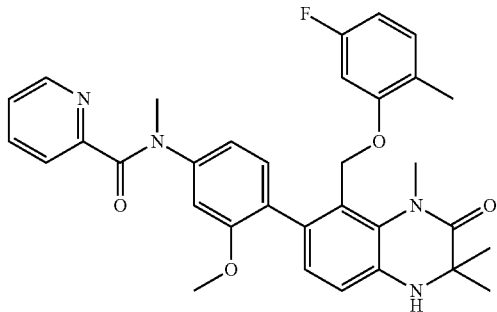

$^1$H-NMR (400 MHz, CDCl$_3$) δ 0.99 (s, 3H), 1.30 (s, 3H), 2.00 (s, 3H), 3.40 (s, 3H), 3.59 (s, 3H), 3.62 (s, 3H), 3.77 (br s, 1H), 4.62 (d, J = 13.1 Hz, 1H), 5.05 (d, J = 13.1 Hz, 1H), 5.97 (d, J = 11.0 Hz, 1H), 6.45 (t, J = 8.3 Hz, 1H), 6.62 (br s, 1H), 6.71 (d, J = 8.1 Hz, 1H), 6.79 (br s, 1H), 6.82 (d, J = 8.1 Hz, 1H), 6.93-6.96 (m, 1H), 7.11 (br s, 1H), 7.15 (d, J = 7.8 Hz, 1H), 7.46 (br s, 1H), 7.54 (br s, 1H), 8.27 (br s, 1H)

| | |
|---|---|
| 8-(5-Fluoro-2-methylphenoxy-methyl)-7-[2-methoxy-4-[N-methyl-N-(pyridin-3-ylcarbonyl)amino]phenyl]-1,3,3-trimethyl-3,4-dihydro-1H-quinoxalin-2-one (Compound No. 16-5)<br />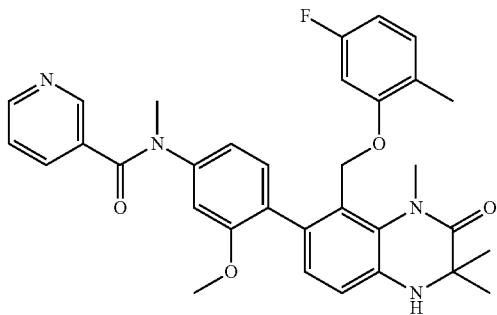 | $^1$H-NMR (400 MHz, CDCl$_3$) δ 1.01 (s, 3H), 1.30 (s, 3H), 2.00 (s, 3H), 3.40 (s, 3H), 3.57 (s, 3H), 3.61 (s, 3H), 3.76 (br s, 1H), 4.65 (d, J = 13.1 Hz, 1H), 5.05 (d, J = 13.1 Hz, 1H), 6.01 (dd, J = 11.2, 2.4 Hz, 1H), 6.45 (td, J = 8.3, 2.4 Hz, 1H), 6.57 (d, J = 1.9 Hz, 1H), 6.71 (d, J = 7.9 Hz, 1H), 6.78 (dd, J = 8.0, 1.9 Hz, 1H), 6.81 (d, J = 7.9 Hz, 1H), 6.92-6.96 (m, 1H), 7.02 (dd, J = 7.8, 4.9 Hz, 1H), 7.20 (d, J = 8.0 Hz, 1H), 7.59 (dt, J = 7.8, 1.9 Hz, 1H), 8.45 (dd, J = 4.9, 1.9 Hz, 1H), 8.62 (d, J = 1.9 Hz, 1H) |

Example 17

7-[4-(3-Chlorophenylaminocarbonyloxy)-2-methoxyphenyl]-8-(5-fluoro-2-methylphenoxymethyl)-1,3,3-trimethyl-3,4-dihydro-1H-quinoxalin-2-one (Compound No. 17-1)

8-(5-Fluoro-2-methylphenoxymethyl)-7-(4-hydroxy-2-methoxyphenyl)-1,3,3-trimethyl-3,4-dihydro-1H-quinoxalin-2-one (Compound No. 11, 20.3 mg, 0.0451 mmol) was dissolved in anhydrous dichloromethane (0.5 mL), then triethylamine (13.6 μL, 0.0977 mmol) and 3-chlorophenyl isocyanate (6 μL, 0.05 mmol) were added to the mixture successively. After the reaction mixture was stirred for 1 hour at room temperature, the mixture was purified by silica gel column chromatography (hexane-ethyl acetate) to give the titled compound (22.4 mg) as a colorless solid. (Yield 82%)

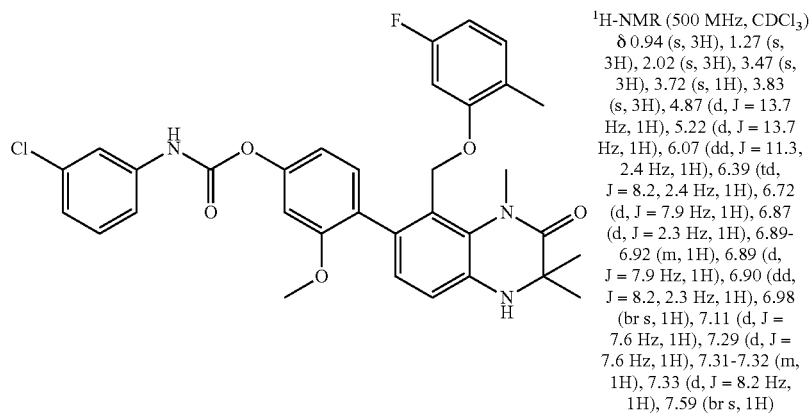

$^1$H-NMR (500 MHz, CDCl$_3$) δ 0.94 (s, 3H), 1.27 (s, 3H), 2.02 (s, 3H), 3.47 (s, 3H), 3.72 (s, 1H), 3.83 (s, 3H), 4.87 (d, J = 13.7 Hz, 1H), 5.22 (d, J = 13.7 Hz, 1H), 6.07 (dd, J = 11.3, 2.4 Hz, 1H), 6.39 (td, J = 8.2, 2.4 Hz, 1H), 6.72 (d, J = 7.9 Hz, 1H), 6.87 (d, J = 2.3 Hz, 1H), 6.89-6.92 (m, 1H), 6.89 (d, J = 7.9 Hz, 1H), 6.90 (dd, J = 8.2, 2.3 Hz, 1H), 6.98 (br s, 1H), 7.11 (d, J = 7.6 Hz, 1H), 7.29 (d, J = 7.6 Hz, 1H), 7.31-7.32 (m, 1H), 7.33 (d, J = 8.2 Hz, 1H), 7.59 (br s, 1H)

Using any compounds among Compounds No. 8-2, 11, 13-2, and available compounds, the following Compounds (No. 17-2~17-17) were obtained by a method similar to that of Compound No. 17-1.

8-(5-Fluoro-2-methylphenoxymethyl)-7-(2-methoxy-4-phenylaminocarbonyloxyphenyl)-1,3,3-trimethyl-3,4-dihydro-1H-quinoxalin-2-one (Compound No. 17-2)

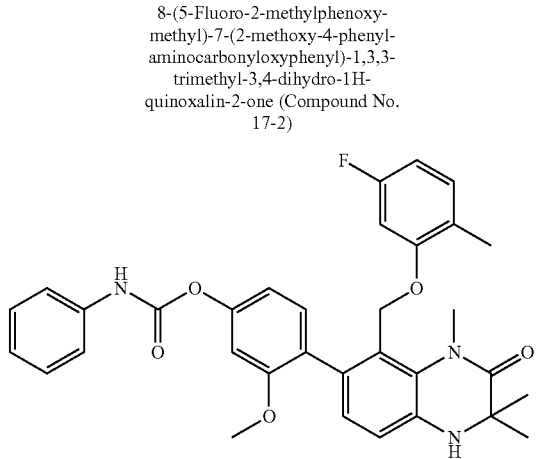 [SMILES: COc1cc(OC(=O)Nc2ccccc2)ccc1-c1ccc2c(c1COc1cc(F)ccc1C)N(C)C(=O)C(C)(C)N2]

$^1$H-NMR (400 MHz, CDCl$_3$)
δ 0.93 (s, 3H), 1.27 (s, 3H), 2.02 (s, 3H), 3.47 (s, 3H), 3.72 (s, 1H), 3.83 (s, 3H), 4.87 (d, J = 13.7 Hz, 1H), 5.22 (d, J = 13.7 Hz, 1H), 6.07 (dd, J = 11.2, 2.4 Hz, 1H), 6.39 (td, J = 8.3, 2.4 Hz, 1H), 6.72 (d, J = 8.0 Hz, 1H), 6.88 (d, J = 2.3 Hz, 1H), 6.89 (d, J = 8.0 Hz, 1H), 6.91 (dd, J = 8.2, 2.3 Hz, 1H), 7.00 (br s, 1H), 7.12-7.15 (m, 1H), 7.31-7.56 (m, 6H)

8-(5-Fluoro-2-methylphenoxymethyl)-7-(2-methoxy-4-propylaminocarbonyloxyphenyl)-1,3,3-trimethyl-3,4-dihydro-1H-quinoxalin-2-one (Compound No. 17-3)

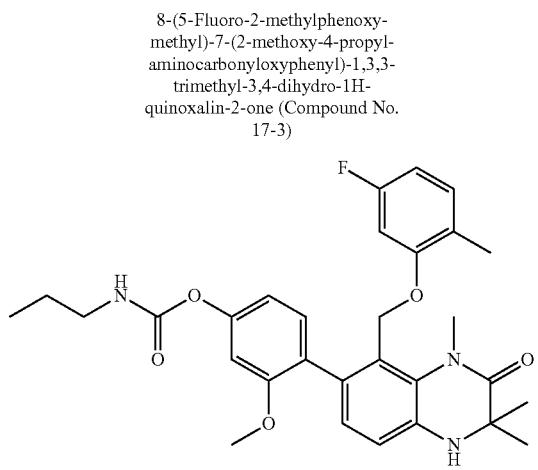 [SMILES: CCCNC(=O)Oc1ccc(-c2ccc3c(c2COc2cc(F)ccc2C)N(C)C(=O)C(C)(C)N3)c(OC)c1]

$^1$H-NMR (500 MHz, CDCl$_3$)
δ 0.92 (s, 3H), 1.00 (t, J = 7.5 Hz, 3H), 1.26 (s, 3H), 1.59-1.67 (m, 2H), 2.01 (s, 3H), 3.25-3.29 (m, 2H), 3.46 (s, 3H), 3.71 (s, 1H), 3.81 (s, 3H), 4.86 (d, J = 13.7 Hz, 1H), 5.07 (t, J = 6.1 Hz, 1H), 5.21 (d, J = 13.7 Hz, 1H) 6.05 (dd, J = 11.2, 2.3 Hz, 1H), 6.38 (td, J = 8.3, 2.3 Hz, 1H), 6.71 (d, J = 8.1 Hz, 1H), 6.82 (d, J = 2.2 Hz, 1H), 6.84 (dd, J = 8.0, 2.2 Hz, 1H), 6.87-6.91 (m, 1H), 6.88 (d, J = 8.1 Hz, 1H), 7.28 (d, J = 8.0 Hz, 1H)

8-(5-Fluoro-2-methylphenoxymethyl)-7-(4-isopropylaminocarbonyloxy-2-methoxyphenyl)-1,3,3-trimethyl-3,4-dihydro-1H-quinoxalin-2-one (Compound No. 17-4)

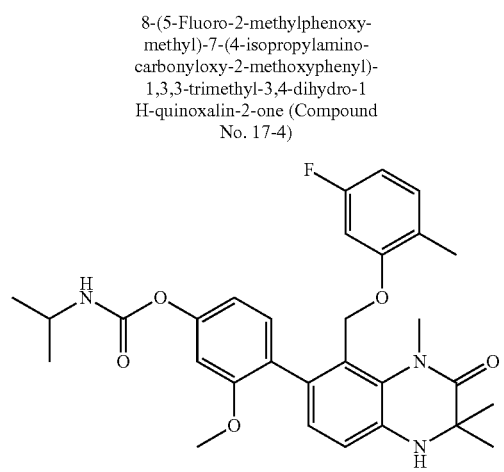 [SMILES: COc1cc(OC(=O)NC(C)C)ccc1-c1ccc2c(c1COc1cc(F)ccc1C)N(C)C(=O)C(C)(C)N2]

$^1$H-NMR (400 MHz, CDCl$_3$)
δ 0.91 (s, 3H), 1.26-1.27 (m, 6H), 1.26 (s, 3H), 2.01 (s, 3H), 3.46 (s, 3H), 3.71 (s, 1H), 3.82 (s, 3H), 3.88-3.97 (m, 1H), 4.86 (d, J = 13.7 Hz, 1H), 4.88-4.90 (m, 1H), 5.22 (d, J = 13.7 Hz, 1H), 6.05 (dd, J = 11.2, 2.4 Hz, 1H), 6.38 (td, J = 8.3, 2.4 Hz, 1H), 6.71 (d, J = 8.1 Hz, 1H), 6.82 (d, J = 2.1 Hz, 1H), 6.84 (dd, J = 8.3, 2.1 Hz, 1H), 6.87-6.91 (m, 1H), 6.88 (d, J = 8.1 Hz, 1H), 7.28 (d, J = 8.3 Hz, 1H)

| | |
|---|---|
| 8-(5-Fluoro-2-methylphenoxy-methyl)-7-[2-methoxy-4-(pyridin-3-ylaminocarbonyloxy)phenyl]-1,3,3-trimethyl-3,4-dihydro-1H-quinoxalin-2-one (Compound No. 17-5)<br>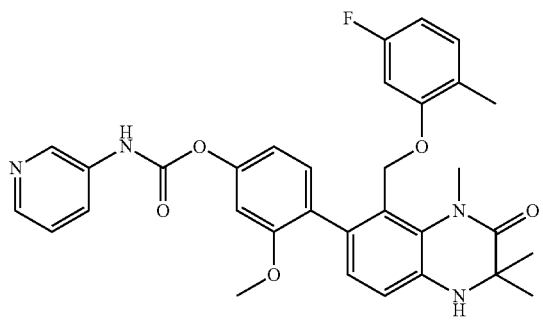 | $^1$H-NMR (500 MHz, CDCl$_3$) δ 0.95 (s, 3H), 1.27 (s, 3H), 2.02 (s, 3H), 3.47 (s, 3H), 3.72 (s, 1H), 3.83 (s, 3H), 4.86 (d, J = 133 (s, 3H), 4.86 (d, J = 13.4 Hz, 1H), 5.21 (d, J = 13.4 Hz, 1H), 6.07 (dd, J = 11.3, 2.4 Hz, 1H), 6.39 (td, J = 8.4, 2.4 Hz, 1H), 6.73 (d, J = 8.2 Hz, 1H), 6.87-6.93 (m, 4H), 7.34 (d, J = 8.0 Hz, 1H), 7.42-7.45 (m, 1H), 8.34 (br s, 1H), 8.39 (d, J = 3.9 Hz, 1H), 8.79 (s, 1H) |
| 7-(4-Cyclohexylaminocarbonyl-oxy-2-methoxyphenyl)-8-(5-fluoro-2-methylphenoxymethyl)-1,3,3-trimethyl-3,4-dihydro-1H-quinoxalin-2-one (Compound No. 17-6)<br>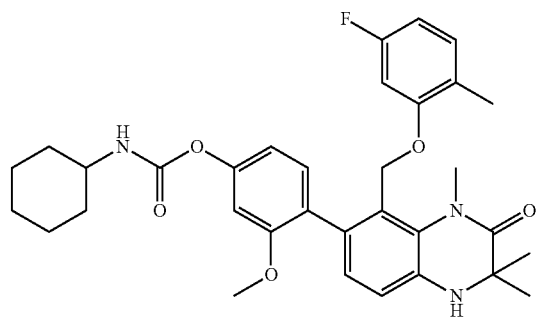 | $^1$H-NMR (500 MHz, CDCl$_3$) δ 0.93 (s, 3H), 1.27 (s, 3H), 1.35-1.77 (m, 10H), 2.01 (s, 3H), 3.46 (s, 3H), 3.58-3.60 (m, 1H), 3.81 (s, 3H), 4.86 (d, J = 13.7 Hz, 1H), 4.94 (d, J = 8.2 Hz, 1H), 5.21 (d, J = 13.7 Hz, 1H), 6.05 (dd, J = 11.0, 2.3 Hz, 1H), 6.38 (td, J = 8.3, 2.3 Hz, 1H), 6.75 (d, J = 7.7 Hz, 1H), 6.83-6.90 (m, 4H), 7.26-7.29 (m, 1H) |
| 8-(5-Fluoro-2-methylphenoxy-methyl)-7-(4-furfurylamino-carbonyloxy-2-methoxyphenyl)-1,3,3-trimethyl-3,4-dihydro-1H-quinoxalin-2-one (Compound No. 17-7)<br>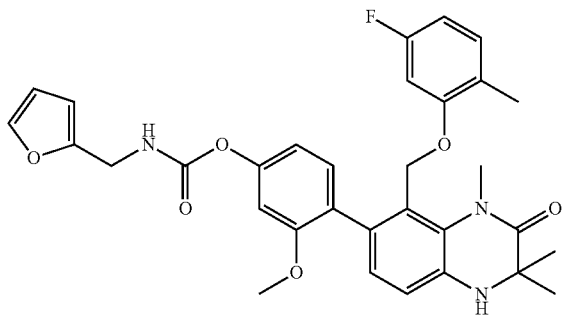 | $^1$H-NMR (500 MHz, CDCl$_3$) δ 0.92 (s, 3H), 1.27 (s, 3H), 2.01 (s, 3H), 3.46 (s, 3H), 3.71 (s, 1H), 3.81 (s, 3H), 4.48 (d, J = 5.8 Hz, 2H), 4.86 (d, J = 13.7 Hz, 1H), 5.21 (d, J = 13.7 Hz, 1H), 5.39 (t, J = 5.8 Hz, 1H), 6.05 (dd, J = 11.2, 2.4 Hz, 1H), 6.30-6.32 (m, 1H), 6.36-6.40 (m, 2H), 6.71 (d, J = 7.9 Hz, 1H), 6.82-6.90 (m, 4H), 7.28 (d, J = 8.0 Hz, 1H), 7.41 (d, J = 1.2 Hz, 1H) |

| | |
|---|---|
| 8-(5-Fluoro-2-methylphenoxy-methyl)-7-[2-methoxy-4-(2-methoxyphenylaminocarbonyloxy)phenyl]-1,3,3-trimethyl-3,4-dihydro-1H-quinoxalin-2-one (Compound No. 17-8)<br>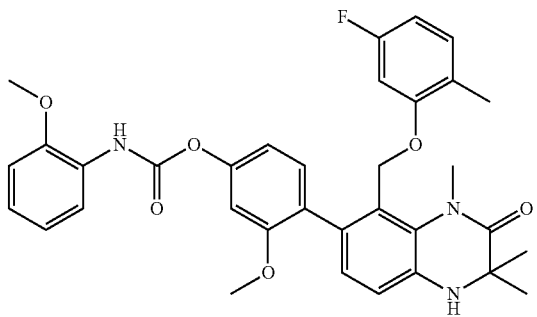 [SMILES: COc1cc(OC(=O)N(C)c2ccccc2)ccc1-c1ccc2c(c1COc1cc(F)ccc1C)N(C)C(=O)C(C)(C)N2] | ¹H-NMR (500 MHz, CDCl₃) δ 0.94 (s, 3H), 1.27 (s, 3H), 2.02 (s, 3H), 3.47 (s, 3H), 3.71 (s, 1H), 3.83 (s, 3H), 3.94 (s, 3H), 4.88 (d, J = 13.6 Hz, 1H), 5.22 (d, J = 13.6 Hz, 1H), 6.07 (dd, J = 11.3, 2.4 Hz, 1H), 6.39 (td, J = 8.2, 2.4 Hz, 1H), 6.72 (d, J = 7.9 Hz, 1H), 6.88-6.93 (m, 3H), 6.90 (d, J = 7.9 Hz, 1H), 6.92 (dd, J = 8.0, 2.3 Hz, 1H), 7.00 (t, J = 7.8 Hz, 1H), 7.07 (t, J = 7.8 Hz, 1H), 7.32 (d, J = 8.0 Hz, 1H), 7.62 (br s, 1H), 8.12 (br s, 1H) |
| 8-(5-Fluoro-2-methylphenoxy-methyl)-7-[2-methoxy-4-(4-methyl-phenylaminocarbonyloxy)phenyl]-1,3,3-trimethyl-3,4-dihydro-1H-quinoxalin-2-one (Compound No. 17-9)<br>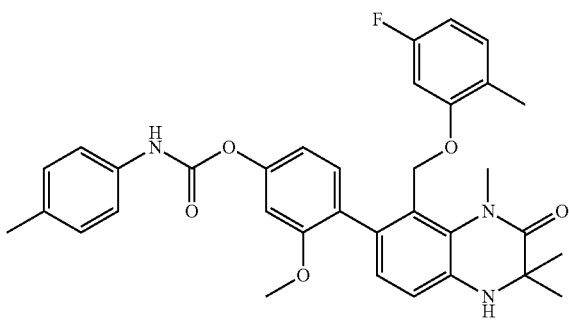 | ¹H-NMR (400 MHz, CDCl₃) δ 0.93 (s, 3H), 1.27 (s, 3H), 2.02 (s, 3H), 2.34 (s, 3H), 3.47 (s, 3H), 3.72 (s, 1H), 3.83 (s, 3H), 4.87 (d, J = 13.7 Hz, 1H), 5.22 (d, J = 13.7 Hz, 1H), 6.07 (dd, J = 11.2, 2.4 Hz, 1H), 6.39 (td, J = 8.3, 2.4 Hz, 1H), 6.72 (d, J = 8.1 Hz, 1H), 6.87-6.92 (m, 1H), 6.88 (d, J = 2.2 Hz, 1H), 6.89 (d, J = 8.1 Hz, 1H), 6,91 (dd, J = 8.1, 2.2 Hz, 1H), 7.17 (d, J = 8.3 Hz, 2H), 7.32 (d, J = 8.1 Hz, 1H), 7.36 (d, J = 8.3 Hz, 2H) |
| 7-(4-Ethoxycarbonylmethylamino-carbonyloxy-2-methoxyphenyl)-8-(5-fluoro-2-methylphenoxy-methyl)-1,3,3-trimethyl-3,4-dihydro-1H-quinoxalin-2-one (Compound No. 17-10)<br>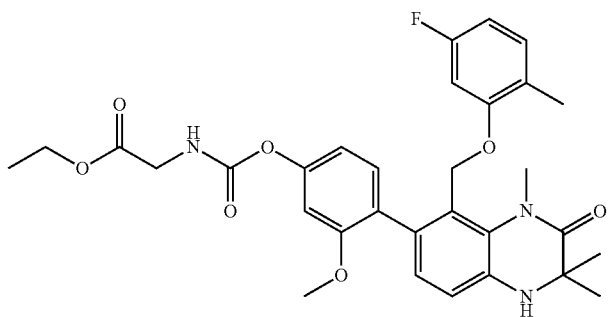 | ¹H-NMR (400 MHz, CDCl₃) δ 0.93 (s, 3H), 1.26 (s, 3H), 1.32 (t, J = 7.2 Hz, 3H), 2.01 (s, 3H), 3.46 (s, 3H), 3.71 (s, 1H), 3.81 (s, 3H), 4.08 (d, J = 5.3 Hz, 2H), 4.27 (q, J = 7.2 Hz, 2H), 4.86 (d, J = 13.4 Hz, 1H), 5.21 (d, J = 13.4 Hz, 1H), 5.58 (t, J = 5.3 Hz, 1H), 6.05 (dd, J = 11.2, 2.4 Hz, 1H), 6.38 (td, J = 8.3, 2.4 Hz, 1H), 6.71 (d, J = 8.0 Hz, 1H), 6.82 (d, J = 2.3 Hz, 1H), 6.86 (dd, J = 8.1, 2.3 Hz, 1H), 6.87-6.91 (m, 1H), 6.88 (d, J = 8.0 Hz, 1H), 7.29 (d, J = 8.1 Hz, 1H) |

| | |
|---|---|
| 8-(5-Fluoro-2-methylphenoxymethyl)-7-[2-methoxy-4-[2-(2-methylacryloyloxy)ethylaminocarbonyloxy]phenyl]-1,3,3-trimethyl-3,4-dihydro-1H-quinoxalin-2-one (Compound No. 17-11)<br>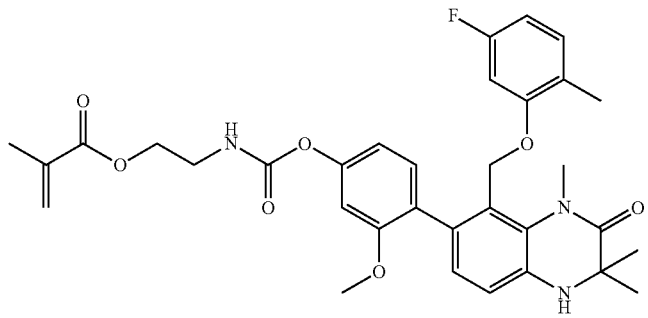 | $^1$H-NMR (400 MHz, CDCl$_3$) δ 0.93 (s, 3H), 1.27 (s, 3H), 1.99 (s, 3H), 2.01 (s, 3H), 3.46 (s, 3H), 3.63 (q, J = 5.6 Hz, 2H), 3.73 (q, J = 5.6 Hz, 2H), 3.71 (s, 1H), 3.81 (s, 3H), 4.34 (t, J = 5.6 Hz, 2H), 4.86 (d, J = 13.7 Hz, 1H), 5.21 (d, J = 13.7 Hz, 1H), 5.36 (t, J = 5.6 Hz, 1H), 5.64 (s, 1H), 6.05 (dd, J = 11.4, 2.5 Hz, 1H), 6.18 (s, 1H), 6.38 (td, J = 8.2, 2.5 Hz, 1H), 6.71 (d, J = 8.0 Hz, 1H), 6.81 (d, J = 2.2 Hz, 1H), 6.84 (dd, J = 8.2, 2.2 Hz, 1H), 6.87-6.91 (m, 1H), 6.88 (d, J = 8.0 Hz, 1H), 7.29 (d, J = 8.2 Hz, 1H) |
| 7-(4-Benzylaminocarbonyloxy-2-methoxyphenyl)-8-(5-fluoro-2-methylphenoxymethyl)-1,3,3-trimethyl-3,4-dihydro-1H-quinoxalin-2-one (Compound No. 17-12)<br>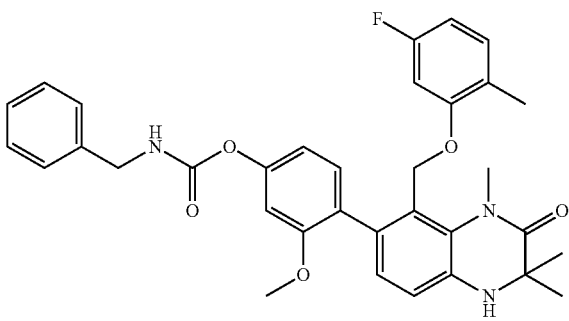 | $^1$H-NMR (400 MHz, CDCl$_3$) δ 0.92 (s, 3H), 1.26 (s, 3H), 2.01 (s, 3H), 3.46 (s, 3H), 3.70 (s, 1H), 3.82 (s, 3H), 4.49 (d, J = 5.9 Hz, 2H), 4.86 (d, J = 13.7 Hz, 1H), 5.21 (d, J = 13.7 Hz, 1H), 5.37 (t, J = 5.9 Hz, 1H), 6.05 (dd, J = 11.2, 2.4 Hz, 1H), 6.38 (td, J = 8.3, 2.4 Hz, 1H), 6.71 (d, J = 8.0 Hz, 1H), 6.84-6.91 (m, 3H), 6.88 (d, J = 8.0 Hz, 1H), 7.29 (d, J = 8.3 Hz, 1H), 7.31-7.39 (m, 5H) |
| 7-[4-(3-Benzylureido)-2-methoxyphenyl]-8-(5-fluoro-2-methylphenoxymethyl)-1,3,3-trimethyl-3,4-dihydro-1H-quinoxalin-2-one (Compound No. 17-13)<br>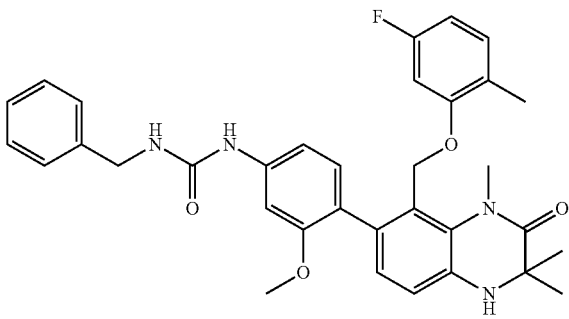 | $^1$H-NMR (400 MHz, CDCl$_3$) δ 0.90 (s, 3H), 1.28 (s, 3H), 2.00 (s, 3H), 3.45 (s, 3H), 3.69 (s, 1H), 3.80 (s, 3H), 4.49 (d, J = 5.8 Hz, 2H), 4.83 (d, J = 13.7 Hz, 1H), 5.12 (t, J = 5.8 Hz, 1H), 5.21 (d, J = 13.7 Hz, 1H), 6.03 (dd, J = 11.2, 2.4 Hz, 1H), 6.37 (td, J = 8.3, 2.4 Hz, 1H), 6.50 (s, 1H), 6.70 (d, J = 8.1 Hz, 1H), 6.76 (dd, J = 8.2, 2.2 Hz, 1H), 6.86 (d, J = 8.1 Hz, 1H), 6.86-6.90 (m, 1H), 7.20 (d, J = 8.2 Hz, 1H), 7.28-7.35 (m, 5H), 7.33 (d, J = 2.2 Hz, 1H) |

| | |
|---|---|
| 8-(5-Fluoro-2-methylphenoxymethyl)-7-[2-methoxy-4-(3-phenylureido)phenyl]-1,3,3-trimethyl-3,4-dihydro-1H-quinoxalin-2-one (Compound No. 17-14)<br>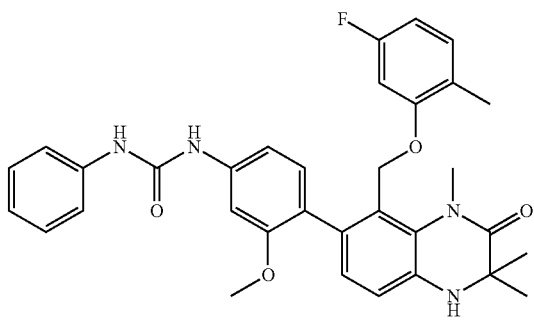 | $^1$H-NMR (400 MHz, CDCl$_3$) δ 0.91 (s, 3H), 1.29 (s, 3H), 2.02 (s, 3H), 3.47 (s, 3H), 3.70 (s, 1H), 3.84 (s, 3H), 4.85 (d, J = 14.0 Hz, 1H), 5.22 (d, J = 14.0 Hz, 1H), 6.05 (dd, J = 11.2, 2.5 Hz, 1H), 6.38 (td, J = 8.2, 2.5 Hz, 1H), 6.62 (s, 1H), 6.71 (d, J = 8.0 Hz, 1H), 6.72 (s, 1H), 6.82 (dd, J = 8.2, 2.1 Hz, 1H), 6.87 (d, J = 8.0 Hz, 1H), 6.87-6.91 (m, 1H), 7.14-7.19 (m, 1H), 7.24 (d, J = 8.2 Hz, 1H), 7.37-7.40 (m, 4H), 7.39 (d, J = 2.1 Hz, 1H) |
| 7-(4-Isopropylaminocarbonyloxy-2-methoxyphenyl)-8-(5-methyl-thiophen-2-ylcarbonyloxymethyl)-1,3,3-trimethyl-3,4-dihydro-1H-quinoxalin-2-one (Compound No. 17-15)<br>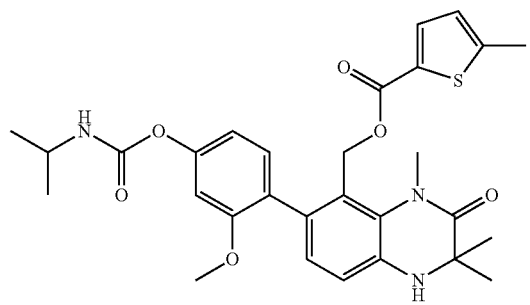 | $^1$H-NMR (500 MHz, CDCl$_3$) δ 1.21 (s, 3H), 1.26 (d, J = 6.1 Hz, 6H), 1.41 (s, 3H), 2.47 (s, 3H), 3.44 (s, 3H), 3.74 (s, 3H), 3.78 (s, 1H), 3.89-3.93 (m, 1H), 4.87 (d, J = 8.0 Hz, 1H), 5.10 (d, J = 13.3 Hz, 1H), 5.29 (d, J = 13.3 Hz, 1H), 6.69 (d, J = 3.9 Hz, 1H), 6.73-6.76 (m, 2H), 6.75 (d, J = 8.1 Hz, 1H), 6.87 (d, J = 8.1 Hz, 1H), 7.23 (d, J = 7.6 Hz, 1H), 7.43 (d, J = 3.9 Hz, 1H) |
| 7-(2-Methoxy-4-phenylaminocarbonyloxyphenyl)-8-(5-methyl-thiophen-2-ylcarbonyloxymethyl)-1,3,3-trimethyl-3,4-dihydro-1H-quinoxalin-2-one (Compound No. 17-16)<br>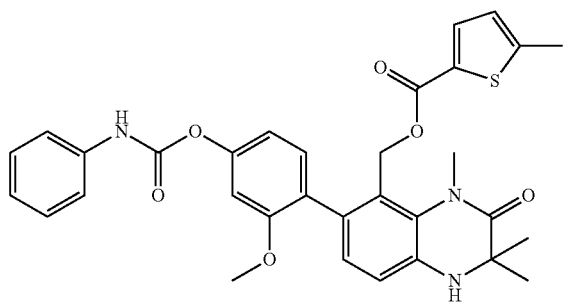 | $^1$H-NMR (500 MHz, CDCl$_3$) δ 1.21 (s, 3H), 1.42 (s, 3H), 2.47 (s, 3H), 3.45 (s, 3H), 3.75 (s, 3H), 3.79 (s, 1H), 5.12 (d, J = 13.3 Hz, 1H), 5.29 (d, J = 13.3 Hz, 1H), 6.69 (d, J = 3.8 Hz, 1H), 6.76 (d, J = 7.9 Hz, 1H), 6.80 (d, J = 2.1 Hz, 1H), 6.82 (dd, J = 7.9, 2.1 Hz, 1H), 6.88 (d, J = 7.9 Hz, 1H), 6.97 (br s, 1H), 7.13 (t, J = 7.5 Hz, 1H), 7.28 (d, J = 7.9 Hz, 1H), 7.36 (t, J = 7.5 Hz, 2H), 7.44 (d, J = 3.8 Hz, 1H), 7.47 (d, J = 7.5 Hz, 2H) |

| | |
|---|---|
| 8-(5-Fluoro-2-methylphenoxy-methyl)-7-[2-methoxy-4-(3-propylureido)phenyl]-1,3,3-trimethyl-3,4-dihydro-1H-quinoxalin-2-one (Compound No. 17-17)<br>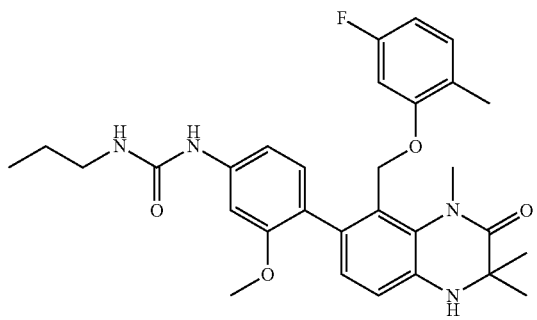 | $^1$H-NMR (500 MHz, CDCl$_3$) δ 0.91 (s, 3H), 0.96 (t, J = 7.2 Hz, 3H), 1.29 (s, 3H), 1.58 (sextet, J = 7.2 Hz, 2H), 2.01 (s, 3H), 3.26 (td, J = 7.2, 5.7 Hz, 2H), 3.47 (s, 3H), 3.69 (s, 1H), 3.83 (s, 3H), 4.73 (t, J = 5.7 Hz, 1H), 4.85 (d, J = 13.6 Hz, 1H), 5.22 (d, J = 13.6 Hz, 1H), 6.04 (dd, J = 11.3, 2.4 Hz 1H), 6.32 (s, 1H), 6.38 (td, J = 8.2, 2.4 Hz, 1H), 6.70 (d, J = 8.1 Hz, 1H), 6.77 (dd, J = 8.1, 2.0 Hz, 1H), 6.87 (d, J = 8.1 Hz, 1H), 6.88-6.90 (m, 1H), 7.22 (d, J = 8.1 Hz, 1H), 7.33 (d, J = 2.0 Hz, 1H) |

Example 18

8-(5-Fluoro-2-methylphenoxymethyl)-7-[2-methoxy-4-(morpholin-4-ylcarbonyloxy)phenyl]-1,3,3-trimethyl-3,4-dihydro-1H-quinoxalin-2-one (Compound No. 18-1)

A mixture of 8-(5-fluoro-2-methylphenoxymethyl)-7-(4-hydroxy-2-methoxyphenyl)-1,3,3-trimethyl-3,4-dihydro-1H-quinoxalin-2-one (Compound No. 11, 153 mg, 0.340 mmol), 1,1'-carbonyldiimiazole (95.6 mg, 0.590 mmol), and 4-dimethylaminopyridine (5.2 mg, 0.043 mmol) was dissolved in anhydrous tetrahydrofuran (3 mL) and stirred for 1 hour at room temperature. After morpholine (58.3 μL, 0.666 mmol) was added to the reaction mixture and the mixture was stirred for 2 hour, the mixture was purified by silica gel column chromatography (hexane-ethyl acetate) to give the titled compound (61.2 mg) as a colorless solid. (Yield 32%)

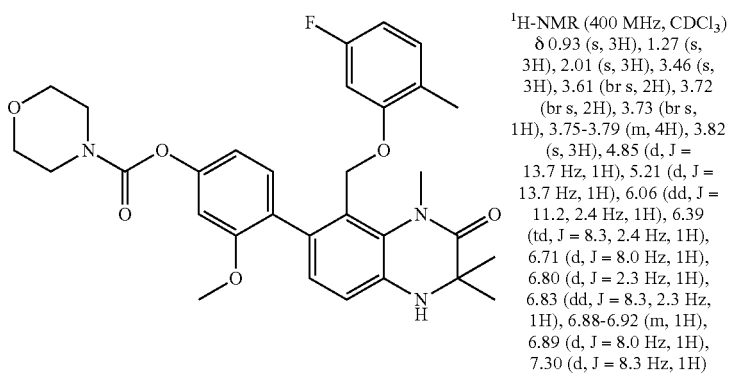

$^1$H-NMR (400 MHz, CDCl$_3$) δ 0.93 (s, 3H), 1.27 (s, 3H), 2.01 (s, 3H), 3.46 (s, 3H), 3.61 (br s, 2H), 3.72 (br s, 2H), 3.73 (br s, 1H), 3.75-3.79 (m, 4H), 3.82 (s, 3H), 4.85 (d, J = 13.7 Hz, 1H), 5.21 (d, J = 13.7 Hz, 1H), 6.06 (dd, J = 11.2, 2.4 Hz, 1H), 6.39 (td, J = 8.3, 2.4 Hz, 1H), 6.71 (d, J = 8.0 Hz, 1H), 6.80 (d, J = 2.3 Hz, 1H), 6.83 (dd, J = 8.3, 2.3 Hz, 1H), 6.88-6.92 (m, 1H), 6.89 (d, J = 8.0 Hz, 1H), 7.30 (d, J = 8.3 Hz, 1H)

Using any compounds among Compounds No. 11 and available compounds, the following Compounds (No. 18-2 and 18-3) were obtained by a method similar to that of Compound. No. 18-1.

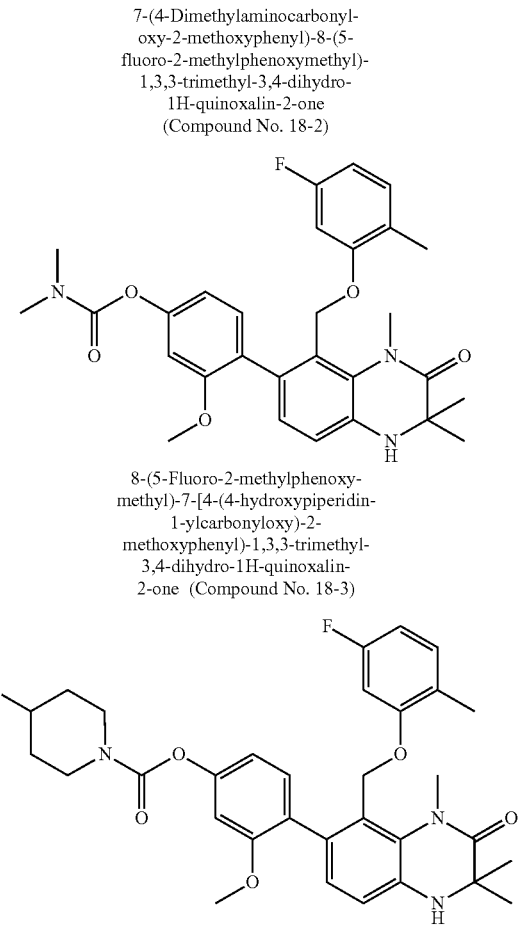

| | |
|---|---|
| 7-(4-Dimethylaminocarbonyl-oxy-2-methoxyphenyl)-8-(5-fluoro-2-methylphenoxymethyl)-1,3,3-trimethyl-3,4-dihydro-1H-quinoxalin-2-one (Compound No. 18-2) | $^{1}$H-NMR (400 MHz, CDCl$_3$) δ 0.92 (s, 3H), 1.27 (s, 3H), 2.01 (s, 3H), 3.05 (s, 3H), 3.14 (s, 3H), 3.46 (s, 3H), 3.71 (s, 1H), 3.81 (s, 3H), 4.86 (d, J = 13.7 Hz, 1H), 5.21 (d, J = 13.7 Hz, 1H), 6.06 (dd, J = 11.2, 2.4 Hz, 1H), 6.38 (td, J = 8.3, 2.4 Hz, 1H), 6.71 (d, J = 7.8 Hz, 1H), 6.80 (d, J = 2.2 Hz, 1H), 6.83 (dd, J = 8.2, 2.2 Hz, 1H), 6.87-6.91 (m, 1H), 6.88 (d, J = 7.8 Hz, 1H), 7.29 (d, J = 8.22 Hz, 1H) |
| 8-(5-Fluoro-2-methylphenoxy-methyl)-7-[4-(4-hydroxypiperidin-1-ylcarbonyloxy)-2-methoxyphenyl]-1,3,3-trimethyl-3,4-dihydro-1H-quinoxalin-2-one (Compound No. 18-3) | $^{1}$H-NMR (400 MHz, CDCl$_3$) δ 0.93 (s, 3H), 1.27 (s, 3H), 1.63-1.65 (m, 2H), 1.97-2.02 (m, 2H), 2.01 (s, 3H), 3.30 (br s, 1H), 3.40 (br s, 1H), 3.46 (s, 3H), 3.70 (s, 1H), 3.82 (s, 3H), 3.96-4.01 (m, 2H), 4.04 (br s, 1H), 4.86 (d, J = 13.7 Hz, 1H), 5.21 (d, J = 13.7 Hz, 1H), 6.06 (dd, J = 11.1, 2.4 Hz, 1H), 6.38 (td, J = 8.3, 2.4 Hz, 1H), 6.71 (d, J = 8.1 Hz, 1H), 6.79 (d, J = 2.2 Hz, 1H), 6.83 (dd, J = 8.2, 2.2 Hz, 1H), 6.88-6.91 (m, 1H), 6.89 (d, J = 8.1 Hz, 1H), 7.29 (d, J = 8.2 Hz, 1H) |

Example 19

8-(5-Fluoro-2-methylphenoxymethyl)-7-[2-methoxy-4-(N-methyl-N-phenylaminocarbonyloxy)phenyl]-1,3,3 trimethyl-3,4-dihydro-1H-quinoxalin-2-one (Compound No. 19)

A mixture 8-(5-fluoro-2-methylphenoxymethyl)-7-(4-hydroxy-2-methoxyphenyl)-1,3,3-trimethyl-3,4-dihydro-1H-quinoxalin-2-one (Compound No. 11, 25.4 mg, 0.0564 mmol) and N-methyl-N-phenylcarbamoyl chloride (20.4 mg, 0.120 mmol) was dissolved in pyridine (1 mL), and stirred for 2 hours at 100° C. The reaction mixture was concentrated, and then the obtained residue was purified by silica gel column chromatography (hexane-ethyl acetate) to give the titled compound (28.7 mg) as a pale yellow amorphous product. (Yield 87%)

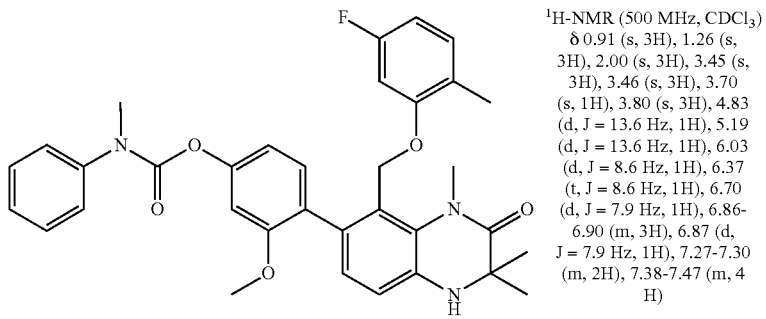

$^{1}$H-NMR (500 MHz, CDCl$_3$) δ 0.91 (s, 3H), 1.26 (s, 3H), 2.00 (s, 3H), 3.45 (s, 3H), 3.46 (s, 3H), 3.70 (s, 1H), 3.80 (s, 3H), 4.83 (d, J = 13.6 Hz, 1H), 5.19 (d, J = 13.6 Hz, 1H), 6.03 (d, J = 8.6 Hz, 1H), 6.37 (t, J = 8.6 Hz, 1H), 6.70 (d, J = 7.9 Hz, 1H), 6.86-6.90 (m, 3H), 6.87 (d, J = 7.9 Hz, 1H), 7.27-7.30 (m, 2H), 7.38-7.47 (m, 4H)

Example 20

7-(4-Aminoacetylamino-2-methoxyphenyl)-8-(5-fluoro-2-methylphenoxymethyl)-1,3,3-trimethyl-3,4-dihydro-1H-quinoxalin-2-one hydrochloride (Compound No. 20)

7-(4-tert-Butoxycarbonylaminoacetylamino-2-methoxyphenyl)-8-(5-fluoro-2-methylphenoxymethyl)-1,3,3-trimethyl-3,4-dihydro-1H-quinoxalin-2-one (Compound No. 15-31, 10.5 mg, 0.0173 mmol) was dissolved in 1,4-dioxane (0.2 mL), 4N 1,4-dioxane solution of hydrochloride (41.3 μL, 0.165 mmol) was added thereto. After the reaction mixture was stirred for 4 hours at room temperature, it was diluted with hexane (10 mL). The precipitated solid was filtered to give the titled compound (7.8 mg) as a pale yellow solid. (Yield 83%)

solvent of tetrahydrofuran (1 mL) and dichloromethane (1 mL), and triethylamine (25 μL, 0.18 mmol) and nicotynoyl chloride hydrochloride (12.0 mg, 0.0674 mmol) were added successively. After the reaction mixture was stirred for 40 minutes at room temperature, it was purified by silica gel column chromatography (hexane-ethyl acetate). The obtained colorless amorphous product was dissolved in N,N-dimethylformamide (1 mL) and piperidine (50 μL) was added thereto. After the reaction mixture was stirred for 20 minutes at room temperature, it was diluted with ethyl acetate (50 mL). The mixture was washed with water (50 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled compound (13.0 mg) as a colorless solid. (Yield 52%)

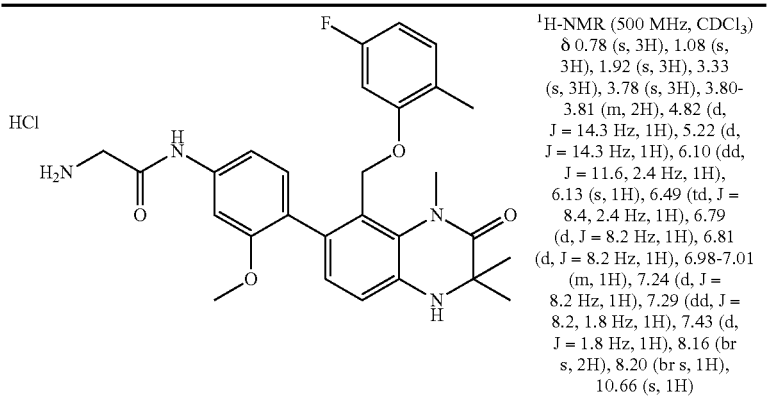

$^1$H-NMR (500 MHz, CDCl$_3$) δ 0.78 (s, 3H), 1.08 (s, 3H), 1.92 (s, 3H), 3.33 (s, 3H), 3.78 (s, 3H), 3.80-3.81 (m, 2H), 4.82 (d, J = 14.3 Hz, 1H), 5.22 (d, J = 14.3 Hz, 1H), 6.10 (dd, J = 11.6, 2.4 Hz, 1H), 6.13 (s, 1H), 6.49 (td, J = 8.4, 2.4 Hz, 1H), 6.79 (d, J = 8.2 Hz, 1H), 6.81 (d, J = 8.2 Hz, 1H), 6.98-7.01 (m, 1H), 7.24 (d, J = 8.2 Hz, 1H), 7.29 (dd, J = 8.2, 1.8 Hz, 1H), 7.43 (d, J = 1.8 Hz, 1H), 8.16 (br s, 2H), 8.20 (br s, 1H), 10.66 (s, 1H)

Example 21

8-(2-Methoxyphenylaminomethyl)-7-[2-methoxy-4-(pyridin-3-ylcarbonyloxy)phenyl]-1,3,3-trimethyl-3,4-dihydro-1H-quinoxalin-2-one (Compound No. 21-1)

7-(4-Hydroxy-2-methoxyphenyl)-8-[N-(2-methoxyphenyl)-N-(9-fluorenylmethoxycarbonyl)aminomethyl]-1,3,3-trimethyl-3,4-dihydro-1H-quinoxalin-2-one (Compound No. 13-1, 30.0 mg, 0.0448 mmol) was dissolved in mixed

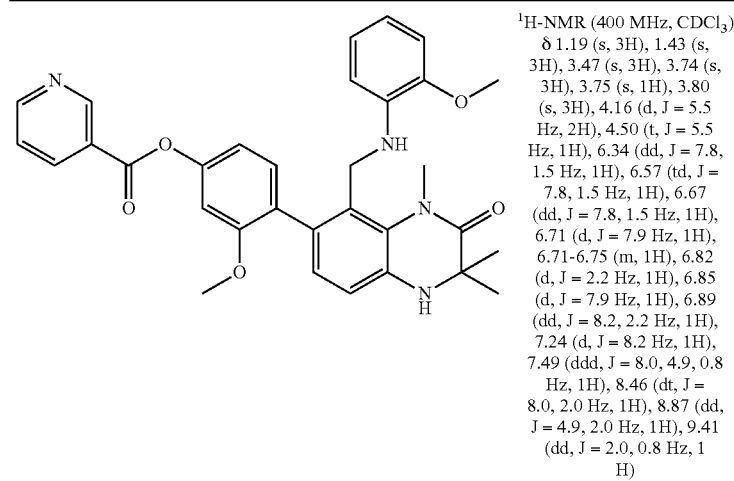

$^1$H-NMR (400 MHz, CDCl$_3$) δ 1.19 (s, 3H), 1.43 (s, 3H), 3.47 (s, 3H), 3.74 (s, 3H), 3.75 (s, 1H), 3.80 (s, 3H), 4.16 (d, J = 5.5 Hz, 2H), 4.50 (t, J = 5.5 Hz, 1H), 6.34 (dd, J = 7.8, 1.5 Hz, 1H), 6.57 (td, J = 7.8, 1.5 Hz, 1H), 6.67 (dd, J = 7.8, 1.5 Hz, 1H), 6.71 (d, J = 7.9 Hz, 1H), 6.71-6.75 (m, 1H), 6.82 (d, J = 2.2 Hz, 1H), 6.85 (d, J = 7.9 Hz, 1H), 6.89 (dd, J = 8.2, 2.2 Hz, 1H), 7.24 (d, J = 8.2 Hz, 1H), 7.49 (ddd, J = 8.0, 4.9, 0.8 Hz, 1H), 8.46 (dt, J = 8.0, 2.0 Hz, 1H), 8.87 (dd, J = 4.9, 2.0 Hz, 1H), 9.41 (dd, J = 2.0, 0.8 Hz, 1H)

Using any compounds among Compounds No. 13-1, 13-3, and available compounds, the following Compounds (No. 21-2~21-24) were obtained by a method similar to that of Compound No. 14-1, 15-1, 17-1 or 18-1 followed by a method similar to that of Compound No. 21-1.

7-[4-(Furan-2-ylcarbonyloxy)-2-methoxyphenyl]-8-(2-methoxyphenylaminomethyl)-1,3,3-trimethyl-3,4-dihydro-1H-quinoxalin-2-one (Compound No. 21-2)

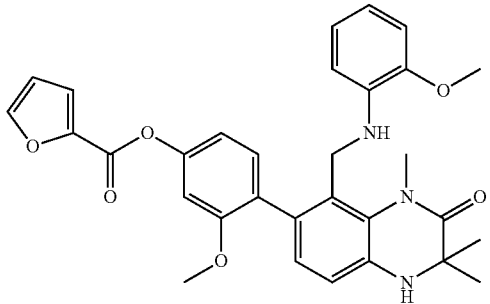

$^1$H-NMR (400 MHz, CDCl$_3$) δ 1.18 (s, 3H), 1.43 (s, 3 H), 3.47 (s, 3H), 3.74 (s, 3H), 3.76 (s, 1H), 3.79 (s, 3H), 4.15 (s, 2H), 4.51 (br s, 1H), 6.33 (dd, J = 7.8, 1.5 Hz, 1H), 6.56 (td, J = 7.8, 1.5 Hz, 1H), 6.61 (dd, J = 3.6, 1.7 Hz, 1H), 6.66 (dd, J = 7.8, 1.5 Hz, 1H), 6.70 (d, J = 8.1 Hz, 1H), 6.72 (td, J = 7.8, 1.5 Hz, 1H), 6.80 (d, J = 2.3 Hz, 1H), 6.84 (d, J = 8.1 Hz, 1H), 6.87 (dd, J = 8.2, 2.3 Hz, 1H), 7.21 (d, J = 8.2 Hz, 1H), 7.40 (dd, J = 3.6, 0.9 Hz, 1H), 7.69 (dd, J = 1.7, 0.9 Hz, 1H)

7-(4-Hydroxy-2-methoxyphenyl)-8-(2-methoxyphenylaminomethyl)-1,3,3-trimethyl-3,4-dihydro-1H-quinoxalin-2-one (Compound No. 21-3)

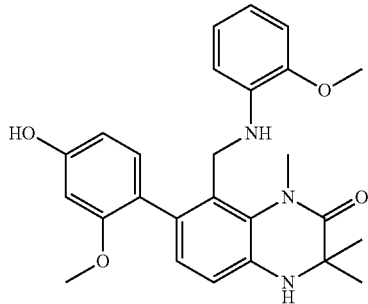

$^1$H-NMR (400 MHz, CDCl$_3$) δ 1.16 (s, 3H), 1.42 (s, 3 H), 3.46 (s, 3H), 3.70 (s, 1H), 3.73 (s, 3H), 3.76 (s, 3H), 4.11 (s, 2H), 4.52 (br s, 1H), 4.90 (s, 1H), 6.33 (dd, J = 7.7, 1.5 Hz, 1H), 6.43 (dd, J = 7.9, 2.3 Hz, 1H), 6.44 (d, J = 2.3 Hz, 1H), 6.56 (td, J = 7.7, 1.5 Hz, 1H), 6.66 (dd, J = 7.7, 1.5 Hz, 1H), 6.68 (d, J = 8.1 Hz, 1H), 6.73 (td, J = 7.7, 1.5 Hz, 1H), 6.80 (d, J = 8.1 Hz, 1H), 7.01 (d, J = 7.9 Hz, 1H)

7-[4-(2-Chlorobenzoyloxy)-2-methoxyphenyl]-8-(2-methoxyphenylaminomethyl)-1,3,3-trimethyl-3,4-dihydro-1H-quinoxalin-2-one (Compound No. 21-4)

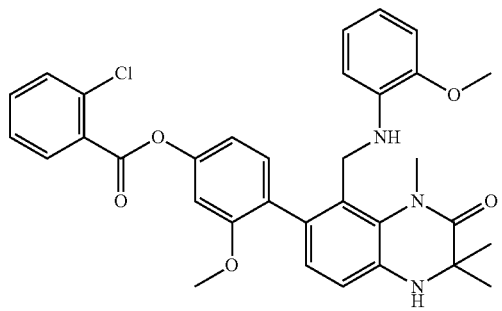

$^1$H-NMR (400 MHz, CDCl$_3$) δ 1.18 (s, 3H), 1.43 (s, 3 H), 3.47 (s, 3H), 3.74 (s, 3H), 3.80 (s, 3H), 4.16 (s, 2H), 4.50 (br s, 1H), 6.33 (d, J = 7.8 Hz, 1H), 6.56 (t, J = 7.8 Hz, 1H), 6.66 (d, J = 7.8 Hz, 1H), 6.70 (d, J = 7.9 Hz, 1H), 6.72 (t, J = 7.8 Hz, 1H), 6.83 (d, J = 2.2 Hz, 1H), 6.84 (d, J = 7.9 Hz, 1H), 6.91 (dd, J = 8.2, 2.2 Hz, 1H), 7.23 (d, J = 8.2 Hz, 1H), 7.39-7.43 (m, 1H), 7.49-7.55 (m, 2 H), 8.06 (dd, J = 8.1, 1.2 Hz, 1H)

| | |
|---|---|
| 7-(4-Butyryloxy-2-methoxyphenyl)-8-(2-methoxyphenylaminomethyl)-1,3,3-trimethyl-3,4-dihydro-1H-quinoxalin-2-one (Compound No. 21-5)<br>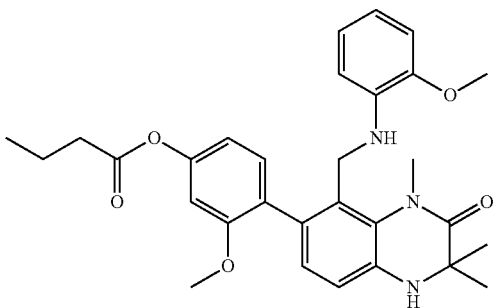 | $^{1}$H-NMR (400 MHz, CDCl$_3$) δ 1.06 (t, J = 7.4 Hz, 3H), 1.17 (s, 3H), 1.42 (s, 3H), 1.75-1.85 (m, 2H), 2.55 (t, J = 7.4 Hz, 2H), 3.46 (s, 3H), 3.73 (s, 4H), 3.77 (s, 3H), 4.13 (br s, 2H), 4.48 (br s, 1H), 6.31 (dd, J = 7.9, 1.5 Hz, 1H), 6.56 (td, J = 7.9, 1.5 Hz, 1H), 6.65 (dd, J = 7.9, 1.5 Hz, 1H), 6.67 (d, J = 2.3 Hz, 1H), 6.69 (d, J = 7.9 Hz, 1H), 6.70-6.73 (m, 1H), 6.74 (dd, J = 8.1, 2.3 Hz, 1H), 6.81 (d, J = 7.9 Hz, 1H), 7.16 (d, J = 8.1 Hz, 1H) |
| 7-[2-Methoxy-4-(2-methoxybenzoyloxy)phenyl]-8-(2-methoxyphenylaminomethyl)-1,3,3-trimethyl-3,4-dihydro-1H-quinoxalin-2-one (Compound No. 21-6)<br>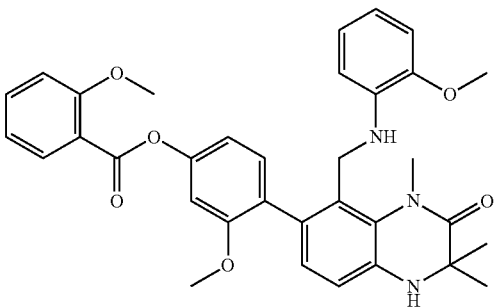 | $^{1}$H-NMR (500 MHz, CDCl$_3$) δ 1.18 (s, 3H), 1.42 (s, 3H), 3.47 (s, 3H), 3.74 (s, 4H), 3.79 (s, 3H), 3.96 (s, 3H), 4.16 (br s, 2H), 4.51 (br s, 1H), 6.33 (dd, J = 7.8, 1.4 Hz, 1H), 6.56 (td, J = 7.8, 1.4 Hz, 1H), 6.66 (dd, J = 7.8, 1.4 Hz, 1H), 6.70 (d, J = 7.9 Hz, 1H), 6.72 (td, J = 7.8, 1.4 Hz, 1H), 6.83 (d, J = 2.1 Hz, 1H), 6.84 (d, J = 7.9 Hz, 1H), 6.88 (dd, J = 8.1, 2.1 Hz, 1H), 7.05-7.08 (m, 1H), 7.05 (d, J = 7.6 Hz, 1H), 7.21 (d, J = 8.1 Hz, 1H), 7.54-7.58 (m, 1H), 8.03 (dd, J = 7.9, 1.8 Hz, 1H) |
| 7-(4-Isopropylaminocarbonyloxy-2-methoxyphenyl)-8-(2-methoxyphenylaminomethyl)-1,3,3-trimethyl-3,4-dihydro-1H-quinoxalin-2-one (Compound No. 21-7)<br>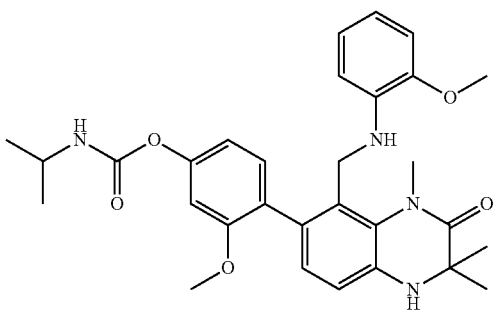 | $^{1}$H-NMR (400 MHz, CDCl$_3$) δ 1.16 (s, 3H), 1.25 (d, J = 7.3 Hz, 6H), 1.41 (s, 3H), 3.45 (s, 3H), 3.73 (s, 4H), 3.77 (s, 3H), 3.88-3.95 (m, 1H), 4.13 (br s, 2H), 4.51 (br s, 1H), 4.87 (d, J = 7.6 Hz, 1H), 6.32 (dd, J = 7.8, 1.3 Hz, 1H), 6.55 (td, J = 7.8, 1.3 Hz, 1H), 6.65 (dd, J = 7.8, 1.3 Hz, 1H), 6.68 (d, J = 7.9 Hz, 1H), 6.69-6.74 (m, 1H), 6.74 (d, J = 2.0 Hz, 1H), 6.77 (dd, J = 8.1, 2.0 Hz, 1H), 6.80 (d, J = 7.9 Hz, 1H), 7.14 (d, J = 8.1 Hz, 1H) |

| | |
|---|---|
| 8-(2-Methoxyphenylaminomethyl)-7-[2-methoxy-4-(thiophen-2-ylcarbonyloxy)phenyl]-1,3,3-trimethyl-3,4-dihydro-1H-quinoxalin-2-one (Compound No. 21-8)<br>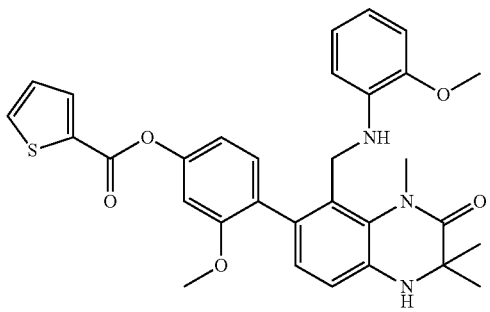 | $^1$H-NMR (500 MHz, CDCl$_3$) δ 1.18 (s, 3H), 1.42 (s, 3 H), 3.47 (s, 3H), 3.74 (s, 4H), 3.79 (s, 3H), 4.15 (br s, 2H), 4.50 (br s, 1H), 6.33 (dd, J = 7.8, 1.4 Hz, 1 H), 6.57 (td, J = 7.8, 1.4 Hz, 1H), 6.66 (dd, J = 7.8, 1.4 Hz, 1H), 6.70 (d, J = 8.1 Hz, 1H), 6.71-6.74 (m, 1H), 6.82 (d, J = 2.1 Hz, 1 H), 6.84 (d, J = 8.1 Hz, 1H), 6.88 (dd, J = 8.2, 2.1 Hz, 1H), 7.19 (dd, J = 5.0, 3.7 Hz, 1H), 7.21 (d, J = 8.2 Hz, 1H), 7.68 (dd, J = 5.0, 1.2 Hz, 1H), 7.99 (dd, J = 3.7, 1.2 Hz, 1H) |
| 7-[2-Methoxy-4-(morpholin-4-ylcarbonyloxy)phenyl]-8-(2-methoxyphenylaminomethyl)-1,3,3-trimethyl-3,4-dihydro-1H-quinoxalin-2-one (Compound No. 21-9)<br>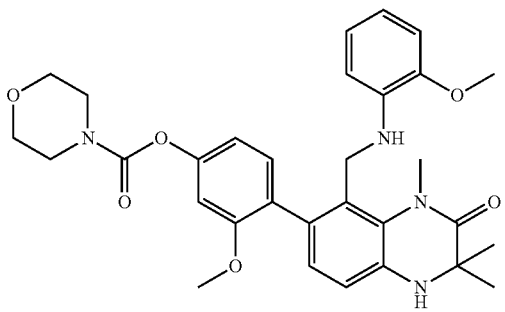 | $^1$H-NMR (500 MHz, CDCl$_3$) δ 1.16 (s, 3H), 1.42 (s, 3 H), 3.45 (s, 3H), 3.59 (br s, 2H), 3.68 (br s, 2H), 3.73 (s, 3H), 3.75-3.77 (m, 5 H), 3.78 (s, 3H), 4.12 (s, 2H), 4.52 (br s, 1H), 6.32 (dd, J = 7.7, 1.5 Hz, 1H), 6.56 (td, J = 7.7, 1.5 Hz, 1H), 6.66 (dd, J = 7.7, 1.4 Hz, 1H), 6.69 (d, J = 7.9 Hz, 1H), 6.71 (d, J = 2.4 Hz, 1H), 6.72 (td, J = 7.7, 1.4 Hz, 1H), 6.76 (dd, J = 8.2, 2.4 Hz, 1H), 6.82 (d, J = 7.9 Hz, 1H), 7.16 (d, J = 8.2 Hz, 1H) |
| 7-[2-Methoxy-4-(4-methoxybenzoyloxy)phenyl]-8-(2-methoxyphenylaminomethyl)-1,3,3-trimethyl-3,4-dihydro-1H-quinoxalin-2-one (Compound No. 21-10)<br>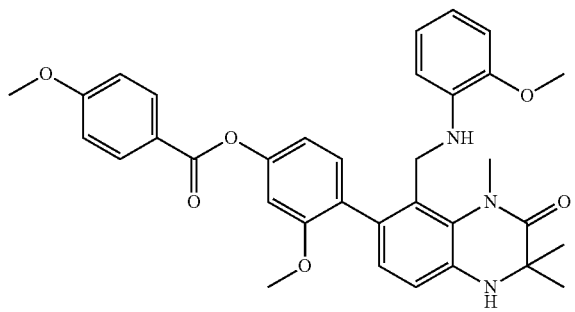 | $^1$H-NMR (500 MHz, CDCl$_3$) δ 1.18 (s, 3H), 1.42 (s, 3 H), 3.47 (s, 3H), 3.74 (s, 4H), 3.79 (s, 3H), 3.91 (s, 3H), 4.16 (d, J = 5.6 Hz, 2H), 4.51 (t, J = 5.6 Hz, 1 H), 6.34 (dd, J = 7.7, 1.4 Hz, 1H), 6.57 (td, J = 7.7, 1.4 Hz, 1H), 6.66 (dd, J = 7.7, 1.4 Hz, 1H), 6.70 (d, J = 7.9 Hz, 1H), 6.73 (td, J = 7.7) 1.4 Hz, 1H), 6.80 (d, J = 2.1 Hz, 1H), 6.85 (d, J = 7.9 Hz, 1H), 6.86 (dd, J = 8.1, 2.1 Hz, 1H), 7.00 (d, J = 8.9 Hz, 2H), 7.21 (d, J = 8.1 Hz, 1H), 8.16 (d, J = 8.9 Hz, 2H) |

| | |
|---|---|
| 8-(2-Methoxyphenylaminomethyl)-7-[2-methoxy-4-(thiophen-3-ylcarbonyloxy)phenyl]-1,3,3-trimethyl-3,4-dihydro-1H-quinoxalin-2-one (Compound No. 21-11)<br>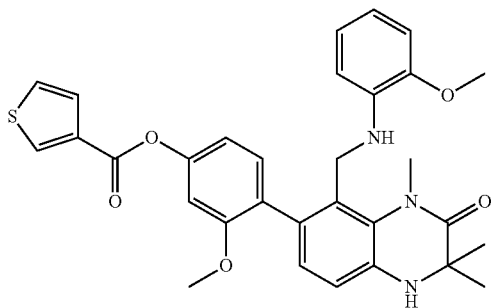 | $^1$H-NMR (400 MHz, CDCl$_3$) δ 1.18 (s, 3H), 1.42 (s, 3 H), 3.47 (s, 3H), 3.74 (s, 4H), 3.79 (s, 3H), 4.16 (s, 2H), 4.51 (br s, 1H), 6.33 (dd, J = 7.8, 1.5 Hz, 1H), 6.57 (td, J = 7.8, 1.5 Hz, 1H), 6.66 (dd, J = 7.8, 1.5 Hz, 1H), 6.70 (d, J = 8.1 Hz, 1H), 6.73 (td, J = 7.8, 1.5 Hz, 1H), 6.79, (d, J = 2.2 Hz, 1H), 6.84 (d, J = 8.1 Hz, 1H), 6.85 (dd, J = 8.2, 2.2 Hz, 1H), 7.21 (d, J = 8.2 Hz, 1H), 7.40 (dd, J = 5.1, 3.0 Hz, 1H), 7.67 (dd, J = 5.1, 1.2 Hz, 1H), 8.32 (dd, J = 3.0, 1.2 Hz, 1H) |
| 7-[2-Methoxy-4-(2-methyl-pyridin-3-ylcarbonyloxy)phenyl]-8-(2-methoxyphenylaminomethyl)-1,3,3-trimethyl-3,4-dihydro-1H-quinoxalin-2-one (Compound No. 21-12)<br>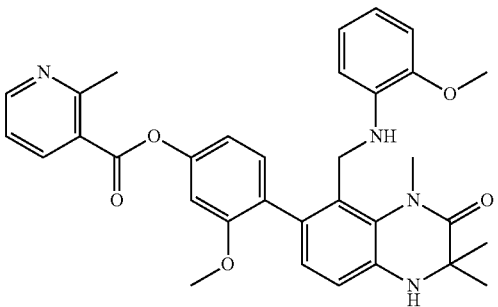 [SMILES: COc1ccccc1NCc1c(-c2ccc(OC(=O)c3cccnc3)cc2OC)ccc2c1N(C)C(=O)C(C)(C)N2] | $^1$H-NMR (500 MHz, CDCl$_3$) δ 1.18 (s, 3H), 1.43 (s, 3H), 2.94 (s, 3H), 3.46 (s, 3 H), 3.74 (s, 4H), 3.80 (s, 3H), 4.16-4.16 (m, 2H), 4.51 (br s, 1H), 6.34 (dd, J = 7.9, 1.3 Hz, 1H), 6.57 (td, J = 7.9, 1.3 Hz, 1H), 6.67 (dd, J = 7.9, 1.3 Hz, 1H), 6.71 (d, J = 7.9 Hz, 1H), 6.74 (td, J = 7.9, 1.3 Hz, 1H), 6.79 (d, J = 2.2 Hz, 1H), 6.84 (d, J = 7.9 Hz, 1 H), 6.86 (dd, J = 8.1, 2.2 Hz, 1H), 7.24 (d, J = 8.1 Hz, 1H), 7.31 (dd, J = 7.8, 4.7 Hz, 1H), 8.44 (dd, J = 7.8, 1.8 Hz, 1H), 8.71 (dd, J = 4.7, 1.8 Hz, 1H) |
| 8-(2-Methoxyphenylaminomethyl)-7-[2-methoxy-4-(thiazol-4-ylcarbonyloxy)phenyl]-1,3,3-trimethyl-3,4-dihydro-1H-quinoxalin-2-one (Compound No. 21-13)<br>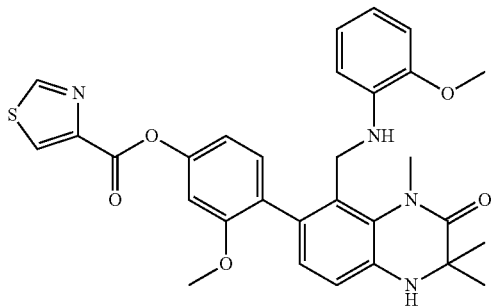 | $^1$H-NMR (400 MHz, CDCl$_3$) δ 1.19 (s, 3H), 1.43 (s, 3H), 3.47 (s, 3H), 3.74 (s, 3 H), 3.77 (s, 1H), 3.79 (s, 3H), 4.15 (br s, 2H), 4.49 (br s, 1H), 6.32 (dd, J = 7.8, 1.4 Hz, 1H), 6.57 (td, J = 7.8, 1.4 Hz, 1H), 6.66 (dd, J = 7.8, 1.4 Hz, 1H), 6.71 (d, J = 8.0 Hz, 1H), 6.72 (td, J = 7.8, 1.4 Hz, 1 H), 6.84 (d, J = 8.0 Hz, 1H), 6.86 (d, J = 2.2 Hz, 1H), 6.92 (dd, J = 8.2, 2.2 Hz, 1H), 7.23 (d, J = 8.2 Hz, 1H), 8.46 (d, J = 2.2 Hz, 1H), 8.95 (d, J = 2.2 Hz, 1 H) |

| | |
|---|---|
| 7-(4-Cyclohexylcarbonyloxy-2-methoxyphenyl)-8-(2-methoxy-phenylaminomethyl)-1,3,3-trimethyl-3,4-dihydro-1H-quinoxalin-2-one (Compound No. 21-14)<br/>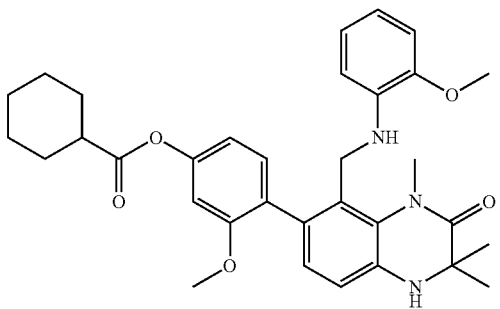 | $^1$H-NMR (400 MHz, CDCl$_3$) δ 1.17 (s, 3H), 1.25-1.39 (m, 4H), 1.42 (s, 3H), 1.58-1.72 (m, 2H), 1.81-1.85 (m, 2H), 2.05-2.09 (m, 2H), 2.52-2.59 (m, 1H), 3.45 (s, 3H), 3.73 (s, 4H), 3.77 (s, 3H), 4.14 (d, J = 3.4 Hz, 2H), 4.48 (br s, 1H), 6.31 (dd, J = 7.8, 1.5 Hz, 1H), 6.55 (td, J = 7.8, 1.5 Hz, 1H), 6.65 (dd, J = 7.8, 1.5 Hz, 1H), 6.65 (d, J = 2.2 Hz, 1H), 6.68 (d, J = 7.9 Hz, 1H), 6.69-6.73 (m, 1H), 6.72 (dd, J = 8.1, 2.2 Hz, 1H), 6.81 (d, J = 7.9 Hz, 1H), 7.16 (d, J = 8.1 Hz, 1H) |
| 7-[2-Methoxy-4-(2-methyl-benzoyloxy)phenyl]-8-(2-methoxy-phenylaminomethyl)-1,3,3-trimethyl-3,4-dihydro-1H-quinoxalin-2-one (Compound No. 21-15)<br/>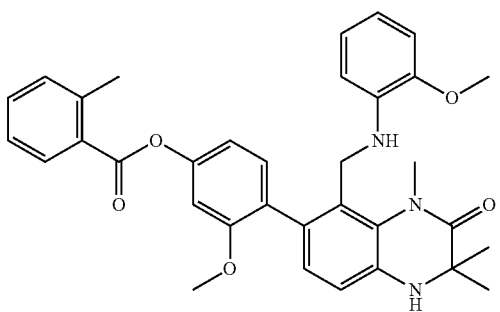 | $^1$H-NMR (400 MHz, CDCl$_3$) δ 1.18 (s, 3H), 1.43 (s, 3H), 2.70 (s, 3H), 3.47 (s, 3H), 3.74 (s, 4H), 3.80 (s, 3H), 4.17 (d, J = 4.9 Hz, 2H), 4.52 (t, J = 4.9 Hz, 1H), 6.34 (dd, J = 7.8, 1.4 Hz, 1H), 6.57 (td, J = 7.8, 1.4 Hz, 1H), 6.67 (dd, J = 7.8, 1.4 Hz, 1H), 6.70 (d, J = 8.0 Hz, 1H), 6.73 (td, J = 7.8, 1.4 Hz, 1H), 6.79 (d, J = 2.1 Hz, 1H), 6.84 (d, J = 8.0 Hz, 1H), 6.86 (dd, J = 8.1, 2.1 Hz, 1H), 7.23 (d, J = 8.1 Hz, 1H), 7.33 (d, J = 7.3 Hz, 1H), 7.34-7.36 (m, 1H), 7.48-7.52 (m, 1H), 8.16-8.18 (m, 1H) |
| 7-(2-Methoxy-4-phenylacetoxy-phenyl)-8-(2-methoxyphenyl-aminomethyl)-1,3,3-trimethyl-3,4-dihydro-1H-quinoxalin-2-one (Compound No. 21-16)<br/>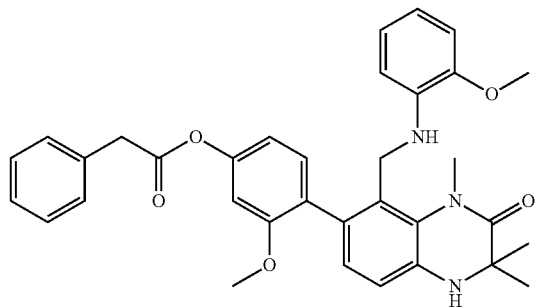 | $^1$H-NMR (400 MHz, CDCl$_3$) δ 1.17 (s, 3H), 1.41 (s, 3H), 3.45 (s, 3H), 3.71 (s, 3H), 3.72 (s, 1H), 3.74 (s, 3H), 3.87 (s, 2H), 4.10-4.13 (m, 2H), 4.46 (br s, 1H), 6.30 (dd, J = 7.8, 1.6 Hz, 1H), 6.55 (td, J = 7.8, 1.6 Hz, 1H), 6.63-6.73 (m, 2H), 6.64 (dd, J = 7.8, 1.6 Hz, 1H), 6.68 (d, J = 7.8 Hz, 1H), 6.71 (dd, J = 8.1, 2.2 Hz, 1H), 6.79 (d, J = 8.1 Hz, 1H), 7.14 (d, J = 8.1 Hz, 1H), 7.32-7.41 (m, 5H) |

| | |
|---|---|
| 7-[2-Methoxy-4-(3-methoxycarbonylbenzoyloxy)phenyl]-8-(2-methoxyphenylaminomethyl)-1,3,3-trimethyl-3,4-dihydro-1H-quinoxalin-2-one (Compound No. 21-17)<br>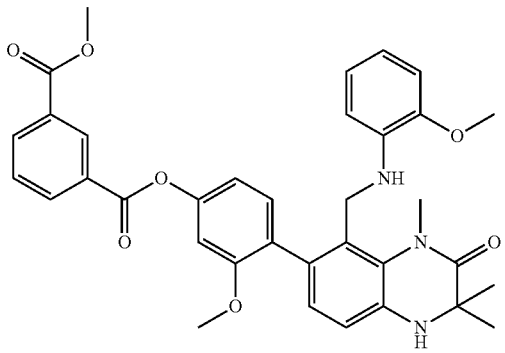 | $^1$H-NMR (400 MHz, CDCl$_3$) δ 1.19 (s, 3H), 1.43 (s, 3 H), 3.47 (s, 3H), 3.75 (s, 4H), 3.80 (s, 3H), 3.98 (s, 3.H), 4.16 (s, 2H), 4.51 (br s, 1H), 6.34 (dd, J = 7.8, 1.5 Hz, 1H), 6.57 (td, J = 7.8, 1.5 Hz, 1H), 6.67 (dd, J = 7.8, 1.5 Hz, 1H), 6.71 (d, J = 8.1 Hz, 1H), 6.74 (td, J = 7.8, 1.5 Hz, 1H), 6.82 (d, J = 2.3 Hz, 1H), 6.85 (d, J = 8.1 Hz, 1H), 6.89 (dd, J = 8.2, 2.3 Hz, 1H), 7.24 (d, J = 8.2 Hz, 1H), 7.63 (t, J = 7.8 Hz, 1 H), 8.32 (dt, J = 7.8, 1.6 Hz, 1H), 8.39 (dt, J = 7.8, 1.6 Hz, 1H), 8.86 (t, J = 1.6 Hz, 1H) |
| 7-[4-(Furan-3-ylcarbonyloxy)-2-methoxyphenyl]-8-(2-methoxyphenylaminomethyl)-1,3,3-trimethyl-3,4-dihydro-1H-quinoxalin-2-one (Compound No. 21-18)<br>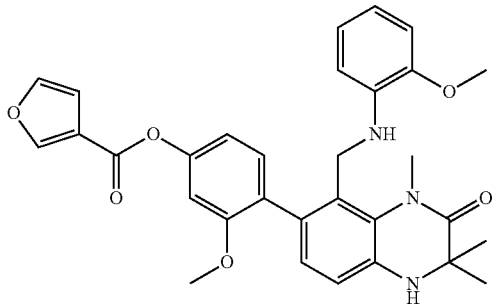 | $^1$H-NMR (400 MHz, CDCl$_3$) δ 1.18 (s, 3H), 1.42 (s, 3 H), 3.46 (s, 3H), 3.74 (s, 4H), 3.79 (s, 3H), 4.15 (s, 2H), 4.50 (br s, 1H), 6.33 (dd, J = 7.7, 1.5 Hz, 1H), 6.56 (td, J = 7.7, 1.5 Hz, 1H), 6.66 (dd, J = 7.7, 1.5 Hz, 1H), 6.70 (d, J = 8.1 Hz, 1H), 6.73 (td, J = 7.7, 1.5 Hz, 1H), 6.77 (d, J = 2.0 Hz, 1H), 6.83 (dd, J = 8.2, 2.0 Hz, 1H), 6.84 (d, J = 8.1 Hz, 1H), 6.88 (dd, J = 1.8, 0.8 Hz, 1H), 7.21 (d, J = 8.2 Hz, 1H), 7.51 (t, J = 1.8 Hz, 1H), 8.21 (dd, J = 1.8, 0.8 Hz, 1H) |
| 7-[4-(3-Acetylbenzoyloxy)-2-methoxyphenyl]-8-(2-methoxyphenylaminomethyl)-1,3,3-trimethyl-3,4-dihydro-1H-quinoxalin-2-one (Compound No. 21-19)<br>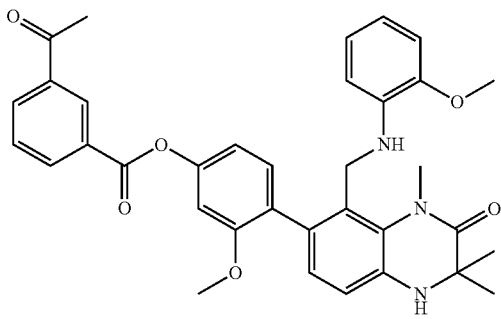 | $^1$H-NMR (500 MHz, CDCl$_3$) δ 1.19 (s, 3H), 1.43 (s, 3H), 2.70 (s, 3H), 3.47 (s, 3 H), 3.75 (s, 4H), 3.81 (s, 3H), 4.16-4.17 (m, 2H), 4.51 (br s, 1H), 6.34 (dd, J = 7.8, 1.4 Hz, 1H), 6.57 (td, J = 7.8, 1.4 Hz, 1H), 6.67 (dd, J = 7.8, 1.4 Hz, 1H), 6.71 (d, J = 8.0 Hz, 1H), 6.74 (td, J = 7.8, 1.4 Hz, 1H), 6.82 (d, J = 2.1 Hz, 1H), 6.85 (d, J = 8.0 Hz, 1 H), 6.89 (dd, J = 8.2, 2.1 Hz, 1H), 7.24 (d, J = 8.2 Hz, 1H), 7.66 (t, J = 7.8 Hz, 1H), 8.25 (dt, J = 7.8, 1.4 Hz, 1H), 8.41 (dt, J = 7.8, 1.4 Hz, 1H), 8.77 (t, J = 1.4 Hz, 1H) |

| Compound | NMR |
|---|---|
| 7-[4-(3-Chlorothiophen-2-ylcarbonyloxy)-2-methoxyphenyl]-8-(2-methoxyphenylamino-methyl)-1,3,3-trimethyl-3,4-dihydro-1H-quinoxalin-2-one (Compound No. 21-20)<br />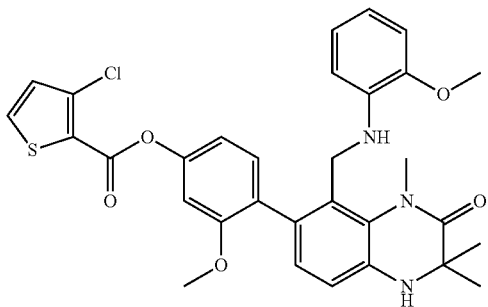 | $^1$H-NMR (400 MHz, CDCl$_3$) δ 1.18 (s, 3H), 1.43 (s, 3H), 3.46 (s, 3H), 3.74 (s, 4 H), 3.80 (s, 3H), 4.15 (br s, 2H), 4.50 (br s, 1H), 6.33 (dd, J = 7.8, 1.5 Hz, 1H), 6.56 (td, J = 7.8, 1.5 Hz, 1H), 6.66 (dd, J = 7.8, 1.5 Hz, 1H), 6.70 (d, J = 7.8 Hz, 1H), 6.73 (td, J = 7.8, 1.5 Hz, 1H), 6.83 (d, J = 7.8 Hz, 1H), 6.83 (d, J = 2.2 Hz, 1H), 6.88 (dd, J = 8.2, 2.2 Hz, 1H), 7.11 (d, J = 5.2 Hz, 1H), 7.21 (d, J = 8.2 Hz, 1H), 7.60 (d, J = 5.2 Hz, 1H) |
| 7-(2-Methoxy-4-methoxycarbonyl-oxyphenyl)-8-(2-methoxy-phenylaminomethyl)-1,3,3-trimethyl-3,4-dihydro-1H-quinoxalin-2-one (Compound No. 21-21)<br />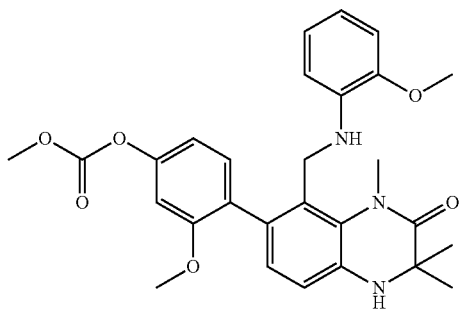 | $^1$H-NMR (500 MHz, CDCl$_3$) δ 1.18 (s, 3H), 1.42 (s, 3 H), 3.46 (s, 3H), 3.72 (s, 3H), 3.73 (s, 1H), 3.77 (s, 3H), 3.92 (s, 3H), 4.14 (br s, 2H), 4.46 (br s, 1H), 6.31 (dd, J = 7.7, 1.4 Hz, 1H), 6.56 (td, J = 7.7, 1.4 Hz, 1H), 6.65 (dd, J = 7.7, 1.4 Hz, 1H), 6.69 (d, J = 8.0 Hz, 1H), 6.72 (td, J = 7.7, 1.4 Hz, 1H), 6.76 (d, J = 2.3 Hz, 1H), 6.81 (d, J = 8.0 Hz, 1H), 6.83 (dd, J = 8.1, 2.3 Hz, 1H), 7.18 (d, J = 8.1 Hz, 1H) |
| 8-(5-Fluoro-2-methylphenyl-aminomethyl)-7-[2-methoxy-4-(2-methylbenzoyloxy)phenyl]-1,3,3-trimethyl-3,4-dihydro-1H-quinoxalin-2-one (Compound No. 21-22)<br />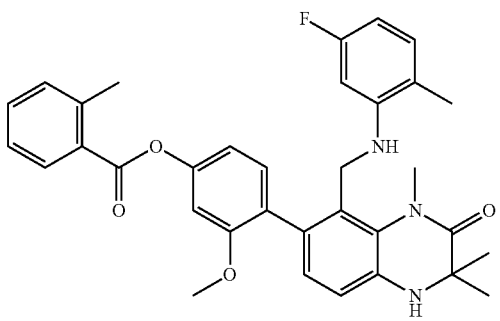 | $^1$H-NMR (400 MHz, CDCl$_3$) δ 1.18 (s, 3H), 1.40 (s, 3 H), 1.87 (s, 3H), 2.70 (s, 3H), 3.43 (s, 3H), 3.77 (s, 1H), 3.80-3.85 (m, 1H), 3.81 (s, 3H), 4.16-4.27 (m, 2 H), 6.03 (dd, J = 11.6, 2.5 Hz, 1H), 6.23 (td, J = 8.3, 2.5 Hz, 1H), 6.72 (d, J = 7.9 Hz, 1H), 6.82-6.86 (m, 1H), 6.84 (d, J = 2.1 Hz, 1H), 6.87 (d, J = 7.9 Hz, 1 H), 6.90 (dd, J = 8.2, 2.1 Hz, 1H), 7.26 (d, J = 8.2 Hz, 1H), 7.33 (d, J = 7.3 Hz, 1H), 7.34 (t, J = 7.3 Hz, 1H), 7.48-7.52 (m, 1H), 8.18 (d, J = 7.3 Hz, 1H) |

7-[2-Methoxy-4-(3-methylfuran-2-ylcarbonyloxy)phenyl]-8-(2-methoxyphenylaminomethyl)-1,3,3-trimethyl-3,4-dihydro-1H-quinoxalin-2-one (Compound No. 21-23)

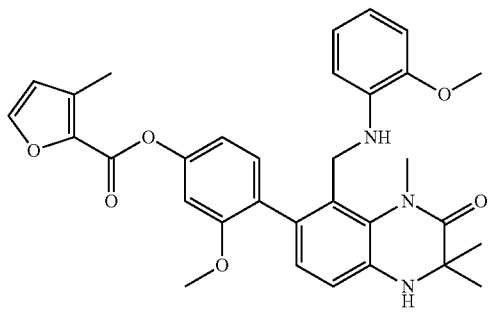

¹H-NMR (400 MHz, CDCl₃)
δ 1.18 (s, 3H), 1.42 (s, 3 H), 2.46 (s, 3H), 3.46 (s, 3H), 3.73 (s, 4H), 3.79 (s, 3H), 4.15 (s, 2H), 4.49 (br s, 1H), 6.32 (dd, J = 7.7, 1.4 Hz, 1H), 6.46 (d, J = 1.4 Hz, 1H), 6.56 (td, J = 7.7, 1.4 Hz, 1H), 6.66 (dd, J = 7.7, 1.4 Hz, 1H), 6.70 (d, J = 8.0 Hz, 1H), 6.72 (td, J = 7.7, 1.4 Hz, 1H), 6.81 (d, J = 2.2 Hz, 1H), 6.84 (d, J = 8.0 Hz, 1H), 6.87 (dd, J = 8.2, 2.2 Hz, 1 H), 7.21 (d, J = 8.2 Hz, 1H), 7.55 (d, J = 1.4 Hz, 1H)

8-(2-Methoxyphenylaminomethyl)-7-[2-methoxy-4-(pyridin-3-ylaminocarbonyloxy)phenyl]-1,3,3-trimethyl-3,4-dihydro-1H-quinoxalin-2-one (Compound No. 21-24)

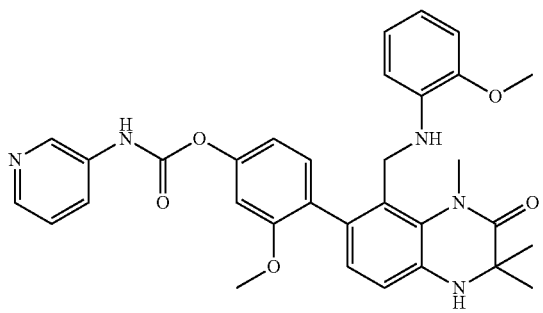

¹H-NMR (500 MHz, CDCl₃)
δ 1.18 (s, 3H), 1.42 (s, 3 H), 3.46 (s, 3H), 3.74 (s, 4H), 3.79 (s, 3H), 4.15 (s, 2H), 4.49 (br s, 1H), 6.33 (dd, J = 7.7, 1.4 Hz, 1H), 6.57 (td, J = 7.7, 1.4 Hz, 1H), 6.66 (dd, J = 7.7, 1.4 Hz, 1H), 6.70 (d, J = 7.9 Hz, 1H), 6.73 (td, J = 7.7, 1.4 Hz, 1H), 6.79 (d, J = 2.1 Hz, 1H), 6.82 (d, J = 7.9 Hz, 1H), 6.84 (dd, J = 8.3, 2.1 Hz, 1H), 7.03 (s, 1H), 7.20 (d, J = 8.3 Hz, 1 H), 7.31 (dd, J = 8.1, 4.7 Hz, 1H), 8.05 (d, J = 8.1 Hz, 1H), 8.38 (dd, J = 4.7, 2.1 Hz, 1H), 8.59 (d, J = 2.1 Hz, 1H)

Example 22

7-[2-Methoxy-4-(2-methylbenzoyloxy)phenyl]-8-(2-methoxy-5-nitrophenoxymethyl)-3,3-dimethyl-3,4-dihydro-1H-quinoxalin-2-one (Compound No. 22)

A mixture of 8-hydroxymethyl-7-[2-methoxy-4-(2-methylbenzoyloxy)phenyl]-3,3-dimethyl-3,4-dihydro-1H-quinoxalin-2-one (Reference Compound No. 23, 40.1 mg, 0.0898 mmol), 2-methoxy-5-nitrophenol (22.8 mg, 0.135 mmol), and tri n-butylphosphine (33.7 μL, 0.135 mmol) was dissolved in anhydrous tetrahydrofuran (1 mL), 1,1'-(azodicarbonyl)dipiperidine (34.0 mg, 0.135 mmol) was added thereto, and then the mixture was stirred at room temperature. After 20 minutes, 2-methoxy-5-nitrophenol (23.1 mg, 0.137 mmol), tri n-butylphosphine (33.7 μL, 0.135 mmol), and 1,1'-(azodicarbonyl)dipiperidine (33.9 mg, 0.134 mmol) were added thereto, and after 80 minutes, 2-methoxy-5-nitrophenol (22.9 mg, 0.135 mmol), tri-n-butylphosphine (33.7 μL, 0.135 mmol), and 1,1'-(azodicarbonyl)dipiperidine (34.0 mg, 0.135 mmol) were added further. The stir was stopped 3 hours later and the reaction mixture was concentrated. The obtained residue was purified by silica gel column chromatography (hexane-ethyl acetate) to give the titled compound (22.1 mg) as a pale yellow amorphous product. (Yield 41%)

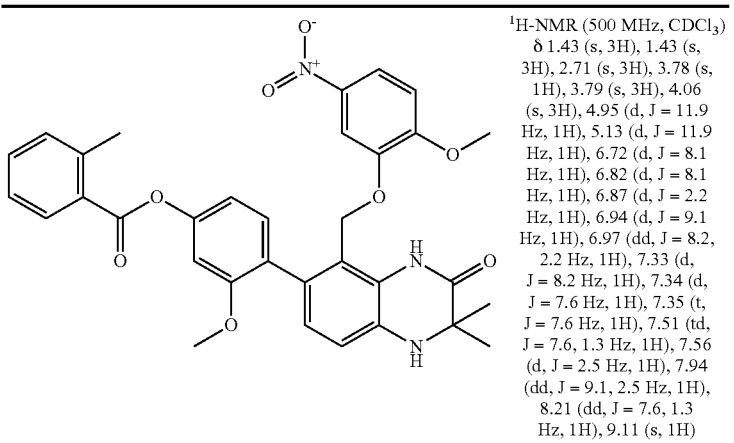

$^1$H-NMR (500 MHz, CDCl$_3$)
δ 1.43 (s, 3H), 1.43 (s, 3H), 2.71 (s, 3H), 3.78 (s, 1H), 3.79 (s, 3H), 4.06 (s, 3H), 4.95 (d, J = 11.9 Hz, 1H), 5.13 (d, J = 11.9 Hz, 1H), 6.72 (d, J = 8.1 Hz, 1H), 6.82 (d, J = 8.1 Hz, 1H), 6.87 (d, J = 2.2 Hz, 1H), 6.94 (d, J = 9.1 Hz, 1H), 6.97 (dd, J = 8.2, 2.2 Hz, 1H), 7.33 (d, J = 8.2 Hz, 1H), 7.34 (d, J = 7.6 Hz, 1H), 7.35 (t, J = 7.6 Hz, 1H), 7.51 (td, J = 7.6, 1.3 Hz, 1H), 7.56 (d, J = 2.5 Hz, 1H), 7.94 (dd, J = 9.1, 2.5 Hz, 1H), 8.21 (dd, J = 7.6, 1.3 Hz, 1H), 9.11 (s, 1H)

Preparation Examples

Hereinafter, typical preparation examples of the present compound are shown.

| 1) Tablet (in 150 mg) | |
|---|---|
| Present compound | 1 mg |
| Lactose | 100 mg |
| Cornstarch | 40 mg |
| Carboxymethyl cellulose calcium | 4.5 mg |
| Hydroxypropyl cellulose | 4 mg |
| Magnesium stearate | 0.5 mg |

A tablet of the above-mentioned formulation is coated with 3 mg of a coating agent (for example, a conventional coating agent such as hydroxypropylmethyl cellulose, macrogol or a silicone resin), whereby an objective tablet can be obtained. In addition, a desired tablet can be obtained by appropriately changing the kind and/or amount of the present compound and additives.

| 2) Capsule (in 150 mg) | |
|---|---|
| Present compound | 5 mg |
| Lactose | 135 mg |
| Carboxymethyl cellulose calcium | 4.5 mg |
| Hydroxypropyl cellulose | 4 mg |
| Magnesium stearate | 1.5 mg |

A desired capsule can be obtained by appropriately changing the kind and/or amount of the present compound and additives.

| 3) Eye drop (in 100 mL) | |
|---|---|
| Present compound | 100 mg |
| Sodium chloride | 900 mg |
| Polysorbate 80 | 500 mg |
| Sodium hydroxide | q.s. |
| Hydrochloric acid | q.s. |
| Sterile purified water | q.s. |

A desired eye drop can be obtained by appropriately changing the kind and/or amount of the present compound and additives.

Pharmacological Test

1. Evaluation Test for Binding Activity to Glucocorticoid Receptor (Hereinafter Referred to as "GR")

In order to evaluate a binding activity to GR, receptor competitor assay was carried out by a fluorescence polarization method. In the assay, a GR competitor assay kit (manufactured by Invitrogen, cat No. P2816) was used, and a procedure was carried out according to the protocol attached to the kit. Hereinafter, the specific method will be described.

(Preparation of Reagents)

GR screening buffer: A buffer containing 10 mM potassium phosphate (pH 7.4), 20 mM sodium molybdate (Na$_2$MoO$_4$), 0.1 mM ethylene diamine tetraacetic acid (EDTA), 5 mM dithiothreitol (DTT), 0.1 mM stabilizing peptide and 2% dimethylsulfoxide was prepared.

4×GS1 solution: Fluormone™ GS1, which is a fluorescent glucocorticoid ligand, was diluted with GR screening buffer, whereby a 4 nM solution was prepared.

4×GR solution: Recombinant human GR was diluted with GR screening buffer, whereby a 16 nM solution was prepared.

(Preparation of Test Compound Solution)

After a test compound was dissolved in dimethylsulfoxide, the resulting solution was diluted with GR screening buffer, whereby a 20 μM test compound solution was prepared.

(Test Method and Measurement Method)

1) The test compound solution was added in an amount of 25 μL into each well of a 96-well plate, and then, 4×GS1 solution and 4×GR solution were added in an amount of 12.5 μL into each well, respectively.

2) The plate was incubated in a dark place at room temperature for 2 to 4 hours.

3) By using a multimode plate reader, Analyst™ HT (manufactured by LJL Biosystems), fluorescence polarization of each well was measured. As the blank, a well containing GR screening buffer in place of the test compound and 4×GS1 solution was used.

4) The same procedure as that in the above 1) to 3) was carried out except that GR screening buffer was used in place of the test compound solution, and the obtained result was taken as the negative control.

5) The same procedure as that in the above 1) to 3) was carried out except that 2 mM dexamethasone was used in place of the test compound solution, and the obtained result was taken as the positive control.

(Calculation Equation of GR Binding Ratio)

A GR binding ratio (%) was calculated from the following equation.

GR binding ratio(%)=100×[1−(fluorescence polarization of test compound solution−fluorescence polarization of positive control solution)/(fluorescence polarization of negative control solution−fluorescence polarization of positive control solution)]

(Test Results and Discussion)

As an example of the test results, the GR binding ratios (%) of the test compounds (Compound 1-4, Compound 2-2, Compound 2-9, Compound 2-16, Compound 3-7, Compound 3-10, Compound 3-15, Compound 3-16, Compound 3-17, Compound 4-5, Compound 4-7, Compound 4-10, Compound 4-11, Compound 5-1, Compound 5-9, Compound 5-14, Compound 5-18, Compound 5-19, Compound 5-21, Compound 5-22, Compound 5-24, Compound 6-4, Compound 6-8, Compound 6-10, Compound 6-12, Compound 6-15, Compound 6-19, Compound 6-23, Compound 6-27, Compound 6-32, Compound 6-38, Compound 8-2, Compound 9-1, Compound 11, Compound 13-2, Compound 14-2, Compound 14-4, Compound 14-11, Compound 14-21, Compound 14-22, Compound 14-30, Compound 14-33, Compound 14-35, Compound 14-36, Compound 14-37, Compound 14-44, Compound 15-1, Compound 15-2, Compound 15-4, Compound 15-6, Compound 15-9, Compound 15-11, Compound 15-13, Compound 15-17, Compound 15-22, Compound 15-24, Compound 16-3, Compound 17-5, Compound 17-16, Compound 18-1, Compound 18-2, Compound 21-3, Compound 21-5, Compound 21-12, Compound 21-13, Compound 21-22, Compound 22) are shown in Table I.

TABLE I

| Test compound | GR Binding ratio (%) |
| --- | --- |
| Compound 1-4 | 91 |
| Compound 2-2 | 99 |
| Compound 2-9 | 99 |
| Compound 2-16 | 100 |
| Compound 3-7 | 100 |
| Compound 3-10 | 100 |
| Compound 3-15 | 100 |
| Compound 3-16 | 100 |
| Compound 3-17 | 100 |
| Compound 4-5 | 100 |
| Compound 4-7 | 100 |
| Compound 4-10 | 100 |
| Compound 4-11 | 100 |
| Compound 5-1 | 100 |
| Compound 5-9 | 100 |
| Compound 5-14 | 100 |
| Compound 5-18 | 100 |
| Compound 5-19 | 100 |
| Compound 5-21 | 100 |
| Compound 5-22 | 99 |
| Compound 5-24 | 100 |
| Compound 6-4 | 98 |
| Compound 6-8 | 98 |
| Compound 6-10 | 100 |
| Compound 6-12 | 100 |
| Compound 6-15 | 100 |
| Compound 6-19 | 100 |
| Compound 6-23 | 98 |
| Compound 6-27 | 100 |
| Compound 6-32 | 89 |
| Compound 6-38 | 100 |
| Compound 8-2 | 100 |
| Compound 9-1 | 100 |
| Compound 11 | 100 |
| Compound 13-2 | 91 |
| Compound 14-2 | 100 |
| Compound 14-4 | 100 |
| Compound 14-11 | 100 |
| Compound 14-21 | 100 |
| Compound 14-22 | 100 |
| Compound 14-30 | 100 |
| Compound 14-33 | 100 |
| Compound 14-35 | 93 |
| Compound 14-36 | 88 |
| Compound 14-37 | 93 |
| Compound 14-44 | 100 |
| Compound 15-1 | 100 |
| Compound 15-2 | 100 |
| Compound 15-4 | 98 |
| Compound 15-6 | 100 |
| Compound 15-9 | 100 |
| Compound 15-11 | 100 |
| Compound 15-13 | 100 |
| Compound 15-17 | 95 |
| Compound 15-22 | 100 |
| Compound 15-24 | 94 |
| Compound 16-3 | 86 |
| Compound 17-5 | 91 |
| Compound 17-16 | 88 |
| Compound 18-1 | 100 |
| Compound 18-2 | 99 |
| Compound 21-3 | 100 |
| Compound 21-5 | 98 |
| Compound 21-12 | 100 |
| Compound 21-13 | 94 |
| Compound 21-22 | 100 |
| Compound 22 | 100 |

As is apparent from Table I, the present compound showed an excellent GR binding activity. Accordingly, the present compound can be used as a GR modulator, and is useful for a preventive or therapeutic agent particularly for GR-related diseases, that is, metabolic disorders, inflammatory diseases, autoimmune diseases, allergic diseases, central nervous system diseases, cardiovascular diseases, homeostasis-related diseases, glaucoma and the like.

INDUSTRIAL APPLICABILITY 1,2,3,4-tetrahydroquinoxaline derivative or the salt according to the present invention has a binding activity to GR and is useful for GR modulator of nonsteroidal compound.

The invention claimed is:

1. A compound represented by the following formula (1) or a salt thereof:

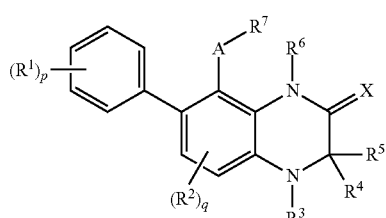

(1)

wherein $R^1$ represents a halogen atom, a lower alkyl group which may have at least a substituent, a lower cycloalkyl group which may have at least a substituent, an aryl group which may have at least a substituent, a heterocyclic group which may have at least a substituent, a hydroxy group, an ester of a hydroxy group, a lower alkoxy group which may have at least a substituent, a lower cycloalkyloxy group which may have at least a substituent, an aryloxy group which may have at least a substituent, a heterocyclic oxy group which may have at least a substituent, a mercapto group, an ester of a mercapto group, a lower alkylthio group which may have at least a substituent, a lower cycloalkylthio group which may have at least a substituent, an arylthio group which may have at least a substituent, a heterocyclic thio group which may have at least a substituent, an amino group, a lower alkylamino group which may have at least a substituent, a lower cycloalkylamino group which may have at least a substituent, an arylamino group which may have at least a substituent, a heterocyclic amino group which may have at least a substituent, an amide of an amino group, an amide of a lower alkylamino group which may have at least a substituent, an amide of a lower cycloalkylamino group which may have at least a substituent, an amide of an arylamino group which may have at least a substituent, an amide of a heterocyclic amino group which may have at least a substituent, a formyl group, a lower alkylcarbonyl group which may have at least a substituent, a lower cycloalkylcarbonyl group which may have at least a substituent, an arylcarbonyl group which may have at least a substituent, a heterocyclic carbonyl group which may have at least a substituent, a carboxy group, an ester of a carboxy group, an amide of a carboxy group, a lower alkylsulfonyl group which may have at least a substituent, a lower cycloalkylsulfonyl group which may have at least a substituent, an arylsulfonyl group which may have at least a substituent, a heterocyclic sulfonyl group which may have at least a substituent, a sulfonic acid group, an ester of a sulfonic acid group, an amide of a sulfonic acid group, a nitro group or a cyano group;

p represents an integer of 0 to 5;

in the case where p is 2 to 5, each $R^1$ may be the same or different;

$R^2$ represents a halogen atom, a lower alkyl group which may have at least a substituent, a hydroxy group, an ester of a hydroxy group or a lower alkoxy group which may have at least a substituent;

q represents an integer of 0 to 2;

in the case where q is 2, each $R^2$ may be the same or different;

$R^3$ represents a hydrogen atom, a lower alkyl group which may have at least a substituent, a lower alkenyl group which may have at least a substituent, a lower alkylcarbonyl group which may have at least a substituent, a lower alkenylcarbonyl group which may have at least a substituent or an arylcarbonyl group which may have at least a substituent;

$R^4$ and $R^5$ are the same or different and represent a halogen atom, a lower alkyl group which may have at least a substituent, a lower alkenyl group which may have at least a substituent, a lower alkynyl group which may have at least a substituent, a lower cycloalkyl group which may have at least a substituent, an aryl group which may have at least a substituent or a heterocyclic group which may have at least a substituent;

$R^4$ and $R^5$ may be combined together to form a 3- to 8-membered lower cycloalkane ring which may have at least a substituent;

$R^6$ represents a hydrogen atom, a lower alkyl group which may have at least a substituent, a lower alkenyl group which may have at least a substituent, a lower alkynyl group which may have at least a substituent, a lower cycloalkyl group which may have at least a substituent, an aryl group which may have at least a substituent or a heterocyclic group which may have at least a substituent;

A represents a lower alkylene group which may have at least a substituent;

$R^7$ represents $OR^8$, $NR^8R^9$, $SR^8$, $S(O)R^8$ or $S(O)_2R^8$;

$R^8$ and $R^9$ are the same or different and represent a hydrogen atom, a lower alkyl group which may have at least a substituent, a lower alkenyl group which may have at least a substituent, a lower alkynyl group which may have at least a substituent, a lower cycloalkyl group which may have at least a substituent, an aryl group which may have at least a substituent, a heterocyclic group which may have at least a substituent, a formyl group, a lower alkylcarbonyl group which may have at least a substituent, a lower alkenylcarbonyl group which may have at least a substituent, a lower alkynylcarbonyl group which may have at least a substituent, a lower cycloalkylcarbonyl group which may have at least a substituent, an arylcarbonyl group which may have at least a substituent, a heterocyclic carbonyl group which may have at least a substituent, a carboxy group, a lower alkoxycarbonyl group which may have at least a substituent, a lower alkenyloxycarbonyl group which may have at least a substituent, a lower alkynyloxycarbonyl group which may have at least a substituent, a lower cycloalkyloxycarbonyl group which may have at least a substituent, an aryloxycarbonyl group which may have at least a substituent, a heterocyclic oxycarbonyl group which may have at least a substituent, a lower alkylsulfonyl group which may have at least a substituent, a lower alkenylsulfonyl group which may have at least a substituent, a lower alkynylsulfonyl group which may have at least a substituent, a lower cycloalkylsulfonyl group which may have at least a substituent, an arylsulfonyl group which may have at least a substituent, a heterocyclic sulfonyl group which may have at least a substituent, an aminocarbonyl group, a lower alkylaminocarbonyl group which may have at least a substituent, a lower alkenylaminocarbonyl group which may have at least a substituent, a lower alkynylaminocarbonyl group which may have at least a substituent, a lower cycloalkylaminocarbonyl group which may have at least a substituent, an arylaminocarbonyl group which may have at least a substituent or a heterocyclic aminocarbonyl group which may have at least a substituent;

in the case where $R^7$ is $NR^8R^9$, $R^8$ and $R^9$ may be combined together to form a 3- to 8-membered nitrogen-containing heterocyclic ring which may have at least a substituent; and X represents O or S.

2. The compound or a salt thereof according to claim 1, wherein in the formula (1), $R^1$ represents a halogen atom, a lower alkyl group, a lower cycloalkyl group, an aryl group, a heterocyclic group, a hydroxy group, an ester of a hydroxy group, a lower alkoxy group, a lower cycloalkyloxy group, an aryloxy group, a heterocyclic oxy group, a mercapto group, an ester of a mercapto group, a lower alkylthio group, a lower cycloalkylthio group, an arylthio group, a heterocyclic thio group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxy group, an ester of a carboxy group, an amide of a carboxy group, a lower alkylsulfonyl group, a lower cycloalkylsulfonyl group, an arylsulfonyl group, a heterocyclic sulfonyl group, a sulfonic acid group, an ester of a sulfonic acid group, an amide of a sulfonic acid group, a nitro group or a cyano group;

in the case where $R^1$ is a lower alkyl group, a lower alkoxy group, a lower alkylthio group, a lower alkylamino group, an amide of a lower alkylamino group, a lower alkylcarbonyl group or a lower alkylsulfonyl group, the lower alkyl group, lower alkoxy group, lower alkylthio group, lower alkylamino group, amide of a lower alkylamino group, lower alkylcarbonyl group or lower alkylsulfonyl group may have one or a plurality of groups selected from a halogen atom, a lower cycloalkyl group, an aryl group, a heterocyclic group, a hydroxy group, an ester of a hydroxy group, a lower alkoxy group, a lower alkoxy group substituted with at least a halogen atom, a lower cycloalkyloxy group, an aryloxy group, a heterocyclic oxy group, a lower alkylthio group, a lower cycloalkylthio group, an arylthio group, a heterocyclic thio group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxy group, an ester of a carboxy group, an amide of a carboxy group, a lower alkylsulfonyl group, a lower cycloalkylsulfonyl group, an arylsulfonyl group, a heterocyclic sulfonyl group, a sulfonic acid group, an ester of a sulfonic acid group, an amide of a sulfonic acid group, a nitro group and a cyano group as substituents;

in the case where $R^1$ is a lower cycloalkyl group, an aryl group, a heterocyclic group, a lower cycloalkyloxy group, an aryloxy group, a heterocyclic oxy group, a lower cycloalkylthio group, an arylthio group, a heterocyclic thio group, a lower cycloalkylamino group, an arylamino group, a heterocyclic amino group, an amide of a lower cycloalkylamino group, an amide of an arylamino group, an amide of a heterocyclic amino group, a lower cycloalkylcarbonyl group, an arylcarbonyl group, a heterocyclic carbonyl group, a lower cycloalkylsulfonyl group, an arylsulfonyl group or a heterocyclic sulfonyl group, the lower cycloalkyl group, aryl group, heterocyclic group, lower cycloalkyloxy group, aryloxy group, heterocyclic oxy group, lower cycloalkylthio group, arylthio group, heterocyclic thio group, lower cycloalkylamino group, arylamino group, heterocyclic amino group, amide of a lower cycloalkylamino group, amide of an arylamino group, amide of a heterocyclic amino group, lower cycloalkylcarbonyl group, arylcarbonyl group, heterocyclic carbonyl group, lower cycloalkylsulfonyl group, arylsulfonyl group or heterocyclic sulfonyl group may have one or a plurality of groups selected from a halogen atom, a lower alkyl group, a lower alkyl group substituted with at least a halogen atom, a hydroxy group, an ester of a hydroxy group, a lower alkoxy group, a lower alkoxy group substituted with at least a halogen atom, a lower alkylthio group, an amino group, a lower alkylamino group, an amide of an amino group, an amide of a lower alkylamino group, a lower alkylcarbonyl group, a carboxy group, an ester of a carboxy group, an amide of a carboxy group, a lower alkylsulfonyl group, a sulfonic acid group, an ester of a sulfonic acid group, an amide of a sulfonic acid group, a nitro group and a cyano group as substituents;

p represents an integer of 0 to 3;

in the case where p is 2 or 3, each $R^1$ may be the same or different;

$R^2$ represents a halogen atom, a lower alkyl group, a hydroxy group or a lower alkoxy group;

q represents an integer of 0 to 2;

in the case where q is 2, each $R^2$ may be the same or different;

$R^3$ represents a hydrogen atom, a lower alkyl group, a lower alkenyl group, a lower alkylcarbonyl group, a lower alkenylcarbonyl group or an arylcarbonyl group;

in the case where $R^3$ is a lower alkyl group or a lower alkylcarbonyl group, the lower alkyl group or lower alkylcarbonyl group may have one or a plurality of substituents selected from the group consisting of a halogen atom and an aryl group;

in the case where $R^3$ is an arylcarbonyl group, the arylcarbonyl group may have one or a plurality of substituents selected from the group consisting of a halogen atom, a lower alkyl group, a lower alkyl group substituted with at least a halogen atom, a lower alkoxy group and a lower alkoxy group substituted with at least a halogen atom;

$R^4$ and $R^5$ are the same or different and represent a halogen atom, a lower alkyl group, a lower cycloalkyl group, aryl or a heterocyclic group;

in the case where $R^4$ or $R^5$ is a lower alkyl group, the lower alkyl group may have one or a plurality of substituents selected from the group consisting of a halogen atom, a lower cycloalkyl group, an aryl group, a heterocyclic group, a hydroxy group, an ester of a hydroxy group, a lower alkoxy group, a lower alkoxy group substituted with at least a halogen atom, a lower cycloalkyloxy group, an aryloxy group, a heterocyclic oxy group, a lower alkylthio group, a lower cycloalkylthio group, an arylthio group, a heterocyclic thio group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxy group, an ester of a carboxy group, an amide of a carboxy group, a nitro group and a cyano group;

in the case where $R^4$ or $R^5$ is a lower cycloalkyl group, aryl or a heterocyclic group, the lower cycloalkyl group, aryl or heterocyclic group may have one or a plurality of substituents selected from the group consisting of a halogen atom, a lower alkyl group, a lower alkyl group substituted with at least a halogen atom, a hydroxy group, an ester of a hydroxy group, a lower alkoxy group, a lower alkoxy group substituted with at least a halogen atom, a lower alkylthio group, an amino group, a lower alkylamino group, an amide of an amino group, an amide of a lower alkylamino group, a lower alkylcarbonyl group, a carboxy group, an ester of a carboxy group, an amide of a carboxy group, a lower alkylsulfonyl group, a sulfonic acid group, an ester of a sulfonic acid group, an amide of a sulfonic acid group, a nitro group and a cyano group;

$R^4$ and $R^5$ may be combined together to form a 3- to 8-membered lower cycloalkane ring;

$R^6$ represents a hydrogen atom, a lower alkyl group, a lower alkenyl group, a lower alkynyl group or a lower cycloalkyl group;

in the case where $R^6$ is a lower alkyl group, a lower alkenyl group, a lower alkynyl group or a lower cycloalkyl group, the lower alkyl group, lower alkenyl group, lower alkynyl group or lower cycloalkyl group may have one or a plurality of substituents selected from the group consisting of a halogen atom and an aryl group as substituents;

A represents a lower alkylene group which may be substituted with at least a hydroxy group or a halogen atom;

$R^7$ represents $OR^8$, $NR^8R^9$ or $SR^8$;

$R^8$ and $R^9$ may be the same or different and represent a hydrogen atom, a lower alkyl group, a lower alkenyl group, a lower alkynyl group, a lower cycloalkyl group, an aryl group, a heterocyclic group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, a lower alkoxycarbonyl group, a lower alkenyloxycarbonyl group, a lower alkynyloxycarbonyl group, a lower cycloalkyloxycarbonyl group, an aryloxycarbonyl group, a heterocyclic oxycarbonyl group, a lower alkylsulfonyl group, a lower alkenylsulfonyl group, a lower alkynylsulfonyl group, a lower cycloalkylsulfonyl group, an arylsulfonyl group, a heterocyclic sulfonyl group, an aminocarbonyl group, a lower alkylaminocarbonyl group, a lower alkenylaminocarbonyl group, a lower alkynylaminocarbonyl group, a lower cycloalkylaminocarbonyl group, an arylaminocarbonyl group or a heterocyclic aminocarbonyl group;

in the case where $R^8$ or $R^9$ is a lower alkyl group, a lower alkenyl group, a lower alkynyl group, a lower alkylcarbonyl group, a lower alkenylcarbonyl group, a lower alkynylcarbonyl group, a lower alkoxycarbonyl group, a lower alkenyloxycarbonyl group, a lower alkynyloxycarbonyl group, a lower alkylsulfonyl group, a lower alkenylsulfonyl group, a lower alkynylsulfonyl group, a lower alkylaminocarbonyl group, a lower alkenylaminocarbonyl group or a lower alkynylaminocarbonyl group, the lower alkyl group, lower alkenyl group, lower alkynyl group, lower alkylcarbonyl group, lower alkenylcarbonyl group, lower alkynylcarbonyl group, lower alkoxycarbonyl group, lower alkenyloxycarbonyl group, lower alkynyloxycarbonyl group, lower alkylsulfonyl group, lower alkenylsulfonyl group, lower alkynylsulfonyl group, lower alkylaminocarbonyl group, lower alkenylaminocarbonyl group or lower alkynylaminocarbonyl group may have one or a plurality of substituents selected from the group consisting of a halogen atom, a lower cycloalkyl group, an aryl group, a heterocyclic group, a hydroxy group, an ester of a hydroxy group, a lower alkoxy group, a lower alkoxy group substituted with at least a halogen atom, a lower cycloalkyloxy group, an aryloxy group, a heterocyclic oxy group, a lower alkylthio group, a lower cycloalkylthio group, an arylthio group, a heterocyclic thio group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxy group, an ester of a carboxy group, an amide of a carboxy group, a lower alkylsulfonyl group, a lower cycloalkylsulfonyl group, an arylsulfonyl group, a heterocyclic sulfonyl group, a sulfonic acid group, an ester of a sulfonic acid group, an amide of a sulfonic acid group, a nitro group and a cyano group;

in the case where $R^8$ or $R^9$ is a lower cycloalkyl group, an aryl group, a heterocyclic group, a lower cycloalkylcarbonyl group, an arylcarbonyl group, a heterocyclic carbonyl group, a lower cycloalkyloxycarbonyl group, an aryloxycarbonyl group, a heterocyclic oxycarbonyl group, a lower cycloalkylsulfonyl group, an arylsulfonyl group, a heterocyclic sulfonyl group, a lower cycloalkylaminocarbonyl group, an arylaminocarbonyl group or a heterocyclic aminocarbonyl group, the lower cycloalkyl group, aryl group, heterocyclic group, lower cycloalkylcarbonyl group, arylcarbonyl group, heterocyclic carbonyl group, lower cycloalkyloxycarbonyl group, aryloxycarbonyl group, heterocyclic oxycarbonyl group, lower cycloalkylsulfonyl group, arylsulfonyl group, heterocyclic sulfonyl group, lower cycloalkylaminocarbonyl group, arylaminocarbonyl group or heterocyclic aminocarbonyl group may have one or a plurality of substituents selected from the group consisting of a halogen atom, a lower alkyl group, a lower alkyl group substituted with at least a halogen atom, a lower alkyl group substituted with at least a hydroxy group, a lower alkenyl group, a lower alkynyl group, a lower cycloalkyl group, an aryl group, a heterocyclic group, a hydroxy group, an ester of a hydroxy group, a lower alkoxy group, a lower alkoxy group substituted with at least a halogen atom, a lower alkenyloxy group, a lower alkynyloxy group, a lower cycloalkyloxy group, an aryloxy group, a heterocyclic oxy group, a lower alkylthio group, a lower cycloalkylthio group, an arylthio group, a heterocyclic thio group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxy group, an ester of a carboxy group, an amide of a carboxy group, a lower alkylsulfonyl group, a lower cycloalkylsulfonyl group, an arylsulfonyl group, a heterocyclic sulfonyl group, a sulfonic acid group, an ester of a sulfonic acid group, an amide of a sulfonic acid group, a nitro group and a cyano group;

in the case where $R^7$ is $NR^8R^9$, $R^8$ and $R^9$ may be combined together to form a 5- or 6-membered nitrogen-containing heterocyclic ring; and X represents O or S.

3. The compound or a salt thereof according to claim 1, wherein in the formula (1), $R^1$ represents a halogen atom, a lower alkyl group, a hydroxy group, an ester of a hydroxy group, a lower alkoxy group, a lower alkylthio group, an amino group, a lower alkylamino group, an amide of an amino group, an amide of a lower alkylamino group, a lower alkylcarbonyl group, a carboxy group, an ester of a carboxy group, an amide of a carboxy group, a lower alkylsulfonyl group, a nitro group or a cyano group;

in the case where $R^1$ is a lower alkyl group, a lower alkoxy group, a lower alkylthio group, a lower alkylamino group, an amide of a lower alkylamino group, a lower alkylcarbonyl group or a lower alkylsulfonyl group, the lower alkyl group, lower alkoxy group, lower alkylthio group, lower alkylamino group, amide of a lower alkylamino group, lower alkylcarbonyl group or lower alkylsulfonyl group may have one or a plurality of substituents selected from the group consisting of a halogen atom, a lower cycloalkyl group, an aryl group, a heterocyclic group, a hydroxy group, an ester of a hydroxy group, a lower alkoxy group, a lower alkoxy group substituted with at least a halogen atom, a lower cycloalkyloxy group, an aryloxy group, a heterocyclic oxy group, a lower alkylthio group, a lower cycloalkylthio group, an arylthio group, a heterocyclic thio group, an amino group, a lower alkylamino group, a lower cycloalkylamino group, an arylamino group, a heterocyclic amino group, an amide of an amino group, an amide of a lower alkylamino group, an amide of a lower cycloalkylamino group, an amide of an arylamino group, an amide of a heterocyclic amino group, a lower alkylcarbonyl group, a lower cycloalkylcarbonyl group, an arylcarbonyl group, a heterocyclic carbonyl group, a carboxy group, an ester of a carboxy group, an amide of a carboxy group, a lower alkylsulfonyl group, a lower cycloalkylsulfonyl group, an arylsulfonyl group, a heterocyclic sulfonyl group, a sulfonic acid group, an ester of a sulfonic acid group, an amide of a sulfonic acid group, a nitro group and a cyano group;

p represents an integer of 0 to 3;

in the case where p is 2 or 3, each $R^1$ may be the same or different;

q represents 0;

$R^3$ represents a hydrogen atom, a lower alkyl group, a lower alkenyl group, a lower alkylcarbonyl group, a lower alkenylcarbonyl group or an arylcarbonyl group;

in the case where $R^3$ is a lower alkyl group, the lower alkyl group may have one or a plurality of aryl groups as substituents;

in the case where $R^3$ is an arylcarbonyl group, the arylcarbonyl group may have one or a plurality of substituents selected from the group consisting of a halogen atom and a lower alkyl group;

$R^4$ and $R^5$ are the same or different and represent a halogen atom, a lower alkyl group, a lower cycloalkyl group, aryl or a heterocyclic group;

in the case where $R^4$ or $R^5$ is a lower alkyl group, the lower alkyl group may have one or a plurality of substituents selected from the group consisting of a halogen atom, a hydroxy group, an ester of a hydroxy group, a lower alkoxy group, a lower alkoxy group substituted with at least a halogen atom, a lower alkylthio group, an amino group, a lower alkylamino group, an amide of an amino group, an amide of a lower alkylamino group, a lower alkylcarbonyl group, a carboxy group, an ester of a carboxy group, an amide of a carboxy group, a nitro group and a cyano group;

in the case where $R^4$ or $R^5$ is a lower cycloalkyl group, aryl or a heterocyclic group, the lower cycloalkyl group, aryl or heterocyclic group may have one or a plurality of substituents selected from the group consisting of a halogen atom, a lower alkyl group, a lower alkyl group substituted with at least a halogen atom, a hydroxy group, an ester of a hydroxy group, a lower alkoxy group, a lower alkoxy group substituted with at least a halogen atom, a lower alkylthio group, an amino group, a lower alkylamino group, an amide of an amino group, an amide of a lower alkylamino group, a lower alkylcarbonyl group, a carboxy group, an ester of a carboxy group, an amide of a carboxy group, a lower alkylsulfonyl group, a nitro group and a cyano group;

$R^4$ and $R^5$ may be combined together to form a 3- to 8-membered lower cycloalkane ring;

$R^6$ represents a hydrogen atom, a lower alkyl group, a lower alkenyl group, a lower alkynyl group or a lower cycloalkyl group;

in the case where $R^6$ is a lower alkyl group, a lower alkenyl group, a lower alkynyl group or a lower cycloalkyl group, the lower alkyl group, lower alkenyl group, lower alkynyl group or lower cycloalkyl group may have one or a plurality of substituents selected from the group consisting of a halogen atom and an aryl group;

A represents a lower alkylene group;

$R^7$ represents $OR^8$, $NR^8R^9$ or $SR^8$;

$R^8$ and $R^9$ are the same or different and represent a hydrogen atom, a lower alkyl group, a lower alkenyl group, a lower alkynyl group, a lower cycloalkyl group, an aryl group, a heterocyclic group, a formyl group, a lower alkylcarbonyl group, a lower alkenylcarbonyl group, a lower alkynylcarbonyl group, a lower cycloalkylcarbonyl group, an arylcarbonyl group, a heterocyclic carbonyl group, a carboxy group, a lower alkoxycarbonyl group, a lower alkenyloxycarbonyl group, a lower alkynyloxycarbonyl group, a lower cycloalkyloxycarbonyl group, an aryloxycarbonyl group, a heterocyclic oxycarbonyl group, a lower alkylsulfonyl group, a lower alkenylsulfonyl group, a lower alkynylsulfonyl group, a lower cycloalkylsulfonyl group, an arylsulfonyl group, a heterocyclic sulfonyl group, an aminocarbonyl group, a lower alkylaminocarbonyl group, a lower alkenylaminocarbonyl group, a lower alkynylaminocarbonyl group, a lower cycloalkylaminocarbonyl group, an arylaminocarbonyl group or a heterocyclic aminocarbonyl group;

in the case where $R^8$ or $R^9$ is a lower alkyl group, a lower alkenyl group, a lower alkynyl group, a lower alkylcarbonyl group, a lower alkenylcarbonyl group, a lower alkynylcarbonyl group, a lower alkoxycarbonyl group, a lower alkenyloxycarbonyl group, a lower alkynyloxycarbonyl group, a lower alkylsulfonyl group, a lower alkenylsulfonyl group, a lower alkynylsulfonyl group, a lower alkylaminocarbonyl group, a lower alkenylaminocarbonyl group or a lower alkynylaminocarbonyl group, the lower alkyl group, lower alkenyl group, lower alkynyl group, lower alkylcarbonyl group, lower alkenylcarbonyl group, lower alkynylcarbonyl group, lower alkoxycarbonyl group, lower alkenyloxycarbonyl group, lower alkynyloxycarbonyl group, lower alkylsulfonyl group, lower alkenylsulfonyl group, lower alkynylsulfonyl group, lower alkylaminocarbonyl group, lower alkenylaminocarbonyl group or lower alkynylaminocarbonyl group may have one or a plurality of substituents selected from the group consisting of a halogen atom, a lower cycloalkyl group, an aryl group, a heterocyclic group, a hydroxy group, an ester of a hydroxy group, a lower alkoxy group, a lower alkoxy group substituted with at least a halogen atom, a lower alkylthio group, an amino group, a lower alkylamino group, an amide of an amino group, an amide of a lower alkylamino group, a lower alkylcarbonyl group, a carboxy group, an ester of a carboxy group, an amide of a carboxy group, a lower alkylsulfonyl group, a nitro group and a cyano group;

in the case where $R^8$ or $R^9$ is a lower cycloalkyl group, an aryl group, a heterocyclic group, a lower cycloalkylcarbonyl group, an arylcarbonyl group, a heterocyclic carbonyl group, a lower cycloalkyloxycarbonyl group, an aryloxycarbonyl group, a heterocyclic oxycarbonyl group, a lower cycloalkylsulfonyl group, an arylsulfonyl group, a heterocyclic sulfonyl group, a lower cycloalkylaminocarbonyl group, an arylaminocarbonyl group or a heterocyclic aminocarbonyl group, the lower cycloalkyl group, aryl group, heterocyclic group, lower cycloalkylcarbonyl group, arylcarbonyl group, heterocyclic carbonyl group, lower cycloalkyloxycarbonyl group, aryloxycarbonyl group, heterocyclic oxycarbonyl group, lower cycloalkylsulfonyl group, arylsulfonyl group, heterocyclic sulfonyl group, lower cycloalkylaminocarbonyl group, arylaminocarbonyl group or heterocyclic aminocarbonyl group may have one or a plurality of substituents selected from the group consisting of a halogen atom, a lower alkyl group, a lower alkyl group substituted with at least a halogen atom, a lower alkyl group substituted with at least a hydroxy group, a lower alkenyl group, a lower alkynyl group, a lower cycloalkyl group, an aryl group, a heterocyclic group, a hydroxy group, an ester of a hydroxy group, a lower alkoxy group, a lower alkoxy group substituted with at least a halogen atom, a lower alkenyloxy group, a lower alkynyloxy group, a lower alkylthio group, an amino group, a lower alkylamino group, an amide of an amino group, an amide of a lower alkylamino group, a lower alkylcarbonyl group, a carboxy group, an ester of a carboxy group, an amide of a carboxy group, a lower alkylsulfonyl group, a nitro group and a cyano group;

in the case where $R^7$ is $NR^8R^9$, $R^8$ and $R^9$ may be combined together to form a 5- or 6-membered nitrogen-containing heterocyclic ring; and X represents O.

4. The compound or a salt thereof according to any one of claims 1 to 3, wherein in the formula (1), A represents a methylene group.

5. A pharmaceutical composition, comprising a therapeutically effective amount of the compound or a salt thereof according to any one of claims 1 to 3 in combination with a pharmaceutically acceptable carrier.

* * * * *